US007074794B2

(12) United States Patent
Kitajima et al.

(10) Patent No.: US 7,074,794 B2
(45) Date of Patent: Jul. 11, 2006

(54) PROLINE DERIVATIVES AND THE USE THEREOF AS DRUGS

(75) Inventors: Hiroshi Kitajima, Tokyo (JP); Hiroshi Sakashita, Tokyo (JP); Fumihiko Akahoshi, Tokyo (JP); Yoshiharu Hayashi, Tokyo (JP)

(73) Assignee: Mitsubishi Pharma Corporation, Osaka (JP)

( * ) Notice: Subject to any disclaimer, the term of this patent is extended or adjusted under 35 U.S.C. 154(b) by 109 days.

(21) Appl. No.: 10/344,255

(22) PCT Filed: Aug. 10, 2001

(86) PCT No.: PCT/JP01/06906

§ 371 (c)(1),
(2), (4) Date: Feb. 10, 2003

(87) PCT Pub. No.: WO02/14271

PCT Pub. Date: Feb. 21, 2002

(65) Prior Publication Data

US 2004/0106655 A1 Jun. 3, 2004

(30) Foreign Application Priority Data

Aug. 10, 2000 (JP) .......................................... 2000-24217
Dec. 28, 2000 (JP) ........................................ 2000-400296

(51) Int. Cl.
*A61K 31/495* (2006.01)
*C07D 403/04* (2006.01)

(52) U.S. Cl. .................. 514/252.12; 544/358; 544/359; 544/371; 548/190; 548/194; 514/254.05; 514/365

(58) Field of Classification Search ................. 544/358, 544/359, 371; 548/190, 194; 574/252.12, 574/254.05; 514/365
See application file for complete search history.

(56) References Cited

U.S. PATENT DOCUMENTS 6,399,629 B1 * 6/2002 Chamberland et al. ...... 514/313
6,495,582 B1 * 12/2002 Hale et al. .................. 514/378
6,593,357 B1 * 7/2003 Green et al. ................ 514/406

FOREIGN PATENT DOCUMENTS

CA 2333603 5/1999
WO 95/15309 6/1995
WO 98/19998 5/1998
WO 99/61431 12/1999

OTHER PUBLICATIONS

KJL Augustyns et al., "Pyrrolidides: Synthesis and Structure–Activity Relationship as Inhibitors of Dipeptidyl Peptidase IV", European Journal of Medicinal Chemistry, vol. 32, No. 4, 1997, pp. 301–309.
Heymann et al., FEBS Letters, vol. 91, pp. 360–364 (1978).
Schon et al., Biomedica Biochimica Acta, vol. 44, K9–K15 (1985).
Johnson et al., Journal of Cell Biology, vol. 121, pp. 1423–1432 (1993).
Callebaut et al., Science, vol. 262, pp. 2045–2050 (1993).
Deacon et al., American Journal of Physiology, vol. 271, E458–E464 (1996).
Deacon et al., Journal of Clinical Endocrinology and Metabolism, vol. 80, pp. 952–957 (1995).
Knudsen et al., European Journal of Pharmacology, vol. 318, pp. 429–435 (1996).
Augustyns et al., Current Medicinal Chemistry, vol. 6, p. 311–327 (1999).
Ashworth et al., Bioorganic & Medicinal Chemistry Letters, vol. 6, pp. 1163–1166 (1996).

* cited by examiner

*Primary Examiner*—Golam M M Shameem
(74) *Attorney, Agent, or Firm*—Wenderoth, Lind & Ponack, L.L.P.

(57) ABSTRACT

The present invention aims at providing compounds having therapeutic effects due to a DPP-IV inhibitory action, and satisfactory as pharmaceutical products.

The present inventors have found that derivatives having a substituent introduced into the γ-position of proline represented by the formula (I)

(I)

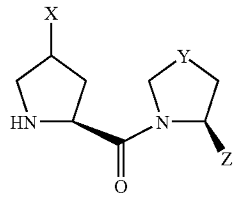

wherein each symbol is as defined in the specification, have a potent DPP-IV inhibitory activity, and completed the present invention by increasing the stability.

8 Claims, No Drawings

PROLINE DERIVATIVES AND THE USE THEREOF AS DRUGS

This application is a U.S. national stage of International Application No. PCT/JP01/06906, filed Aug. 10, 2001.

TECHNICAL FIELD

The present invention relates to a proline derivative showing a dipeptidyl peptidase IV (DPP-IV) inhibitory activity, which is useful for the treatment or prophylaxis of diabetes, obesity, HIV infection, cancer metastasis, dermopathy, prostatic hyperplasia, periodontitis, autoimmune disease and the like, and a salt thereof.

BACKGROUND ART

DPP-IV is a serine protease, which recognizes an amino acid sequence having proline (or alanine or hydroxyproline) the penultimate position from the N-terminal and produces dipeptide Xaa-Pro (Xaa shows an optional amino acid and Pro shows L-proline). DPP-IV is widely distributed in mammalian tissues and is known to be present particularly in blood, kidney, intestinal epithelium and placenta.

While the physiological role of DPP-IV in mammal has not been completely elucidated, its involvement in a broad range of functions of living organisms such as degradation of neuropeptide [Heymann et al., FEBS Letters vol. 91, 360–364 (1978)], activation of T cell [Schon et al., Biomedica Biochimica Acta vol. 44, K9–K15 (1985)], adhesion of metastatic tumor cell to endothelium [Johnson et al., Journal of Cell Biology, vol. 121, 1423–1432 (1993)], invasion of HIV virus into lymphocytes [Callebaut et al., Science vol. 262, 2045–2050 (1993)] and the like is being clarified. Of these, the role of DPP-IV as an enzyme that inactivates glucagon-like peptide (GLP-1), which is a biogenic substance having a strong insulin secretion ability and controls postprandial blood glucose level, has been drawing attention [Deacon et al., Journal of Clinical Endocrinology and Metabolism, vol. 80, 952–957 (1995)].

GLP-1 is known to be metabolized in several minutes in a living organism. In the metabolism, that by DPP-IV is particularly important, because it quickly cleaves GLP-1 and produces inert GLP-1 [Deacon et al., American Journal of Physiology, vol. 271, E458–E464 (1996)]. In addition, it is considered that physiological action of GLP-1 becomes attenuated further because this inert GLP-1 shows an antagonistic action on GLP-1 receptor [Knudsen et al., European Journal of Pharmacology, vol. 318, 429–435 (1996)]. Therefore, a method for suppressing cleavage of GLP-1 by inhibition of DPP-IV is considered to be the most superior approach for reinforcing GLP-1 action. That is, a DPP-IV inhibitor is expected to be a superior treatment method of curing postprandial hyperglycemia without side effects, such as prolonged hypoglycemia and the like, for non insulin-dependent diabetic (type II diabetes) patients.

Patent applications relating to DPP-IV inhibitors include the following.

Japanese Patent Application under PCT laid-open under kohyo No. 9-509921 discloses (S)-2-cyano-1-L-prolinepyrrolidine derivative. The L-α-amino acid corresponding to the L-proline moiety of the compound disclosed therein characteristically has a lipophilic side chain.

In addition, WO99/61431 describes DPP-IV inhibitory activities of a compound consisting of natural amino acid and thiazolidine or pyrrolidine.

DISCLOSURE OF THE INVENTION

While there have been reported many DPP-IV inhibitors till date [Augustyns et al., Current Medicinal Chemistry, vol. 6, 311–327 (1999)], none of the compounds shows sufficient inhibitory activity or sufficient stability and safety in living organisms, and they are unsatisfactory as a pharmaceutical product. Therefore, the development of a compound which exhibits a therapeutic effect through the inhibition of DPP-IV action and satisfactory as a pharmaceutical product has been demanded.

In view of the above-mentioned points, the present inventors have conducted intensive studies with the aim of developing a novel DPP-IV inhibitor. As a result, the present inventors have found that a derivative having a substituent introduced into the γ-position of proline has a potent DPP-IV inhibitory activity, and made the stability higher, which resulted in the completion of the present invention.

Accordingly, the present invention relates to the following compounds.

(1) An L-proline derivative of the formula (I)

(I)

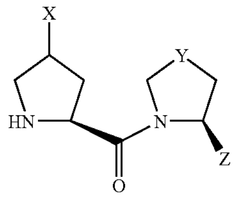

wherein

X shows —$NR^1R^2$ wherein $R^1$ and $R^2$ may be the same or different and each is independently a hydrogen atom, alkyl, cycloalkyl, cycloalkylalkyl, aryl, arylalkyl, heteroaryl or heteroarylalkyl, or may be bonded to each other to form a heterocycle optionally containing 1 or 2 nitrogen atoms or oxygen atoms, the heterocycle optionally being condensed with an aromatic ring optionally having substituents, and the heterocycle optionally being a spiro ring, —$NR^3COR^4$ wherein $R^3$ and $R^4$ are the same or different and each is independently a hydrogen atom, alkyl, cycloalkyl, cycloalkylalkyl, aryl, arylalkyl, arylalkenyl, heteroaryl or heteroarylalkyl, —$NR^5CONR^6R^7$ or —$NR^5CH_2CH_2NR^6R^7$ wherein $R^5$, $R^6$ and $R^7$ are the same or different and each is independently hydrogen atom, alkyl, acyl, cycloalkyl, cycloalkylalkyl, aryl, arylalkyl, heteroaryl or heteroarylalkyl, or $R^6$ and $R^7$ may be bonded to each other to form a heterocycle optionally containing 1 or 2 nitrogen atoms or oxygen atoms, the heterocycle optionally being condensed with an aromatic ring optionally having substituents, —$NR^8SO_2R^9$ wherein $R^8$ and $R^9$ are the same or different and each is independently a hydrogen atom, alkyl, cycloalkyl, cycloalkylalkyl, aryl, arylalkyl, heteroaryl or heteroarylalkyl, or —$OR^{10}$ or —$OCOR^{11}$ wherein $R^{10}$ and $R^{11}$ are each a hydrogen atom, alkyl, cycloalkyl, cycloalkylalkyl, aryl, arylalkyl, heteroaryl or heteroarylalkyl, Y is $CH_2$, CH—OH, S, S═O or $SO_2$, Z is a hydrogen atom or a cyano, and of the above-mentioned groups, alkyl, aryl, arylalkyl, arylalkenyl, heteroaryl, heteroarylalkyl, cycloalkyl, cycloalkylalkyl and heterocycle each optionally have substituents, or a pharmaceutically acceptable salt thereof.

(2) The L-proline derivative described in the aforementioned (1), wherein X of the formula (I) is a substituent selected from the formulas (II)

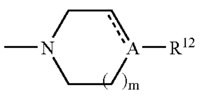

(III)

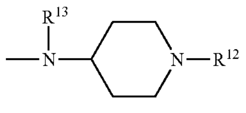

wherein

=== is a single bond or a double bond, $R^{12}$ is alkyl, cycloalkyl, cycloalkylalkyl, aryl, arylalkyl, heteroaryl, heteroarylalkyl, $—NR^{14}R^{15}$, $—OR^{16}$, $—COR^{17}$, $—CO_2R^{18}$, $—CONR^{19}R^{20}$ or $—SO_2R^{21}CH_2$ wherein $R^{14}$, $R^{15}$, $R^{16}$, $R^{17}$, $R^{18}$, $R^{19}$, $R^{20}$ and $R^{21}$ are the same or different and each is independently a hydrogen atom, alkyl, cycloalkyl, cycloalkylalkyl, aryl, arylalkyl, heteroaryl, heteroarylalkyl or haloalkyl, or $R^{14}$ and $R^{15}$, and $R^{19}$ and $R^{20}$ may be bonded to each other to form heterocycles each optionally containing 1 or 2 nitrogen atoms or oxygen atoms, said heterocycle optionally being condensed with an aromatic ring optionally having substituents, $R^{13}$ is a hydrogen atom, alkyl, cycloalkyl, cycloalkylalkyl, aryl, arylalkyl, heteroaryl or heteroarylalkyl, m is 1 or 2, and A is a carbon atom or a nitrogen atom, provided that i) when A is a carbon atom, A may be substituted by a hydroxyl group, carboxyl or alkoxycarbonyl, and ii) when A is a nitrogen atom, === is a single bond, of the above-mentioned groups, alkyl, cycloalkyl, cycloalkylalkyl, aryl, arylalkyl, heteroaryl, heteroarylalkyl and heterocycle each optionally have substituents, or a pharmaceutically acceptable salt thereof.

(3) The L-proline derivative described in the aforementioned (1) or (2), wherein X of the formula (I) is a substituent selected from the formulas (IV)

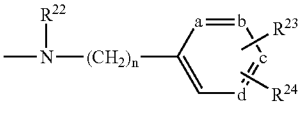

(V)

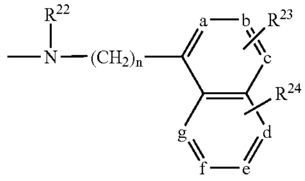

(VI)

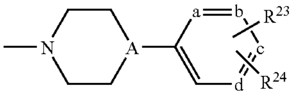

-continued (VII)

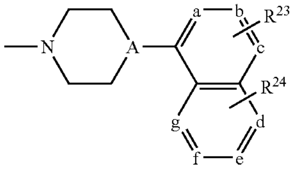

wherein $R^{22}$ is a hydrogen atom, alkyl, cycloalkyl, cycloalkylalkyl, aryl, arylalkyl, heteroaryl or heteroarylalkyl, $R^{23}$ and $R^{24}$ are the same or different and each is independently a hydrogen atom, alkyl, aryl, arylalkyl, heteroaryl, heteroarylalkyl, halogen, haloalkyl, cyano, nitro, $—NR^{25}R^{26}$, $—NHSO_2R^{27}$, $—OR^{28}$, $—COOR^{29}$, $—CONHSO_2R^{30}$, $—SO_2OR^{31}$, $—SO_2R^{32}$ or $—CONR^{33}R^{34}$ wherein $R^{25}$, $R^{26}$, $R^{27}$, $R^{28}$, $R^{29}$, $R^{30}R^{31}$, $R^{32}$, $R^{33}$ and $R^{34}$ are the same or different and each is independently a hydrogen atom, alkyl, cycloalkyl, cycloalkylalkyl, aryl, arylalkyl, heteroaryl, heteroarylalkyl or haloalkyl, or $R^{25}$ and $R^{26}$, and $R^{33}$ and $R^{34}$ may be bonded to each other to form heterocycles each optionally containing 1 or 2 nitrogen atoms or oxygen atoms, said heterocycle optionally being condensed with an aromatic ring optionally having substituents, a, b, c, d, e, f and g are all carbon atoms, or any one or two thereof is(are) nitrogen atom(s) and the rest is a carbon atom, n is 0, 1, 2 or 3, and A is a carbon atom or a nitrogen atom, provided that when A is a carbon atom, A may be substituted by a hydroxyl group, carboxyl or alkoxycarbonyl, and of the above-mentioned groups, alkyl, aryl, arylalkyl, heteroaryl, heteroarylalkyl, cycloalkyl, cycloalkylalkyl and heterocycle each optionally have substituents, or a pharmaceutically acceptable salt thereof.

(4) The L-proline derivative of any of the aforementioned (1) to (3), wherein, in the formula (I), the asymmetric carbon, to which X is bonded, is expressed by an S configuration, X is a group of the formula (VI) or (VII), $R^{23}$ and $R^{24}$ are the same or different and each is nitro, cyano, $C_{1-6}$alkyl, $C_{1-6}$alkyloxy, halogen or haloalkyl, Y is a sulfur atom and Z is a hydrogen atom, or a pharmaceutically acceptable salt thereof.

(5) The L-proline derivative of the aforementioned (1), wherein, in the formula (I), X is a hydroxyl group, phenylamino optionally having substituents, 2-pyridylamino optionally having substituents, 3-pyridazinylamino optionally having substituents or 2-pyrimidinylamino optionally having substituents, and the asymmetric carbon, to which X is bonded, is expressed by an S configuration, or a pharmaceutically acceptable salt thereof.

(6) A compound of the formula (I-a)

(I-a)

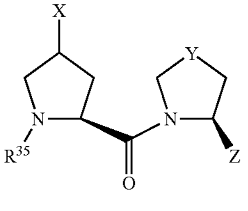

wherein

X shows $—NR^1R^2$ wherein $R^1$ and $R^2$ may be the same or different and each is independently a hydrogen atom, alkyl, cycloalkyl, cycloalkylalkyl, aryl, arylalkyl, heteroaryl or heteroarylalkyl, or may be bonded to each other to form a heterocycle optionally containing 1 or 2 nitrogen atoms or oxygen atoms, the heterocycle optionally being condensed with an aromatic ring optionally having substituents, and the heterocycle optionally being a spiro ring, —$NR^3COR^4$ wherein $R^3$ and $R^4$ are the same or different and each is independently a hydrogen atom, alkyl, cycloalkyl, cycloalkylalkyl, aryl, arylalkyl, arylalkenyl, heteroaryl or heteroarylalkyl, —$NR^5CONR^6R^7$ or —$NR^5CH_2CH_2NR^6R^7$ wherein $R^5$, $R^6$ and $R^7$ are the same or different and each is independently a hydrogen atom, alkyl, acyl, cycloalkyl, cycloalkylalkyl, aryl, arylalkyl, heteroaryl or heteroarylalkyl, or $R^6$ and $R^7$ may be bonded to each other to form a heterocycle optionally containing 1 or 2 nitrogen atoms or oxygen atoms, said heterocycle optionally being condensed with an aromatic ring optionally having substituents, or —$NR^8SO_2R^9$ wherein $R^8$ and $R^9$ are the same or different and each is independently a hydrogen atom, alkyl, cycloalkyl, cycloalkylalkyl, aryl, arylalkyl, heteroaryl or heteroarylalkyl, Y is $CH_2$, CH—OH, S, S═O or $SO_2$, Z is a hydrogen atom or a cyano, $R^{35}$ is —$COR^{41}$ wherein $R^{41}$ is a hydrogen atom, alkyl, cycloalkyl, cycloalkylalkyl, aryl, arylalkyl, heteroaryl or heteroarylalkyl, or —$COOR^{42}$ wherein $R^{42}$ is alkyl, cycloalkyl, cycloalkylalkyl, aryl, arylalkyl, heteroaryl or heteroarylalkyl, and of the above-mentioned groups, alkyl, cycloalkyl, cycloalkylalkyl, aryl, arylalkyl, arylalkenyl, heteroaryl, heteroarylalkyl and heterocycle each optionally have substituents.

(7) A compound of the formula (I-b)

(I-b)

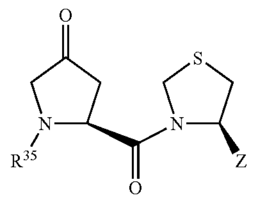

wherein

Z is a hydrogen atom or a cyano, and $R^{35}$ is —$COR^{41}$ wherein $R^{41}$ is a hydrogen atom, alkyl, cycloalkyl, cycloalkylalkyl, aryl, arylalkyl, heteroaryl or heteroarylalkyl, or —$COOR^{42}$ wherein $R^{42}$ is alkyl, cycloalkyl, cycloalkylalkyl, aryl, arylalkyl, heteroaryl or heteroarylalkyl, and of the above-mentioned groups, alkyl, cycloalkyl, cycloalkylalkyl, aryl, arylalkyl, heteroaryl and heteroarylalkyl each optionally have substituents.

The present invention further relates to the following compositions for pharmaceutical agents.

(8) A pharmaceutical composition containing an L-proline derivative of any of the aforementioned (1)–(5) or a pharmaceutically acceptable salt thereof, and a pharmacologically acceptable carrier.

(9) A DPP-IV inhibitor containing an L-proline derivative of any of the aforementioned (1)–(5) or a pharmaceutically acceptable salt thereof as an active ingredient.

(10) A therapeutic agent for the disease where DPP-IV is involved, which contains an L-proline derivative of any of the aforementioned (1)–(5) or a pharmaceutically acceptable salt thereof as an active ingredient.

(11) The therapeutic agent of the aforementioned (10), wherein the aforementioned disease is diabetes, obesity, HIV infection, cancer metastasis, dermopathy, prostatic hyperplasia, periodontitis or autoimmune disease.

The symbols used in the present specification are explained in the following.

Alkyl is preferably linear or branched alkyl having 1 to 8 carbon atoms, such as methyl, ethyl, propyl, isopropyl, butyl, isobutyl, tert-butyl, pentyl, hexyl, octyl and the like.

Acyl is preferably linear or branched and has 1 to 8 carbon atoms, such as formyl, acetyl, propionyl, butyryl, isobutyryl, valeryl, isovaleryl, hexanoyl and the like.

Cycloalkyl preferably has 3 to 7 carbon atoms, and is exemplified by cyclopropyl, cyclopentyl, cyclohexyl, cycloheptyl and the like.

Cycloalkylalkyl has a cycloalkyl moiety, which is equivalent to that mentioned above, and an alkyl moiety which is preferably linear or branched and has 1 to 3 carbon atoms. Examples thereof include cyclopropylmethyl, 2-cyclobutylethyl, 3-cyclopentylpropyl, cyclohexylmethyl, 2-cyclohexylethyl, cycloheptylmethyl and the like.

Aryl is preferably phenyl, naphthyl or ortho fused bicyclic group having 8 to 10 ring atoms wherein at least one ring is an aromatic ring (e.g., indenyl) and the like.

Arylalkyl has an aryl moiety, which is equivalent to that mentioned above, and an alkyl moiety which is preferably linear or branched and has 1 to 3 carbon atoms. Examples thereof include benzyl, benzhydryl, phenethyl, 3-phenylpropyl, 1-naphthylmethyl, 2-(1-naphthyl)ethyl, 2-(2-naphthyl)ethyl, 3-(2-naphthyl)propyl and the like.

Arylalkenyl has an aryl moiety, which is equivalent to that mentioned above, and an alkenyl moiety which has 2 or 3 carbon atoms and is linear or branched. Examples thereof include styryl and the like.

Heteroaryl is preferably a 5 or 6-membered ring group having carbon and 1–4 hetero atoms (oxygen, sulfur or nitrogen), an ortho fused bicyclic heteroaryl having 8 to 10 ring atoms, which is derived therefrom, particularly a benz derivative, those derived from fusing a propenylene, trimethylene or tetramethylene group therewith, stable N-oxide thereof and the like. Examples thereof include pyrrolyl, furyl, thienyl, oxazolyl, isoxazolyl, imidazolyl, thiazolyl, isothiazolyl, pyrazolyl, triazolyl, tetrazolyl, 1,3,5-oxadiazolyl, 1,2,4-oxadiazolyl, 1,3,4-oxadiazolyl, 1,2,4-thiadiazolyl, pyridyl, pyrazinyl, pyrimidinyl, pyridazinyl, 1,2,4-triazinyl, 1,2,3-triazinyl, 1,3,5-triazinyl, benzoxazolyl, benzisoxazolyl, benzothiazolyl, benzisothiazolyl, benzimidazolyl, oxazolopyridyl, imidazopyridazinyl, thianaphthenyl, isothianaphthenyl, benzofuranyl, isobenzofuranyl, benzothienyl, chromenyl, isoindolyl, indolyl, indolinyl, indazolyl, isoquinolyl, quinolyl, phthalazinyl, quinoxalinyl, quinazolinyl, cinnolinyl, 2,1,3-benzoxadiazolyl, benzoxazinyl and the like.

Heteroarylalkyl has a heteroaryl moiety, which is equivalent to that mentioned above, and an alkyl moiety which is preferably has 1 to 3 carbon atoms and linear or branched. Examples thereof include 2-pyrrolylmethyl, 2-pyridylmethyl, 3-pyridylmethyl, 4-pyridylmethyl, 2-thienylmethyl, 2-(2-pyridyl)ethyl, 2-(3-pyridyl)ethyl, 2-(4-pyridyl)ethyl, 3-(2-pyrrolyl)propyl, 4-imidazolylmethyl and the like.

Heterocycle is a saturated or unsaturated monocyclic 4 to 7-membered ring group or 10 or 11-membered ring group, which is a spiro ring, having carbon and at least one nitrogen, and optionally other hetero atom (oxygen or sulfur). Examples thereof include azetidinyl, pyrrolidinyl, piperidino, piperazinyl, morpholino, 1,4-diazepanyl, 1,2,5,6-tetrahydropyridyl, thiomorpholino, oxothiomorpholino, dioxothiomorpholino, 3-azaspiro[5,5]undecyl, 1,3,8-triazaspiro[4,5]decyl and the like.

Moreover, the above-mentioned heterocycle may be condensed with an aromatic ring (e.g., benzene ring, pyridine ring and the like) optionally having substituents. Examples thereof include indolinyl, isoindolinyl, 1,2,3,4-tetrahydroquinolyl, 1,2,3,4-tetrahydroisoquinolyl, phthalimido, indolyl and the like.

Halogen is exemplified by chlorine, bromine, fluorine and iodine.

Haloalkyl is exemplified by trifluoromethyl, 2,2,2-trifluoroethyl, pentafluoroethyl and the like.

Of the above-mentioned substituents, alkyl, cycloalkyl, cycloalkylalkyl, aryl, arylalkyl, arylalkenyl, heteroaryl, heteroarylalkyl and heterocycle are optionally substituted by the following 1 or more substituents.

The substituents may be, for example, halogen, hydroxyl group, nitro, cyano, trifluoromethyl, alkyl, alkoxy, alkylthio, formyl, acyloxy, oxo, phenyl, 2-pyridyl, 3-pyridyl, 4-pyridyl, 4-piperidinyl, 2-morpholinoethyl, 3-picolyl, arylalkyl, $-COOR_a$, $-CH_2COOR_a$, $-OCH_2COOR_a$, $-CONR_bR_c$, $-CH_2CQNR_b R_c$ (Q is =O or =S), $-OCH_2CONR_bR_c$, $-COO(CH_2)_2NR_eR_f$, $-SO_2T_1$, $-CONR_dSO_2T_1$, $-NR_eR_f$, $-NR_gCHO$, $-NR_gCOT_2$, $-NR_gCOOT_2$, $-NR_gCONR_iR_j$, $-NR_kSO_2T_3$, $-SO_2NR_lR_m$, $-SO_2NR_nCOT_4$, methylenedioxy, ethyleneoxy and the like.

These substituents may have substituents, and phenyl, 2-pyridyl and 4-piperidinyl having substituents are exemplified by 4-cyanophenyl, 4-chlorophenyl, 4-methoxyphenyl, 5-cyano-2-pyridyl, 1-ethoxycarbonyl-4-piperidinyl and the like.

In the above-mentioned substituents of the substituents, halogen, alkyl and arylalkyl are exemplified by those mentioned above.

Alkoxy is linear or branched and preferably has 1 to 8 carbon atoms. Examples thereof include methoxy, ethoxy, propoxy, butoxy, pentyloxy, hexyloxy, octyloxy and the like. Alkylthio is linear or branched and preferably has 1 to 8 carbon atoms. Examples thereof include methylthio, ethylthio, propylthio, butylthio, pentylthio, hexylthio, octylthio and the like. Acyloxy is linear or branched and preferably has 1 to 8 carbon atoms. Examples thereof include formyloxy, acetyloxy, propionyloxy, butyryloxy, valeryloxy, pivaloyloxy, hexanoyloxy, benzoyloxy and the like.

$R_a$–$R_n$ show hydrogen, alkyl (as defined above) or arylalkyl (as defined above). $R_b$ and $R_c$, $R_e$ and $R_f$, $R_i$ and $R_j$, and $R_l$ and $R_m$ of $-NR_bR_c$, $-NR_eR_f$, $-NR_iR_j$ and $-NR_lR_m$ may be respectively bonded to each other to form heterocycles each optionally having 1 or 2 nitrogen atoms or oxygen atoms, and the heterocycle may be condensed with an aromatic ring optionally having substituents (as defined above, and optionally substituted by the aforementioned substituents). Moreover, $-NR_eR_f$ may show a heteroaryl having =O (e.g., 2-pyrrolidinon-1-yl, succinimido, oxazolidin-2-on-3-yl, 2-benzoxazolinon-3-yl, phthalimido, cis-hexahydrophthalimido and the like). $T_1$–$T_4$ show hydrogen atom, alkyl, cycloalkyl, cycloalkylalkyl, aryl, arylalkyl, heteroaryl, heteroarylalkyl or haloalkyl, which may be substituted by the aforementioned substituents.

Due to the asymmetric carbon, to which X is bonded, in compound (I), compound (I) can be present as an optically active compound or a diastereomer mixture, and the diastereomer mixture can be separated into each optically active compound by a known method.

The compound (I) can show polymorphism, and can be present as two or more tautomers.

Therefore, the present invention encompasses any of the above-mentioned stereoisomers, optical isomers, polymorphs, tautomers, optional mixtures thereof and the like.

The pharmaceutically acceptable salt of compound (I) includes, for example, inorganic acid addition salts (e.g., salts with hydrochloric acid, hydrobromic acid, hydriodic acid, sulfuric acid, nitric acid, phosphoric acid and the like), organic acid addition salts (e.g., salts with methanesulfonic acid, benzenesulfonic acid, p-toluenesulfonic acid, formic acid, acetic acid, trifluoroacetic acid, oxalic acid, citric acid, malonic acid, fumaric acid, glutaric acid, adipic acid, maleic acid, tartaric acid, succinic acid, mandelic acid, malic acid, pantothenic acid, methylsulfuric acid and the like), salts with. amino acids (e.g., salts with glutamic acid, aspartic acid and the like), and the like.

The L-proline derivative of the present invention can be produced by the following method.

Scheme 1 shows a production method of a compound of the formula (I) wherein X is $-OR^{10}$ or $-OCOR^{11}$.

Scheme 1

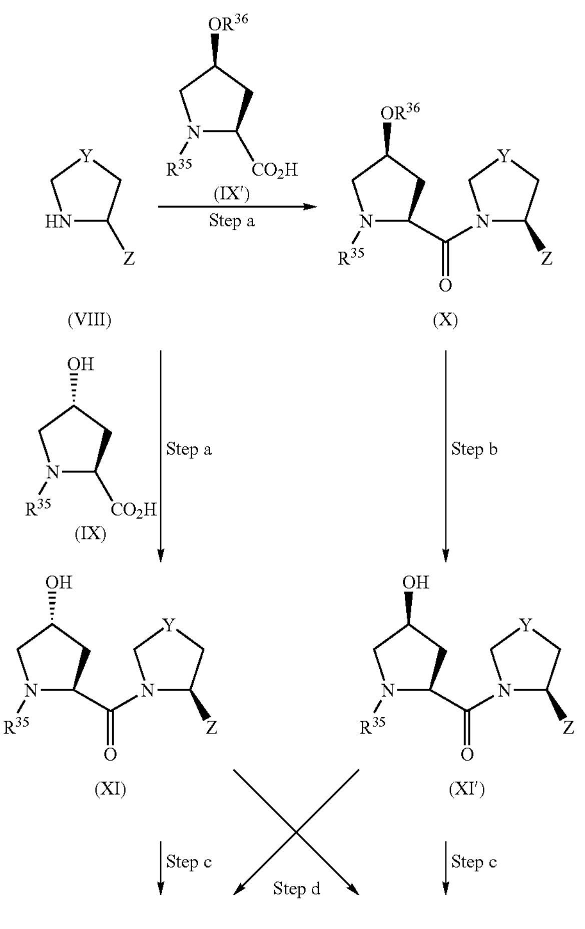

-continued

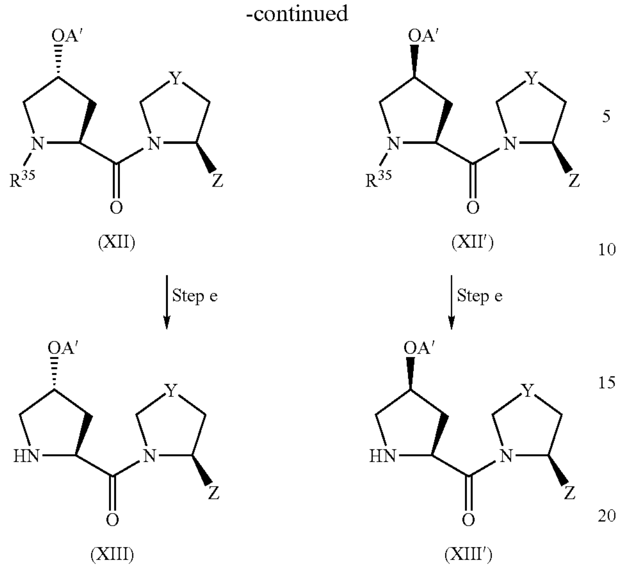

wherein $R^{35}$ is an amino acid-protecting group (e.g., tert-butoxycarbonyl (Boc) and benzyloxycarbonyl (Cbz)), $R^{36}$ is a hydroxyl-protecting group (e.g., tert-butyldimethylmethylsilyl, triisopropylsilyl and tert-butyldiphenylsilyl), A' is $R^{10}$ or $COR^{11}$ and other symbols are as defined above.

When Z of a compound of the formula (VIII) is cyano, this compound can be prepared by a method described in a reference [Ashworth et al., Bioorganic & Medicainal Chemistry Letters, vol. 6, 1163–1166 (1996)] or a conventional method based on such reference. A compound of the formula (IX') [hereinafter to be referred to as compound (IX')] can be prepared by silylation of hydroxyl group of hydroxyproline derivative by a conventional method.

Step a: Compound (VIII) is Reacted with Compound (IX) to Give Amide Compound (XI), or Compound (VIII) is Reacted with Compound (IX') to Give Amide Compound (X).

As a condensation agent for activating carboxylic acid of compound (IX) or (IX'), there are recited, for example, dicyclohexylcarbodiimide (DCC), N-(3-dimethylaminopropyl)-N'-ethylcarbodiimide (EDC), hydrochloride thereof, 2-ethoxy-1-ethoxycarbonyl-1,2-dihydroxyquinoline (EEDQ), carbodiimidazole (CDI), diethylphosphoryl cyanide, benzotriazol-1-yloxytrispyrrolidinophosphonium hexafluorophosphate (PyBOP), diphenylphosphoryl azide (DPPA), isobutyl chloroformate, diethylacetyl chloride, trimethylacetyl chloride and the like. These condensation agent may be used alone, or an additive such as N-hydroxysuccinimide (HONSu), hydroxybenzotriazole (HOBT) or 3-hydroxy-4-oxo-3,4-dihydro-1,2,3-benzotriazine (HOOBT), 4-dimethylaminopyridine (DMAP) and the like is used in combination.

This reaction is generally carried out in an inert solvent and the inert solvent to be used may be any as long as it is aprotic. Preferable examples include acetonitrile, tetrahydrofuran, dichloromethane, chloroform, N,N-dimethylformamide (DMF) and the like. This condensation is carried out generally at a temperature of from −30° C. to 80° C., preferably from −10° C. to 25° C.

Step b: Compound (X) is Deprotected to Give Compound (XI').

This reaction can be carried out in an inert solvent such as tetrahydrofuran and the like, using tetrabutylammonium fluoride and the like. The reaction mixture is preferably buffered with an acid such as acetic acid and the like generally at a temperature of from −30° C. to 70° C. for 10 min to 24 hr.

Step c: Compound (XI) is Reacted to Give Compound (XII), or Compound (XI') is Reacted to Give Compound (XII').

By acylation of hydroxyl group of compound (XI) or (XI') by a general method, a compound of the formula (XII) or (XII'), wherein A' is $COR^{11}$, can be obtained. The synthetic method of compound (XII) or (XII'), wherein $R^{11}$ is alkyl, cycloalkyl, cycloalkylalkyl, aryl, arylalkyl, heteroaryl or heteroarylalkyl, is exemplified by a method including use of an active carboxylic acid derivative such as acid halide, a method including use of a carboxylic acid and a coupling agent, and the like.

A compound of the formula (XII) or (XII') wherein A' is $R^{10}$ can be obtained by converting hydroxyl group of compound (XI) or (XI') to alcoholate, which is followed by nucleophilic substitution of alkyl halide and the like. The reaction is carried out in the presence of a base such as sodium hydride and the like, using alkyl halide and the like in an inert solvent such as tetrahydrofuran and the like, generally at a temperature of from −80° C. to 60° C., preferably from −50° C. to 25° C.

Step d: Compound (XI) is Reacted to Give Compound (XII'), or Compound (XI') is Reacted to Give Compound (XII).

The reaction is carried out in the presence of phosphines such as triphenylphosphine, tributylphosphine and the like and diazodicarboxylic acid diester, using $R^{11}COOH$ or aryl or heteroaryl having a hydroxyl group, and the like in an inert solvent such as toluene, tetrahydrofuran and the like, generally at a temperature of from −30° C. to 110° C., preferably from 0° C. to 25° C.

A compound of the formula (XII') or (XII), wherein A' is $COR^{11}$, can be obtained by sulfonylation of hydroxyl group of compound (XI) or (XI'), and reacting the compound with carboxylic acid salt. The sulfonylation is carried out in the presence of a base such as pyridine, triethylamine and the like using p-toluenesulfonyl chloride, methanesulfonyl chloride, trifluoromethanesulfonyl chloride and the like, in an inert solvent such as dichloromethane, 1,2-dichloroethane and the like generally from −30° C. to 60° C. for 10 min to 24 hr. The subsequent reaction with carboxylic acid salt is carried out in the presence of an inorganic base such as potassium carbonate, sodium carbonate and the like using $R^{11}COOH$ in an inert solvent such as acetone, hexamethylphosphoramide and the like generally from 0° C. to 120° C. for 10 min to 24 hr.

Step e: Compound (XII) is Deprotected to Give Compound (XIII), or Compound (XII') is Deprotected to Give Compound (XIII').

When, in this reaction, the protecting group is Boc group, for example, the compound is reacted in a solvent such as acetonitrile, tetrahydrofuran, 1,4-dioxane, ethyl acetate, methanol, ethanol, chloroform and the like, using an acid such as hydrogen chloride, trifluoroacetic acid and the like generally from −30° C. to 60° C. for 10 min to 24 hr for deprotection.

Scheme 2 shows a production method of a compound of the formula (I) wherein X is $—NR^1R^2$.

Scheme 2

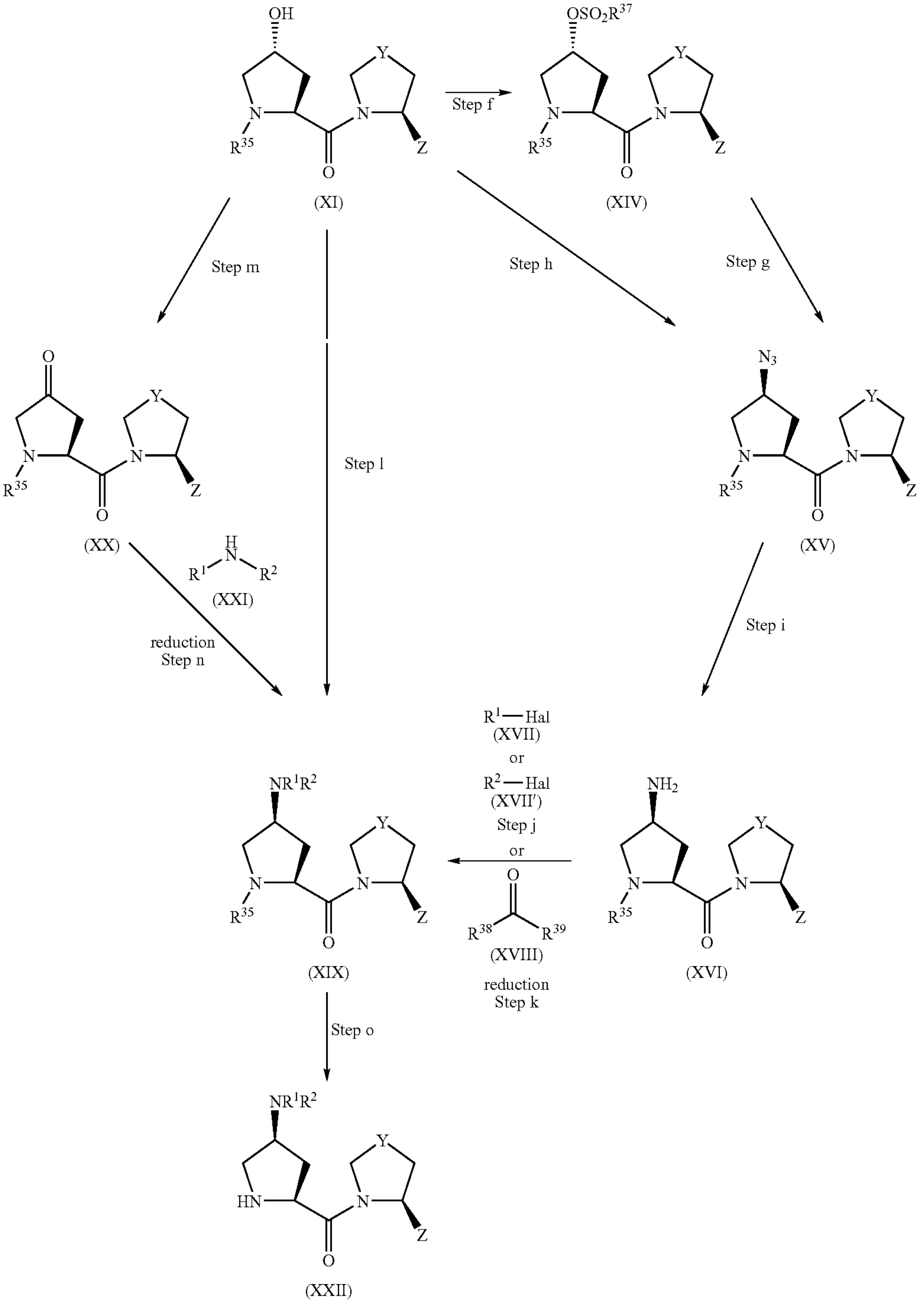

wherein $OSO_2R^{37}$ is a leaving group (e.g., tosylate (OTs), mesylate (OMs) or triflate (OTf)), Hal is halogen, $R^{38}$ and $R^{39}$ are the same or different and each is independently hydrogen atom, alkyl, cycloalkyl, cycloalkylalkyl, aryl, arylalkyl, heteroaryl or heteroarylalkyl, or may be bonded to each other to form a heterocycle optionally containing 1 or 2 nitrogen atoms or oxygen atoms, or the heterocycle may be condensed with an aromatic ring optionally having substituents, and other symbols are as defined above.

Step f: Hydroxyl Group of Compound (XI) is Sulfonylated to Give Compound (XIV).

This reaction is carried out in the presence of a base such as pyridine, triethylamine and the like, using p-toluenesulfonyl chloride, methanesulfonyl chloride, trifluoromethanesulfonyl chloride and the like in an inert solvent such as dichloromethane, 1,2-dichloroethane and the like generally at a temperature of from −30° C. to 60° C. for 10 min to 24 hr.

Step g: Compound (XIV) is Subjected to Azidation to Give Compound (XV).

The reaction is carried out using a metal azide, such as s sodium azide, in a solvent such as N,N-dimethylformamide and the like generally at a temperature of from 0° C. to 120° C. for 30 min to 24 hr.

Step h: Compound (XV) is Directly Obtained from Compound (XI).

The reaction is carried out in the presence of phosphines such as triphenylphosphine, tributylphosphine and the like, and diazodicarboxylic acid diester using hydrogen azide, DPPA, zinc azide bispyridine complex salt and the like in an inert solvent such as toluene, tetrahydrofuran and the like generally at a reaction temperature of from −30° C. to 100° C.

Step i: Compound (XV) is Reduced to Give Compound (XVI).

For this reaction, catalytic reduction using palladium, platinum, nickel and the like, reduction by metalhydride, reduction by triphenylphosphine, thiol, sulfide, diborane, or transition metal and the like are mentioned.

Step j: Compound (XVI) is Reacted with Compound (XVII) or (XVII') to Give Compound (XIX).

The reaction is carried out in the presence of a base such as triethylamine, diisopropylethylamine and the like in an inert solvent such as N-methyl-2-pyrrolidone, N,N-dimethylformamide, tetrahydrofuran and the like at a temperature of from 0° C. to near boiling point of solvent, preferably from 0° C. to 80° C.

Step k: Compound (XVI) is Reacted with Compound (XVIII), which is Followed by Reduction to Give Compound (XIX).

This reaction is carried out in the presence of sodium borohydride, sodium cyanoborohydride, sodium triacetoxyborohydride and the like in an inert solvent such as methanol, ethanol, dichloromethane, 1,2-dichloroethane, tetrahydrofuran, acetonitrile, 1,4-dioxane and the like, and using, where necessary, an acid catalyst such as acetic acid, p-toluenesulfonic acid, boron trifluoride diethylether complex and the like, generally at a temperature of from 0° C. to 100° C. for 10 min to 20 hr.

By repeating Step j or k as necessary, compound (XIX) wherein $R^1$ and $R^2$ may be the same or different can be obtained.

Step l: Compound (XIX) is Directly Obtained from Compound (XI).

The reaction is carried out in the presence of phosphines such as triphenylphosphine, tributylphosphine and the like and diazodicarboxylic acid diester using iminodicarbonates, sulfonamides, a nitrogen-containing compound having N-H hydrogen and having high acidity, and the like in an inert solvent such as toluene, tetrahydrofuran and the like.

Step m: Compound (XI) is Oxidized to Give (XX).

This reaction is carried out by, for example, a method using pyridine sulfur trioxide complex and dimethyl sulfoxide at room temperature. Examples of useful other methods include a method using alkaline potassium permanganate solution; a method using oxalyl chloride, dimethyl sulfoxide and tertiary amine; a method using acetic anhydride and dimethyl sulfoxide; a method using EDC and dimethyl sulfoxide with dichloroacetic acid as a catalyst; a method using chromium oxide (XI) pyridine complex in dichloromethane; a method using aqueous sodium hypochlorite solution with TEMPO free radical as a catalyst in the presence of sodium bromide in ethyl acetate and toluene, and the like.

Step n: Compound (XX) is Reacted with Compound (XXI), which is Followed by Reduction to Give Compound (XIX).

This reaction is carried out in the presence of sodium borohydride, sodium cyanoborohydride, sodium triacetoxyborohydride and the like, in an inert solvent such as methanol, ethanol, dichloromethane, 1,2-dichloroethane, tetrahydrofuran, acetonitrile, 1,4-dioxane and the like, and using as necessary an acidic catalyst, such as acetic acid, p-toluenesulfonic acid, boron trifluoride diethyl ether complex and the like generally at a temperature of from 0° C. to 100° C. for 10 min to 20 hr.

The compound (XXI) can be synthesized by a known method.

Step o is the Same as Step e of Scheme 1.

The production method of a compound of the formula (I) wherein X is $—NR^3COR^4$ is shown in Scheme 3.

Scheme 3

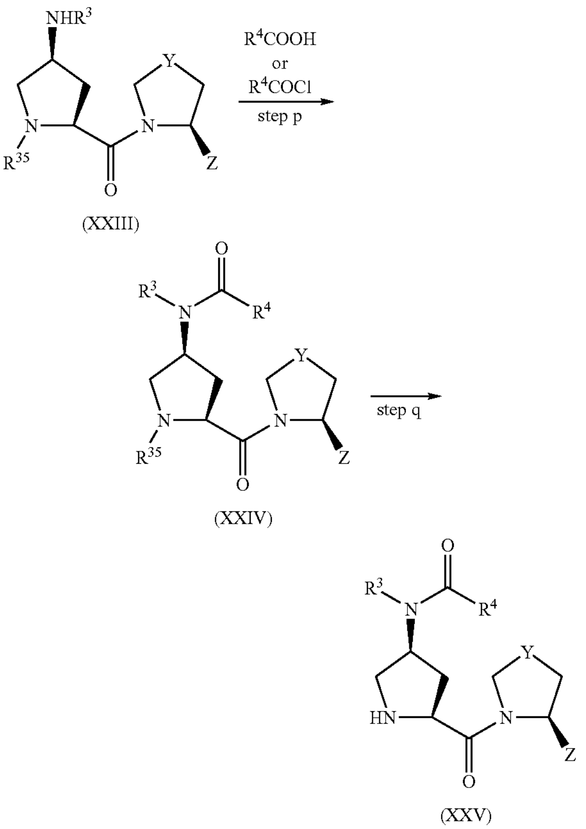

wherein each symbol in the formula is as defined above.

The compound (XXIII) is the same as compound (XVI) obtained in Scheme 2 or a compound (XIX) wherein one of $R^1$ and $R^2$ is hydrogen atom.

Step p: Compound (XXIII) is Reacted to Give Amide Compound (XXIV).

The reaction is carried out using $R^4COCl$ or $R^4CO_2H$ after conversion to an acid halide with thionyl chloride, thionyl bromide and the like or conversion to a mixed acid anhydride with pivaloyl chloride, isobutyl chloroformate and the like, in the presence of a tertiary base such as triethylamine, pyridine, N,N-dimethylaniline and the like, in an inert solvent such as toluene, hexane, tetrahydrofuran, 1,4-dioxane, ethyl acetate, chloroform, N,N-dimethylformamide, dimethyl sulfoxide, hexamethylphosphoramide and the like, generally from 0° C. to 120° C. for 10 min to 10 hr.

For the reaction with $R^4CO_2H$, a condensation agent shown in Step a can be also used and the reaction is carried out in an inert solvent such as acetonitrile, tetrahydrofuran, dichloromethane, chloroform, N,N-dimethylformamide and the like generally at a temperature of from −30° C. to 80° C., preferably from −10° C. to 25° C.

Step q is the same as Step e of Scheme 1.

The production method of a compound of the formula (I) wherein X is —$NR^5CONR^6R^7$ is shown in Scheme 4.

Scheme 4

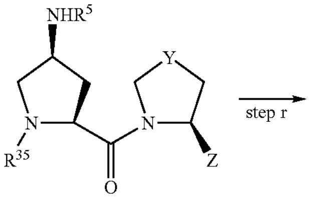

(XXVI)

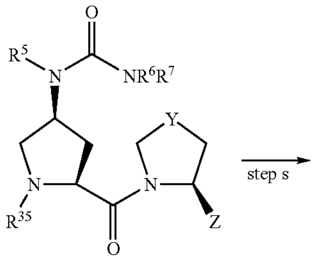

(XXVII)

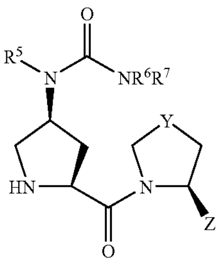

(XXVIII)

wherein each symbol in the formula is as defined above.

The compound (XXVI) is the same as compound (XVI) obtained in Scheme 2 or a compound (XIX) wherein one of $R^1$ and $R^2$ is hydrogen atom.

Step r: Compound (XXVI) is Reacted to Give Urea Compound (XXVII).

The reaction is carried out using isocyanate such as $R^6$—NCO and the like in an inert solvent such as toluene, chloroform, dichloromethane, tetrahydrofuran and the like generally at a temperature of from −20° C. to 80° C., preferably from 0° C. to 25° C.

Alternatively, there is a method using, for example, carbodiimidazole, phosgene, diphosgene (trichloromethyl chloroformate), triphosgene [bis(trichloromethyl)carbonate] and the like, together with an amine represented by $R^6R^7NH$ and a tertiary base such as triethylamine and the like.

Step s is the same as Step e of Scheme 1.

The production method of a compound of the formula (I) wherein X is —$NR^8SO_2R^9$ is shown in Scheme 5.

Scheme 5

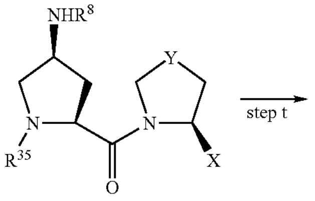

(XXIX)

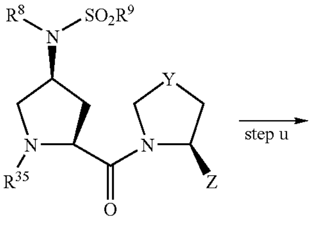

(XXX)

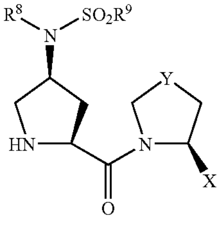

(XXXI)

wherein each symbol in the formula is as defined above.

The compound (XXIX) is the same as compound (XVI) obtained in Scheme 2 or a compound (XIX) wherein one of $R^1$ and $R^2$ is hydrogen atom.

Step t: Compound (XXIX) is Reacted to Give Sulfonamide Compound (XXX).

The reaction is carried out using sulfonyl chloride such as $R^9$—$SO_2Cl$ and the like in the presence of an organic base such as triethylamine, pyridine and the like or an inorganic base such as sodium carbonate, potassium carbonate, sodium hydroxide and the like, in a solvent such as water, toluene, chloroform, dichloromethane, tetrahydrofuran and the like generally at a temperature of from −20° C. to 80° C.

Alternatively, there is a method wherein compound (XXIX) and sulfuryl chloride are reacted in the presence of a tertiary base such as triethylamine and the like in an inert solvent such as chloroform, dichloromethane, tetrahydrofuran and the like to give sulfamyl chloride, which is reacted with aryl compound in the presence of a Lewis acid such as aluminum chloride and the like.

Step u is the same as Step e of Scheme 1.

A different production method of compound (XXII) is shown in Scheme 6. This production method is useful when both $R^1$ and $R^2$ are not hydrogen atoms.

Scheme 6

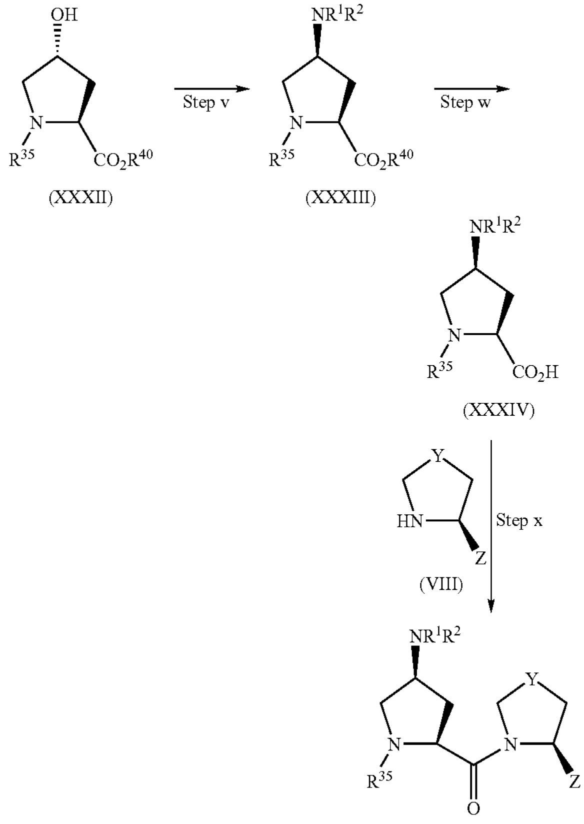

(XXXII) (XXXIII) (XXXIV) (VIII) (XIX)

wherein $R^{40}$ is alkyl such as methyl, ethyl and the like, benzyl and the like, and other symbols are as defined above.

Step v is the same as the method for conversion of compound (XI) to compound (XIX) shown in Scheme 2.

Step w: Ester-Protected Carboxyl Group of Compound (XXXIII) is Deprotected to Give Compound (XXXIV).

For reaction, general deprotection can be used. For example, sodium hydroxide, potassium hydroxide, sodium carbonate, potassium carbonate and the like are hydrolyzed under alkali conditions, or when $R^{40}$ is benzyl, catalytic hydrogenation and the like are conducted in the presence of platinum, palladium and the like, in an inert solvent such as methanol, ethanol and the like for deprotection.

Step x: Compound (VIII) and Compound (XXXIV) are Reacted to Give Amide Compound (XIX).

The reaction is carried out using a condensation agent shown in Step a, in an inert solvent such as acetonitrile, tetrahydrofuran, dichloromethane, chloroform, N,N-dimethylformamide and the like generally at a temperature of from −30° C. to 80° C., preferably from −10° C. to 25° C.

The compound of the formula (XXIV) shown in Scheme 3, the compound of the formula (XXVII) shown in Scheme 4 and the compound of the formula (XXX) shown in Scheme 5 can be produced by the routes shown in Scheme 6.

The production method of compound (XXII), wherein the asymmetric, carbon, to which $NR^1R^2$ is bonded, is shown by S configuration, is shown in Scheme 2 using the compound of the formula (XI) as a starting material, and in Scheme 6, using the compound of the formula (XXXII) as a starting material.

Besides the above-mentioned, a compound (XXII'), wherein the asymmetric carbon, to which $NR^1R^2$ is bonded, is shown by R configuration, (XXII')

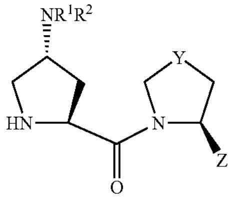

wherein each symbol in the formula is as defined above, can be also produced by a method similar to the one mentioned above using compound (XI')

(XI')

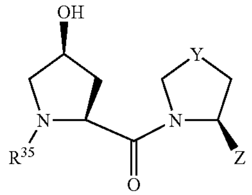

wherein each symbol in the formula is as defined above, or a compound (XXXII')

(XXXII')

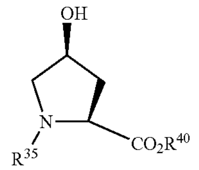

wherein each symbol in the formula is as defined above, as a starting material.

When Z in each formula shows cyano, each compound up to an intermediate is produced with Z of the formula as a carbamoyl group and dehydrated by a known method for conversion thereof to cyano group.

This reaction is carried out using diphosphorus pentaoxide, phosphorus oxychloride-imidazole, trifluoroacetic acid anhydride, p-toluenesulfonyl chloride-pyridine and the like as a dehydrating agent in an inert solvent such as dichloromethane, pyridine and the like.

The L-proline derivative of the formula (I) of the present invention produced in this manner can be obtained at an optional purity by applying a known separation and purification means as necessary, such as concentration, extraction, chromatography, reprecipitation, recrystallization and the like.

The L-proline derivative of the formula (I) can be prepared into an acid addition salt as necessary with an inorganic acid such as hydrochloric acid, hydrobromic acid, hydriodic acid, sulfuric acid, nitric acid, phosphoric acid and the like or an organic acid such as methanesulfonic acid, benzenesulfonic acid, p-toluenesulfonic acid, formic acid, acetic acid, trifluoroacetic acid, oxalic acid, citric acid, malonic acid, fumaric acid, glutaric acid, adipic acid, maleic acid, tartaric acid, succinic acid, mandelic acid, malic acid, pantothenic acid, methylsulfuric acid and the like. In addition, it is also present as a solvate such as hydrate and the like.

The compound of the formula (I) or a pharmacologically acceptable salt of the present invention has a superior DPP-IV inhibitory activity in mammals (e.g., human, dog, cat, rat and the like).

Therefore, the compound of the present invention (I) or a pharmacologically acceptable salt thereof is useful as a DPP-IV inhibitor and useful for the prophylaxis or treatment of various diseases considered to be caused by DPP-IV, for example, for the prophylaxis or treatment of diseases where GLP-1 is considered to be involved (e.g., diabetes, obesity and the like), and the like.

The compound (I) of the present invention can be administered to a same subject with other therapeutic drug for diabetes, therapeutic drug for diabetic complications, anti-hyperlipidemic agent, antihypertensive agent and the like at the same time or timelag. As used herein, examples of the therapeutic drug for diabetes include insulin sensitivity increasing agent, α-glucosidase inhibitor, biguanide agent and the like. Examples of the therapeutic drug for diabetic complications include aldose reductase inhibitor. As the anti-hyperlipidemic agent, statin compound, which is a cholesterol synthetase inhibitor, squalene synthetase inhibitor, fibrates having triglyceride lowering effect, and the like can be mentioned. As the antihypertensive agent, calcium antagonist, angiotensin converting enzyme inhibitor, angiotensin II antagonist and the like can be mentioned. When the compound of the present invention is used on combination with multiple agents, the mixing ratio thereof can be appropriately determined depending on the subject of administration, age and body weight of the administration subject, symptom, administration time, dosage form, administration method, combination and the like.

When the compound (I) of the present invention or an acid addition salt thereof is used as the aforementioned pharmaceutical agent, it is used on its own or admixed with an appropriate pharmacologically acceptable carrier, an excipient, a diluent and the like in the form of powder, granule, tablet, capsule, injection and the like, and administered orally or parenterally. The above-mentioned preparation contains an effective amount of compound (I) or a pharmacologically acceptable salt thereof.

While the dose of the compound (I) or a pharmacologically acceptable salt thereof varies depending on the administration route, target disease, symptom, body weight and age of patients, and the compound to be used, it can be determined as appropriately according to the administration object. Generally, when orally administered to an adult, 0.01–1000 mg/kg body weight/day, preferably 0.05–500 mg/kg body weight/day, is preferably administered once a day or in several doses a day.

EXAMPLES

The present invention is explained in detail by referring to Reference Examples and Examples, which are not to be construed as limitative.

$^1$H-NMR was measured at 300 MHz unless particularly indicated. The chemical shift of $^1$H-NMR relative delta (δ) value was expressed in parts per million (ppm) using tetramethylsilane (TMS) as the internal standard. For the coupling constant, obvious multiplicity is shown in hertz (Hz) using s (singlet), d (doublet), t (triplet), q (quartet), quint (quintet), m (multiplet), dd (doublet of doublets), td (triplet of doublets), brs (broad singlet) and the like. Thin-layer chromatography used was manufactured by Merck, and column chromatography was performed using silica gel manufactured by Fuji silysia chemical.

For drying organic solutions in extraction, anhydrous sodium sulfate or anhydrous magnesium sulfate was used, unless particularly indicated.

Reference Example 1

Synthesis of (S)-1-((2S,4S)-1-tert-butoxycarbonyl-4-hydroxy-2-pyrrolidinylcarbonyl)-2-cyanopyrrolidine (1) N-tert-Butoxycarbonyl-L-cis-4-hydroxyproline (23.1 g) and imidazole (30.0 g) were dissolved in DMF (300 mL). tert-Butyldimethylsilyl chloride (33.3 g) was added thereto. After stirring at room temperature for 16 hr, water (300 mL) was gradually added under ice-cooling. The reaction solution was acidified with 10% aqueous citric acid solution and extracted with ethyl acetate. The extract was washed 3 times with water and with brine, and dried. The solvent was distilled away under reduced pressure. The residue was purified by silica gel chromatography to give N-tert-butoxycarbonyl-L-cis-4-tert-butyldimethylsilyloxyproline (27.4 g) as a white solid.

(2) The above-mentioned compound (27.4 g) and (S)-2-cyanopyrrolidine hydrochloride (10.4 g) were dissolved in DMF (250 mL), and triethylamine (10.9 mL), HOBT (14.3 g) and EDC hydrochloride (18.0 g) were added successively. The mixture was stirred at room temperature for 15 hr. The reaction mixture was added to saturated aqueous sodium hydrogencarbonate solution, and extracted with ethyl acetate. The extract was washed with water and brine, and dried. The solvent was evaporated under reduced pressure. The residue was purified by silica gel chromatography to give (S)-1-[(2S,4S)-1-tert-butoxycarbonyl-4-tert-butyldimethylsilyloxy-2-pyrrolidinylcarbonyl]-2-cyanopyrrolidine (25.3 g) as a slightly yellow oil.

(3) The above-mentioned compound (25.3 g) was dissolved in tetrahydrofuran (300 mL), and a 1.0 mol/L solution (60 mL) of tetrabutylammonium fluoride in tetrahydrofuran was added dropwise under ice-cooling. The mixture was stirred at room temperature for 3 hr, and the solvent was evaporated under reduced pressure. The residue was added to brine, and extracted with ethyl acetate. The extract was dried, and the solvent was evaporated under reduced pressure. The residue was purified by silica gel chromatography to give the title compound (20.6 g) as a white solid.

$^1$H-NMR(DMSO-$d_6$)δ1.25–1.45(9H,m), 1.50–1.64(1H,m), 1.95–2.30(4H,m), 2.98–3.13(1H,m), 3.30–3.67(4H,m), 4.13–4.26(1H,m), 4.30–4.42(1H,m), 4.77–4.88(1H,m), 5.16 (1H,d,J=6.5 Hz).

Reference Example 2

Synthesis of (S)-1-((2S,4R)-1-tert-butoxycarbonyl-4-hydroxy-2-pyrrolidinylcarbonyl)-2-cyanopyrrolidine N-tert-Butoxycarbonyl-L-trans-4-hydroxyproline (68.4 g) and (S)-2-cyanopyrrolidine hydrochloride (39.2 g) were dissolved in DMF (350 mL), and triethylamine (41.4 mL), HOBT (49.9 g), and EDC hydrochloride (62.5 g) were successively added. The mixture was stirred at room temperature for 15 hr. The reaction mixture was concentrated and brine and saturated aqueous sodium hydrogencarbonate solution were added to the residue. The precipitated crystals were collected by filtration. The filtrate was extracted with ethyl acetate and the extract was dried. The solvent was evaporated under reduced pressure. The residue and the crystals were combined and washed with ethyl acetate to give the title compound (60.7 g) as a white solid.

$^1$H-NMR($CDCl_3$)δ1.30–1.45(9H,m), 1.54–2.38(5H,m), 3.30–3.93(5H,m), 4.49–4.89(3H,m).

Reference Example 3

Synthesis of (S)-1-((2S,4S)-4-amino-1-tert-butoxycarbonyl-2-pyrrolidinylcarbonyl)-2-cyanopyrrolidine (1) (S)-1-((2S,4R)-1-tert-Butoxycarbonyl-4-hydroxy-2-pyrrolidinylcarbonyl)-2-cyanopyrrolidine (title compound of Reference Example 2, 60.7 g) and triethylamine (30.1 mL) were dissolved in DMF (300 mL). Methanesulfonyl chloride (16 mL) was added thereto under ice-cooling. After stirring at room temperature for 3 hr, the reaction mixture was washed with water and dried. The solvent was evaporated under reduced pressure. Ethanol was added to the residue to give (S)-1-((2S,4R)-1-tert-butoxycarbonyl-4-methanesulfonyloxy-2-pyrrolidinylcarbonyl)-2-cyanopyrrolidine (64.1 g) as a white solid.

(2) The above-mentioned compound (64.1 g) and sodium azide (11.8 g) were dissolved in DMF (250 mL), and the mixture was stirred at 85° C. for 5 hr. The reaction mixture was added to water and the precipitated crystals were collected by filtration to give (S)-1-((2S,4S)-4-azido-1-tert-butoxycarbonyl-2-pyrrolidinylcarbonyl)-2-cyanopyrrolidine (50.1 g) as a white solid.

(3) The above-mentioned compound (50.1 g) was dissolved in ethanol (500 mL). The mixture was stirred under a hydrogen atomosphere (1 atm) in the presence of 5% palladium/barium sulfate (5.9 g). The reaction mixture was filtrated and the filtrate was concentrated under reduced pressure. Diethyl ether was added thereto and the precipitated solid was collected by filtration to give the title compound (45.5 g) as a white solid.

$^1$H-NMR($CDCl_3$)δ1.23–1.52(10H,m), 1.60–2.47(8H,m), 2.86–3.00(1H,m), 3.43–3.65(3H,m), 4.25–4.40(1H,m), 4.75–5.02(1H,m).

Reference Example 4

Synthesis of (2S,4R)-1-tert-butoxycarbonyl-4-(5-cyano-2-pyridyl)aminopyrrolidine-2-carboxylic acid (1) N-tert-Butoxycarbonyl-L-cis-4-hydroxyproline (24.5 g) and triethylamine (15.4 mL) were dissolved in dichloromethane (500 mL). Methanesulfonyl chloride (8.1 mL) was added thereto under ice-cooling. After stirring at room temperature for 3 hr, the reaction mixture was washed with water and dried. The solvent was evaporated under reduced pressure. The residue was dissolved in DMF (250 mL) and sodium azide (7.15 g) was added. The mixture was stirred at 80° C. for 3 hr, added to water and extracted with ethyl acetate. The extract was dried, and the solvent was evaporated under reduced pressure. The residue was purified by silica gel chromatography to give methyl (2S,4R)-4-azido-1-tert-butoxycarbonylpyrrolidine-2-carboxylate (18.4 g) as an oil.

(2) The above-mentioned compound (18.3 g) was dissolved in methanol (200 mL), and the mixture was stirred under a hydrogen atomosphere (1 atm) in the presence of 5% palladium/carbon (5.9 g). The reaction mixture was filtrated and the filtrate was concentrated under reduced pressure to give methyl (2S,4R)-4-amino-1-tert-butoxycarbonylpyrrolidine-2-carboxylate (16.6 g) as an oil.

(3) The above-mentioned compound (3.32 g) and triethylamine (1.4 mL) were dissolved in tetrahydrofuran (20 mL), and 2-chloro-5-cyanopyridine (1.0 g) was added thereto. The mixture was stirred at 80° C. for 4 hr. The reaction mixture was added to water and extracted with ethyl acetate. The extract was washed with saturated aqueous sodium hydrogencarbonate solution and brine, and dried. The solvent was evaporated under reduced pressure, and the residue was purified by silica gel chromatography to give methyl (2S,4R)-1-tert-butoxycarbonyl-4-(5-cyano-2-pyridylamino)pyrrolidine-2-carboxylate (1.2 g) as a white solid.

(4) The above-mentioned compound (0.94 g) was dissolved in methanol (30 mL), and 1 mol/L aqueous sodium hydroxide solution (3.0 mL) was added thereto. The mixture was stirred at room temperature for 15 hr. The reaction mixture was concentrated and 5% aqueous citric acid solution was added to the residue. The mixture was extracted with ethyl acetate, and the extract was washed with brine and dried. The solvent was evaporated under reduced pressure to give the title compound (0.75 g) as amorphous.

$^1$H-NMR($CDCl_3$)δ1.33–1.57(9H,m), 2.14–2.68(2H,m), 3.27–3.55(1H,m), 3.82–4.00(1H,m), 4.33–4.57(2H,m), 6.23 (1H,brs), 6.50(1H,d,J=8.7 Hz), 7.64(1H,dd,J=8.7,2.1 Hz)8.33(1H,d,J=2.1 Hz).

Reference Example 5

Synthesis of (2S,4S)-4-(2-benzoxazolyl)amino-1-tert-butoxycarbonylpyrrolidine-2-carboxylic acid (1) N-tert-Butoxycarbonyl-L-trans-4-hydroxyproline (20.7 g) and triethylamine (15.4 mL) were dissolved in dichloromethane (400 mL). p-Toluenesulfonic acid chloride (16.8 g) was added thereto under ice-cooling. After stirring at room temperature for 15 hr, the reaction mixture was washed with water and dried. The solvent was evaporated under reduced pressure and the residue was purified by silica gel chromatography to give methyl (2S,4R)-1-tert-butoxycarbonyl-4-(p-toluenesulfonyloxy)pyrrolidine-2-carboxylate (11.7 g).

(2) The above-mentioned compound (11.7 g) was dissolved in DMF (100 mL), and sodium azide (1.95 g) was added thereto. The mixture was stirred at 80° C. for 3 hr. The reaction mixture was added to water, and extracted with ethyl acetate. The extract was dried, and the solvent was evaporated under reduced pressure. The residue was purified by silica gel chromatography to give methyl (2S,4S)-4-azide-1-tert-butoxycarbonylpyrrolidine-2-carboxylate (7.99 g) as an oil.

(3) The above-mentioned compound (7.99 g) was dissolved in methanol (150 mL). The mixture was stirred under a hydrogen atomosphere (1 atm) in the presence of 10% palladium/carbon (2 g). The reaction mixture was filtrated and the filtrate was concentrated under reduced pressure to give methyl (2S,4S)-4-amino-1-tert-butoxycarbonylpyrrolidine-2-carboxylate (7.23 g) as an oil.

(4) The above-mentioned compound (2.4 g) and triethylamine (1.4 mL) were dissolved in tetrahydrofuran (20 mL), and 2-chlorobenzoxazole (0.82 mL) was added thereto. The mixture was stirred at 60° C. for 3 hr. The reaction mixture was added to water, and extracted with ethyl acetate. The extract was ashed with saturated aqueous sodium hydrogencarbonate solution and dried. The solvent was evaporated under reduced pressure and the residue was purified by silica gel chromatography to give methyl (2S,4S)-4-(2-benzoxazolyl)amino-1-tert-butoxycarbonylpyrrolidine-2-carboxylate (1.49 g) as amorphous.

(5) The above-mentioned compound (1.49 g) was dissolved in methanol (50 mL), and 1 mol/L aqueous sodium hydroxide solution (5.0 mL) was added thereto. The mixture was stirred for 15 hr and concentrated. The residue was extracted with water and the extract was washed with ethyl acetate. 5% Aqueous citric acid solution was added thereto to give the title compound (1.39 g) as a white solid.

$^1$H-NMR(DMSO-$d_6$)δ1.28–1.50(9H,m), 1.93–2.08(1H, m), 2.53–2.75(1H,m), 3.18–3.30(1H,m), 3.77–4.33(2H,m), 6.97–7.40(4H,m), 8.06–8.16(1H,m), 12.63(1H,brs).

Reference Example 6

Synthesis of (2S,4R)-4-(2-benzoxazolyl)amino-1-tert-butoxycarbonylpyrrolidine-2-carboxylic acid (1) Methyl (2S,4R)-4-amino-1-tert-butoxycarbonylpyrrolidine-2-carboxylate [product of Reference Example 4(2), 3.32 g] and triethylamine (1.4 mL) were dissolved in tetrahydrofuran (20 mL). 2-Chlorobenzoxazole (0.86 mL) was added thereto and the mixture was stirred at room temperature for 48 hr. The reaction mixture was added to water and extracted with ethyl acetate. The extract was washed with saturated aqueous sodium hydrogencarbonate solution and brine, and dried. The solvent was evaporated under reduced pressure and the residue was purified by silica gel chromatography to give methyl (2S,4R)-4-(2-benzoxazolyl)amino-1-tert-butoxycarbonylpyrrolidine-2-carboxylate (1.48 g) as a white solid.

(2) The above-mentioned compound (1.31 g) was dissolved in methanol (30 mL) and 1 mol/L aqueous sodium hydroxide solution (4.4 mL) was added thereto. The mixture was stirred at room temperature for 15 hr and the reaction mixture was concentrated. To the residue was added 5% aqueous citric acid solution and the mixture was extracted with ethyl acetate. The extract was washed with brine and dried. The solvent was evaporated under reduced pressure to give the title compound (1.11 g) as a white solid.

$^1$H-NMR($CDCl_3$)δ1.32–1.68(9H,m), 2.20–2.80(2H,m), 3.37–3.62(1H,m), 3.88–4.10(1H,m), 4.37–4.68(2H,m), 7.01–7.43(4H,m).

Reference Example 7

Synthesis of (2S,4S)-4-benzoylamino-1-tert-butoxycarbonylpyrrolidine-2-carboxylic acid (1) Methyl (2S,4S)-4-amino-1-tert-butoxycarbonylpyrrolidine-2-carboxylate [product of Reference Example 5(3), 2.4 g] and triethylamine (2.0 mL) were dissolved in tetrahydrofuran (20 mL), and benzoyl chloride (1.1 mL) was added thereto. The mixture was stirred for 1 hr. The reaction mixture was added to water and extracted with ethyl acetate. The extract was washed with saturated aqueous sodium hydrogencarbonate solution and dried. The solvent was evaporated under reduced pressure and the residue was purified by silica gel chromatography to give methyl (2S,4S)-4-benzoylamino-1-tert-butoxycarbonylpyrrolidine-2-carboxylate (1.63 g) as a white solid.

(2) The above-mentioned compound (1.5 g) was dissolved in methanol (50 mL) and 1 mol/L aqueous sodium hydroxide solution (4.7 mL) was added thereto. The mixture was stirred for 15 hr. The reaction mixture was concentrated and 5% aqueous citric acid solution was added to the residue. The mixture was extracted with ethyl acetate, and the extract was washed with brine and dried. The solvent was evaporated under reduced pressure to give the title compound (1.1 g) as amorphous.

Reference Example 8

Synthesis of (2S,4R)-4-benzoylamino-1-tert-butoxycarbonylpyrrolidine-2-carboxylic acid (1) The product (3.32 g) of Reference Example 4(2) and triethylamine (1.4 mL) were dissolved in tetrahydrofuran (20 mL), and benzoyl chloride (0.87 mL) was added thereto. The mixture was stirred for 1 hr. The reaction mixture was added to water and extracted with ethyl acetate. The extract was washed with saturated aqueous sodium hydrogencarbonate solution and dried. The solvent was evaporated under reduced pressure and the residue was purified by silica gel chromatography to give methyl (2S,4R)-4-benzoylamino-1-tert-butoxycarbonylpyrrolidine-2-carboxylate (2.4 g) as amorphous.

(2) The above-mentioned compound (2.4 g) was dissolved in methanol (80 mL), and 1 mol/L aqueous sodium hydroxide solution (8.2 mL) was added thereto. The mixture was stirred for 15 hr. The reaction mixture was concentrated and 5% aqueous citric acid solution was added to the residue. The mixture was extracted with ethyl acetate, and the extract was washed with brine and dried. The solvent was evaporated under reduced pressure to give the title compound (1.9 g) as a white solid.

$^1$H-NMR($CDCl_3$)δ1.33–1.55(9H,m), 2.12–2.75(2H,m), 3.31–3.60(1H,m), 3.84–4.00(1H,m), 4.30–4.81(2H,m), 6.16–6.55(4H,m), 7.38–7.80(5H,m).

Reference Example 9

Synthesis of 3-[(2S,4R)-1-tert-butoxycarbonyl-4-hydroxy-2-pyrrolidinylcarbonyl]-1,3-thiazolidine N-tert-Butoxycarbonyl-L-trans-4-hydroxyproline (69.4 g) and thiazolidine (29.4 g) were dissolved-in DMF (300 mL), and HOBT (50.5 g) and EDC hydrochloride (63.3 g) were successively added thereto. The mixture was stirred at room temperature for 18 hr and the reaction mixture was concentrated. To the concentrate were added brine and saturated aqueous sodium hydrogencarbonate solution, and the mixture was extracted with ethyl acetate. The extract was dried, and the solvent was evaporated under reduced pressure to give the title compound (56.3 g) as a colorless transparent oil.

$^1$H-NMR($CDCl_3$)δ1.41–1.45(9H,m), 1.95–2.34(2H,m) 2.62–3.25(2H,m), 3.40–3.98(4H,m),4.40–4.90(4H,m).

Reference Example 10

Synthesis of 3-((2S,4S)-4-amino-1-tert-butoxycarbonyl-2-pyrrolidinylcarbonyl)-1,3-thiazolidine (1) 3-((2S,4R)-1-tert-Butoxycarbonyl-4-hydroxy-2-pyrrolidinylcarbonyl)-1,3-thiazolidine (title compound of Reference Example 9, 56.3 g) and triethylamine (28.5 mL) were dissolved in dichloromethane (1.0 l), and methanesulfonyl chloride (15.1 mL) was added thereto under ice-cooling. After stirring under ice-cooling for 1 hr, the reaction mixture was washed with water and dried. The solvent was evaporated under reduced pressure to give 3-((2S,4R)-1-tert-butoxycarbonyl-4-methanesulfonyloxy-2-pyrrolidinylcarbonyl)-1,3-thiazolidine (70.5 g) as. an oil.

(2) The above-mentioned compound (70.5 g) and sodium azide (13.3 g) were dissolved in DMF (500 mL), and the mixture was stirred at 80° C. for 5 hr. The reaction mixture was concentrated under reduced pressure and water was added thereto. The mixture was extracted with ethyl acetate, and the organic layer was dried and concentrated. The residue was purified by silica gel chromatography to give 3-((2S,4S)-4-azido-1-tert-butoxycarbonyl-2-pyrrolidinylcarbonyl)-1,3-thiazolidine (39.5 g) as a white solid.

(3) The above-mentioned compound (26.7 g) was dissolved in ethanol (270 mL) and the mixture was stirred under a hydrogen atomosphere (1 atm) for 18 hr in the presence of 10% palladium carbon catalyst (13.4 g). The reaction mixture was filtrated and the filtrate was concentrated under reduced pressure to give the title compound (24.5 g) as a black solid.

$^1$H-NMR($CDCl_3$)δ1.40–1.45(9H,m), 1.70–1.83(1H,m), 2.07(2H,brs), 2.32–2.56(1H,m), 2.90–3.19(2H,m), 3.25–3.58(2H,m), 3.60–4.14(3H,m), 4.31–4.80(3H,m).

Reference Example 11

Synthesis of 3-((2S,4S)-1-tert-butoxycarbonyl-4-hydroxy-2-pyrrolidinylcarbonyl)-1,3-thiazolidine (1) N-tert-Butoxycarbonyl-L-cis-4-tert-butyldimethylsilyloxyproline [product of Reference Example 1 (1), 5.55 g] and thiazolidine (1.4 mL) were dissolved in DMF (55 mL), and triethylamine (2.24 mL), HOBT (2.96 g) and EDC hydrochloride (3.70 g) were successively added thereto. The mixture was stirred at room temperature for 13 hr. The reaction mixture was added to saturated aqueous sodium hydrogencarbonate solution, and extracted with ethyl acetate. The extract was washed with water and brine and dried. The solvent was evaporated under reduced pressure and the residue was purified by silica gel chromatography to give 3-[(2S,4S)-1-tert-butoxycarbonyl-4-tert-butyldimethylsilyloxy-2-pyrrolidinylcarbonyl]-1,3-thiazolidine (3.41 g) as a white solid.

(2) The above-mentioned compound (3.36 g) was dissolved in tetrahydrofuran (50 mL), and a 1.0 mol/L solution (9 mL) tetrabutylammonium fluoride in tetrahydrofuran was added dropwise under ice-cooling. The mixture was stirred at room temperature for 18 hr, and the solvent was evaporated under reduced pressure. The residue was added to brine and extracted with ethyl acetate. The extract was dried and the solvent was evaporated under reduced pressure. The residue was purified by silica gel chromatography to give the title compound (2.44 g) as a white solid.

$^1$H-NMR(DMSO-$d_6$)δ1.25–1.45(9H,m), 1.52–1.70(1H,m), 2.35–2.50(1H,m), 2.95–3.20(3H,m), 3.50–3.80(3H,m), 4.10–4.25(1H,m), 4.37–4.78(3H,m), 5.18(1H,brs).

Reference Example 12

Synthesis of 3-((S)-1-tert-butoxycarbonyl-4-oxo-2-yrrolidinylcarbonyl)-1,3-thiazolidine The title compound (55.4 g) of Reference Example 9 and triethylamine (46 mL) were dissolved in dichloromethane (350 mL). A solution of sulfur trioxide pyridine complex (52.4 g) in dimethyl sulfoxide (150 mL) was added thereto under ice-cooling, and the mixture was stirred for 2 hr. Saturated aqueous sodium hydrogencarbonate solution was added to the reaction mixture, and the mixture was extracted with ethyl acetate. The extract was washed with brine and dried. The solvent was evaporated under reduced pressure and the residue was purified by silica gel chromatography to give the title compound (30.3 g) as a white solid.

$^1$H-NMR($CDCl_3$)δ1.47(9H,s), 2.45–2.57(1H,m), 2.70–2.93(1H,m), 2.97–3.22(2H,m), 3.66–3.78(0.6H,m), 3.80–4.10(3H,m), 4.28–4.38(0.4H,m), 4.45–5.08(3H,m).

Reference Example 13

Synthesis of (2S,4S)-1-tert-butoxycarbonyl-4-(1-indolyl)pyrrolidine-2-carboxylic acid (1) N-tert-Butoxycarbonyl-L-trans-4-hydroxyproline benzyl ester (20.3 g) and triethylamine (17.6 mL) were dissolved in dichloromethane (120 mL), and a solution of sulfur trioxide pyridine complex (25.1 g) in dimethyl sulfoxide (60 mL) was added thereto under ice-cooling, and the mixture was stirred for 5 hr. Saturated aqueous sodium hydrogencarbonate solution was added to the reaction mixture, and the mixture was extracted with ethyl acetate. The extract was washed with brine and dried. The solvent was evaporated under reduced pressure and the residue was purified by silica gel chromatography to give benzyl (S)-1-tert-butoxycarbonyl-4-oxopyrrolidine-2-carboxylate (9.76 g) as an oil.

(2) The above-mentioned compound (2.50 g), indoline (1.05 mL) and acetic acid (0.45 mL) were dissolved in 1,2-dichloroethane (40 mL), and sodium triacetoxyborohydride (3.32 g) was added hereto. The mixture was stirred at room temperature for 6 hr and saturated aqueous sodium hydrogencarbonate solution was added to the reaction mixture. The mixture was extracted with ethyl acetate, and the extract was washed with brine and dried. The solvent was evaporated under reduced pressure and the residue was purified by silica gel chromatography to give benzyl (2S-,4S)-1-tert-butoxycarbonyl-4-(1-indolinyl)pyrrolidine-2-carboxylate (2.59 g) as an oil.

(3) The above-mentioned compound (2.53 g) was dissolved in acetone (50 mL) and manganese dioxide (7.51 g) was added thereto. The mixture was stirred at room temperature for 12 hr and the reaction mixture was filtrated. The filtrate was concentrated under reduced pressure and the residue was purified by silica gel chromatography to give benzyl (2S,4S)-1-tert-butoxycarbonyl-4-(1-indolyl)pyrrolidine-2-carboxylate (2.43 g) as an oil.

(4) The above-mentioned compound (2.42 g) was dissolved in methanol (50 mL) and the mixture was stirred under a hydrogen atomosphere (1 atm) for 20 hr in the presence of 10% palladium/carbon (0.25 g). The reaction mixture was filtrated and the filtrate was concentrated under reduced pressure to give the title compound (1.91 g) as a pale-green solid.

$^1$H-NMR($CDCl_3$)δ1.49(9H,s), 2.37–3.00(2H,m), 3.60–3.85(1H,m), 4.05–4.25(1H,m), 4.40–4.60(1H,m), 4.95–5.10(1H,m), 6.54(1H,s), 7.13(1H,t,J=7.7 Hz), 7.18–7.28(2H,m), 7.38(1H,d,J=8.2 Hz), 7.62(1H,d,J=7.7 Hz).

Reference Example 14

Synthesis of 1-((S)-1-tert-butoxycarbonyl-4-oxo-2-pyrrolidinylcarbonyl)pyrrolidine (1) N-tert-Butoxycarbonyl-L-trans-4-hydroxyproline (46.25 g) and pyrrolidine (18 mL) were dissolved in DMF (200 mL), and HOBT (45.5 g) and EDC hydrochloride (46.0 g) were successively added thereto. The mixture was stirred at room temperature for 13 hr, and the solvent was evaporated under reduced pressure. Saturated aqueous sodium hydrogencarbonate solution was added to the residue, and the mixture was extracted with ethyl acetate. The extract was dried and the solvent was evaporated under reduced pressure to give 1-((2S,4R)-1-tert-butoxycarbonyl-4-hydroxy-2-pyrrolidinylcarbonyl)pyrrolidine (59.3 g) as an oil.

(2) The above-mentioned compound (59.3 g) and triethylamine (41 mL) were dissolved in dichloromethane (350 mL), and a solution of sulfur trioxide pyridine complex (46.5 g) in dimethyl sulfoxide (100 mL) was added thereto under ice-cooling. The mixture was stirred for 2 hr and saturated aqueous sodium hydrogencarbonate solution was added to the reaction mixture. The mixture was extracted with ethyl acetate, and the extract was washed with brine and dried. The solvent was evaporated under reduced pressure. The residue was purified by silica gel chromatography to give the title compound (11.9 g) as a white solid.

$^1$H-NMR($CDCl_3$)δ1.47(9H,s), 1.80–2.08(4H,m), 2.42–2.53(1H,m), 2.68–2.88(1H,m), 3.35–3.58(3H,m), 3.62–4.13(3H,m), 4.85(0.4H,d,J=9.0 Hz), 4.99(0.6H,d,J=8.7 Hz).

Reference Example 15

Synthesis of 3-((2S,4R)-4-amino-1-tert-butoxycarbonyl-2-pyrrolidinylcarbonyl)-1,3-thiazolidine (1) The title compound (13.6 g) of Reference Example 11 was dissolved in dichloromethane (250 mL), and triethylamine (7 mL) was added thereto. Methanesulfonyl chloride. (3.64 mL) was added to the reaction mixture under ice-cooling, and the mixture was stirred for 1 hr. Water was added to the reaction mixture and the organic layer was separated. The solvent was evaporated under reduced pressure and the residue was dissolved in DMF (200 mL). Sodium azide (3.25 g) was added thereto and he mixture was stirred at 85° C. for 3 hr with heating. The reaction mixture was concentrated under reduced pressure and water was added to the residue. The mixture was extracted with ethyl acetate and the extract was concentrated under reduced pressure. The residue was purified by silica gel chromatography to give 3-((2S,4R)-4-azido-1-tert-butoxycarbonyl-2-pyrrolidinylcarbonyl)-1,3-thiazolidine (9.9 g).

(2) The above-mentioned compound (9.9 g) was dissolved in ethanol (150 mL) and the mixture was stirred at room temperature for 18 hr under a hydrogen atomosphere (1 atm) in the presence of 10% palladium/carbon (10 g). The reaction mixture was filtrated and the filtrate was concentrated under reduced pressure to give the title compound (10.1 g) as a black solid.

$^1$H-NMR(500 MHz,DMSO-$d_6$)δ1.30(4.5H,s), 1.38(4.5H, s), 1.42–1.52(1H,m), 2.05(2H,brs), 2.33–2.45(1H,m), 2.92–3.88(7H,m), 4.37–4.72(3H,m).

Example 1

Synthesis of (S)-2-cyano-1-((2S,4S)-4-hydroxy-2-pyrrolidinylcarbonyl)pyrrolidine trifluoroacetate (S)-1-((2S,4S)-1-tert-Butoxycarbonyl-4-hydroxy-2-pyrrolidinylcarbonyl)-2-cyanopyrrolidine (title compound of Reference Example 1, 544 mg) was dissolved in dichloromethane (18 mL), and trifluoroacetic acid (1.8 mL) was added thereto. The mixture was stirred at room temperature for 18 hr, and the solvent was evaporated under reduced pressure. Ethanol and diethyl ether were added to the residue and the precipitated powder was collected by filtration to give the title compound (350 mg) as powdery white crystals.

$^1$H-NMR(DMSO-$d_6$)δ1.68–2.85(6H,m), 3.10–3.30(2H, m), 3.44–3.70(2H,m), 4.30–4.60(2H,m), 4.78–5.09(1H,m), 5.35–5.50(1H,m), 9.18(2H,brs).

Example 2

Synthesis of (S)-2-cyano-1-((2S,4R)-4-hydroxy-2-pyrrolidinylcarbonyl)pyrrolidine hydrochloride The title compound (309 mg) of Reference Example 2 was dissolved in 4 mol/L hydrochloric acid-1,4-dioxane (2 mL), and the mixture was stirred at room temperature for 18 hr. The solvent was evaporated under reduced pressure and the residue was purified by HPLC to give the title compound (36 mg) as powdery white crystals.

$^1$H-NMR(DMSO-$d_6$)δ1.85–2.44(6H,m), 3.05–3.72(4H, m), 4.41–4.60(2H,m), 4.78–5.16(1H,m), 5.55–5.70(1H,m).

Example 3

Synthesis of (S)-1-((2S,4S)-4-amino-2-pyrrolidinylcarbonyl)-2-cyanopyrrolidine dihydrochloride (S)-1-((2S,4S)-4-Amino-1-tert-butoxycarbonyl-2-pyrrolidinylcarbonyl)-2-cyanopyrrolidine (title compound of Reference Example 3, 308 mg) was dissolved in 4 mol/L hydrochloric acid-1,4-dioxane (1.25 mL), and the mixture was stirred at room temperature for 27 hr. The solvent was evaporated under reduced pressure and tetrahydrofuran was added thereto. The precipitated solid was collected by filtration to give the title compound (214 mg).

$^1$H-NMR(DMSO-$d_6$)δ1.85–2.35(5H,m), 2.80–2.93(1H, m), 3.27–3.68(4H,m), 3.83–3.98(1H,m), 4.52–4.64(1H,m), 4.84(1H,d,J=4.5,7.8 Hz), 8.81(3H,brs).

Example 4

Synthesis of (S)-1-((2S,4S)-4-anilino-2-pyrrolidinylcarbonyl)-2-cyanopyrrolidine trifluoroacetate (1) The title compound (6.18 g) of Reference Example 2 and triethylamine (8.4 mL) were dissolved in dimethyl sulfoxide (15 mL). Sulfur trioxide pyridine complex (9.54 g) was added thereto. After stirring at room temperature for 1 hr, water was added to the reaction mixture, and the mixture was extracted with ethyl acetate. The extract was washed with water and dried. The solvent was evaporated under reduced pressure and the residue was purified by silica gel chromatography to give (S)-1-((2S)-1-tert-butoxycarbonyl-4-oxo-2-pyrrolidinylcarbonyl)-2-cyanopyrrolidine (6.0 g) as an oil.

(2) The above-mentioned compound (1.5 g) and aniline (0.43 mL) were dissolved in methanol (25 mL), and the mixture was stirred at room temperature for 6 hr in the presence of molecular sieve 3A (1.5 g). Sodium cyanoborohydride (0.315 g) and acetic acid (0.4 mL) were added to the reaction mixture, and the mixture was stirred for 1 hr. The reaction mixture was filtrated and the filtrate was evaporated under reduced pressure. Saturated aqueous sodium hydrogencarbonate solution was added to the residue, and the mixture was extracted with ethyl acetate. The extract was dried, and the solvent was evaporated under reduced pressure. The residue was purified by silica gel chromatography to give (S)-1-((2S,4S)-4-anilino-1-tert-butoxycarbonyl-2-pyrrolidinylcarbonyl)-2-cyanopyrrolidine (0.74 g) as amorphous.

(3) The above-mentioned compound (0.82 g) was dissolved in dichloromethane (21 mL) and trifluoroacetic acid (2.1 mL) was added thereto. The mixture was stood at room temperature for 15 hr, and the solvent was evaporated under reduced pressure. The residue was purified by HPLC and freeze-dried to give the title compound (0.246 g) as amorphous.

$^1$H-NMR(DMSO-$d_6$)δ1.52–2.33(5H,m), 2.87–3.22(2H, m), 3.75–5.13(8H,m), 6.50–6.67(3H,m), 7.03–7.20(2H,m), 8.91(1H,brs), 9.88(1H,brs).

Example 5

Synthesis of (S)-2-cyano-1-[(2S,4S)-4-(4-nitrophenyl)amino-2-pyrrolidinylcarbonyl]pyrrolidine hydrochloride (1) The title compound (0.924 g) of Reference Example 3, diisopropylethylamine (1.7 mL) and 4-fluoronitrobenzene (0.53 mL) were dissolved in N-methyl-2-pyrrolidone (10 mL), and the mixture was stirred at 80° C. for 15 hr. Water was added to the reaction mixture and the mixture was extracted with ethyl acetate. The extract was dried, and the solvent was evaporated under reduced pressure. The residue was purified by silica gel chromatography to give (S)-1-[(2S,4S)-1-tert-butoxycarbonyl-4-(4-nitrophenyl)amino-2-pyrrolidinylcarbonyl]-2-cyanopyrrolidine (1.14 g) as amorphous.

(2) The above-mentioned compound (1.13 g) was dissolved in ethyl acetate (3.5 mL), and 4 mol/L hydrochloric acid-ethyl acetate (3.4 mL) was added thereto. The mixture was stood at room temperature for 15 hr. The precipitated solid was collected by filtration to give the title compound (0.67 g).

$^1$H-NMR(DMSO-$d_6$)δ1.74–2.37(6H,m), 2.90–3.10(1H, m), 3.27–3.97(3H,m), 4.37–4.70(2H,m), 4.80–5.20(1H,m), 6.90–7.34(2H,m), 7.88–8.03(2H,m), 9.09(1H,brs), 10.98 (1H,brs).

Example 6

Synthesis of (S)-2-cyano-1-[(2S,4S)-4-(4-cyanophenyl)amino-2-pyrrolidinylcarbonyl] pyrrolidine hydrochloride (1) The title compound (924 mg) of Reference Example 3, diisopropylethylamine (1.7 mL) and 4-fluorobenzonitrile (606 mg) were dissolved in N-methyl-2-pyrrolidone (10 mL), and the mixture was stirred at 100° C. for 15 hr. Water was added to the reaction mixture, and the mixture was extracted with ethyl acetate. The extract was dried and the solvent was evaporated under reduced pressure. The residue was purified by silica gel chromatography to give (S)-2-cyano-1-[(2S,4S)-1-tert-butoxycarbonyl-4-(4-cyanophenyl) amino-2-pyrrolidinylcarbonyl]pyrrolidine (340 mg) as amorphous.

(2) The above-mentioned compound (420 mg) was dissolved in ethyl acetate (1.2 mL), and 4 mol/L hydrochloric acid-ethyl acetate (1.2 mL) was added thereto. The mixture was stood at room temperature for 15 hr and the precipitated solid was collected by filtration to give the title compound (289 mg).

$^1$H-NMR(DMSO-$d_6$)δ1.62–1.80(1H,m), 1.97–2.33(4H, m), 2.90–3.24(2H,m), 3.64–3.96(3H,m), 4.20–4.63(2H,m), 4.80–5.13(1H,m), 6.70(2H,d,J=8.7 Hz), 7.53(2H,d,J=8.7 Hz), 9.00(1H,brs), 10.50(1H,brs).

Example 7

Synthesis of (S)-2-cyano-1-[(2S,4S)-4-(2-cyanophenyl)amino-2-pyrrolidinylcarbonyl] pyrrolidine hydrochloride (1) The title compound (924 mg) of Reference Example 3, diisopropylethylamine (1.7 mL) and 2-fluorobenzonitrile (0.54 mL) were dissolved in N-methyl-2-pyrrolidone (10 mL), and the mixture was stirred at 100° C. for 15 hr. Water was added to the reaction mixture, and the mixture was extracted with ethyl acetate. The extract was dried and the solvent was evaporated under reduced pressure. The residue was purified by silica gel chromatography to give (S)-1-[(2S,4S)-1-tert-butoxycarbonyl-4-(2-cyanophenyl)amino-2-pyrrolidinylcarbonyl]-2-cyanopyrrolidine (177 mg) as amorphous.

(2) The above-mentioned compound (115 mg) was dissolved in ethyl acetate (0.5 mL), and 4 mol/L hydrochloric acid-ethyl acetate (0.35 mL) was added thereto. The mixture was stood at room temperature for 15 hr. The precipitated solid was collected by filtration to give the title compound (46 mg).

$^1$H-NMR(DMSO-$d_6$)1.70–2.36(6H,m), 2.93–3.74(3H, m), 4.28–4.66(2H,m), 4.81–5.15(1H,m), 6.33(1H,d,J=8.1 Hz), 6.77(1H,dd,J=8.4,8.1 Hz), 6.90(1H,d,J=8.4 Hz), 7.39–7.60(2H,m).

Example 8

Synthesis of (S)-2-cyano-1-[(2S,4S)-4-(2-fluoro-4-nitrophenyl)amino-2-pyrrolidinylcarbonyl] pyrrolidine hydrochloride (1) The title compound (0.924 g) of Reference Example 3, diisopropylethylamine (1.7 mL) and 3,4-difluoronitrobenzene (0.55 mL) were dissolved in N-methyl-2-pyrrolidone (10 mL), and the mixture was stirred at 80° C. for 15 hr. Water was added to the reaction mixture and the mixture was extracted with ethyl acetate. The extract was dried and the solvent was evaporated under reduced pressure. The residue was purified by silica gel chromatography to give (S)-1-[(2S,4S)-1-tert-butoxycarbonyl-4-(2-fluoro-4-nitrophenyl)amino-2-pyrrolidinylcarbonyl]-2-cyanopyrrolidine (0.95 g) as amorphous.

(2) The above-mentioned compound (0.95 g) was dissolved in ethyl acetate (3 mL), and 4 mol/L hydrochloric acid-ethyl acetate (2.65 mL) was added thereto. The mixture was stood at room temperature for 15 hr and the precipitated solid was collected by filtration to give the title compound (0.63 g).

$^1$H-NMR(DMSO-$d_6$)δ1.74–2.37(6H,m), 2.90–3.10(1H, m), 3.27–3.97(3H,m), 4.37–4.70(2H,m), 4.80–5.20(1H,m), 6.90–7.34(2H,m), 7.88–8.03(2H,m), 9.09(1H,brs), 10.98 (1H,brs).

Example 9

Synthesis of (S)-2-cyano-1-[(2S,4S)-4-(4-cyano-2-fluorophenyl)amino-2-pyrrolidinylcarbonyl] pyrrolidine hydrochloride (1) The title compound (924 mg) of-Reference Example 3, diisopropylethylamine (1.7 mL) and 3,4-difluorobenzonitrile (700 mg) were dissolved in N-methyl-2-pyrrolidone (10 mL), and the mixture was stirred at 80° C. for 15 hr. Water was added to the reaction mixture and the mixture was extracted with ethyl acetate. The extract was dried and the solvent was evaporated under reduced pressure. The residue was purified by silica gel chromatography to give (S)-1-[(2S,4S)-1-tert-butoxycarbonyl-4-(4-cyano-2-fluorophenyl)amino-2-pyrrolidinylcarbonyl]-2-cyanopyrrolidine (920 mg) as amorphous.

(2) The above-mentioned compound (920 mg) was dissolved in ethyl acetate (2.5 mL), and 4 mol/L hydrochloric acid-ethyl acetate (2.2 mL) was added thereto. The mixture was stood at room temperature for 15 hr and the precipitated solid was collected by filtration to give the title compound (756 mg).

$^1$H-NMR(DMSO-$d_6$)δ1.67–2.35(6H,m), 2.88–3.06(1H, m), 3.22–3.73(3H,m), 4.27–4.64(2H,m), 4.86–5.13(1H,m), 6.73(1H,d,J=6.3 Hz), 7.82–7.92(1H,m), 7.51(1H,dd,J=8.4, 1.5 Hz), 7.61(1H,dd,J=12.0,1.5 Hz), 8.98(1H,brs), 10.75 (1H,brs).

Example 10

Synthesis of (S)-1-[(2S,4S)-4-(4-bromo-2-cyanophenyl)amino-2-pyrrolidinylcarbonyl]-2-cyanopyrrolidine hydrochloride (1) The title compound (924 mg) of Reference Example 3, diisopropylethylamine (1.7 mL) and 3-bromo-6-fluorobenzonitrile (1000 mg) were dissolved in N-methyl-2-pyrrolidone (10 mL) and the mixture was stirred at 80° C. for 5 hr. Water was added to the reaction mixture and the mixture was extracted with ethyl acetate. The extract was dried and the solvent was evaporated under reduced pressure. The residue was purified by silica gel chromatography to give (S)-1-[(2S,4S)-1-tert-butoxycarbonyl-4-(4-bromo-2-cyanophenyl)amino-2-pyrrolidinylcarbonyl]-2-cyanopyrrolidine (904 mg) as amorphous.

(2) The above-mentioned compound (900 mg) was dissolved in ethyl acetate (2 mL) and 4 mol/L hydrochloric acid-ethyl acetate (1.8 mL) was added thereto. The mixture was stood at room temperature for 15 hr and the precipitated solid was collected by filtration to give the title compound (501 mg).

$^1$H-NMR(DMSO-$d_6$)δ1.70–2.34(4H,m), 2.93–3.07(1H, m), 3.42–3.65(3H,m), 4.33–4.61(2H,m), 4.82–5.10(1H,m), 6.56(1H,d,J=8.7 Hz), 6.94(1H,dd,J=8.1,1.8 Hz), 7.12(1H,d, J=1.8 Hz), 7.49(1H,d,J=8.1 Hz), 8.96(1H,brs), 10.02(1H, brs).

Example 11

Synthesis of (S)-2-cyano-1-[(2S,4S)-4-(3,4-dicyanophenyl)amino-2-pyrrolidinylcarbonyl]pyrrolidine hydrochloride (1) The title compound (0.924 g) of Reference Example 3, diisopropylethylamine (1.7 mL) and 3-fluorophthalonitrile (0.73 g) were dissolved in N-methyl-2-pyrrolidone (10 mL), and the mixture was stirred at 80° C. for 4 hr. Water was added to the reaction mixture and the mixture was extracted with ethyl acetate. The extract was dried and the solvent was evaporated under reduced pressure. The residue was purified by silica gel chromatography to give (S)-1-[(2S,4S)-1-tert-butoxycarbonyl-4-(3,4-dicyanophenyl)amino-2-pyrrolidinylcarbonyl]-2-cyanopyrrolidine (1.05 g) as amorphous.

(2) The above-mentioned compound (1.04 g) was dissolved in ethyl acetate (5 mL) and 4 mol/L hydrochloric acid-ethyl acetate (3.0 mL) was added thereto. The mixture was stood at room temperature for 15 hr and the precipitated solid was collected by filtration to give the title compound (0.794 g).

$^1$H-NMR(DMSO-$d_6$)δ1.62–1.79(1H,m), 1.95–2.35(3H, m), 2.90–3.28(2H,m), 3.53–3.71 (2H,m), 4.23–4.64(2H,m), 4.80–5.13(1H,m), 7.01(1H,dd,J=9.0,2.4 Hz), 7.24(1H,d,J=2.4 Hz), 7.65(1H,d,J=6.3 Hz), 7.78(1H,d,J=9.0 Hz), 9.06 (1H,brs), 10.62(1H,brs).

Example 12

Synthesis of (S)-1-[(2S,4S)-4-(3-chloro-4-cyanophenyl)amino-2-pyrrolidinylcarbonyl]-2-cyanopyrrolidine hydrochloride (1) The title compound (0.924 g) of Reference Example 3, diisopropylethylamine (1.7 mL) and 2-chloro-4-fluorobenzonitrile (0.78 g) were dissolved in N-methyl-2-pyrrolidone (10 mL), and the mixture was stirred at 80° C. for 4 hr. Water was added to the reaction mixture and the mixture was extracted with ethyl acetate. The extract was dried and the solvent was evaporated under reduced pressure. The residue was purified by silica gel chromatography to give (S)-1-[(2S,4S)-1-tert-butoxycarbonyl-4-(3-chloro-4-cyanophenyl)amino-2-pyrrolidinylcarbonyl]-2-cyanopyrrolidine (0.94 g) as amorphous.

(2) The above-mentioned compound (0.93 g) was dissolved in ethyl acetate (3 mL) and 4 mol/L hydrochloric acid-ethyl acetate (2.6 mL) was added thereto. The mixture was stood at room temperature for 15 hr and the precipitated solid was collected by filtration to give the title compound (0.73 g).

$^1$H-NMR(DMSO-$d_6$)δ1.58–1.80(1H,m), 1.96–2.37(3H, m), 2.92–3.22(2H,m), 3.53–3.67(2H,m), 4.22–4.60(2H,m), 4.80–5.10(1H,m), 6.67(1H,dd,J=8.7,2.4 Hz), 6.84(1H,d,J=2.4 Hz), 7.24(1H,d,J=6.9 Hz), 7.61(1H,d,J=8.7 Hz), 9.02 (1H,brs), 9.97(1H,brs).

Example 13

Synthesis of (S)-2-cyano-1-[(2S,4S)-4-(4-cyano-2,6-difluorophenyl)amino-2-pyrrolidinylcarbonyl]pyrrolidine hydrochloride (1) The title compound (0.924 g) of Reference Example 3, diisopropylethylamine (1.7 mL) and 3,4,5-trifluorobenzonitrile (0.79 g) were dissolved in N-methyl-2-pyrrolidone (10 mL), and the mixture was stirred at 80° C. for 3 hr. Water was added to the reaction mixture and the mixture was extracted with ethyl acetate. The extract was dried and the solvent was evaporated under reduced pressure. The residue was purified by silica gel chromatography to give (S)-1-[(2S,4S)-1-tert-butoxycarbonyl-4-(4-cyano-2,6-difluorophenyl)amino-2-pyrrolidinylcarbonyl]-2-cyanopyrrolidine (1.08 g) as amorphous.

(2) The above-mentioned compound (1.08 g) was dissolved in ethyl acetate (3 mL) and 4 mol/L hydrochloric acid-ethyl acetate (2.4 mL) was added thereto. The mixture was stood at room temperature for 15 hr and the precipitated solid was collected by filtration to give the title compound (0.706 g).

$^1$H-NMR(DMSO-$d_6$)δ1.72–2.33(6H,m), 2.77–2.92(1H, m), 3.20–3.70(3H,m), 4.42–5.09(3H,m), 6.38(1H,d,J=8.4 Hz), 7.51–7.70(2H,m), 8.97(1H,brs), 10.73(1H,brs).

Example 14

Synthesis of (S)-2-cyano-1-[(2S,4S)-4-(3-trifluoromethyl-2-pyridyl)amino-2-pyrrolidinylcarbonyl]pyrrolidine trifluoroacetate (1) The title compound (1.86 g) of Reference Example 3, diisopropylethylamine (3.14 mL) and 2-chloro-3-trifluoromethylpyridine (1.09 g) were dissolved in N-methyl-2-pyrrolidone (36 mL), and the mixture was stirred at 120° C. for 8 hr. The reaction mixture was added to saturated aqueous sodium hydrogencarbonate solution, and the mixture was extracted with ethyl acetate. The extract was dried and the solvent was evaporated under reduced pressure. The residue was purified by silica gel chromatography to give (S)-1-[(2S,4S)-1-tert-butoxycarbonyl-4-(3-trifluoromethyl-2-pyridyl)amino-2-pyrrolidinylcarbonyl]-2-cyanopyrrolidine (0.099 g).

(2) The above-mentioned compound (99 mg) was dissolved in dichloromethane (2.2 mL) and trifluoroacetic acid (0.2 mL) was added thereto. The mixture was stood at room temperature for 18 hr. The reaction mixture was concentrated under reduced pressure and purified by HPLC to give the title compound (3.2 mg) as amorphous.

$^1$H-NMR(DMSO-$d_6$)δ1.80–2.40(5H,m), 2.80–2.98(1H, m), 3.30–3.65(4H,m), 4.40–4.78(1H,m), 4.80–4.89(1H,m), 4.90–5.10(1H,m), 6.58(1H,d,J=7.8 Hz), 6.73–6.89(1H,m), 7.86(1H,d,J=6.6 Hz), 8.33(1H,d,J=3.9 Hz), 8.84(1H,brs), 9.56(1H,brs).

Example 15

Synthesis of (S)-2-cyano-1-[(2S,4S)-4-(3-nitro-2-pyridyl)amino-2-pyrrolidinylcarbonyl]pyrrolidine trifluoroacetate (1) The title compound (928 mg) of Reference Example 3, diisopropylethylamine (1.57 mL) and 2-chloro-3-nitropyridine (476 mg) were dissolved in N-methyl-2-pyrrolidone (18 mL), and the mixture was stirred at 80° C. for 3 hr. The reaction mixture was added to saturated aqueous sodium hydrogencarbonate solution, and the mixture was extracted with ethyl acetate. The extract was dried and the solvent was evaporated under reduced pressure. The residue was purified by silica gel chromatography to give (S)-1-[(2S,4S)-1-tert-butoxycarbonyl-4-(3-nitro-2-pyridyl)amino-2-pyrrolidinylcarbonyl]-2-cyanopyrrolidine (851 mg) as a yellow oil.

(2) The above-mentioned compound (851 mg) was dissolved in dichloromethane (20 mL) and trifluoroacetic acid (2.0 mL) was added thereto. The mixture was stood at room temperature for 18 hr. The reaction mixture was concentrated under reduced pressure and diethyl ether was added to the residue. The precipitated product was collected by filtration to give a yellow powder (677 mg). This powder (257 mg) was purified by HPLC to give the title compound (152 mg) as a yellow powder.

$^{1}$H-NMR(DMSO-$d_6$)δ1.89–2.37(5H,m), 2.86–3.04(1H, m), 3.38–3.65(4H,m), 4.49–4.70(1H,m), 4.79–4.90(1H,m), 5.00–5.22(1H,m), 6.88(1H,dd,J=8.4,4.8 Hz), 8.38–8.60(3H, m), 9.03(1H,brs), 9.73(1H,brs).

Example 16

Synthesis of (S)-2-cyano-1-[(2S,4S)-4-(3-cyano-2-pyridyl)amino-2-pyrrolidinylcarbonyl]pyrrolidine hydrochloride (1) The title compound (1.86 g) of Reference Example 3, diisopropylethylamine (3.14 mL) and 2-chloro-3-cyanopyridine (0.831 g) were dissolved in N-methyl-2-pyrrolidone (36 mL), and the mixture was stirred at 100° C. for 9 hr. The reaction mixture was added to saturated aqueous sodium hydrogencarbonate solution, and the mixture was extracted with ethyl acetate. The extract was dried and the solvent was evaporated under reduced pressure. The residue was purified by silica gel chromatography to give (S)-1-[(2S,4S)-1-tert-butoxycarbonyl-4-(3-cyano-2-pyridyl) amino-2-pyrrolidinylcarbonyl]-2-cyanopyrrolidine (0.487 g).

(2) The above-mentioned compound (0.464 g) was dissolved in ethyl acetate (1.13 mL) and 4 mol/L hydrochloric acid-ethyl acetate (1.41 mL) was added thereto. The mixture was stood at room temperature for 3 hr. The precipitated solid was collected by filtration to give the title compound (0.370 g) as a pale-brown powder.

$^{1}$H-NMR(DMSO-$d_6$)δ1.72–2.31(5H,m), 2.81–2.98(1H, m), 3.20–3.36(1H,m), 3.40–3.69(3H,m), 4.45–4.67(1H,m), 4.75–5.11(1H,m), 6.78(1H,dd,J=7.5,4.8 Hz), 7.35(1H,d,J=7.5 Hz), 7.99(1H,dd,J=7.5,1.8 Hz), 8.33(1H,dd,J=5.1,1.8 Hz), 8.88(1H,brs), 10.50(1H,brs).

Example 17

Synthesis of (S)-2-cyano-1-[(2S,4S)-4-(4-cyano-2-pyridyl)amino-2-pyrrolidinylcarbonyl]pyrrolidine trifluoroacetate (1) The title compound (928 mg) of Reference Example 3, diisopropylethylamine (1.57 mL) and 2-chloro-4-cyanopyridine (416 mg) were dissolved in N-methyl-2-pyrrolidone (18 mL), and the mixture was stirred at 120° C. for 18 hr. The reaction mixture was added to saturated aqueous sodium hydrogencarbonate solution, and extracted with ethyl acetate. The extract was dried and the solvent was evaporated under reduced pressure. The residue was purified by silica gel chromatography to give (S)-1-[(2S,4S)-1-tert-butoxycarbonyl-4-(4-cyano-2-pyridyl)amino-2-pyrrolidinylcarbonyl]-2-cyanopyrrolidine (134 mg).

(2) The above-mentioned compound (134 mg) was dissolved in dichloromethane (3.3 mL) and trifluoroacetic acid (0.3 mL) was added thereto. The mixture was stirred at room temperature for 18 hr. The reaction mixture was concentrated under reduced pressure and diethyl ether was added to the residue. The precipitated product was collected by filtration to give a pale-brown powder (64 mg). This powder (64 mg) was purified by HPLC to give the title compound (8 mg) as a white solid.

$^{1}$H-NMR(DMSO-$d_6$)δ1.64–1.86(1H,m), 1.86–2.37(4H, m), 2.80–3.00(1H,m), 3.06–3.28(1H,m), 3.42–3.69(3H,m), 4.42–4.70(2H,m), 4.75–5.10(1H,m), 6.89(1H,s), 6.93(1H,d, J=5.2 Hz), 7.44(1H,d,J=6.2 Hz), 8.23(1H,d,J=4.7 Hz), 8.96 (1H,brs), 9.81(1H,brs).

Example 18

Synthesis of (S)-2-cyano-1-[(2S,4S)-4-(5-cyano-2-pyridyl)amino-2-pyrrolidinylcarbonyl]pyrrolidine dihydrochloride (1) The title compound (462 mg) of Reference Example 3, triethylamine (0.42 mL) and 2-chloro-5-cyanopyridine (210 mg) were dissolved in DMF (10 mL), and the mixture was stirred at 90° C. for 24 hr. Water was added to the reaction mixture and the mixture was extracted with ethyl acetate. The extract was dried and the solvent was evaporated under reduced pressure. The residue was purified by silica gel chromatography to give (S)-1-[(2S,4S)-1-tert-butoxycarbonyl-4-(5-cyano-2-pyridyl)amino-2-pyrrolidinylcarbonyl]-2-cyanopyrrolidine (310 mg) as amorphous.

(2) The above-mentioned compound (310 mg) was dissolved in tetrahydrofuran (3 mL) and 4 mol/L hydrochloric acid-ethyl acetate (2 mL) was added thereto. The mixture was stood at room temperature for 15 hr and the solvent was evaporated under reduced pressure. The residue was purified by HPLC and freeze-dried to give the title compound (150 mg) as amorphous.

$^{1}$H-NMR(DMSO-$d_6$)δ1.77–2.33(2.81–3.23(2H,m), 4.00–5.15(6H,m), 6.61(1H,d,J=8.7 Hz), 7.77(1H,d,J=8.7 Hz), 7.91(1H,d,J=6.0 Hz), 8.46(1H,s), 8.98(1H,brs), 9.91 (1H,brs).

Example 19

Synthesis of (S)-1-[(2S,4R)-4-(5-cyano-2-pyridyl)amino-2-pyrrolidinylcarbonyl]-2-cyanopyrrolidine dihydrochloride (1) (2S,4R)-1-tert-Butoxycarbonyl-4-(5-cyano-2-pyridyl)aminopyrrolidine-2-carboxylic acid (title compound of Reference Example 4, 0.73 g) and (S)-2-cyanopyrrolidine hydrochloride (0.29 g) were dissolved in DMF (10 mL), and triethylamine (0.62 mL), HOBT (0.34 g) and EDC hydrochloride (0.42 g) were successively added thereto. The mixture was stirred at room temperature for 15 hr. Water was added to the reaction mixture and the mixture was extracted with ethyl acetate. The extract was dried and evaporated under reduced pressure. The residue was purified by silica gel chromatography to give (S)-1-[(2S,4S)-1-tert-butoxycarbonyl-4-(5-cyano-2-pyridyl) amino-2-pyrrolidinylcarbonyl]-2-cyanopyrrolidine (0.58 g) as amorphous.

(2) The above-mentioned compound (0.57 g) was dissolved in 4 mol/L hydrochloric acid-1,4-dioxane (4 mL), and the mixture was stood at room temperature for 15 hr. The solvent was evaporated under reduced pressure, and the residue was purified by HPLC and freeze-dried to give the title compound (0.181 g) as amorphous.

$^{1}$H-NMR(DMSO-$d_6$)δ1.93–2.68(6H,m), 3.13–3.70(4H, m), 4.58–5.10(3H,m), 6.61(1H,d,J=8.7 Hz), 7.79(1H,dd,J=8.7,1.8 Hz), 7.98(1H,brs), 8.48(1H,d,J=1.8 Hz), 8.87(1H, brs), 9.78(1H,brs).

Example 20

Synthesis of (S)-2-cyano-1-[(2S,4S)-4-(5-trifluoromethyl-2-pyridyl)amino-2-pyrrolidinylcarbonyl]pyrrolidine 2 trifluoroacetate (1) The title compound (0.924 g) of Reference Example 3, diisopropylethylamine (1.7 mL) and 2-chloro-5- trifluoromethylpyridine (0.54 g) were dissolved in N-methyl-2-pyrrolidone (10 mL), and the mixture was stirred at 120° C. for 8 hr. Water was added to the reaction mixture and the mixture was extracted with ethyl acetate. The extract was dried and the solvent was evaporated under reduced pressure. The residue was purified by silica gel chromatography to give (S)-1-[(2S,4S)-1-tert-butoxycarbonyl-4-(5-trifluoromethyl-2-pyridyl)amino-2-pyrrolidinylcarbonyl]-2-cyanopyrrolidine (0.40 g) as amorphous.

(2) The above-mentioned compound (0.40 g) was dissolved in dichloromethane (9 mL) and trifluoroacetic acid (0.9 mL) was added thereto. The mixture was stood at room temperature for hr, and the solvent was evaporated under reduced pressure. The residue was purified by HPLC and freeze-dried to give the title compound (0.163 g) as amorphous.

$^1$H-NMR(DMSO-$d_6$)δ1.68–2.32(5H,m), 2.85–3.26(2H, m), 4.38–5.12(8H,m), 6.65(1H,d,J=9.0 Hz), 7.66(1H,d,J=6.3 Hz), 7.72(1H,dd,J=9.0,2.4 Hz), 8.35(1H,s), 8.96(1H, brs), 9.80(1H,brs).

Example 21

Synthesis of (S)-2-cyano-1-[(2S,4S)-4-(5-nitro-2-pyridyl)amino-2-pyrrolidinylcarbonyl]pyrrolidine dihydrochloride (1) The title compound (0.462 g) of Reference Example 3, triethylamine (0.42 mL) and 2-chloro-5-nitropyridine (0.24 g) were dissolved in DMF (6 mL), and the mixture was stirred at 100° C. for 8 hr. Water was added to the reaction mixture and the mixture was extracted with ethyl acetate. The extract was dried and the solvent was evaporated under reduced pressure. The residue was purified by silica gel chromatography to give (S)-1-[(2S,4S)-1-tert-butoxycarbonyl-4-(5-nitro-2-pyridyl)amino-2-pyrrolidinylcarbonyl]-2-cyanopyrrolidine (0.50 g) as amorphous.

(2) The above-mentioned compound (0.50 g) was dissolved in tetrahydrofuran (3 mL) and 4 mol/L hydrochloric acid-1,4-dioxane (3 mL) was added thereto. The mixture was stood at room temperature for 15 hr and the precipitated solid was collected by filtration to give the title compound (0.445 g).

$^1$H-NMR(DMSO-$_6$)δ1.69–2.37(5H,m), 2.80–3.26(2H, m), 3.47–3.76(3H,m), 4.50–5.15(3H,m), 6.67(1H,d,J=9.3 Hz), 8.18(1H,dd,J=9.3,3.0 Hz), 8.58(1H,s), 8.90–9.12(2H, m), 10.65(1H,brs).

Example 22

Synthesis of (S)-2-cyano-1-[(2S,4S)-4-(3,5-dinitro-2-pyridyl)amino-2-pyrrolidinylcarbonyl]pyrrolidine trifluoroacetate (1) The title compound (0.928 g) of Reference Example 3, diisopropylethylamine (1.57 mL) and 2-chloro-3,5-dinitropyridine (0.611 g) were dissolved in N-methyl-2-pyrrolidone (18 mL), and the mixture was stirred at room temperature for 2 hr. The reaction mixture was added to saturated aqueous sodium hydrogencarbonate solution, and the mixture was extracted with ethyl acetate. The extract was dried and the solvent was evaporated under reduced pressure. The residue was purified by silica gel chromatography to give (S)-1-[(2S,4S)-1-tert-butoxycarbonyl-4-(3,5-dinitro-2-pyridyl)amino-2-pyrrolidinylcarbonyl]-2-cyanopyrrolidine (1.21 g) as a yellow oil.

(2) The above-mentioned compound (1.18 g) was dissolved in dichloromethane (25 mL) and trifluoroacetic acid (2.5 mL) was added thereto. The mixture was stirred at room temperature for 18 hr. The reaction mixture was concentrated under reduced pressure and diethyl ether was added to the residue. The precipitated yellow powder was collected by filtration to give the title compound (1.12 g).

$^1$H-NMR(DMSO-$d_6$)δ1.68–2.33(5H,m), 2.84–3.08(1H, m), 3.32–3.68(4H,m), 4.49–4.70(1H,m), 4.76–4.90(1H,m), 5.11–5.37(1H,m), 9.01(1H,s), 9.04(1H,brs), 9.25(1H,brs), 9.28(1H,s), 9.84(1H,brs).

Example 23

Synthesis of (S)-1-[(2S,4S)-4-(6-chloro-3-pyridazinyl)amino-2-pyrrolidinylcarbonyl]-2-cyanopyrrolidine hydrochloride (1) The title compound (928 mg) of Reference Example 3, diisopropylethylamine (1.57 mL) and 2,6-dichloropyridazine (447 mg) were dissolved in N-methyl-2-pyrrolidone (18 mL), and the mixture was stirred at 120° C. for 5 hr. The reaction mixture was added to saturated aqueous sodium hydrogencarbonate solution, and the mixture was extracted with ethyl acetate. The extract was dried and the solvent was evaporated under reduced pressure. The residue was purified by silica gel chromatography to give (S)-1-[(2S,4S)-1-tert-butoxycarbonyl-4-(6-chloro-3-pyridazinyl)amino-2-pyrrolidinylcarbonyl]-2-cyanopyrrolidine (58 mg).

(2) The above-mentioned compound (57 mg) was dissolved in ethyl acetate (1.0 mL) and 4 mol/L hydrochloric acid-ethyl acetate (0.2 mL) was added thereto. The mixture was stood at room temperature for 4 hr and the precipitated solid was collected by filtration to give the title compound (31 mg).

$^1$H-NMR(DMSO-$d_6$)δ11.69–2.35(5H,m), 2.88–3.01(1H, m), 3.09–3.29(1H,m), 3.50–3.70(3H,m), 4.50–4.72(2H,m), 4.76–5.15(1H,m), 7.00(1H,d,J=9.3 Hz), 7.48(1H,d,J=9.3 Hz), 7.71(1H,brs), 9.00(1H,brs), 10.31(1H,brs).

Example 24

Synthesis of (S)-2-cyano-1-[(2S,4S)-4-(2-pyrimidinyl)amino-2-pyrrolidinylcarbonyl] pyrrolidine hydrochloride (1) The title compound (1.85 g) of Reference Example 3, diisopropylethylamine (3.14 mL) and 2-chloropyrimidine (0.687 g) were dissolved in N-methyl-2-pyrrolidone (30 mL), and the mixture was stirred at 100° C. for 24 hr. The reaction mixture was added to saturated aqueous sodium hydrogencarbonate solution, and extracted with ethyl acetate. The extract was dried and the solvent was evaporated under reduced pressure. The residue was purified by silica gel chromatography to give (S)-1-[(2S,4S)-1-tert-butoxycarbonyl-4-(2-pyrimidinyl)amino-2-pyrrolidinylcarbonyl]-2-cyanopyrrolidine (0.950 g) as a pale-brown powder.

(2) The above-mentioned compound (0.833 g) was dissolved in ethyl acetate (2.16 mL) and 4 mol/L hydrochloric acid-ethyl acetate (2.69 mL) was added thereto. The mixture was stood at room temperature for 18 hr. The precipitated solid was collected by filtration to give the title compound (0.626 g).

$^1$H-NMR(DMSO-$d_6$)δ1.70–2.35(5H,m), 2.80–2.95(1H, m), 3.10–3.30(1H,m), 3.42–3.90(3H,m), 4.49–4.73(2H,m), 4.80–5.14(1H,m), 6.74(1H,t,J=5.1 Hz), 7.67(1H,brs), 8.38 (2H,d,J=5.1 Hz), 8.89(1H,brs), 10.37(1H,brs).

Example 25

Synthesis of (S)-2-cyano-1-[(2S,4S)-4-(4-trifluoromethyl-2-pyrimidinyl)amino-2-pyrrolidinylcarbonyl]pyrrolidine hydrochloride (1) The title compound (1.85 g) of Reference Example 3, diisopropylethylamine (3.14 mL) and 2-chloro-4-trifluoromethylpyrimidine (1.10 g) were dissolved in N-methyl-2-pyrrolidone (30 mL), and the mixture was stirred at room temperature for 18 hr. The reaction mixture was added to saturated aqueous sodium hydrogencarbonate solution, and the mixture was extracted with ethyl acetate. The extract was dried and the solvent was evaporated under reduced pressure. The residue was purified by silica gel chromatography to give (S)-1-[(2S,4S)-1-tert-butoxycarbonyl-4-(4-trifluoromethyl-2-pyrimidinyl)amino-2-pyrrolidinylcarbonyl]-2-cyanopyrrolidine (2.44 g).

(2) The above-mentioned compound (2.27 g) was dissolved in ethyl acetate (4.99 mL) and 4 mol/L hydrochloric acid-ethyl acetate (6.24 mL) was added thereto. The mixture was stood at room temperature for 4 hr. The precipitated solid was collected by filtration to give the title compound (1.94 g).

$^1$H-NMR(DMSO-$d_6$)δ1.72–2.35(5H,m), 2.78–2.99(1H, m), 3.10–3.30(1H,m), 3.36–3.88(3H,m), 4.47–4.72(2H,m), 4.79–5.13(1H,m), 7.11(1H,d,J=5.1 Hz), 8.20(1H,brs), 8.69 (1H,d,J=4.2 Hz), 8.94(1H,brs), 10.73(1H,brs).

Example 26

Synthesis of (S)-1-[(2S,4S)-4-(2-benzoxazolyl) amino-2-pyrrolidinylcarbonyl]-2-cyanopyrrolidine hydrochloride (1) (2S,4S)-4-(2-Benzoxazolyl)amino-1-tert-butoxycarbonylpyrrolidine-2-carboxylic acid (title compound of Reference Example 5, 1.04 g) and (S)-2-cyanopyrrolidine hydrochloride (0.40 g) were dissolved in DMF (5 mL), and triethylamine (0.84 mL), HOBT (0.51 g) and EDC hydrochloride (0.63 g) were successively added thereto. The mixture was stirred at room temperature for 15 hr. Water was added to the reaction mixture, and the mixture was extracted with ethyl acetate. The extract was dried and evaporated under reduced pressure. The residue was purified by silica gel chromatography to give (S)-1-[(2S,4S)-4-(2-benzoxazolyl)amino-1-tert-butoxycarbonyl-2-pyrrolidinylcarbonyl]1-2-cyanopyrrolidine (0.86 g) as amorphous.

(2) The above-mentioned compound (0.86 g) was dissolved in 4 mol/L hydrochloric acid-1,4-dioxane (6 mL), and the mixture was stood at room temperature for 15 hr. The precipitated white solid was collected by filtration to give the title compound (0.828 g).

$^1$H-NMR(DMSO-$d_6$)δ1.70–2.36(5H,m), 2.87–3.50(2H, m), 4.20–5.15(3H,m), 7.00–7.49(4H,m), 8.24–8.38(1H,m), 8.97(1H,brs), 10.26(1H,brs).

Example 27

Synthesis of (S)-1-[(2S,4R)-4-(2-benzoxazolyl) amino-2-pyrrolidinylcarbonyl]-2-cyanopyrrolidine hydrochloride (1) (2S,4R)-4-(2-Benzoxazolyl)amino-1-tert-butoxycarbonylpyrrolidine-2-carboxylic acid (title compound of Reference Example 6, 1.0 g) and (S)-2-cyanopyrrolidine hydrochloride (0.38 g) were dissolved in DMF (10 mL), and triethylamine (0.81 mL), HOBT (0.49 g) and EDC hydrochloride (0.61 g) were successively added thereto. The mixture was stirred at room temperature for 15 hr. Water was added to the reaction mixture, and mixture was extracted with ethyl acetate. The extract was dried and the residue was evaporated under reduced pressure. The residue was purified by silica gel chromatography to give (S)-1-[(2S,4R)-4-(2-benzoxazolyl)amino-1-tert-butoxycarbonyl-2-pyrrolidinylcarbonyl]-2-cyanopyrrolidine (0.91 g) as amorphous.

(2) The above-mentioned compound (0.91 g) was dissolved in 4 mol/L hydrochloric acid-1,4-dioxane (6 mL), and the mixture was stood at room temperature for 15 hr. The precipitated white solid was collected by filtration to give the title compound (0.841 g).

$^1$H-NMR(DMSO-$d_6$)δ1.93–2.73(6H,m), 3.30–3.94(4H, m), 4.36–5.18(3H,m), 6.96–7.50(4H,m), 8.42–9.05(2H,m), 10.17(1H,brs).

Example 28

Synthesis of (S)-1-[(2S,4S)-4-(4-chlorophenylmethyl)amino-2-pyrrolidinylcarbonyl]-2-cyanopyrrolidine dihydrochloride (1) The title compound (1.54 g) of Reference Example 3 and 4-chlorobenzaldehyde (0.703 g) were dissolved in methanol (15 mL), and the mixture was stirred at room temperature for 1 hr. Sodium cyanoborohydride (0.315 g) and acetic acid (0.4 mL) were added to the reaction mixture, and the mixture was stirred for 1 hr. The reaction mixture was filtrated and the filtrate was evaporated under reduced pressure. Saturated aqueous sodium hydrogencarbonate solution was added to the residue, and the mixture was extracted with ethyl acetate. The extract was dried and the solvent was evaporated under reduced pressure. The residue was purified by silica gel chromatography to give (S)-1-[(2S,4S)-1-tert-butoxycarbonyl-4-(4-chlorophenylmethyl) amino-2-pyrrolidinylcarbonyl]-2-cyanopyrrolidine (1.67 g) as amorphous.

(2) The above-mentioned compound (0.643 g) was dissolved in ethyl acetate (1.9 mL) and 4 mol/L hydrochloric acid-ethyl acetate (1.9 mL) was added thereto. The mixture was stood at room temperature for 15 hr. The precipitated solid was collected by filtration to give the title compound (0.62 g).

$^1$H-NMR(DMSO-$d_6$)δ2.00–2.37(5H,m), 2.90–3.05(1H, m), 3.52–3.73(4H,m), 3.86–4.04(1H,m), 4.24(2H,s), 4.48–4.54(1H,m), 4.80–5.17(1H,m), 7.53(2H,d,J=8.4 Hz), 7.66(2H,d,J=8.4 Hz), 9.07(1H,brs), 10.20(2H,brs), 10.72 (1H,brs).

Example 29

Synthesis of (S)-2-cyano-1-[(2S,4S)-4-(4-nitrophenylmethyl)amino-2-pyrrolidinylcarbonyl] pyrrolidine dihydrochloride (1) The title compound (1.54 g) of Reference Example 3 and 4-nitrobenzaldehyde (6.801 g) were dissolved in methanol (15 mL), and the mixture was stirred at room temperature for 1 hr. Sodium cyanoborohydride (0.315 g) and acetic acid (0.4 mL) were added to the reaction mixture, and the mixture was stirred for 1 hr. The reaction mixture was filtrated and the filtrate was evaporated under reduced pressure. Saturated aqueous sodium hydrogencarbonate solution was added to the residue and the mixture was extracted with chloroform. The extract was dried and the solvent was evaporated under reduced pressure. The residue was purified by silica gel chromatography to give (S)-1-[(2S,4S)-1-tert-butoxycarbonyl-4-(4-nitrophenylmethyl)amino-2-pyrrolidinylcarbonyl]-2-cyanopyrrolidine (1.15 g) as amorphous.

(2) The above-mentioned compound (1.15 g) was dissolved in ethyl acetate (3 mL) and 4 mol/L hydrochloric acid-ethyl acetate (3.3 mL) was added thereto. The mixture was stood at room temperature for 15 hr. The precipitated solid was collected by filtration to give the title compound (0.975 g).

$^1$H-NMR(DMSO-$d_6$)δ1.96–2.37(5H,m), 2.93–3.07(1H, m), 3.66–3.75(3H,m), 3.93–4.10(1H,m), 4.40(2H,s), 4.50–4.67(1H,m), 4.80–5.17(1H,m), 7.92(2H,d,J=8.7 Hz), 8.31(2H,d,J=8.7 Hz), 9.10(1H,brs), 10.10–11.30(2H,m).

Example 30

Synthesis of (S)-2-cyano-1-[(2S,4s)-4-(4-phenoxyphenylmethyl)amino-2-pyrrolidinylcarbonyl]pyrrolidine dihydrochloride (1) The title compound (0.924 g) of Reference Example 3 and 4-phenoxybenzaldehyde (0.594 g) were dissolved in methanol (15 mL), and the mixture was stirred at room temperature for 1 hr. Sodium cyanoborohydride (0.189 g) and acetic acid (0.2 mL) were added to the reaction mixture, and the mixture was stirred for 1 hr. The reaction mixture was evaporated under reduced pressure. Saturated aqueous sodium hydrogencarbonate solution was added to the residue and the mixture was extracted with ethyl acetate. The extract was dried and the solvent was evaporated under reduced pressure. The residue was purified by silica gel chromatography to give (S)-1-[(2S,4S)-1-tert-butoxycarbonyl-4-(4-phenoxyphenylmethyl)amino-2-pyrrolidinylcarbonyl]-2-cyanopyrrolidine (0.99 g) as amorphous.

(2) The above-mentioned compound (0.99 g) was dissolved in ethyl acetate (2 mL) and 4 mol/L hydrochloric acid-ethyl acetate (2.5 mL) was added thereto. The mixture was stood at room temperature for 15 hr. The precipitated solid was collected by filtration to give the title compound (0.95 g).

$^1$H-NMR(DMSO-$d_6$)δ1.95–2.38(5H,m), 2.90–3.16(1H, m), 3.40–3.70(4H,m), 3.89–4.03(1H,m), 4.21(2H,s), 4.50–4.67(1H,m), 4.80–5.17(1H,m), 6.94–7.22(5H,m), 7.34–7.48(2H,m), 7.64(2H,d,J=8.4 Hz), 9.10(1H,brs), 10.17 (2H,brs), 10.90(1H,brs).

Example 31

Synthesis of (S)-2-cyano-1-[(2S,4S)-4-(4-cyanophenylmethyl)amino-2-pyrrolidinylcarbonyl] pyrrolidine dihydrochloride (1) The title compound (924 mg) of Reference Example 3 and 4-cyanobenzaldehyde (589 mg) were dissolved in methanol (15 mL), and the mixture was stirred at room temperature for 1 hr. Sodium cyanoborohydride (283 mg) and acetic acid (0.4 mL) were added to the reaction mixture, and the mixture was stirred for 1 hr. The reaction mixture was filtrated and the filtrate was evaporated under reduced pressure. Saturated aqueous sodium hydrogencarbonate solution was added to the residue and the mixture was extracted with ethyl acetate. The extract was dried and the solvent was evaporated under reduced pressure. The residue was purified by silica gel chromatography to give (S)-1-[(2S,4S)-1-tert-butoxycarbonyl-4-(4-cyanophenylmethyl)amino-2-pyrrolidinylcarbonyl]-2-cyanopyrrolidine (940 mg) as amorphous.

(2) The above-mentioned compound (940 mg) was dissolved in ethyl acetate (3.0 mL) and 4 mol/L hydrochloric acid-ethyl acetate (2.8 mL) was added thereto. The mixture was stood at room temperature for 15 hr. The precipitated solid was collected by filtration to give the title compound (655 mg).

$^1$H-NMR(DMSO-$d_6$)δ1.94–2.37(6H,m), 2.89–3.09(1H, m), 3.27–3.80(3H,m), 3.90–4.10(1H,m), 4.23–4.44(2H,s), 4.53–4.69(1H,m), 4.80–5.20(1H,m), 7.87(2H,d,J=8.4 Hz), 7.94(2H,d,J=8.4 Hz), 9.18(1H,brs), 10.60(2H,brs).

Example 32

Synthesis of (S)-1-{(2S,4S)-4-[N-(4-cyanophenylmethyl)-N-methylamino]-2-pyrrolidinylcarbonyl}-2-cyanopyrrolidine dihydrochloride (1) (S)-1-[(2S,4S)-1-tert-Butoxycarbonyl-4-(4-cyanophenylmethyl)amino-2-pyrrolidinylcarbonyl]-2-cyanopyrrolidine [product of Example 31 (1), 1.04 g] and 37% formaldehyde solution (0.7 mL) were dissolved in acetonitrile (15 mL), and the mixture was stirred at room temperature for 1 hr. Sodium cyanoborohydride (0.240 g) and acetic acid (0.4 mL) were added to the reaction mixture, and the mixture was stirred for 1 hr. The reaction mixture was evaporated under reduced pressure. Saturated aqueous sodium hydrogencarbonate solution was added to the residue and the mixture was extracted with chloroform. The extract was dried and the solvent was evaporated under reduced pressure. The residue was purified by silica gel chromatography to give (S)-1-{(2S,4S)-1-tert-butoxycarbonyl-4-[N-(4-cyanophenylmethyl)-N-methylamino]-2-pyrrolidinylcarbonyl}-2-cyanopyrrolidine (0.71 g) as amorphous.

(2) The above-mentioned compound (0.70 g) was dissolved in ethyl acetate (2.0 mL) and 4 mol/L hydrochloric acid-ethyl acetate (2.0 mL) was added thereto. The mixture was stood at room temperature for 15 hr. The precipitated solid was collected by filtration to give the title compound (0.548 g).

$^1$H-NMR(DMSO-$d_6$)δ2.00–2.42(5H,m), 2.59(3H,s), 2.88–3.18(1H,m), 3.50–5.20(9H,m), 7.89(2H,d,J=8.1 Hz), 7.97(2H,d,J=8.1 Hz), 9.26(1H,brs), 10.96(1H,brs), 12.42 (1H,brs).

Example 33

Synthesis of (S)-2-cyano-1-{(2S,4S)-4-[N,N-bis(4-cyanophenylmethyl)amino]-2-pyrrolidinylcarbonyl}pyrrolidine dihydrochloride (1) The title compound (0.924 g) of Reference Example 3, 4-cyanobenzyl bromide (1.27 g) and diisopropylethylamine (1.6 mL) were dissolved in N-methyl-2-pyrrolidone (10 mL), and the mixture was stirred at room temperature for 15 hr. Water was added to the reaction mixture and the mixture was extracted with ethyl acetate. The extract was dried and the solvent was evaporated under reduced pressure. The residue was purified by silica gel chromatography to give (S)-1-{(2S,4S)-1-tert-butoxycarbonyl-4-[N,N-bis(4-cyanophenylmethyl)amino]-2-pyrrolidinylcarbonyl}-2-cyanopyrrolidine (1.11 g) as a white solid.

(2) The above-mentioned compound (0.95 g) was dissolved in ethyl acetate (2.2 mL) and 4 mol/L hydrochloric acid-ethyl acetate (2.2 mL) was added thereto. The mixture was stood at room temperature for 15 hr. The precipitated solid was collected by filtration to give the title compound (0.85 g).

$^1$H-NMR(DMSO-$d_6$)δ1.72–2.37(5H,m), 2.62–2.79(1H, m), 3.06–3.43(2H,m), 3.53–4.50(8H,m), 4.80–5.14(1H,m), 7.55(4H,d,J=8.1 Hz), 7.79(4H,d,J=8.1 Hz), 8.90(1H,brs), 10.10(1H,brs).

Example 34

Synthesis of (S)-2-cyano-1-[(2S,4S)-4-(3-pyridylmethyl)amino-2-pyrrolidinylcarbonyl]pyrrolidine 3 trifluoroacetate (1) The title compound (928 mg) of Reference Example 3 and nicotinaldehyde (321 mg) were dissolved in methanol (16 mL), and the mixture was stirred at room temperature for 30 min. Sodium cyanoborohydride (189 mg) and several drops of acetic acid were added to the reaction mixture, and the mixture was stirred at room temperature for 18 hr. The reaction mixture was filtrated and the filtrate was evaporated under reduced pressure. Saturated aqueous sodium hydrogencarbonate solution was added to the residue and the mixture was extracted with ethyl acetate. The extract was dried and the solvent was evaporated under reduced pressure. The residue was purified by silica gel chromatography to give (S)-1-[(2S,4S)-1-tert-butoxycarbonyl-4-(3-pyridylmethyl)amino-2-pyrrolidinylcarbonyl]-2-cyanopyrrolidine (591 mg).

(2) The above-mentioned compound (557 mg) was dissolved in dichloromethane (14 mL) and trifluoroacetic acid (1.4 mL) was added thereto. The mixture was stood at room temperature for 18 hr. The reaction solvent was concentrated under reduced pressure, and diethyl ether was added to the residue. The precipitated solid was collected by filtration to give the title compound (704 mg).

$^1$H-NMR(DMSO-$d_6$)δ1.70–2.40(5H,m), 2.91–3.14(1H, m), 3.29–3.73(5H,m), 4.31(2H,s), 4.52–4.70(1H,m), 4.78–5.15(1H,m), 7.58(1H,dd,J=7.8,5.0 Hz), 8.02(1H,d,J=7.9 Hz), 8.68(1H,dd,J=4.9, 1.4 Hz), 8.75(1H,d,J=1.7 Hz).

Example 35

Synthesis of (S)-2-cyano-1-((2S,4S)-4-phenethylamino-2-pyrrolidinylcarbonyl)pyrrolidine 2 trifluoroacetate (1) The title compound (462 mg) of Reference Example 3 and phenylacetaldehyde (0.18 mL) were dissolved in methanol (15 mL), and the mixture was stirred at room temperature for 1 hr. Sodium cyanoborohydride (94 mg) and acetic acid (0.1 mL) were added to the reaction mixture, and the mixture was stirred for 15 hr. The reaction mixture was filtrated and the filtrate was evaporated under reduced pressure. Saturated aqueous sodium hydrogencarbonate solution was added to the residue and the mixture was extracted with ethyl acetate. The extract was dried and the solvent was evaporated under reduced pressure. The residue was purified by silica gel chromatography to give (S)-1-((2S,4S)-1-tert-butoxycarbonyl-4-phenethylamino-2-pyrrolidinylcarbonyl)-2-cyanopyrrolidine (300 mg) as amorphous.

(2) The above-mentioned compound (300 mg) was dissolved in dichloromethane (7.3 mL) and trifluoroacetic acid (0.73 mL) was added thereto. The mixture was stood at room temperature for 15 hr. The solvent was evaporated under reduced pressure, and the residue was purified by HPLC and freeze-dried to give the title compound (150 mg) as amorphous.

$^1$H-NMR(DMSO-$d_6$)δ1.85–2.38(5H,m), 2.83–3.08(3H, m), 3.15–3.74(4H,m), 3.75–5.18(5H,m), 7.17–7.40(5H,m).

Example 36

Synthesis of (S)-2-cyano-1-((2S,4S)-4-cyclohexylamino-2-pyrrolidinylcarbonyl)pyrrolidine dihydrochloride (1) The title compound (924 mg) of Reference Example 3 and cyclohexanone (0.34 mL) were dissolved in methanol (15 mL), and the mixture was stirred at room temperature for 1 hr. Sodium cyanoborohydride (200 mg) and acetic acid (0.4 mL) were added to the reaction mixture, and the mixture was stirred for 15 hr. The reaction mixture was evaporated under reduced pressure. Saturated aqueous sodium hydrogencarbonate solution was added to the residue and the mixture was extracted with ethyl acetate. The extract was dried and the solvent was evaporated under reduced pressure. The residue was purified by silica gel chromatography to give (S)-1-(2S,4S)-1-tert-butoxycarbonyl-4-cyclohexylamino-2-pyrrolidinylcarbonyl)-2-cyanopyrrolidine (440 mg) as amorphous.

(2) The above-mentioned compound (430 mg) was dissolved in ethyl acetate (1.5 mL) and 4 mol/L hydrochloric acid-ethyl acetate (1.4 mL) was added thereto. The mixture was stood at room temperature for 15 hr. The precipitated solid was collected by filtration to give the title compound (338 mg).

$^1$H-NMR(DMSO-$d_6$)δ1.01–1.47(5H,m), 1.54–2.38(10H, m), 2.88–3.07(2H,m), 3.38–3.70(4H,m), 3.95–4.13(1H,m), 4.40–4.61(1H,m), 4.80–5.14(1H,m), 9.68(1H,brs), 9.89(1H, brs).

Example 37

Synthesis of (S)-2-cyano-1-((2S,4S)-4-diethylamino-2-pyrrolidinylcarbonyl)pyrrolidine dihydrochloride (1) The title compound (924 mg) of Reference Example 3 and 90% aqueous acetaldehyde solution (1.7 mL) were dissolved in methanol (15 mL), and the mixture was stirred at room temperature for 3 hr. Sodium cyanoborohydride (440 mg) and acetic acid (0.4 mL) were added to the reaction mixture, and the mixture was stirred for 1 hr. The reaction mixture was evaporated under reduced pressure. Saturated aqueous sodium hydrogencarbonate solution was added to the residue and the mixture was extracted with ethyl acetate. The extract was dried and the solvent was evaporated under reduced pressure. The residue was purified by silica gel chromatography to give (S)-1-((2S,4S)-1-tert-butoxycarbonyl-4-diethylamino-2-pyrrolidinylcarbonyl)-2-cyanopyrrolidine (720 mg) as amorphous.

(2) The above-mentioned compound (720 mg) was dissolved in ethyl acetate (2 mL) and 4 mol/L hydrochloric acid-ethyl acetate (2.5 mL) was added thereto. The mixture was stood at room temperature for 15 hr. The precipitated solid was collected by filtration to give the title compound (713 mg.).

$^1$H-NMR(DMSO-$d_6$)δ1.20–1.30(6H,m), 1.94–2.36(1H, m), 2.87–3.38(6H,m), 3.52–4.18(8H,m), 4.45–4.64(1H,m), 4.82–4.90(1H,m), 9.38(1H,brs), 11.30(1H,brs), 11.82(1H, brs).

Example 38

Synthesis of (S)-2-cyano-1-[(2S,4S)-4-(1-piperidino)-2-pyrrolidinylcarbonyl]pyrrolidine dihydrochloride (1) The title compound (924 mg) of Reference Example 3 and 50% aqueous glutaraldehyde solution (0.8 mL) were dissolved in methanol (15 mL), and the mixture was stirred at room temperature for 3 hr. Sodium cyanoborohydride (630 mg) and acetic acid (0.4 mL) were added the reaction mixture-and the mixture was stirred for 1 hr. The reaction mixture was evaporated under reduced pressure. Saturated aqueous sodium hydrogencarbonate solution was added to the residue and the mixture was extracted with ethyl acetate. The extract was dried and the solvent was evaporated under reduced pressure. The residue was purified by silica gel chromatography to give (S)-1-[(2S,4S)-1-tert-butoxycarbonyl-4-(1-piperidino)-2-pyrrolidinylcarbonyl]-2-cyanopyrrolidine (480 mg) as amorphous.

(2) The above-mentioned compound (470 mg) was dissolved in ethyl acetate (2 mL) and 4 mol/L hydrochloric acid-ethyl acetate (1.6 mL) was added thereto. The mixture was stood at room temperature for 15 hr. The precipitated solid was collected by filtration to give the title compound (485 mg).

$^1$H-NMR(DMSO-$d_6$)δ1.30–1.50(1H,m), 1.61–1.90(5H, m), 1.99–2.32(3H,m), 2.83–3.09(2H,m), 3.31–3.80(8H,m), 3.90–4.07(1H,m), 4.40–4.62(1H,m), 4.80–5.20(1H,m), 9.27 (1H,brs), 11.10(1H,brs), 11.64(1H,brs).

Example 39

Synthesis of (S)-2-cyano-1-{(2S,4S)-4-[N,N-bis (ethoxycarbonylmethyl)amino]-2-pyrrolidinylcarbonyl}pyrrolidine dihydrochloride (1) The title compound (0.924 g) of Reference Example 3, ethyl bromoacetate (0.73 mL) and diisopropylethylamine (1.6 mL) were dissolved in N-methyl-2-pyrrolidone (10 mL), and the mixture was stirred at room temperature for 15 hr. Water was added to the reaction mixture and the mixture was extracted with ethyl acetate. The extract was dried and the solvent was evaporated under reduced pressure. The residue was purified by silica gel chromatography to give (S)-1-{(2S,4S)-1-tert-butoxycarbonyl-4-[N,N-bis (ethoxycarbonylmethyl)amino]-2-pyrrolidinylcarbonyl}-2-cyanopyrrolidine (0.95 g) as a white solid.

(2) The above-mentioned compound (0.80 g) was dissolved in ethyl acetate (2 mL) and 4 mol/L hydrochloric acid-ethyl acetate (2 mL) was added thereto. The mixture was stood at room temperature for 15 hr. The precipitated solid was collected by filtration to give the title compound (0.65 g).

$^1$H-NMR(DMSO-$d_6$)δ1.19(6H,t,J=7.2 Hz), 1.57–1.74 (1H,m), 1.93–2.34(4H,m), 2.96–3.42(2H,m), 3.75–4.50 (12H,m), 4.78–5.12(1H,m), 8.80(1H,brs), 10.19(1H,brs).

Example 40

Synthesis of (S)-1-((2S,4S)-4-benzoylamino-2-pyrrolidinylcarbonyl)-2-cyanopyrrolidine hydrochloride (1) (2S,4S)-4-Benzoylamino-1-tert-butoxycarbonylpyrrolidine-2-carboxylic acid (title compound of Reference Example 7, 1.1 g) and (S)-2-cyanopyrrolidine hydrochloride (0.44 g) were dissolved in DMF (10 mL), and triethylamine (0.98 mL), HOBT (0.54 g) and EDC hydrochloride (0.67 g) were successively added. The mixture was stirred at room temperature for 15 hr. Water was added to the reaction mixture and the mixture was extracted with ethyl acetate. The extract was dried and evaporated under reduced pressure. The residue was purified by silica gel chromatography to give (S)-1-((2S,4R)-4-benzoylamino-1-tert-butoxycarbonyl-2-pyrrolidinylcarbonyl)-2-cyanopyrrolidine (1.0 g) as a white solid.

(2) The above-mentioned compound (0.91 g) was dissolved in tetrahydrofuran (3 mL) and 4 mol/L hydrochloric acid-1,4-dioxane (6 mL) was added thereto. The mixture was stood at room temperature for 15 hr. The precipitated white solid was collected by filtration to give the title compound (541 mg).

$^1$H-NMR(DMSO-$d_6$)δ1.63–2.36(5H,m), 2.75–2.93((1H, m), 3.21–3.80(4H,m), 4.51–5.13(3H,m), 7.40–7.90(2H,m), 8.52–9.00(2H,m), 10.06(1H,brs).

Example 41

Synthesis of (S)-1-((2S,4R)-4-benzoylamino-2-pyrrolidinylcarbonyl)-2-cyanopyrrolidine hydrochloride (1) (2S,4R)-4-Benzoylamino-1-tert-butoxycarbonylpyrrolidine-2-carboxylic acid (title compound of Reference Example 8, 1.6 g) and (S)-2-cyanopyrrolidine hydrochloride (0.63 g) were dissolved in DMF (10 mL), and triethylamine (1.32 mL), HOBT (0.79 g) and EDC hydrochloride (0.99 g) were successively added. The mixture was stirred at room temperature for 15 hr. Water was added to the reaction mixture and the mixture was extracted with ethyl acetate. The extract was dried and evaporated under reduced pressure. The residue was purified by silica gel chromatography to give (S)-1-((2S,4R)-4-benzoylamino-1-tert-butoxycarbonyl-2-pyrrolidinylcarbonyl)-2-cyanopyrrolidine (1.2 g) as a white solid.

(2) The above-mentioned compound (0.97 g) was dissolved in 4 mol/L hydrochloric acid-1,4-dioxane (6 mL). The mixture was stood at room temperature for 15 hr. The precipitated white solid was collected by filtration to give the title compound (0.814 g).

$^1$H-NMR(DMSO-$d_6$)δ1.96–2.65(6H,m), 3.23–3.71(4H, m), 4.42–5.15(3H,m), 7.51–7.97(5H,m), 8.67–9.03(2H,m), 9.92(1H,brs).

Example 42

Synthesis of (S)-1-[(2S,4S)-4-(4-chlorobenzoyl) amino-2-pyrrolidinylcarbonyl]-2-cyanopyrrolidine hydrochloride (1) The title compound (462 mg) of Reference Example 3 and triethylamine (0.42 mL) were dissolved in dichloromethane (30 mL), and 4-chlorobenzoyl chloride (0.19 mL) was added under ice-cooling. The mixture was stirred at room temperature for 24 hr. Water was added to the reaction mixture and the mixture was extracted with dichloromethane. The extract was dried and evaporated under reduced pressure. The residue was purified by silica gel chromatography to give (S)-1-[(2S,4S)-1-tert-butoxycarbonyl-4-(4-chlorobenzoyl)amino-2-pyrrolidinylcarbonyl]-2-cyanopyrrolidine (617 mg) as amorphous.

(2) The above-mentioned compound (610 mg) was dissolved in tetrahydrofuran (4 mL) and 4 mol/L hydrochloric acid-1,4-dioxane (3.4 mL) was added thereto. The mixture was stirred at room temperature for 24 hr. The solvent was evaporated under reduced pressure, and the concentrate was purified by HPLC and freeze-dried to give the title compound (340 mg) as amorphous.

$^1$H-NMR(DMSO-$d_6$)δ1.87–2.34(5H,m), 2.78–2.93(1H, m), 3.20–3.75(4H,m), 4.54–4.72(2H,m), 4.85(1H,dd,J=7.8, 4.7 Hz), 7.58(2H,d,J=8.5 Hz), 7.86(2H,d,J=8.5 Hz), 8.70 (1H,d,J=6.8 Hz), 8.88(1H,brs), 9.74(1H,brs).

Example 43

Synthesis of (S)-2-cyano-1-[(2S,4s)-4-(4-trifluoromethylbenzoyl)amino-2-pyrrolidinylcarbonyl]pyrrolidine hydrochloride (1) The title compound (462 mg) of Reference Example 3, 4-trifluoromethylbenzoic acid (285 mg) and triethylamine (0.42 mL) were dissolved in DMF (30 mL), and HOBT (241 mg) and EDC hydrochloride (302 mg) were successively added under ice-cooling. The mixture was stirred at room temperature for 22 hr. The solvent was evaporated under reduced pressure, and saturated aqueous sodium hydrogencarbonate solution was added to the concentrate. The mixture was extracted with ethyl acetate. The extract was washed with brine, dried and evaporated under reduced pressure. The residue was purified by silica gel chromatography to give (S)-1-[(2S,4S)-1-tert-butoxycarbonyl-4-(4-trifluoromethylbenzoyl)amino-2-pyrrolidinylcarbonyl]-2-cyanopyrrolidine (640 mg) as a colorless oil.

(2) The above-mentioned compound (640 mg) was dissolved in tetrahydrofuran (15 mL) and 4 mol/L hydrochloric acid-1,4-dioxane (3.3 mL) was added thereto. The mixture was stirred at room temperature for 24 hr. The solvent was evaporated under reduced pressure and the concentrate was purified by HPLC and freeze-dried to give the title compound (163 mg) as amorphous.

$^1$H-NMR(DMSO-$d_6$)δ1.92–2.37(5H,m), 2.82–2.96(1H, m), 3.24–3.65(4H,m), 4.67–4.76(2H,m), 4.89(1H,dd,J=7.8, 4.7),7.90(2H,d,J=8.2 Hz), 8.06(2R,d,J=8.2 Hz), 8.90(1H,d, J-6.7 Hz), 9.0–10.0(2H,m).

Example 44

Synthesis of (S)-2-cyano-1-[(2S,4S)-4-(4-cyanobenzoyl)amino-2-pyrrolidinylcarbonyl]pyrrolidine hydrochloride (1) The title compound (462 mg) of Reference Example 3, 4-cyanobenzoic acid (221 mg) and triethylamine (0.42 mL) were dissolved in DMF (30 mL), HOBT (241 mg) and EDC hydrochloride (302 mg) were successively added under ice-cooling. The mixture was stirred at room temperature for 21 hr. The solvent was evaporated under reduced pressure, and saturated aqueous sodium hydrogencarbonate solution was added to the concentrate. The mixture was extracted with ethyl acetate. The extract was washed with brine, dried and evaporated under reduced pressure. The residue was purified by silica gel chromatography to give (S)-1-[(2S,4S)-1-tert-butoxycarbonyl-4-(4-cyanobenzoyl)amino-2-pyrrolidinylcarbonyl]-2-cyanopyrrolidine (548 mg) as amorphous.

(2) The above-mentioned compound (548 mg) was dissolved in tetrahydrofuran (15 mL) and 4 mol/L hydrochloric acid-1,4-dioxane (3.1 mL) was added thereto. The mixture was stirred at room temperature for 5 days. The solvent was evaporated under reduced pressure, and the concentrate was purified by HPLC and freeze-dried to give the title compound (177 mg) as amorphous.

$^1$H-NMR(DMSO-$d_6$)δ1.93–2.36(5H,m), 2.80–2.96(1H, m), 3.26–3.68(4H,m), 4.58–4.76(2H,m), 4.88(1H,dd,J=7.7, 4.8 Hz), 8.00(4H,s), 8.93(1H,d,J=6.6 Hz), 9.0–10.0(2H,m).

Example 45

Synthesis of (S)-2-cyano-1-((2S,4S)-4-nicotinoylamino-2-pyrrolidinylcarbonyl)pyrrolidine 2 trifluoroacetate (1) The title compound (462 mg) of Reference Example 3 and triethylamine (0.63 mL) were dissolved in tetrahydrofuran (10 mL), and nicotinoyl chloride hydrochloride (285 mg) was added thereto. The mixture was stirred at room temperature for 15 hr. Water was added to the reaction mixture and the mixture was extracted with ethyl acetate. The extract was dried and the solvent was evaporated under reduced pressure. The residue was purified by silica gel chromatography to give (S)-1-((2S,4S)-1-tert-butoxycarbonyl-4-nicotinoylamino-2-pyrrolidinylcarbonyl)-2-cyanopyrrolidine (190 mg) as amorphous.

(2) The above-mentioned compound (180 mg) was dissolved in dichloromethane (5 mL), and trifluoroacetic acid (0.5 mL) was added thereto. The mixture was stood at room temperature for 15 hr. The solvent was evaporated under reduced pressure, and the residue was purified by HPLC and freeze-dried to give the title compound (96 mg) as amorphous.

$^1$H-NMR(DMSO-$d_6$)δ1.86–2.36(5H,m), 2.80–2.97(1H, m), 3.24–3.68(4H,m), 4.49–5.13(3H,m), 7.58(1H,dd,J=7.8, 4.8 Hz), 8.24(1H,d,J=7.8 Hz), 8.76(1H,d,J=4.8 Hz), 8.87 (1H,d,J=6.6 Hz), 9.03(1H,s), 9.93(1H,brs).

Example 46

Synthesis of (S)-2-cyano-1-((2S,4S)-4-isonicotinoylamino-2-pyrrolidinylcarbonyl)pyrrolidine 2 trifluoroacetate (1) The title compound (462 mg) of Reference Example 3 and triethylamine (0.63 mL) were dissolved in tetrahydrofuran (10 mL), and isonicotinoyl chloride hydrochloride (285 mg) was added thereto. The mixture was stirred at room temperature for 15 hr. Water was added to the reaction mixture and the mixture was extracted with ethyl acetate. The extract was dried and the solvent was evaporated under reduced pressure. The residue was purified by silica gel chromatography to give (S)-1-((2S,4S)-1-tert-butoxycarbonyl-4-isonicotinoylamino-2-pyrrolidinylcarbonyl)-2-cyanopyrrolidine (670 mg) as amorphous.

(2) The above-mentioned compound (650 mg) was dissolved in dichloromethane (16 mL) and trifluoroacetic acid (1.6 mL) was added thereto. The mixture was stood at room temperature for 15 hr. The solvent was evaporated under reduced pressure, and the residue was purified by HPLC and freeze-dried to give the title compound (412 mg) as amorphous.

$^1$H-NMR(DMSO-$d_6$)δ1.87–2.36(5H,m), 2.79–2.96(1H, m), 3.20–3.68(4H,m), 4.48–5.15(3H,m), 7.80(2H,d,J=6.0 Hz), 8.70–9.13(4H,m), 9.93(1H,brs).

Example 47

Synthesis of (S)-2-cyano-1-((2S,4S)-4-glycylamino-2-pyrrolidinylcarbonyl)pyrrolidine dihydrochloride (1) The title compound (464 mg) of Reference Example 3 and N-methylmorpholine (0.16 mL) were dissolved in tetrahydrofuran (10 mL), and isobutyl chloroformate (0.19 mL) was added thereto at −20° C. The mixture was stirred for 30 min, and a solution of N-tert-butoxycarbonylglycine (463 mg) and triethylamine (0.21 mL) in DMF (3 mL) was added thereto at −20° C. The mixture was stirred at room temperature for 20 hr. Saturated aqueous sodium hydrogencarbonate solution was added to the reaction mixture and the mixture was extracted with ethyl acetate. The extract was washed with brine, dried and evaporated under reduced pressure. The residue was purified by silica gel chromatography to give (S)-1-[(2S,4S)-1-tert-butoxycarbonyl-4-(N-tert-butoxycarbonylglycyl)amino-2-pyrrolidinylcarbonyl]-2-cyanopyrrolidine (680 mg) as amorphous.

(2) The above-mentioned compound (360 mg) was dissolved in 1,4-dioxane (1 mL) and 4 mol/L hydrochloric acid-1,4-dioxane (4 mL) was added thereto. The mixture was stirred at room temperature for 4 hr. The precipitated solid was collected by filtration to give the title compound (262 mg) as a white solid.

$^1$H-NMR(DMSO-d$_6$)δ1.7–2.3(5H,m), 2.78(1H,m), 3.5 (2H,m), 4.26–4.60(2H,m), 4.84(1H,dd,J=7.9,4.6 Hz), 8.24 (3H,brs), 8.7–9.1(2H,m), 10.71(1H,brs).

Example 48

Synthesis of (S)-2-cyano-1-[(2S,4S)-4-(ethoxyoxalyl)amino-2-pyrrolidinylcarbonyl]pyrrolidine trifluoroacetate (1) The title compound (464 mg) of Reference Example 3 and triethylamine (0.63 mL) were dissolved in tetrahydrofuran (10 mL), and ethyl chloroglyoxylate (0.18 mL) was added thereto under ice-cooling. The mixture was stirred for 2 hr and the solvent was evaporated under reduced pressure. Saturated aqueous sodium hydrogencarbonate solution was added to the concentrate and the mixture was extracted with ethyl acetate. The extract was washed with brine and dried. The solvent was evaporated under reduced pressure and the residue was purified by silica gel chromatography to give (S)-1-[(2S,4S)-1-tert-butoxycarbonyl-4-(ethoxyoxalyl)amino-2-pyrrolidinylcarbonyl]-2-cyanopyrrolidine (615 mg) as amorphous.

(2) The above-mentioned compound (492 mg) was dissolved in acetonitrile (10 mL), and trifluoroacetic acid (2 mL) was added thereto under ice-cooling. The mixture was stood at room temperature for 28 hr. The solvent was evaporated under reduced pressure, and the residue was purified by HPLC and freeze-dried to give the title compound (168 mg) as amorphous.

$^1$H-NMR(DMSO-d$_6$)δ1.27(3H,t,J=7.1 Hz), 1.82–2.35 (5H,m), 2.82(1H,m), 3.26(1H,dd,J=11.5,7.1 Hz), 3.45(1H, dd,J=11.5,7.1 Hz), 3.5(2H,m), 4.24(2H,q,J=7.1 Hz), 4.43–4.62(2H,m), 4.85(1H,dd,J=7.8,4.8 Hz), 8.89(1H,brs), 9.18(1H,d,J=7.8 Hz), 9.78(1H,brs).

Example 49

Synthesis of (S)-2-cyano-1-[(2S,4S)-4-(4-pyridyl)oxy-2-pyrrolidinylcarbonyl]pyrrolidine dihydrochloride (1) The title compound (464 mg) of Reference Example 2, 4-hydroxypyridine (144 mg) and triphenylphosphine (393 mg) were dissolved in tetrahydrofuran (20 mL), and 40% toluene solution (0.71 mL) of diethyl diazodicarboxylate was added thereto. The mixture was stirred for 9 days. The solvent was evaporated under reduced pressure, and the concentrate was purified by HPLC and freeze-dried to give (S)-1-[(2S,4S)-1-tert-butoxycarbonyl-4-(4-pyridyl)oxy-2-pyrrolidinylcarbonyl]-2-cyanopyrrolidine (178 mg) as amorphous.

(2) The above-mentioned compound (173 mg) was dissolved in ethyl acetate (1.0 mL) and 4 mol/L hydrochloric acid-ethyl acetate (0.6 mL) was added thereto. The mixture was stood at room temperature for 5 hr. The precipitated white solid was collected by filtration to give the title compound (159 mg).

$^1$H-NMR(DMSO-d$_6$)δ1.73–2.42(5H,m), 2.87–3.03(1H, m), 3.2–3.8(4H,m), 4.66–4.87(2H,m), 5.53–5.67(m,1H), 7.52(1H,d,J=7.2 Hz), 8.78(1H,d,J=7.2 Hz), 8.81(1H,d,J=7.2 Hz), 8.96(1H,brs), 10.86(1H,brs).

Example 50

Synthesis of (S)-1-[(2S,4S)-4-(4-aminobenzoyl)oxy-2-pyrrolidinylcarbonyl]-2-cyanopyrrolidine dihydrochloride (1) The title compound (619 mg) of Reference Example 1 and triethylamine (0.84 mL) were dissolved in dichloromethane (10 mL), and 4-nitrobenzoyl chloride (557 mg) and 4-dimethylaminopyridine (24 mg) were added thereto. The mixture was stirred at room temperature for 14 hr. Saturated aqueous sodium hydrogencarbonate solution was added to the reaction mixture and the mixture was extracted with chloroform. The extract was washed with brine and dried. The solvent was evaporated under reduced pressure, and the residue was purified by silica gel chromatography and recrystallized from ethyl acetate-hexane to give (S)-1-[(2S,4S)-1-tert-butoxycarbonyl-4-(4-nitrobenzoyl)oxy-2-pyrrolidinylcarbonyl]-2-cyanopyrrolidine (800 mg) as pale-brown crystals.

(2) The above-mentioned compound (600 mg) was dissolved in ethyl acetate (15 mL), and the mixture was stirred under a hydrogen atomosphere (1 atm) in the presence of 10% palladium/carbon (123 mg) for 3 hr. The reaction mixture was filtrated and the filtrate was concentrated under reduced pressure. The residue was crystallized from ethyl acetate-hexane to give (S)-1-[(2S,4S)-4-(4-aminobenzoyl)oxy-1-tert-butoxycarbonyl-2-pyrrolidinylcarbonyl]-2-cyanopyrrolidine (96 mg) as white crystals.

(3) The above-mentioned compound (518 mg) was dissolved in ethyl acetate (1.2 mL) and 4 mol/L hydrochloric acid-ethyl acetate (1.5 mL) was added thereto. The mixture was stood at room temperature for 15 hr. The precipitated pale-brown solid was collected by filtration to give the title compound (378 mg).

$^1$H-NMR(DMSO-d$_6$)δ1.97–2.38(5H,m), 2.76–2.88(1H, m), 3.40–3.70(4H,m), 4.63–4.76(1H,m), 4.88(1H,dd,J=7.9, 5.3 Hz), 5.42–5.50(m,1H),6.71(1H,d,J=8.7 Hz), 7.72(1H,d, J=8.7 Hz), 8.88(1H,brs), 10.84(1H,brs).

Example 51

Synthesis of (S)-2-cyano-1-((2S,4S)-4-nicotinoyloxy-2-pyrrolidinylcarbonyl)pyrrolidine dihydrochloride (1) The title compound (619 mg) of Reference Example 1 and triethylamine (0.84 mL) were dissolved in dichloromethane (10 mL), and nicotinoyl chloride hydrochloride (534 mg) and 4-dimethylaminopyridine (23 mg) were added thereto. The mixture was stirred at room temperature for 15 hr. Saturated aqueous sodium hydrogencarbonate solution was added to the reaction mixture and the mixture was extracted with chloroform. The extract was washed with brine and dried. The solvent was evaporated under reduced pressure and the residue was purified by silica gel chromatography and recrystallized from ethyl acetate-hexane to give (S)-1-((2S,4S)-1-tert-butoxycarbonyl-4-nicotinoyloxy-2-pyrrolidinylcarbonyl)-2-cyanopyrrolidine (731 mg) as pale-yellow crystals.

(2) The above-mentioned compound (414 mg) was dissolved in ethyl acetate (2 mL) and 4 mol/L hydrochloric acid-ethyl acetate (1.25 mL) was added thereto. The mixture was stood at room temperature for 18 hr. The precipitated white solid was collected by filtration to give the title compound (524 mg).

$^1$H-NMR(DMSO-$d_6$)δ1.97–2.45(5H,m), 2.81–2.96(1H, m), 3.45–3.85(4H,m), 4.67–4.78(1H,m), 4.86(1H,dd,J=7.9, 5.0 Hz), 5.60–5.67(m,1H),7.65(1H,dd,J=8.0,5.1 Hz), 8.40–8.47(1H,m), 8.88(1H,dd,J=5.0,1.6 Hz), 9.02(1H,brs), 9.17(1H,d,J=1.8 Hz), 10.94(1H,brs).

Example 52

Synthesis of (S)-2-cyano-1-((2S,4S)-4-isonicotinoyloxy-2-pyrrolidinylcarbonyl)pyrrolidine dihydrochloride (1) The title compound (752 mg) of Reference Example 1 and triethylamine (0.84 mL) were dissolved in dichloromethane (10 mL), and isonicotinoyl chloride hydrochloride (712 mg) and 4-dimethylaminopyridine (40 mg) were added thereto. The mixture was stirred at room temperature for 22 hr. Saturated aqueous sodium hydrogencarbonate solution was added to the reaction mixture, and the mixture was extracted with chloroform. The extract was washed with brine and dried. The solvent was evaporated under reduced pressure. The residue was purified by silica gel chromatography and crystallized from diethyl ether to give (S)-1-((2S, 4S)-1-tert-butoxycarbonyl-4-isonicotinoyloxy-2-pyrrolidinylcarbonyl)-2-cyanopyrrolidine (576 mg) as white crystals.

(2) The above-mentioned compound (414 mg) was dissolved in ethyl acetate (1.0 mL) and 4 mol/L hydrochloric acid-ethyl acetate (1.25 mL) was added thereto. The mixture was stood at room temperature for 18 hr. The precipitated white solid was collected by filtration to give the title compound (458 mg).

$^1$H-NMR(DMSO-$d_6$)δ1.97–2.47(5H,m), 2.79–2.92(1H, m), 3.5–3.8(4H,m), 4.68–4.81(1H,m), 4.87(1H,dd,J=7.9,5.3 Hz), 5.60–5.67(m,1H),7.97(2H,d,J=6.0 Hz), 8.83(2H,d,J= 6.0 Hz), 8.97(1H,brs), 10.98(1H,brs).

Example 53

Synthesis of 3-((2S,4S)-4-amino-2-pyrrolidinylcarbonyl)-1,3-thiazolidine dihydrochloride 3-((2S,4S)-4-Amino-1-tert-butoxycarbonyl-2-pyrrolidinylcarbonyl)-1,3-thiazolidine (title compound of Reference Example 10, 400 mg) was dissolved in ethyl acetate (3.0 mL), and 4 mol/L hydrochloric acid-ethyl acetate (3.75 mL) was added thereto. The mixture was stood at room temperature for 3 hr. The reaction mixture was concentrated under reduced pressure, and the residue was dissolved in ethanol (100 mL). Activated carbon (0.4 g) was added thereto and the activated carbon was filtered off. The filtrate was concentrated and diethyl ether was added thereto. The precipitated solid was collected by filtration to give the title compound (28.8 mg) as a white powder.

$^1$H-NMR(DMSO-$d_6$)δ1.85–2.06(1H,m), 2.71–2.93(1H, m), 2.99–3.20(2H,m), 3.40–3.98(5H,m), 4.37–4.78(3H,m), 8.86(5H,brs).

Example 54

Synthesis of 3-[(2S,4S)-4-(4-cyanophenyl)amino-2-pyrrolidinylcarbonyl]-1,3-thiazolidine hydrochloride (1) The title compound (1810 mg) of Reference Example 10, diisopropylethylamine (3.14 mL) and 4-fluorobenzonitrile (727 mg) were dissolved in N-methyl-2-pyrrolidone (18 mL), and the mixture was stirred at 100° C. for 24 hr. The reaction mixture was poured into saturated aqueous sodium hydrogencarbonate solution, and the mixture was extracted with ethyl acetate. The extract was dried and the solvent was evaporated under reduced pressure. The residue was purified by silica gel chromatography to give 3-[(2S,4S)-1-tert-butoxycarbonyl-4-(4-cyanophenyl)amino-2-pyrrolidinylcarbonyl]-1,3-thiazolidine (170 mg) as a pale-brown oil.

(2) The above-mentioned compound (170 mg) was dissolved in ethyl acetate (0.42 mL) and 4 mol/L hydrochloric acid-ethyl acetate (0.53 mL) was added thereto. The mixture was stirred at room temperature for 18 hr. The precipitated solid was collected by filtration to give the title compound (69.3 mg) as a pale-brown powder.

$^1$H-NMR(DMSO-$d_6$)δ1.64–1.80(1H,m), 2.84–3.20(4H, m), 3.45–3.96(3H,m), 4.15–4.34(1H,m), 4.39–4.78(3H,m), 6.70(2H,d,J=8.8 Hz), 6.85–7.01(1H,m), 7.52(1H,d,J=8.7 Hz), 9.45(2H,brs).

Example 55

Synthesis of 3-[(2S,4S)-4-(4-nitrophenyl)amino-2-pyrrolidinylcarbonyl]-1,3-thiazolidine hydrochloride (1) The title compound (904 mg) of Reference Example 10, diisopropylethylamine (1.57 mL) and 4-fluoronitrobenzene (423 mg) were dissolved in N-methyl-2-pyrrolidone (9 mL), and the mixture was stirred at 80° C. for 24 hr. The reaction mixture was poured into saturated aqueous sodium hydrogencarbonate solution, and the mixture was extracted with ethyl acetate. The extract was dried and the solvent was evaporated under reduced pressure. The residue was purified by silica gel chromatography to give 3-[(2S,4S)-1-tert-butoxycarbonyl-4-(4-nitrophenyl)amino-2-pyrrolidinylcarbonyl]-1,3-thiazolidine (919 mg) as yellow amorphous.

(2) The above-mentioned compound (795 mg) was dissolved in ethyl acetate (3.8 mL) and 4 mol/L hydrochloric acid-ethyl acetate (2.4 mL) was added thereto. The mixture was stirred at room temperature for 18 hr. The precipitated solid was collected by filtration to give the title compound (647 mg) as a yellow powder.

$^1$H-NMR(DMSO-$d_6$)δ1.68–1.87(1H,m), 2.88–3.30(4H, m), 3.48–3.98(3H,m), 4.24–4.80(4H,m), 6.72(2H,d,J=9.3 Hz), 7.40–7.56(1H,m), 8.04(2H,d,J=7.5 Hz), 9.51(2H,brs).

Example 56

Synthesis of 3-[(2S,4S)-4-(4-methanesulfonylphenyl)amino-2-pyrrolidinylcarbonyl]-1,3-thiazolidine hydrochloride (1) The title compound (904 mg) of Reference Example 10, diisopropylethylamine (1.57 mL) and 4-fluorophenyl methyl sulfone (523 mg) were dissolved in N-methyl-2-pyrrolidone (9 mL), and the mixture was stirred at 100° C. for 18 hr. The reaction mixture was poured into saturated aqueous sodium hydrogencarbonate solution, and the mixture was extracted with ethyl acetate. The extract was dried and the solvent was evaporated under reduced pressure. The residue was purified by silica gel chromatography to give 3-[(2S,4S)-1-tert-butoxycarbonyl-4-(4-methanesulfonylphenyl)amino-2-pyrrolidinylcarbonyl]-1,3-thiazolidine (27 mg).

(2) The above-mentioned compound (27 mg) was dissolved in ethyl acetate (0.2 mL) and 4 mol/L hydrochloric acid-ethyl acetate (0.1 mL) was added thereto. The mixture was stirred at room temperature for 18 hr. The precipitated solid was collected by filtration to give the title compound (19.4 mg).

$^1$H-NMR(DMSO-$d_6$)δ1.65–1.82(1H,m), 2.89–3.23(7H, m), 3.49–3.98(3H,m), 4.18–4.78(4H,m), 6.74(2H,d,J=9.0 Hz), 6.80–6.92(1H,m), 6.63(2H,d,J=9.0 Hz), 9.30(2H,brs).

Example 57

Synthesis of 3-[(2S,4S)-4-(2-cyanophenyl)amino-2-pyrrolidinylcarbonyl]-1,3-thiazolidine hydrochloride (1) The title compound (1810 mg) of Reference Example 10, diisopropylethylamine (3.14 mL) and 2-fluorobenzonitrile (727 mg) were dissolved in N-methyl-2-pyrrolidone (18 mL), and the mixture was stirred at 80° C. for 32 hr. The reaction mixture was poured into saturated aqueous sodium hydrogencarbonate solution, and the mixture was extracted with ethyl acetate. The extract was dried and the solvent was evaporated under reduced pressure. The residue was purified by silica gel chromatography to give 3-[(2S,4S)-1-tert-butoxycarbonyl-4-(2-cyanophenyl)amino-2-pyrrolidinylcarbonyl]-1,3-thiazolidine (88 mg).

(2) The above-mentioned compound (88 mg) was dissolved in ethyl acetate (0.4 mL) and 4 mol/L hydrochloric acid-ethyl acetate (0.3 mL) was added thereto. The mixture was stirred at room temperature for 18 hr. The precipitated solid was collected by filtration to give the title compound (25 mg).

$^1$H-NMR(DMSO-$d_6$)δ1.74–1.95(1H,m), 2.85–3.16(3H, m), 3.30–3.92(4H,m), 4.27–4.79(4H,m), 6.15–6.27(1H,m), 6.77(1H,t,J=7.5 Hz), 6.87(1H,d,J=8.4 Hz), 7.38–7.59(2H, m), 8.90(1H,brs), 10.80(1H,brs).

Example 58

Synthesis of 3-[(2S,4S)-4-(5-cyano-2-pyridyl)amino-2-pyrrolidinylcarbonyl]-1,3-thiazolidine dihydrochloride (1) The title compound (904 mg) of Reference Example 10, diisopropylethylamine (1.57 mL) and 2-chloro-5-cyanopyridine (416 mg) were dissolved in N-methyl-2-pyrrolidone (9 mL), and the mixture was stirred at 80° C. for 18 hr. The reaction mixture was added to saturated aqueous sodium hydrogencarbonate solution, and the mixture was extracted with ethyl acetate. The extract was dried and the solvent was evaporated under reduced pressure. The residue was purified by silica gel chromatography to give 3-[(2S,4S)-1-tert-butoxycarbonyl-4-(5-cyano-2-pyridyl)amino-2-pyrrolidinylcarbonyl]-1,3-thiazolidine (807 mg) as white amorphous.

(2) The above-mentioned compound (711 mg) was dissolved in ethyl acetate (1.76 mL) and 4 mol/L hydrochloric acid-ethyl-acetate (2.20 mL) was added thereto. The mixture was stood at room temperature for 18 hr. The precipitated solid was collected by filtration to give the title compound (709 mg) as a white powder.

$^1$H-NMR(DMSO-$d_6$)δ1.74–1.94(1H,m), 2.78–2.94(1H, m), 2.97–3.26(3H,m), 3.40–3.77(3H,m), 4.40–4.80(4H,m), 6.64(1H,d,J=9.0 Hz), 7.77(1H,dd,J=8.7,2.4 Hz), 8.08(1H, brs), 8.46(1H,d,J=1.8 Hz), 8.86(1H,brs), 10.37(1H,brs).

Example 59

Synthesis of 3-[(2S,4S)-4-(3,4-dicyanophenyl)amino-2-pyrrolidinylcarbonyl]-1,3-thiazolidine hydrochloride (1) The title compound (0.904 g) of Reference Example 10, diisopropylethylamine (1.57 mL) and 4-fluorophthalonitrile (0.438 g) were dissolved in N-methyl-2-pyrrolidone (9 mL), and the mixture was stirred at 80° C. for 4 hr. The reaction mixture was poured into saturated aqueous sodium hydrogencarbonate solution, and the mixture was extracted with ethyl acetate. The extract was dried and the solvent was evaporated under reduced pressure. The residue was purified by silica gel chromatography to give 3-[(2S,4S)-1-tert-butoxycarbonyl-4-(3,4-dicyanophenyl)amino-2-pyrrolidinylcarbonyl]-1,3-thiazolidine (1.08 g) as white amorphous.

(2) The above-mentioned compound (0.924 g) was dissolved in ethyl acetate (2.16 mL) and 4 mol/L hydrochloric acid-ethyl acetate (2.70 mL) was added thereto. The mixture was stirred at room temperature for 18 hr. The precipitated solid was collected by filtration to give the title compound (0.782 g) as a yellow powder.

$^1$H-NMR(DMSO-$d_6$)δ1.66–1.84(1H,m), 2.90–3.27(4H, m), 3.49–3.95(3H,m), 4.20–4.40(1H,m), 4.40–5.79(3H,m), 7.00(1H,dd,J=8.7,2.4 Hz), 7.22(1H,s), 7.52–7.67(1H,m), 7.76(1H,d,J=9.0 Hz).

Example 60

Synthesis of 3-[(2S,4S)-4-(3-chloro-4-cyanophenyl)amino-2-pyrrolidinylcarbonyl]-1,3-thiazolidine hydrochloride (1) The title compound (0.904 g) of Reference Example 10, diisopropylethylamine (1.57 mL) and 2-chloro-4-fluorobenzonitrile (0.467 g) were dissolved in N-methyl-2-pyrrolidone 9 mL), and the mixture was stirred at 80° C. for 8 hr. The reaction mixture was poured into saturated aqueous sodium hydrogencarbonate solution, and the mixture was extracted with ethyl acetate. The extract was dried and the solvent was evaporated under reduced pressure. The residue was purified by silica gel chromatography to give 3-[(2S,4S)-1-tert-butoxycarbonyl-4-(3-chloro-4-cyanophenyl)amino-2-pyrrolidinylcarbonyl]-1,3-thiazolidine (0.630 g) as a colorless transparent oil.

(2) The above-mentioned compound (0.630 g) was dissolved in ethyl acetate (2.88 mL) and 4 mol/L hydrochloric acid-ethyl acetate (1.80 mL) was added thereto. The mixture was stirred at room temperature for 18 hr, and the precipitated solid was collected by filtration to give the title compound (0.465 g) as a white powder.

$^1$H-NMR(DMSO-$d_6$)δ1.65–1.81(1H,m), 2.84–2.99(1H, m), 2.99–3.22(3H,m), 3.48–3.95(3H,m), 4.16–4.37(1H,m), 4.39–4.78(3H,m), 6.68(1H,dd,J=8.7,2.1 Hz), 6.85(1H,d,J=1.8 Hz), 7.30–7.45(1H,m), 7.60(1H,d,J=8.7 Hz), 9.60(2H, brs).

Example 61

Synthesis of 3-[(2S,4S)-4-(2-benzoxazolyl)amino-2-pyrrolidinylcarbonyl]-1,3-thiazolidine hydrochloride (1) The title compound (904 mg) of Reference Example 10, diisopropylethylamine (1.57 mL) and 2-chlorobenzoxazole (461 mg) were dissolved in N-methyl-2-pyrrolidone (9 mL), and the mixture was stirred at room temperature for 1 hr. The reaction mixture was poured into saturated aqueous sodium hydrogencarbonate solution, and the mixture was extracted with ethyl acetate. The extract was dried and the solvent was evaporated under reduced pressure. The residue was purified by silica gel chromatography to give 3-[(2S,4S)-4-(2-benzoxazolyl)amino-1-tert-butoxycarbonyl-2-pyrrolidinylcarbonyl]-1,3-thiazolidine (975 mg) as white amorphous.

(2) The above-mentioned compound (862 mg) was dissolved in ethyl acetate (4.1 mL) and 4 mol/L hydrochloric acid-ethyl acetate (2.6 mL) was added thereto. The mixture was stirred at room temperature for 8 hr. The precipitated solid was collected by filtration to give the title compound (656 mg) as a white powder.

$^1$H-NMR(DMSO-$d_6$)δ1.94–2.13(1H,m), 2.85–2.99(1H, m), 3.00–3.20(2H,m), 3.31–4.00(4H,m), 4.40–4.82(4H,m), 7.07(1H,td,J=7.8,1.2 Hz), 7.18(1H,td,J=7.8,1.2 Hz), 7.33 (1H,d,J=7.2 Hz), 7.42(1H,d,J=7.5 Hz), 8.61(1H,brs), 8.89 (1Hbrs), 10.59(1H,brs).

Example 62

Synthesis of 3-((2S,4S)-4-benzylamino-2-pyrrolidinylcarbonyl)-1,3-thiazolidine dihydrochloride (1) The title compound (904 mg) of Reference Example 10 and benzaldehyde (318 mg) were dissolved in methanol (16 mL), and the mixture was stirred at room temperature for 30 min. Sodium cyanoborohydride (189 mg) and several drops of acetic acid were added to the reaction mixture, and the mixture was stirred for 6 hr. The reaction mixture was evaporated under reduced pressure. Saturated aqueous sodium hydrogencarbonate solution was added to the residue and the mixture was extracted with ethyl acetate. The extract was dried and the solvent was evaporated under reduced pressure. The residue was purified by silica gel chromatography to give 3-[(2S,4S)-4-benzylamino-1-tert-butoxycarbonyl-2-pyrrolidinylcarbonyl]-1,3-thiazolidine (742 mg) as a colorless transparent oil.

(2) The above-mentioned compound (742 mg) was dissolved in ethyl acetate (3.8 mL) and 4 mol/L hydrochloric acid-ethyl acetate (2.4 mL) was added thereto. The mixture was stirred at room temperature for 18 hr and the precipitated solid was collected by filtration to give the title compound (540 mg) as a white powder.

$^1$H-NMR(DMSO-$d_6$)δ2.10–2.32(1H,m), 2.86–3.20(3H, m), 3.49–4.03(5H,m), 4.21(2H,s), 4.39–4.80(3H,m), 7.31–7.52(3H,m), 7.52–7.72(2H,m), 10.17(4H,brs).

Example 63

Synthesis of 3-[(2S,4S)-4-(4-cyanophenylmethyl)amino-2-pyrrolidinylcarbonyl]-1,3-thiazolidine dihydrochloride (1) The title compound (904 mg) of Reference Example 10 and 4-cyanobenzaldehyde (393 mg) were dissolved in methanol (16 mL), and the mixture was stirred at room temperature for 30 min. Sodium cyanoborohydride (189 mg) and several drops of acetic acid were added to the reaction mixture, and the mixture was stirred for 18 hr. The reaction mixture was evaporated under reduced pressure. Saturated aqueous sodium hydrogencarbonate solution was added to the residue and the mixture was extracted with ethyl acetate. The extract was dried and the solvent was evaporated under reduced pressure. The residue was purified by silica gel chromatography to give 3-[(2S,4S)-1-tert-butoxycarbonyl-4-(4-cyanophenylmethyl)amino-2-pyrrolidinylcarbonyl]-1,3-thiazolidine (389 mg) as a colorless transparent oil.

(2) The above-mentioned compound (389 mg) was dissolved in ethyl acetate (0.9 mL) and 4 mol/L hydrochloric acid-ethyl acetate (1.2 mL) was added thereto. The mixture was stood at room temperature for 18 hr. The precipitated solid was collected by filtration to give the title compound (286 mg) as a white powder.

$^1$H-NMR(DMSO-$d_6$)δ2.06–2.34(1H,m), 2.85–3.01(1H, m), 3.01–3.20(2H,m), 3.50–4.06(5H,m), 4.30(2H,s), 4.41–4.79(3H,m), 7.80(2H,d,J=8.1 Hz), 7.95(2H,d,J=8.4 Hz), 9.05(1H,brs), 10.30(3H,brs).

Example 64

Synthesis of 3-{(2S,4S)-4-[N-(4-cyanophenylmethyl)-N-methylamino]-2-pyrrolidinylcarbonyl}-1,3-thiazolidine dihydrochloride (1) 3-[(2S,4S)-1-tert-Butoxycarbonyl-4-(4-cyanophenylmethyl)amino-2-pyrrolidinylcarbonyl]-1,3-thiazolidine [product of Example 63 (1), 1.35 g] and 37% formaldehyde solution (0.788 mL) were dissolved in acetonitrile (20 mL), and the mixture was stirred at room temperature for 30 min. Sodium cyanoborohydride (0.305 g) and several drops of acetic acid were added to the reaction mixture, and the reaction mixture was stirred for 1 hr. The reaction mixture was evaporated under reduced pressure. Saturated aqueous sodium hydrogencarbonate solution was added to the residue and the mixture was extracted with ethyl acetate. The extract was dried and the solvent was evaporated under reduced pressure. The residue was purified by silica gel chromatography to give 3-{(2S,4S)-1-tert-butoxycarbonyl-4-[N-(4-cyanophenylmethyl)-N-methylamino]-2-pyrrolidinylcarbonyl}-1,3-thiazolidine (0.953 g) as white amorphous.

(2) The above-mentioned compound (0.818 g) was dissolved in ethyl acetate (3.8 mL) and 4 mol/L hydrochloric acid-ethyl acetate (2.4 mL) was added thereto. The mixture was stirred at room temperature for 5 hr. The precipitated solid was collected by filtration to give the title compound (0.683 g) as a white powder.

$^1$H-NMR(DMSO-$d_6$)δ2.20–2.48(1H,m), 2.57(3H,s), 2.80–3.20(3H,m), 3.57–4.17(5H,m), 4.20–4.85(5H,m), 7.88 (2H,d,J=7.8 Hz), 7.96(2H,d,J=8.4 Hz), 9.12(1H,brs), 10.95 (1H,brs), 12.50(1H,brs).

Example 65

Synthesis of 3-[(2S,4R)-4-(7-methoxy-2-phenyl-4-quinolyl)oxy-2-pyrrolidinylcarbonyl]-1,3-thiazolidine trihydrochloride (1) N-tert-Butoxycarbonyl-L-trans-hydroxyproline (5.67 g) was dissolved in dimethyl sulfoxide (70 mL), and potassium tert-butoxide (6.88 g) was gradually added thereto at room temperature. The mixture was stirred for 1.5 hr. 4-Chloro-7-methoxy-2-phenylquinoline (7.28 g) was gradually added to this solution, and the mixture was stirred for 17 hr. Water was added to the reaction mixture and the mixture was washed with ethyl acetate/hexane (1/1). The aqueous layer was adjusted to pH 4 with 1 mol/L hydrochloric acid, and the precipitate was collected by filtration to give (2S,4R)-1-tert-butoxycarbonyl-4-(7-methoxy-2-phenyl-4-quinolyl)oxy-2-pyrrolidine-2-carboxylic acid (8.00 g) as a white solid.

(2) Using the above-mentioned compound (546 mg) and in the same manner as in Reference Example 9, 3-[(2S,4R)-1-tert-butoxycarbonyl-4-(7-methoxy-2-phenyl-4-quinolyl)oxy-2-pyrrolidinylcarbonyl]-1,3-thiazolidine (568 mg) was obtained as a white solid.

(3) Using the above-mentioned compound (554 mg) and in the same manner as in Example 5 (2), the title compound (521 mg) was obtained as a white powder.

$^1$H-NMR(500 MHz,DMSO-$d_6$)δ2.40–2.50(1H,m), 2.96–3.12(3H,m), 3.68–3.97(4H,m), 3.99(3H,s), 4.48–4.94

(3H,m), 4.98(1H,brs), 7.43(1H,d,J=8.1 Hz), 7.69–7.70(4H, m), 7.91(1H,brs), 8.26(2H,d,J=7.4 Hz), 8.57(1H,brs), 9.10 (1H,brs), 11.00(1H,brs).

Example 66

Synthesis of 3-((2S,4S)-4-benzoyloxy-2-pyrrolidinylcarbonyl)-1,3-thiazolidine (1) Using the title compound (643 mg) of Reference Example 11 and benzoyl chloride (0.44 mL), and in the same manner as in Example 50 (1), 3-((2S,4S)-4-benzoyloxy-1-tert-butoxycarbonyl-2-pyrrolidinylcarbonyl)-1,3-thiazolidine (515 mg) was obtained as an oil.

(2) The above-mentioned compound (413 mg) was dissolved in ethyl acetate (4 mL) and 4 mol/L hydrochloric acid-ethyl acetate (1.3 mL) was added thereto. The mixture was stirred at room temperature for 14 hr and the solvent was evaporated under reduced pressure. The residue was added to aqueous sodium hydrogencarbonate solution and extracted with ethyl acetate. The extract was washed with brine and dried. The solvent was evaporated under reduced pressure and the residue was purified by silica gel chromatography to give the title compound (315 mg) as an oil.

$^1$H-NMR(DMSO-$d_6$)δ1.83–1.93(1H,m), 2.45–2.57(1H, m), 2.87(1H,dd,J=12.8,4.2 Hz), 2.99(1H,t,J=6.3 Hz), 3.08 (1H,t,J=6.3 Hz), 3.19(1H,d,J=12.8 Hz), 3.57–3.77(1.5H,m), 3.83–3.98(1.5H,m), 4.42(0.5H,d,J=9.5 Hz), 4.48–4.58(1H, m), 4.72(0.5H,d,J=9.5 Hz), 5.28–5.36(1H,m), 7.52(2H,t,J=7.4 Hz), 7.65(1H,t,J=7.4 Hz), 7.93(2H,d,J=7.4 Hz).

Example 67

Synthesis of 3-[(2S,4S)-4-(4-cyanobenzoyl)oxy-2-pyrrolidinylcarbonyl]-1,3-thiazolidine (1) Using the title compound (445 mg) of Reference Example 11 and 4-cyanobenzoyl chloride (371 mg), and in the same manner as in Example 50 (1), 3-[(2S,4S)-1-tert-butoxycarbonyl-4-(4-cyanobenzoyl)oxy-2-pyrrolidinylcarbonyl]-1,3-thiazolidine (519 mg) was obtained as a pale-brown solid.

(2) Using the above-mentioned compound (386 mg), and in the same manner as in Example 66 (2), the title compound (280 mg) was obtained as a pale-yellow solid.

$^1$H-NMR(DMSO-$d_6$)δ1.88–1.97(1H,m), 2.46–2.58(1H, m), 2.88(1H,dd,J=12.9,4.0 Hz), 2.99(1H,t,J=6.3 Hz), 3.09 (1H,t,J=6.3 Hz), 3.23(1H,d,J=12.9 Hz), 3.57–3.76(1.5H,m), 3.84–3.99(1.5H,m), 4.42(0.5H,d,J=9.5 Hz), 4.48–4.57(1H, m), 4.72(0.5H,d,J=9.5 Hz), 5.33–5.38(1H,m), 8.01(2H,d,J=8.3 Hz), 8.07(2H,d,J=8.3 Hz).

Example 68

Synthesis of 3-((2S,4S)-4-anilino-2-pyrrolidinylcarbonyl)-1,3-thiazolidine dihydrochloride (1) The title compound (501 mg) of Reference Example 12, aniline (0.20 mL) and acetic acid (0.10 mL) were dissolved in methanol (10 mL), and the mixture was stirred at room temperature for 1.5 hr. Sodium cyanoborohydride (145 mg) was added to the reaction mixture and the mixture was stirred for 2 hr. The reaction mixture was evaporated under reduced pressure. Saturated aqueous sodium hydrogencarbonate solution was added to the residue and the mixture was extracted with ethyl acetate. The extract was washed with brine and dried. The solvent was evaporated under reduced pressure, and the residue was purified by silica gel chromatography and crystallized from diethyl ether to give 3-((2S,4S)-4-anilino-1-tert-butoxycarbonyl-2-pyrrolidinylcarbonyl)-1,3-thiazolidine (156 mg) as white crystals.

(2) The above-mentioned compound (142 mg) was dissolved in ethyl acetate (2 mL) and 4 mol/L hydrochloric acid-ethyl acetate (0.5 mL) was added thereto. The mixture was stirred at room temperature for 12 hr. The precipitated solid was collected by filtration to give the title compound (89 mg) as a white powder.

$^1$H-NMR(DMSO-$d_6$)δ1.64–1.78(1H,m), 2.84–2.97(1H, m), 3.00–3.19(3H,m), 3.43–3.55(1H,m), 3.60–4.20(5H,m), 4.41–4.76(3H,m), 6.56–6.67(3H,m), 7.13(2H,t,J=7.2 Hz), 8.79(1H,brs), 10.29(1H,brs).

Example 69

Synthesis of 3-[(2S,4S)-4-(4-aminophenyl)amino-2-pyrrolidinylcarbonyl]-1,3-thiazolidine hydrochloride The title compound (200 mg) of Example 55 was dissolved in ethanol (10 mL), and 4 mol/L hydrochloric acid-1,4-dioxane (0.28 mL) and 10% palladium/carbon (100 mg) were added. The mixture was stirred under a hydrogen atomosphere (1 atm) at room temperature for 18 hr. The reaction mixture was filtrated and the filtrate was concentrated under reduced pressure, and the obtained solid was washed with ethanol to give the title compound (13 mg) as a white powder.

$^1$H-NMR(DMSO-$d_6$)δ1.58–1.80(1H,m), 2.83–3.00(1H, m), 3.00–3.20(3H,m), 3.60–3.90(3H,m), 4.08–4.25(1H,m), 4.39–4.79(3H,m), 6.67(2H,d,J=8.7 Hz), 7.15(2H,d,J=8.7 Hz), 8.81(1H,brs), 10.00(3H,brs), 10.25(1H,brs).

Example 70

Synthesis of 3-[(2S,4S)-4-(p-anisidino)-2-pyrrolidinylcarbonyl]-1,3-thiazolidine dihydrochloride (1) The title compound (450 mg) of Reference Example 12, p-anisidine (222 mg) and acetic acid (0.09 mL) were dissolved in 1,2-dichloroethane (8 mL), and sodium triacetoxyborohydride (636 mg) was added thereto. The mixture was stirred at room temperature for 3 hr. Saturated aqueous sodium hydrogencarbonate solution was added to the reaction mixture, and the mixture was extracted with ethyl acetate. The extract was washed with brine and dried. The solvent was evaporated under reduced pressure, and the residue was purified by silica gel chromatography to give 3-[(2S,4S)-4-(p-anisidino)-1-tert-butoxycarbonyl-2-pyrrolidinylcarbonyl]-1,3-thiazolidine (515 mg) as a white solid.

(2) The above-mentioned compound (448 mg) was dissolved in ethyl acetate (10 mL) and 4 mol/L hydrochloric acid-ethyl acetate (1.4 mL) was added thereto. The mixture was stirred at room temperature for 13 hr. The precipitated solid was collected by filtration to give the title compound (223 mg) as a white powder.

$^1$H-NMR(DMSO-$d_6$)δ1.77–1.90(1H,m), 2.77–2.89(1H, m), 3.00–3.14(3H,m), 3.20–4. 20(1H,m), 3.60–4.20(6H,m), 4.40–4.72(3H,m), 6.87(4H,s), 8.84(1H,brs), 10.33(1H,brs).

Example 71

Synthesis of 3-[(2S,4S)-4-(4-chlorophenyl)amino-2-pyrrolidinylcarbonyl]-1,3-thiazolidine dihydrochloride (1) Using the title compound (450 mg) of Reference Example 12 and p-chloroaniline (230 mg), and in the same manner as in Example 70 (1), 3-[(2S,4S)-1-tert-butoxycarbonyl-4-(4-chlorophenyl)amino-2-pyrrolidinylcarbonyl]-1,3-thiazolidine (415 mg) was obtained as an oil.

(2) Using the above-mentioned compound (412 mg), and in the same manner as in Example 70 (2) the title compound (297 mg) was obtained as a white powder.

$^1$H-NMR(DMSO-$d_6$)δ1.63–1.78(1H,m), 2.84–2.97(1H,m), 3.00–3.17(3H,m), 3.5–3.92(3H,m), 4.07–4.18(1H,m), 4.40–4.73(3H,m), 6.62(2H,d,J=8.8 Hz), 7.15(2H,d,J=8.8 Hz), 8.86(1H,brs), 10.23(1H,brs).

Example 72

Synthesis of 3-[(2S,4S)-4-(2-chloro-4-cyanophenyl)amino-2-pyrrolidinylcarbonyl]-1,3-thiazolidine hydrochloride (1) The title compound (904 mg) of Reference Example 10, diisopropylethylamine (1.57 mL) and 3-chloro-4-fluorobenzonitrile (467 mg) were dissolved in N-methyl-2-pyrrolidone (9 mL), and the mixture was stirred at 80° C. for 8 hr. The reaction solution wag added to saturated aqueous sodium hydrogencarbonate solution, extracted with ethyl acetate. The extract was dried and the solvent was evaporated under reduced pressure. The residue was purified by silica gel chromatography to give 3-[(2S,4S)-1-tert-butoxycarbonyl-4-(2-chloro-4-cyanophenyl)amino-2-pyrrolidinylcarbonyl]-1,3-thiazolidine (460 mg) as a white solid.

(2) The above-mentioned compound (395 mg) was dissolved in ethyl acetate (1.8 mL) and 4 mol/L hydrochloric acid-ethyl acetate (1.13 mL) was added thereto. The mixture was stirred at room temperature for 4 hr, and the precipitated solid was collected by filtration to give the title compound (177 mg) as a white powder.

$^1$H-NMR(DMSO-$d_6$)δ1.80–1.99(1H,m), 2.82–3.17(3H,m), 3.25–3.94(4H,m), 4.36–4.54(2H,m), 4.54–4.80(2H,m), 6.42(1H,d,J=7.8 Hz), 6.93(1H,d,J=8.7 Hz), 7.64(1H,dd,J=8.4,1.8 Hz), 7.82(d,J=1.8 Hz).

Example 73

Synthesis of 3-[(2S,4S)-4-(3-chloro-4-methoxyphenyl)amino-2-pyrrolidinylcarbonyl]-1,3-thiazolidine dihydrochloride (1) Using the title compound (450 mg) of Reference Example 12 and 3-chloro-4-methoxyaniline (284 mg), and in the same manner as in Example 70 (1), 3-[(2S,4S)-1-tert-butoxycarbonyl-4-(3-chloro-4-methoxyphenyl)amino-2-pyrrolidinylcarbonyl]-1,3-thiazolidine (569 mg) was obtained as an oil.

(2) Using the above-mentioned compound (561 mg), and in the same manner as in Example 70 (2), the title compound (429 mg) was obtained as a pale-brown powder.

$^1$H-NMR(DMSO-$d_6$)δ1.62–1.76(1H,m), 2.82–2.95(1H,m), 3.00–3.18(3H,m), 3.5–3.92(6H,m), 4.07–4.18(1H,m), 4.40–4.73(3H,m), 6.61(1H,dd,J=8.8,2.7 Hz), 6.75(1H,d,J=2.7 Hz), 6.98(1H,d,J=8.8 Hz), 8.80(1H,brs), 10.15(1H,brs).

Example 74

Synthesis of 3-[(2S,4S)-4-(3,4-methylenedioxyphenyl)amino-2-pyrrolidinylcarbonyl]-1,3-thiazolidine dihydrochloride (1) Using the title compound (450 mg) of Reference Example 12 and 3,4-methylenedioxyaniline (249 mg), and in the same manner as in Example 70 (1), 3-[(2S,4S)-1-tert-butoxycarbonyl-4-(3,4-methylenedioxyphenyl)amino-2-pyrrolidinylcarbonyl]-1,3-thiazolidine (553 mg) was obtained as a pale-brown-reddish solid.

(2) Using the above-mentioned compound (549 mg), and in the same manner as in Example 70 (2), the title compound (457 mg) as obtained as a pale-brown-reddish powder.

$^1$H-NMR(DMSO-$d_6$)δ1.72–1.85(1H,m), 2.820–2.93(1H,m), 3.00–3.28(3H,m), 3.45–3.57(1H,m), 3.60–3.95(2H,m), 4.08–4.20(1H,m), 4.42–4.75(3H,m), 5.92(2H,s), 6.25–6.32(1H,m), 6.53(1H,s), 6.76–6.83(1H,m), 8.89(1H,brs), 10.36(1H,brs).

Example 75

Synthesis of 3-[(2S,4S)-4-(5-trifluoromethyl-2-pyridyl)amino-2-pyrrolidinylcarbonyl]-1,3-thiazolidine dihydrochloride (1) The title compound (904 mg) of Reference Example 10, diisopropylethylamine (1.57 mL) and 2-chloro-5-trifluoromethylpyridine (545 mg) were dissolved in N-methyl-2-pyrrolidone (9 mL), and the mixture was stirred at 80° C. for 18 hr. The reaction solution was added to saturated aqueous sodium hydrogencarbonate solution, and extracted with ethyl acetate. The extract was dried and the solvent was evaporated under reduced pressure. The residue was purified by silica gel chromatography to give 3-[(2S,4S)-1-tert-butoxycarbonyl-4-(5-trifluoromethyl-2-pyridyl)amino-2-pyrrolidinylcarbonyl]-1,3-thiazolidine (143 mg).

(2) The above-mentioned compound (143 mg) was dissolved in ethyl acetate (0.64 mL) and 4 mol/L hydrochloric acid-ethyl acetate (0.32 mL) was added thereto. The mixture was stirred at room temperature for 18 hr. The precipitated solid was collected by filtration to give the title compound (65 mg) as a brown powder.

$^1$H-NMR(DMSO-$d_6$)δ1.71–1.93(1H,m), 2.80–2.98(1H,m), 3.00–3.28(3H,m), 3.34–3.99(3H,m), 4.40–4.80(4H,m), 6.68(1H,d,J=9.0 Hz), 7.74(1H,dd,J=8.7,2.4 Hz), 7.83(1H,brs), 8.35(1H,d,J=1.2 Hz), 8.91(1H,brs), 10.22(1H,brs).

Example 76

Synthesis of 3-[(2S,4S)-4-(6-cyano-5-trifluoromethyl-2-pyridyl)amino-2-pyrrolidinylcarbonyl]-1,3-thiazolidine hydrochloride (1) 2-Chloro-5-trifluoromethylpyridine (5 g) was dissolved in chloroform (150 mL) and m-chloroperbenzoic acid (14.3 g) was added thereto. The mixture was stirred at 60° C. for 30 hr. Aqueous sodium thiosulfate solution and saturated aqueous sodium hydrogencarbonate solution were added to the reaction mixture, and after stirring, the mixture was extracted with chloroform. The extract was washed successively with saturated aqueous sodium hydrogencarbonate solution and brine, and dried. The solvent was evaporated under reduced pressure and the residue was purified by silica gel chromatography to give 2-chloro-5-trifluoromethylpyridine 1-oxide (0.64 g).

(2) The above-mentioned compound (610 mg) was dissolved in acetonitrile (5 mL), and triethylamine (0.861 mL) and trimethylsilyl cyanide (1.16 mL) were added thereto. The mixture was refluxed for 4 hr. Saturated aqueous sodium hydrogencarbonate solution was added to the reaction mixture, and the mixture was extracted with ethyl acetate. The extract was washed with brine and the solvent was evaporated under reduced pressure. The residue was purified by silica gel chromatography to give 6-chloro-3-trifluoromethylpyridine-2-carbonitrile (401 mg) as a red oil.

(3) The above-mentioned compound (381 mg), the title compound (556 mg) of Reference Example 10 and diisopropylethylamine (0.96 mL) were dissolved in N-methyl-2-pyrrolidone (6 mL), and the mixture was stirred at room temperature for 18 hr. The reaction solution was added to saturated aqueous sodium hydrogencarbonate solution and extracted with ethyl acetate. The extract was dried and the solvent was evaporated under reduced pressure. The residue was purified by silica gel chromatography to give 3-[(2S,4S)-1-tert-butoxycarbonyl-4-(6-cyano-5-trifluoromethyl-2-pyridyl)amino-2-pyrrolidinylcarbonyl]-1,3-thiazolidine (509 mg) as a colorless transparent oil.

(4) The above-mentioned compound (481 mg) was dissolved in ethyl acetate (2.04 mL) and 4 mol/L hydrochloric acid-ethyl acetate (1.02 mL) was added thereto. The mixture was stirred at room temperature for 8 hr. The reaction solvent was evaporated under reduced pressure, and the obtained solid was washed with ethyl acetate to give the title compound (272 mg) as a white powder.

$^1$H-NMR(DMSO-$d_6$)δ1.71–1.95(1H,m), 2.77–2.98(1H, m), 2.99–3.27(3H,m), 3.48–3.99(3H,m), 4.40–4.80(4H,m), 6.96(1H,d,J=9.0 Hz), 7.93(1H,d,J=9.0 Hz), 8.40(1H,t,J=6.0 Hz), 9.55(1H,brs).

Example 77

Synthesis of 3-[(2S,4S)-4-(5,6-dicyano-2-pyridyl)amino-2-pyrrolidinylcarbonyl]-1,3-thiazolidine hydrochloride (1) 2-Chloropyridine-5-carbonitrile (7.01 g) was dissolved in acetonitrile (70 mL), and urea hydrogen peroxide addition compound (10 g) was added. Trifluoroacetic anhydride was added dropwise to the reaction mixture under ice-cooling and the mixture was stirred at room temperature for 18 hr. The reaction mixture was added to aqueous sodium thiosulfate solution and the mixture was extracted with chloroform. The extract was washed successively with saturated aqueous sodium hydrogencarbonate solution and brine and dried. The solvent was evaporated under reduced pressure and the residue was purified by silica gel chromatography to give 2-chloro-5-cyanopyridine 1-oxide (0.779 g) as a white solid.

(2) Using the above-mentioned compound (779 mg), and in the same manner as in Example 76 (2), 6-chloro-2,3-dicyanopyridine (198 mg) was obtained as a brown solid.

(3) Using the above-mentioned compound (196 mg) and the title compound (361 mg) of Reference Example 10, and in the same manner as in Example 76 (3), 3-[(2S,4S)-1-tert-butoxycarbonyl-4-(5,6-dicyano-2-pyridyl)amino-2-pyrrolidinylcarbonyl]-1,3-thiazolidine (338 mg) was obtained as a white solid.

(4) The above-mentioned compound (338 mg) was dissolved in ethyl acetate (1.58 mL) and 4 mol/L hydrochloric acid-ethyl acetate (0.79 mL) was added thereto. The mixture was stirred at room temperature for 6 hr. The precipitated solid was collected by filtration to give the title compound (178 mg) as a pale-yellow powder.

$^1$H-NMR(DMSO-$d_6$)δ1.71–1.98(1H,m), 2.80–3.00(1H, m), 3.00–3.24(3H,m), 3.49–4.00(3H,m), 4.39–4.90(3H,m), 6.94(1H,d,J=9.0 Hz), 7.97(1H,d,J=8.7 Hz), 8.70(1H,brs), 9.55(2H,brs).

Example 78

Synthesis of 3-[(2S,4S)-4-(3-cyanophenylmethyl)amino-2-pyrrolidinylcarbonyl]-1,3-thiazolidine dihydrochloride (1) Using the title compound (3.62 g) of-Reference Example 10 and 3-cyanobenzaldehyde (1.57 g), and in the same manner as in Example 63 (1), 3-[(2S,4S)-1-tert-butoxycarbonyl-4-(3-cyanophenylmethyl)amino-2-pyrrolidinylcarbonyl]-1,3-thiazolidine (2.01 g) was obtained.

(2) The above-mentioned compound (313 mg) was dissolved in ethyl acetate (1.50 mL) and 4 mol/L hydrochloric acid-ethyl acetate (0.94 mL) was added thereto. The mixture was stirred at room temperature for 18 hr. The precipitated solid was collected by filtration to give the title compound (217 mg) as a white powder.

$^1$H-NMR(DMSO-$d_6$)δ2.09–2.30(1H,m), 2.87–3.01(1H, m), 3.07(1H,t,J=6.3 Hz), 3.15(1H,t,J=6.0 Hz), 3.50–4.05 (5H,m), 4.27(2H,s), 4.40–4.78(3H,m), 7.67(1H,t,J=7.8 Hz), 7.84–8.00(2H,m), 8.10(1H,s), 10.28(3H,brs).

Example 79

Synthesis of 3-[(2S,4S)-4-(4-trifluoromethylphenylmethyl)amino-2-pyrrolidinylcarbonyl]-1,3-thiazolidine dihydrochloride (1) Using the title compound (1.81 g) of Reference Example 10 and 4-(trifluoromethyl)benzaldehyde (1.05 g), and in the same manner as in Example 63 (1), 3-[(2S,4S)-1-tert-butoxycarbonyl-4-(4-trifluoromethylphenylmethyl)amino-2-pyrrolidinylcarbonyl]-1,3-thiazolidine (1.69 g) was obtained.

(2) The above-mentioned compound (488 mg) was dissolved in ethyl acetate (2.12 mL) and 4 mol/L hydrochloric acid-ethyl acetate (1.33 mL) was added thereto. The mixture was stirred at room temperature for 18 hr and the precipitated solid was collected by filtration to give the title compound (375 mg) as a white powder.

$^1$H-NMR(DMSO-$d_6$)δ2.10–2.32(1H,m), 2.86–3.00(1H, m), 2.50(1H,t,J=1.8 Hz), 2.51(1H,t,J=1.8 Hz), 3.50–4.02 (5H,m), 4.32(2H,s), 4.41–4.80(3H,m), 7.78–7.92(4H,m), 10.35(3H,brs).

Example 80

Synthesis of 3-{(2S,4S)-4-[bis(4-cyanophenylmethyl)]amino-2-pyrrolidinylcarbonyl}-1,3-thiazolidine dihydrochloride (1) The title compound (0.904 g) of Reference Example 10, 4-cyanobenzyl bromide (1.29 g) and diisopropylethylamine (1.57 mL) were dissolved in N-methyl-2-pyrrolidone (9 mL), and the mixture was stirred at room temperature for 18 hr. The reaction mixture was added to saturated aqueous sodium hydrogencarbonate solution, and the mixture was extracted with ethyl acetate. The extract was dried and the solvent was evaporated under reduced pressure. The residue was purified by silica gel chromatography to give 3-{(2S,4S)-1-tert-butoxycarbonyl-4-[bis(4-cyanophenylmethyl)]amino-2-pyrrolidinylcarbonyl}-1,3-thiazolidine (1.27 g).

(2) The above-mentioned compound (1.13 g) was dissolved in ethyl acetate (4.24 mL) and 4 mol/L hydrochloric acid-ethyl acetate (2.65 mL) was added thereto. The mixture was stirred at room temperature for 18 hr and the precipitated solid was collected by filtration to give the title compound (444 mg) as a white powder.

$^1$H-NMR(DMSO-$d_6$)δ1.81–1.94(1H,m), 2.57–2.79(1H, m), 3.00–3.95(11H,m), 4.39–4.75(3H,m), 7.55(4H,d,J=8.1 Hz), 7.79(4H,d,J=8.1 Hz), 8.78(1H,brs), 10.19(1H,brs).

Example 81

Synthesis of 3-[(2S,4S)-4-(4-imidazolylmethyl)amino-2-pyrrolidinylcarbonyl]-1,3-thiazolidine trihydrochloride (1) Using the title compound (904 mg) of Reference Example 10 and 4-imidazolecarboxyaldehyde (288 mg), and in the same manner as in Example 63 (1), 3-[(2S,4S)-1-tert-butoxycarbonyl-4-(4-imidazolylmethyl)amino-2-pyrrolidinylcarbonyl]-1,3-thiazolidine (221 mg) was obtained.

(2) The above-mentioned compound (221 mg) was dissolved in ethyl acetate (1.16 mL) and 4 mol/L hydrochloric acid-ethyl acetate (0.72 mL) was added thereto. The mixture was stirred at room temperature for 18 hr. The precipitated solid was collected by filtration, and washed with ethanol to give the title compound (7.7 mg) as a white powder.

$^1$H-NMR(DMSO-$d_6$)δ2.04–2.26(1H,m), 2.88–4.10(8H, m), 4.25–4.80(5H,m), 7.82(1H,s), 9.07(1H,s).

Example 82

Synthesis of 3-{(2S,4S)-4-[N-benzyl-N-(5-cyano-2-pyridyl)amino]-2-pyrrolidinylcarbonyl}-1,3-thiazolidine hydrochloride (1) 3-[(2S,4S)-1-tert-Butoxycarbonyl-4-(5-cyano-2-pyridyl)amino-2-pyrrolidinylcarbonyl]-1,3-thiazolidine [product of Example 58(1)] (305 mg) was dissolved in DMF (10 mL), and potassium tert-butoxide (93 mg) was added under ice cooling. After stirring the mixture for 10 min, benzyl bromide (94 μl) was added, and the mixture was stirred at room temperature for 3 days. 10% citric acid solution was added to the reaction mixture, and the mixture was extracted with ethyl acetate. The extract was washed successively with saturated aqueous sodium hydrogencarbonate solution and brine, and dried. The solvent was evaporated under reduced pressure and the residue was purified by silica gel chromatography to give 3-{(2S,4S)-4-[N-benzyl-N-(5-cyano-2-pyridyl)amino]-1-tert-butoxycarbonyl-2-pyrrolidinylcarbonyl}-1,3-thiazolidine (202 mg) as a pale-yellow solid.

(2) The above-mentioned compound (196 mg) was dissolved in ethyl acetate (2 ml) and 4 mol/L hydrochloric acid-ethyl acetate (0.5 mL) was added thereto. The mixture was stirred at room temperature for 17 hr. The precipitated solid was collected by filtration to give the title compound (112 mg) as a pale-yellow powder.

$^1$H-NMR(DMSO-$d_6$)δ1.91–1.99(1H,m), 2.69–2.76(1H, m), 3.00–3.11(2H,m), 3.28–3.34(1H,m), 3.41–3.48(1H,m), 3.58–3.90(2H,m), 4.41–4.47(1H,m), 4.58–4.81(4H,m), 5.43–5.48(1H,m), 6.65(1H,d,J=9.0 Hz), 7.17–7.38(5H,m), 7.88(1H,dd,J=9.0,2.1 Hz), 8.54(1H,d,J=2.1 Hz), 8.84(1H, brs), 10.21(1H,brs).

Example 83

Synthesis of 3-[(2S,4S)-4-(1-indolyl)-2-pyrrolidinylcarbonyl]-1,3-thiazolidine hydrochloride (1) The title compound (950 mg) of Reference Example 13 and thiazolidine (0.27 mL) were dissolved in DMF (20 mL), and HOBT (666 mg) and EDC hydrochloride (666 mg) were added successively. The mixture was stirred at room temperature for 4 hr. The reaction mixture was added to saturated aqueous sodium hydrogencarbonate solution, and extracted with ethyl acetate. The extract was washed with brine and dried. The solvent was evaporated under reduced pressure and the residue was purified by silica gel chromatography to give 3-[(2S,4S)-1-tert-butoxycarbonyl-4-(1-indolyl)-2-pyrrolidinylcarbonyl]-1,3-thiazolidine (978 mg) as a white solid.

(2) Using the above-mentioned compound (665 mg), and in the same manner as in Example 68 (2), the title compound (486 mg) was obtained as a red powder.

$^1$H-NMR(DMSO-$d_6$)δ2.14–2.28(1H,m), 2.98–3.18(4H, m), 3.4–3.97(3H,m), 4.43–4.87(3H,m), 5.38–5.55(1H,m), 6.55(1H,d,J=3.3 Hz), 7.07(1H,t,J=7.1 Hz), 7.20(1H,d,J=7.1 Hz), 7.48–7.63(3H,m), 9.25(1H,brs), 10.45(1H,brs).

Example 84

Synthesis of 3-[(2S,4S)-4-(1-indolinyl)-2-pyrrolidinylcarbonyl]-1,3-thiazolidine dihydrochloride (1) Using the title compound (601 mg) of Reference Example 12 and indoline (0.27 mL), and in the same manner as in Example 70 (1), 3-[(2S,4S)-1-tert-butoxycarbonyl-4-(1-indolinyl)-2-pyrrolidinylcarbonyl]-1,3-thiazolidine (460 mg) was obtained as a white solid.

(2) Using the above-mentioned compound (436 mg), and in the same manner as in Example 70 (2), the title compound (373 mg) was obtained as a white powder.

$^1$H-NMR(DMSO-$d_6$)δ1.83–1.97(1H,m), 2.62–2.77(1H, m), 2.88(2H,t,J=8.2 Hz), 3.04(1H,t,J=7.0 Hz), 3.12(1H,t,J=6.2 Hz), 3.20–3.95(6H,m), 4.40–4.78(4H,m), 6.55–6.68(2H, m), 6.98–7.09(2H,m), 8.84(1H,brs), 10.31(1H,brs).

Example 85

Synthesis of 1-[(2S,4S)-4-(1-indolinyl)-2-pyrrolidinylcarbonyl]pyrrolidine dihydrochloride (1) Using the title compound (565 mg) of Reference Example 14 and indoline (0.27 mL), and in the same manner as in Example 70 (1), 1-[(2S,4S)-1-tert-butoxycarbonyl-4-(1-indolinyl)-2-pyrrolidinylcarbonyl]pyrrolidine (653 mg) was obtained as a white solid.

(2) Using the above-mentioned compound (648 mg), and in the same manner as in Example 70 (2), the title compound (491 mg) was obtained as a white powder.

$^1$H-NMR(DMSO-$d_6$)δ1.75–1.97(5H,m), 2.60–2.72(1H, m), 2.88(2H,t,J=8.2 Hz), 3.218–3.60(8H,m), 4.40–4.55(2H, m), 6.56–6.67(2H,m), 6.98–7.09(2H,m), 8.75(1H,brs), 10.41(1H,brs).

Example 86

Synthesis of 3-[(2S,4S)-4-(5-nitro-1-indolinyl)-2-pyrrolidinylcarbonyl]-1,3-thiazolidine hydrochloride (1) Using the title compound (450 mg) of Reference Example 12 and 5-nitroindoline (295 mg), and in the same manner as in Example 70 (1), 3-[(2S,4S)-1-tert-butoxycarbonyl-4-(5-nitro-1-indolinyl)-2-pyrrolidinylcarbonyl]-1,3-thiazolidine (153 mg) was obtained as an oil.

(2) Using the above-mentioned compound (153 mg), and in the same manner as in Example 70 (2), the title compound (116 mg) was obtained as a yellow powder.

$^1$H-NMR(DMSO-$d_6$)δ1.92–2.06(1H,m), 2.67–2.80(1H, m), 3.00–3.17(4H,m), 3.27–3.94(6H,m), 4.42–4.78(4H,m), 6.62(1H,d,J=8.9 Hz), 7.87(1H,d,J=2.3 Hz), 8.04(1H,dd,J=8.9,2.3 Hz), 9.1(1H,brs), 10.2(1H,brs).

Example 87

Synthesis of 3-[(2S,4S)-4-(6-nitro-1-indolinyl)-2-pyrrolidinylcarbonyl]-1,3-thiazolidine dihydrochloride (1) Using the title compound (450 mg) of Reference Example 12 and 6-nitroindoline (296 mg), and in the same manner as in Example 70 (1), 3-[(2S,4S)-1-tert-butoxycarbonyl-4-(6-nitro-1-indolinyl)-2-pyrrolidinylcarbonyl]-1,3-thiazolidine (188 mg) was obtained as an oil.

(2) Using the above-mentioned compound (188 mg), and in the same manner as in Example 70 (2), the title compound (80 mg) was obtained as a brown-reddish powder.

$^1$H-NMR(DMSO-$d_6$)δ1.84–2.00(1H,m), 2.64–2.77(1H, m), 3.00–3.17(4H,m), 3.22–3.92(6H,m), 4.41–4.77(4H,m), 7.22–7.32(2H,m), 7.51(1H,dd,J=7.9,1.9 Hz), 8.94(1H,brs), 10.12(1H,brs).

Example 88

Synthesis of 3-[(2S,4S)-4-(5-methoxy-1-indolinyl)-2-pyrrolidinylcarbonyl]-1,3-thiazolidine dihydrochloride (1) Using the title compound (751 mg) of Reference Example 12 and 5-methoxyindoline (410 mg), and in the same manner as in Example 70 (1), 3-[(2S,4S)-1-tert-butoxycarbonyl-4-(5-methoxy-1-indolinyl)-2-pyrrolidinylcarbonyl]-1,3-thiazolidine (1010 mg) was obtained as a white solid.

(2) Using the above-mentioned compound (326 mg), and in the same manner as in Example 70 (2), the title compound (262 mg) was obtained as a white powder.

$^1$H-NMR(DMSO-$d_6$)δ1.80–1.95(1H,m), 2.62–2.75(1H, m), 2.86(2H,t,J=7.9 Hz), 3.04(1H,t,J=7.0 Hz), 3.12(1H,t,J=6.2 Hz), 3.17–3.52(4H,m), 3.65(3H,s), 3.66–4.08(6H,m), 4.28–4.77(4H,m), 6.54(1H,d,J=8.5 Hz), 6.63(1H,dd,J=8.5, 2.4 Hz), 6.75(1H,d,J=2.4 Hz), 8.83(1H,brs), 10.40(1H,brs).

Example 89

Synthesis of 3-[(2S,4S)-4-(5-hydroxy-1-indolinyl)-2-pyrrolidinylcarbonyl]-1,3-thiazolidine dihydrochloride (1) Using the title compound (872 mg) of Reference Example 12 and 5-hydroxyindoline (390 mg), and in the same manner as in Example 70 (1), 3-[(2S,4S)-1-tert-butoxycarbonyl-4-(5-hydroxy-1-indolinyl)-2-pyrrolidinylcarbonyl]-1,3-thiazolidine (538 mg) was obtained as a pale-brown solid.

(2) Using the above-mentioned compound (163 mg), and in the same manner as in Example 70 (2), the title compound (101 mg) was obtained as a white powder.

$^1$H-NMR(DMSO-$d_6$)δ1.85–2.00(1H,m), 2.63–2.78(1H, m), 2.88(2H,t,J=7.7 Hz), 3.04(1H,t,J=6.6 Hz), 3.12(1H,t,J=6.2 Hz), 3.24–3.95(6H,m), 4.27–4.76(4H,m), 6.51–6.68(3H, m), 8.96(1H,brs), 10.43(1H,brs).

Example 90

Synthesis of 3-[(2S,4S)-4-(5-acetoxy-1-indolinyl)-2-pyrrolidinylcarbonyl]-1,3-thiazolidine dihydrochloride (1) Using 3-[(2S,4S)-1-tert-butoxycarbonyl-4-(5-hydroxy-1-indolinyl)-2-pyrrolidinylcarbonyl]-1,3-thiazolidine [product of Example 89 (1), 174 mg] and acetyl chloride (50 μL), and in the same manner as in Example 50 (1), 3-[(2S,4S)-4-(5-acetoxy-1-indolinyl)-1-tert-butoxycarbonyl-2-pyrrolidinylcarbonyl]-1,3-thiazolidine (136 mg) was obtained as an oil.

(2) Using the above-mentioned compound (136 mg), and in the same manner as in Example 70 (2), the title compound (77 mg) was obtained as a pale-brown powder.

$^1$H-NMR(DMSO-$d_6$)δ1.83–1.96(1H,m), 2.20(3H,s), 2.63–2.77(1H,m), 2.89(2H,t,J=8.1 Hz), 3.05(1H,t,J=6.8 Hz), 3.12(1H,t,J=6.2 Hz), 3.18–3.53(4H,m), 3.61–3.93(2H, m), 4.36–4.77(4H,m), 6.56(1H,d,J=8.4 Hz), 6.76(1H,dd,J=8.4,2.3 Hz), 6.83(1H,d,J=2.3 Hz), 8.91(1H,brs), 10.19(1H, brs).

Example 91

Synthesis of 3-[(2S,4S)-4-(5-benzoyloxy-1-indolinyl)-2-pyrrolidinylcarbonyl]-1,3-thiazolidine dihydrochloride (1) Using the product (199 mg) of Example 89 (1) and benzoyl chloride (83 μL), and in the same manner as in Example 50 (1), 3-[(2S,4S)-4-(5-benzoyloxy-1-indolinyl)-1-tert-butoxycarbonyl-2-pyrrolidinylcarbonyl]-1,3-thiazolidine (173 mg) was obtained as a pale-brown solid.

(2) Using the above-mentioned compound (173 mg), and in the same manner as in Example 7.0 (2), the title compound (116 mg) was obtained as a pale-brown powder.

$^1$H-NMR(DMSO-$d_6$)δ1.84–1.98(1H,m), 2.66–2.78(1H, m), 2.93(2H,t,J=8.3 Hz), 3.05(1H,t,J=6.7 Hz), 3.13(1H,t,J=6.2 Hz), 3.23–3.56(4H,m), 3.6–3.95(2H,m), 4.42–4.78(4H, m), 6.62(1H,d,J=8.4 Hz), 6.93(1H,dd,J=8.4,2.2 Hz), 6.99 (1H,d,J=2.2 Hz), 7.60(2H,t,J=7.5 Hz), 7.74(1H,t,J=7.5 Hz), 8.10(2H,d,J=7.5 Hz), 8.93(1H,brs), 10.37(1H,brs).

Example 92

Synthesis of 3-[(2S,4S)-4-(5-fluoro-1-indolinyl)-2-pyrrolidinylcarbonyl]-1,3-thiazolidine dihydrochloride (1) Using the title compound (496 mg) of Reference Example 12 and 5-fluoroindoline (200 mg), and in the same manner as in Example 70 (1), 3-[(2S,4S)-1-tert-butoxycarbonyl-4-(5-fluoro-1-indolinyl)-2-pyrrolidinylcarbonyl]-1,3-thiazolidine (492 mg) was obtained as a pale-brown solid.

(2) Using the above-mentioned compound (487 mg), and in the same manner as in Example 70 (2), the title compound (357 mg) was obtained as a white powder.

$^1$H-NMR(DMSO-$d_6$)δ1.80–1.95(1H,m), 2.62–2.75(1H, m), 2.88(2H,t,J=8.2 Hz), 3.04(1H,t,J=7.0 Hz), 3.11(1H,t,J=6.2 Hz), 3.18–3.52(4H,m), 3.60–3.94(2H,m), 4.35–4.78(4H, m), 6.55(1H,dd,J=8.8,4.3 Hz), 6.85(1H,td,J=8.8,2.6 Hz), 6.94(1H,dd,J=8.5,2.6 Hz), 8.90(1H,brs), 10.44(1H,brs).

Example 93

Synthesis of 3-[(2S,4S)-4-(5-chloro-1-indolinyl)-2-pyrrolidinylcarbonyl]-1,3-thiazolidine hydrochloride (1) Using the title compound (665 mg) of Reference Example 12 and 5-chloroindoline (340 mg), and in the same manner as in Example 70 (1), 3-[(2S,4S)-1-tert-butoxycarbonyl-4-(5-chloro-1-indolinyl)-2-pyrrolidinylcarbonyl]-1,3-thiazolidine (393 mg) was obtained as a white solid.

(2) Using the above-mentioned compound (389 mg), and in the same manner as in Example 70 (2), the title compound (242 mg) was obtained as a white powder.

$^1$H-NMR(DMSO-$d_6$)δ1.81–1.95(1H,m), 2.62–2.74(1H, m), 2.90(2H,t,J=8.3 Hz), 3.04(1H,t,J=7.1 Hz), 3.12(1H,t,J=6.2 Hz), 3.18–3.52(4H,m), 3.60–3.94(2H,m), 4.38–4.77(4H, m), 6.57(1H,d,J=8.3 Hz), 7.03–7.11(2H,m), 8.86(1H,brs), 10.38(1H,brs).

Example 94

Synthesis of 3-[(2S,4S)-4-(5-bromo-1-indolinyl)-2-pyrrolidinylcarbonyl]-1,3-thiazolidine hydrochloride (1) Using the title compound (0.901 g) of Reference Example 12 and 5-bromoindoline (0.713 g), and in the same manner as in Example 70 (1), 3-[(2S,4S)-4-(5-bromo-1-indolinyl)-1-tert-butoxycarbonyl-2-pyrrolidinylcarbonyl]-1,3-thiazolidine (1.31 g) was obtained as a white solid.

(2) Using the above-mentioned compound (340 mg), and in the same manner as in Example 70 (2), the title compound (251 mg) was obtained as a pale-red powder.

$^1$H-NMR(DMSO-$d_6$),δ1.82–1.96(1H,m), 2.62–2.74(1H,m), 2.91(2H,t,J=8.3 Hz), 3.04(1H,t,J=7.0 Hz), 3.12(1H,t,J=6.2 Hz), 3.18–3.54(4H,m), 3.62–3.93(2H,m), 4.37–4.77(4H,m), 6.53(1H,d,J=8.1 Hz), 7.15–7.24(2H,m), 8.91(1H,brs), 10.27(1H,brs).

Example 95

Synthesis of 3-[(2S,4S)-4-(1,2,3,4-tetrahydro-1-quinolyl)-2-pyrrolidinylcarbonyl]-1,3-thiazolidine hydrochloride (1) Using the title compound (450 mg) of Reference Example 12 and 1,2,3,4-tetrahydroquinoline (0.23 mL), and in the same manner as in Example 70 (1), 3-[(2S,4S)-1-tert-butoxycarbonyl-4-(1,2,3,4-tetrahydro-1-quinolyl)-2-pyrrolidinylcarbonyl]-1,3-thiazolidine (100 mg) was obtained as an oil.

(2) Using the above-mentioned compound (100 mg), and in the same manner as in Example 70 (2), the title compound (60 mg) was obtained as a pale-brown-reddish powder.

$^1$H-NMR(DMSO-$d_6$)δ1.76–1.97(3H,m), 2.59–2.73(3H,m), 3.02–3.5(6H,m), 3.62–3.94(2H,m), 4.42–4.86(4H,m), 6.57(1H,d,J=7.2 Hz), 6.80(1H,d,J=8.3 Hz), 6.92(1H,d,J=7.2 Hz), 6.97–7.07(1H,m), 8.84(1H,brs), 10.04(1H,brs).

Example 96

Synthesis of 3-[(2S,4S)-4-(2-isoindolinyl)-2-pyrrolidinylcarbonyl]-1,3-thiazolidine 2 trifluoroacetate (1) The title compound (1.49 g) of Reference Example 10 was dissolved in DMF (50 mL), and potassium carbonate (2.04 g) and α,α'-dibromo-o-xylene (1.37 g) were added thereto. The mixture was stirred at room temperature for 18 hr. Water was added to the reaction mixture and the mixture was extracted with chloroform. The extract was washed with brine and dried. The solvent was evaporated under reduced pressure. The residue was purified by silica gel chromatography to give 3-[(2S,4S)-1-tert-butoxycarbonyl-4-(2-isoindolinyl)-2-pyrrolidinylcarbonyl]-1,3-thiazolidine (1.26 g) as a pale-brown solid.

(2) Using the above-mentioned compound (910 mg), and in the same manner as in Example 1, the title compound (730 mg) was obtained as a brown powder.

$^1$H-NMR(DMSO-$d_6$)δ2.05–2.14(1H,m), 2.88–2.96(1H,m), 3.05–3.17(2H,m), 3.42–4.02(5H,m), 4.44–4.75(7H,m), 7.31–7.37(4H,m).

Example 97

Synthesis of 3-[(2S,4S)-4-(N-methylanilino)-2-pyrrolidinylcarbonyl]-1,3-thiazolidine dihydrochloride (1) Using the title compound (450 mg) of Reference Example 12 and N-methylaniline (0.22 mL), and in the same manner as in Example 70 (1), 3-[(2S,4S)-1-tert-butoxycarbonyl-4-(N-methylanilino)-2-pyrrolidinylcarbonyl]-1,3-thiazolidine (274 mg) was obtained as a white solid.

(2) Using the above-mentioned compound (216 mg), and in the same manner as in Example 70 (2), the title compound (149 mg) was obtained as a white powder.

$^1$H-NMR(DMSO-$d_6$)δ1.83–1.98(1H,m), 2.56–2.69(1H,m), 2.82(3H,s), 3.05(1H,t,J=6.9 Hz), 3.11(1H,t,J=6.2 Hz), 3.20–3.32(1H,m), 3.36–3.50(1,m), 3.62–4.0(4H,m), 4.43–4.82(4H,m), 6.85(1H,t,J=7.5 Hz), 7.02(1H,d,J=7.5 Hz), 7.27(1H,t,J=7.5 Hz), 8.89(1H,brs), 10.44(1H,brs).

Example 98

Synthesis of 3-{(2S,4S)-4-[N-(5-cyano-2-pyridyl)-N-methylamino]-2-pyrrolidinylcarbonyl}-1,3-thiazolidine hydrochloride (1) Using the product (313 mg) of Example 58 (1) and methyl iodide 53 μL, and in the same manner as in Example 82 (1), 3-{(2S,4S)-1-tert-butoxycarbonyl-4-[N-(5-cyano-2-pyridyl)-N-methylamino]-2-pyrrolidinylcarbonyl}-1,3-thiazolidine (200 mg) was obtained as a white powder.

(2) Using the above-mentioned compound (198 mg), and in the same manner as in Example 5 (2), the title compound (165 mg) was obtained as a white powder.

$^1$H-NMR(DMSO-$d_6$)δ1.91–1.99(1H,m), 2.62–2.70(1H,m), 2.98(3H,s), 3.00–3.13(2H,m), 3.30–3.34(2H,m), 3.65–3.93(2H,m), 4.45–4.77(3H,m), 5.51–5.57(1H,m), 6.84 (1H,d,J=9.0 Hz), 7.94(1H,dd,J=9.0,2.4 Hz), 8.52(1H,d,J=2.4 Hz), 8.93(1H,brs), 10.22(1H,brs).

Example 99

Synthesis of 3-{(2S,4S)-4-[N-(3-cyanophenylmethyl)-N-methylamino]-2-pyrrolidinylcarbonyl}-1,3-thiazolidine dihydrochloride (1) Using 3-[(2S,4S)-1-tert-butoxycarbonyl-4-(3-cyanophenylmethyl)amino-2-pyrrolidinylcarbonyl]-1,3-thiazolidine [product of Example 78 (1), 313 mg], and in the same manner as in Example 64 (1), 3-{(2S,4S)-1-tert-butoxycarbonyl-4-[N-(3-cyanophenylmethyl)-N-methylamino]-2-pyrrolidinylcarbonyl}-1,3-thiazolidine (598 mg) was obtained as an oil.

(2) The above-mentioned compound (571 mg) was dissolved in ethyl acetate (2.65 mL) and 4 mol/L hydrochloric acid-ethyl acetate (1.66 mL) was added thereto. The mixture was stirred at room temperature for 18 hr. The precipitated solid was collected by filtration to give the title compound (377 mg) as a white powder.

$^1$H-NMR(DMSO-$d_6$)δ2.20–2.42(1H,m), 2.57(3H,brs), 2.80–3.20(3H,m), 3.55–4.10(5H,m), 4.20–4.85(5H,m), 7.68 (1H,t,J=7.8 Hz), 7.88–8.05(2H,m), 8.14(1H,brs), 9.12(1H,brs), 10.70(1H,brs).

Example 100

Synthesis of 3-{(2S,4S)-4-[N-(4-cyanophenylmethyl)-N-(2-propyl)amino]-2-pyrrolidinylcarbonyl}-1,3-thiazolidine dihydrochloride (1) Using the product (833 mg) of Example 63 (1) and acetone, and in the same manner as in Example 70 (1), 3-{(2S,4S)-1-tert-butoxycarbonyl-4-[N-(4- cyanophenylmethyl)-N-(2-propyl)amino]-2-pyrrolidinylcarbonyl}-1,3-thiazolidine (818 mg) was obtained.

(2) The above-mentioned compound (792 mg) was dissolved in ethyl acetate (3.47 mL) and 4 mol/L hydrochloric acid-ethyl acetate (2.16 mL) was added thereto. The mixture was stirred at room temperature for 18 hr and the precipitated solid was collected by filtration to give the title compound (637 mg) as a white powder.

$^1$H-NMR(DMSO-$d_6$)δ0.90–1.60(6H,m), 1.95–2.45(1H, m), 2.65–3.20(3H,m), 3.40–4.90(11H,m), 7.50–8.30(4H,m).

Example 101

Synthesis of 3-{(2S,4S)-4-[N-butyl-N-(4-cyanophenylmethyl)amino]-2-pyrrolidinylcarbonyl}-1,3-thiazolidine dihydrochloride (1) Using the product (833 mg) of Example 63 (1) and n-butyraldehyde (216 mg), and in the same manner as in Example 70 (1), 3-{(2S,4S)-1-tert-butoxycarbonyl-4-[N-butyl-N-(4-cyanophenylmethyl)amino]-2-pyrrolidinylcarbonyl}-1,3-thiazolidine (837 mg) was obtained.

(2) The above-mentioned compound (830 mg) was dissolved in ethyl acetate (3.51 mL) and 4 mol/L hydrochloric acid-ethyl acetate (2.20 mL) was added thereto. The mixture was stirred at room temperature for 18 hr and the precipitated solid was collected by filtration to give the title compound (607 mg) as a pale-yellow powder.

$^1$H-NMR(DMSO-$d_6$)δ0.80(3H,t,J=7.2 Hz), 1.18(2H, quint,J=6.9 Hz), 1.30–1.90(2H,m), 2.10–2.50(1H,m), 2.60–3.24(5H,m), 3.54–4.87(9H,m), 7.60–8.20(4H,m).

Example 102

Synthesis of 3-{(2S,4S)-4-[N-(4-cyanophenylmethyl)-N-(2-hydroxyethyl)amino]-2-pyrrolidinylcarbonyl}-1,3-thiazolidine dihydrochloride (1) The product (1.67 g) of Example 63 (1) was dissolved in N-methyl-2-pyrrolidone (12 mL), and 2-bromoethanol (1.42 mL) and diisopropylethylamine (2.09 mL) were added thereto. The mixture was stirred at 80° C. for 2 days. The reaction mixture was added to saturated aqueous sodium hydrogencarbonate solution and the mixture was extracted with ethyl acetate. The extract was dried and the solvent was evaporated under reduced pressure. The residue was purified by silica gel chromatography to give 3-{(2S,4S)-1-tert-butoxycarbonyl-4-[N-(4-cyanophenylmethyl)-N-(2-hydroxyethyl)amino]-2-pyrrolidinylcarbonyl}-1,3-thiazolidine (0.480 g).

(2) The above-mentioned compound (480 mg) was dissolved in ethyl acetate (2.08 mL) and 4 mol/L hydrochloric acid-ethyl acetate (1.04 mL) was added thereto. The mixture was stirred at room temperature for 18 hr and the precipitated solid was collected by filtration to give the title compound (351 mg) as a brown powder.

$^1$H-NMR(DMSO-$d_6$)δ1.85–1.97(1H,m), 2.02–2.33(2H, m), 2.70–4.80(14H,m), 7.60–8.00(4H,m), 9.00(1H,brs), 10.50(1H,brs).

Example 103

Synthesis of 3-{(2S,4S)-4-[N-(carboxymethyl)-N-(5-cyano-2-pyridyl)amino]-2-pyrrolidinylcarbonyl]-1,3-thiazolidine trifluoroacetate (1) Using the product (461 mg) of Example 58 (1) and tert-butyl bromoacetate (202 μL), and in the same manner as in Example 82 (1), 3-{(2S,4S)-1-tert-butoxycarbonyl-4-[N-(tert-butoxycarbonylmethyl)-N-(5-cyano-2-pyridyl)amino]-2-pyrrolidinylcarbonyl}-1,3-thiazolidine (344 mg) was obtained as a pale-yellow powder.

(2) Using the above-mentioned compound (340 mg), and by the synthesis in the same manner as in Example 1 and purification by HPLC, the title compound (118 mg) was obtained as a white solid.

$^1$H-NMR(500 MHz,DMSO-$d_6$)δ1.93–1.98(1H,m), 2.66–2.69(1H,m), 3.04–3.12(2H,m), 3.27–3.31(1H,m), 3.40–3.45(1H,m), 3.62–3.87(2H,m), 4.32(2H,s), 4.44–4.71 (3H,m), 5.23(1H,m), 6.81(1H,d,J=7.3 Hz), 7.95(1H,dd,J=7.3,2.3 Hz), 8.51(1H,d,J=2.3 Hz).

Example 104

Synthesis of 3-{(2S,4S)-4-[N-(4-cyanophenylmethyl)-N-(ethoxycarbonylmethyl)amino]-2-pyrrolidinylcarbonyl}-1,3-thiazolidine dihydrochloride (1) The product (0.833 g) of Example 63 (1) was dissolved in N-methyl-2-pyrrolidone (6 mL), and ethyl bromoacetate (0.333 mL) and diisopropylethylamine (1.05 mL) were added thereto. The mixture was stirred at room temperature for 18 hr. The reaction mixture was added to saturated aqueous sodium hydrogencarbonate solution, and the mixture was extracted with ethyl acetate. The extract was dried, and the solvent was evaporated under reduced pressure. The residue was purified by silica gel chromatography to give 3-{(2S,4S)-1-tert-butoxycarbonyl-4-[N-(4-cyanophenylmethyl)-N-(ethoxycarbonylmethyl)amino]-2-pyrrolidinylcarbonyl}-1,3-thiazolidine (1.01 g) as an oil.

(2) The above-mentioned compound (976 mg) was dissolved in ethyl acetate (3.88 mL) and 4 mol/L hydrochloric acid-ethyl acetate (2.43 mL) was added thereto. The mixture was stirred at room temperature for 18 hr and the precipitated solid was collected by filtration to give the title compound (630 mg) as a white powder.

$^1$H-NMR(DMSO-$d_6$)δ1.18-(3H,t,J=7.1 Hz), 1.67–1.90 (1H,m), 2.56–2.75(1H,m), 2.94–3.22(3H,m), 3.25–4.00(8H, m), 4.07(2H,q,J=7.1 Hz), 4.34–4.78(3H,m), 7.54(2H,d,J=8.2 Hz), 7.81(2H,d,J=8.2 Hz), 8.80(1H,brs), 10.40(1H,brs).

Example 105

Synthesis of 3-{(2S,4S)-4-[N-(4-cyanophenylmethyl)-N-(isopropoxycarbonylmethyl)amino]-2-pyrrolidinylcarbonyl}-1,3-thiazolidine dihydrochloride (1) Using the product (0.833 g) of Example 63 (1) and isopropyl bromoacetate (0.259 mL), and in the same manner as in Example 104 (1), 3-{(2S,4S)-1-tert-butoxycarbonyl-4-[N-(4-cyanophenylmethyl)-N-(isopropoxycarbonylmethyl)amino]-2-pyrrolidinylcarbonyl}-1,3-thiazolidine (0.967 g) was obtained as an oil.

(2) The above-mentioned compound (966 mg) was dissolved in ethyl acetate (3.74 mL) and 4 mol/L hydrochloric acid-ethyl acetate (1.87 mL) was added thereto. The mixture was stirred at room temperature for 8 hr. The precipitated solid was collected by filtration to give the title compound (641 mg) as a white powder.

$^1$H-NMR(DMSO-$d_6$)δ1.18(6H,d,J=6.0 Hz), 1.65–1.84 (1H,m), 2.55–2.74(1H,m), 2.95–3.16(3H,m), 3.22–3.47(3H, m), 3.50–3.98(5H,m), 4.39–4.80(3H,m), 4.91(1H,quint,J=6.3 Hz), 7.53(2H,d,J=8.1 Hz), 7.81(2H,d,J=8.4 Hz), 8.70 (1H,brs), 10.25(1H,brs).

Example 106

Synthesis of 3-{(2S,4S)-4-[N-(benzyloxycarbonylmethyl)-N-(4-cyanophenylmethyl)amino}-2-pyrrolidinylcarbonyl]-1,3-thiazolidine dihydrochloride (1) Using the product (0.833 g) of Example 63 (1) and benzyl bromoacetate (0.317 mL), and in the same manner as in Example 104 (1), 3-{(2S,4S)-4-[N-(benzyloxycarbonylmethyl)-N-(4-cyanophenylmethyl)amino]-1-tert-butoxycarbonyl-2-pyrrolidinylcarbonyl}-1,3-thiazolidine (0.992 g) was obtained as an oil.

(2) The above-mentioned compound (992 mg) was dissolved in ethyl acetate (3.51 mL) and 4 mol/L hydrochloric acid-ethyl acetate (1.76 mL) was added thereto. The mixture was stirred at room temperature for 8 hr and the precipitated solid was collected by filtration to give the title compound (680 mg) as a white powder.

$^1$H-NMR(DMSO-$d_6$)δ1.67–1.85(1H,m), 2.53–2.71(1H, m), 2.94–3.20(3H,m), 3.20–4.00(8H,m), 4.37–4.80(3H,m), 5.11(2H,s), 7.29–7.45(5H,m), 7.50(2H,d,J=8.1 Hz), 7.78 (2H,d,J=8.4 Hz), 8.75(1H,brs), 10.15(1H,brs).

Example 107

Synthesis of 3-{(2S,4S)-4-[N-(carboxymethyl)-N-(4-cyanophenylmethyl)amino]-2-pyrrolidinylcarbonyl}-1,3-thiazolidine 2 trifluoroacetate (1) Using the product (0.833 g) of Example 63 (1) and tert-butyl bromoacetate (0.443 mL), and in the same manner as in Example 104 (1), 3-{(2S,4S)-1-tert-butoxycarbonyl-4-[N-(tert-butoxycarbonylmethyl)-N-(4-cyanophenylmethyl) amino]-2-pyrrolidinylcarbonyl}-1,3-thiazolidine (0.990 g) was obtained.

(2) The above-mentioned compound (881 mg) was dissolved in ethyl acetate (3.06 mL) and 4 mol/L hydrochloric acid-ethyl acetate (6.91 mL) was added thereto. The mixture was stirred at room temperature for 3 days. The precipitated solid was purified by HPLC to give the title compound (141 mg) as a white powder.

$^1$H-NMR(DMSO-$d_6$)δ1.65–1.84(1H,m), 2.57–2.74(1H, m), 2.96–3.19(3H,m), 3.22–4.00(8H,m), 4.37–4.72(3H,m), 7.53(2H,d,J=8.4 Hz), 7.81(2H,d,J=8.1 Hz), 8.77(1H,brs), 9.63(1H,brs).

Example 108

Synthesis of 3-{(2S,4S)-4-[N-(4-carbamoylphenylmethyl)-N-(carboxymethyl)amino]-2-pyrrolidinylcarbonyl}-1,3-thiazolidine 2 trifluoroacetate The title compound (41 mg) was obtained as a pale-yellow powder by purification of Example 107 (2) by HPLC.

$^1$H-NMR(DMSO-$d_6$)δ1.67–1.90(1H,m), 2.56–2.79(1H, m), 2.90–4.20(11H,m), 4.36–4.74(3H,m), 7.34(1H,brs), 7.56(2H,d,J=8.1 Hz), 7.84(2H,d,J=8.4 Hz), 7.96(1H,brs), 8.80(1H,brs), 9.60(1H,brs).

Example 109

Synthesis of 3-{(2S,4S)-4-[N-(carbamoylmethyl)-N-(4-cyanophenylmethyl)amino]-2-pyrrolidinylcarbonyl}-1,3-thiazolidine dihydrochloride (1) Using the product (0.833 g) of Example 63 (1) and 2-bromoacetamide (0.276 mL), and in the same manner as in Example 104 (1), 3-{(2S,4S)-1-tert-butoxycarbonyl-4-[N-(carbamoylmethyl)-N-(4-cyanophenylmethyl)amino]-2-pyrrolidinylcarbonyl}-1,3-thiazolidine (0.599 g) was obtained.

(2) The above-mentioned compound (599 mg) was dissolved in ethyl acetate (2.53 mL) and 4 mol/L hydrochloric acid-ethyl acetate (1.27 mL) was added thereto. The mixture was stirred at room temperature for 6 hr and the precipitated solid was collected by filtration to give the title compound (416 mg) as a white powder.

$^1$H-NMR(DMSO-$d_6$)δ1.76–1.99(1H,m), 2.62–2.83(1H, m), 2.90–4.10(11H,m), 4.25–4.80(3H,m), 7.22(1H,brs), 7.44(1H,brs), 7.64(2H,d,J=8.1 Hz), 7.84(2H,d,J=8.4 Hz), 8.82(1H,brs), 10.35(1H,brs).

Example 110

Synthesis of 3-((2S,4S)-4-benzoylamino-2-pyrrolidinylcarbonyl)-1,3-thiazolidine (1) Using the title compound (499 mg) of Reference Example 10 and benzoyl chloride (202 μL), and in the same manner as in Reference Example 7, 3-((2S,4S)-4-benzoylamino-1-tert-butoxycarbonyl-2-pyrrolidinylcarbonyl)-1,3-thiazolidine (652 mg) was obtained as a white powder.

(2) Using the above-mentioned compound (648 mg), and in the same manner as in Example 5 (2), the title compound (250 mg) was obtained as a white powder.

$^1$H-NMR(500 MHz,DMSO-$d_6$)δ1.76–1.81(1H,m), 2.33–2.39(1H,m), 2.91–3.09(5H,m), 3.63–3.95(3H,m), 4.34–4.70(3H,m), 7.44–7.53(3H,m), 7.80–7.82(2H,m), 8.38 (1H,brs).

Example 111

Synthesis of 3-[(2S,4S)-4-(4-cyanobenzoyl)amino-2-pyrrolidinylcarbonyl]-1,3-thiazolidine hydrochloride (1) Using the title compound (543 mg) of Reference Example 10 and 4-cyanobenzoyl chloride (313 mg), and in the same manner as in Reference Example 7, 3-[(2S,4S)-1-tert-butoxycarbonyl-4-(4-cyanobenzoyl)amino-2-pyrrolidinylcarbonyl]-1,3-thiazolidine (804 mg) was obtained as a white powder.

(2) Using the above-mentioned compound (798 mg), and in the same manner as in Example 5 (2), the title compound (513 mg) was obtained as a white powder.

$^1$H-NMR(500 MHz,DMSO-$d_6$)δ2.01–2.06(1H,m), 2.81–2.86(1H,m), 3.03–3.14(2H,m), 3.36–3.50(2H,m), 3.65–3.94(2H,m), 4.45–4.75(4H,m), 7.98–8.06(4H,m), 8.86 (1H,brs), 9.07–9.12(1H,m), 10.49(1H,brs).

Example 112

Synthesis of 3-[(2S,4S)-4-(5-chloro-2-nitrobenzoyl) amino-2-pyrrolidinylcarbonyl]-1,3-thiazolidine hydrochloride (1) Using the title compound (495 mg) of Reference Example 10 and 5-chloro-2-nitrobenzoic acid (300 mg), and in the same manner as in Reference Example 9, 3-[(2S,4S)-1-tert-butoxycarbonyl-4-(5-chloro-2-nitrobenzoyl)amino-2-pyrrolidinylcarbonyl]-1,3-thiazolidine (340 mg) was obtained as a white powder.

(2) Using the above-mentioned compound (338 mg), and in the same manner as in Example 5 (2), the title compound (272 mg) was obtained as a white powder.

$^1$H-NMR(DMSO-$d_6$)δ1.88–1.99(1H,m), 2.79–2.88(1H, m), 3.04–3.15(2H,m), 3.26–3.36(1H,m), 3.47–3.94(3H,m), 4.44–4.75(4H,m), 7.80–7.84(2H,m), 8.11–8.14(1H,m), 9.09–9.12(1H,m), 9.50(2H,brs).

Example 113

Synthesis of 3-[(2S,4S)-4-(2,4-dichlorobenzoyl) amino-2-pyrrolidinylcarbonyl]-1,3-thiazolidine hydrochloride (1) Using the title compound (440 mg) of Reference Example 10 and 2,4-dichlorobenzoic acid (254 mg), and in the same manner as in Reference Example 9, 3-[(2S,4S)-1-tert-butoxycarbonyl-4-(2,4-dichlorobenzoyl)amino-2-pyrrolidinylcarbonyl]-1,3-thiazolidine (356 mg) was obtained as a white powder.

(2) Using the above-mentioned compound (356 mg), and in the same manner as in Example 5 (2), the title compound (211 mg) was obtained as a white powder.

$^1$H-NMR(DMSO-$d_6$)δ1.86–1.99(1H,m), 2.79–2.88(1H, m), 3.04–3.14(2H,m), 3.26–3.31(1H,m), 3.47–3.95(3H,m), 4.43–4.75(4H,m), 7.50–7.56(2H,m), 7.71(1H,s), 8.84–8.88 (1H,m), 9.70(2H,brs).

Example 114

Synthesis of 3-{(2S,4S)-4-[(3-nitrophenyl)acetyl] amino-2-pyrrolidinylcarbonyl}-1,3-thiazolidine hydrochloride (1) Using the title compound (370 mg) of Reference Example 10 and 3-nitrophenylacetic acid (201 mg), and in the same manner as in Reference Example 9, 3-{(2S,4S)-1-tert-butoxycarbonyl-4-[(3-nitrophenyl)acetyl]amino-2-pyrrolidinylcarbonyl}-1,3-thiazolidine (516 mg) was obtained as a white powder.

(2) Using the above-mentioned compound (515 mg), and in the same manner as in Example 5 (2), the title compound (427 mg) was obtained as a white powder.

$^1$H-NMR(500 MHz,DMSO-$d_6$)δ1.86–1.93(1H,m), 2.74–2.78(1H,m), 3.04–3.14(3H,m), 3.40–3.44(1H,m), 3.63 (2H,s), 3.63–3.89(2H,m), 4.36–4.70(4H,m), 7.60–7.63(1H, m), 7.72(1H,d,J=7.7 Hz), 8.12(1H,d,J=8.2 Hz), 8.15(1H,s), 8.65–8.68(1H,m).

Example 115

Synthesis of 3-[(2S,4S)-4-(trans-3-trifluoromethylcinnamoyl)amino-2-pyrrolidinylcarbonyl]-1,3-thiazolidine hydrochloride (1) Using the compound (338 mg) of Reference Example 10 and 3-trifluoromethylcinnamoyl chloride (201 μL), and in the same manner as in Reference Example 7, 3-[(2S,4S)-1-tert-butoxycarbonyl-4-(trans-3-trifluoromethylcinnamoyl) amino-2-pyrrolidinylcarbonyl]-1,3-thiazolidine (274 mg) was obtained as a white powder.

(2) Using the above-mentioned compound (270 mg), and in the same manner as in Example 5 (2), the title compound (230 mg) was obtained as a white powder.

$^1$H-NMR(DMSO-$d_6$)δ1.78–1.88(1H,m), 2.79–2.87(1H, m), 3.04–3.22(3H,m), 3.46–3.52(1H,m), 3.64–3.94(2H,m), 4.46–4.75(4H,m), 6.76(1H,d,J=15.9 Hz), 7.57(1H,d,J=15.9 Hz), 7.64–7.76(2H,m), 7.89–8.03(2H,m), 8.70–8.75(1H,m), 9.60(2H,brs).

Example 116

Synthesis of 3-{(2S,4S)-4-[N-(4-cyanobenzoyl)-N-(4-cyanophenylmethyl)amino]-2-pyrrolidinylcarbonyl}-1,3-thiazolidine hydrochloride (1) The product (0.833 g) of Example 63 (1) was dissolved in dichloromethane (10 mL), and triethylamine (0.418 mL) and 4-cyanobenzoyl chloride (0.331 g) were added thereto. The mixture was stirred at room temperature for 18 hr. The reaction mixture was added to saturated aqueous sodium hydrogencarbonate solution, and the mixture was extracted with ethyl acetate. The extract was dried and the solvent was evaporated under reduced pressure. The residue was purified by silica gel chromatography to give 3-{(2S,4S)-1-tert-butoxycarbonyl-4-[N-(4-cyanobenzoyl)-N-(4-cyanophenylmethyl)amino]-2-pyrrolidinylcarbonyl}-1,3-thiazolidine (0.956 g).

(2) The above-mentioned compound (514 mg) was dissolved in ethyl acetate (1.88 mL) and 4 mol/L hydrochloric acid-ethyl acetate (1.18 mL) was added thereto. The mixture was stirred at room temperature for 18 hr and the precipitated solid was collected by filtration to give the title compound (320 g) as a white powder.

$^1$H-NMR(DMSO-$d_6$)δ1.62–2.39(1H,m), 2.45–2.82(1H, m), 2.90–3.25(2H,m), 3.30–3.95(4H,m), 4.25–5.00(6H,m), 7.30–8.20(8H,m).

Example 117

Synthesis of 3-{(2S,4S)-4-[N-acetyl-N-(5-cyano-2-pyridyl)amino]-2-pyrrolidinylcarbonyl}-1,3-thiazolidine hydrochloride (1) Using the product (340 mg) of Example 58 (1) and acetyl chloride (72 μL), and in the same manner as in Example 82 (1), 3-{(2s,4S)-4-[N-acetyl-N-(5-cyano-2-pyridyl)amino]-1-tert-butoxycarbonyl-2-pyrrolidinylcarbonyl}-1,3-thiazolidine (188 mg) was obtained.

(2) Using the above-mentioned compound (186 mg), and in the same manner as in Example 82 (2), the title compound (121 mg) was obtained as a white powder.

$^1$H-NMR(500 MHz,DMSO-$d_6$)δ1.90–1.95(1H,m), 1.91 (3H,s), 2.75–2.80(1H,m), 3.03–3.11(2H,m), 3.40–3.44(1H, m), 3.50–3.54(1H,m), 3.59–3.63(1H,m), 3.71–3.85(1H,m), 4.39–4.44(1H,m), 4.56–4.69(2H,m), 5.04–5.08(1H,m), 7.75 (1H,d,J=8.3 Hz), 8.50(1H,dd,J=8.3,2.1 Hz), 9.01(1H,d,J=2.1 Hz).

Example 118

Synthesis of 3-((2S,4S)-4-phthalimido-2-pyrrolidinylcarbonyl)-1,3-thiazolidine trifluoroacetate (1) The title compound (1.23 g) of Reference Example 10 was suspended in toluene (20 mL), and phthalic anhydride (632 mg) and triethylamine (60 μL) were added thereto. The mixture was refluxed for 5 hr. To the reaction mixture was added 10% citric acid solution and the mixture was extracted with ethyl acetate. The extract was washed successively with saturated aqueous sodium hydrogencarbonate solution and brine, and dried. The solvent was evaporated under reduced pressure. The residue was purified by silica gel chromatography to give 3-((2S,4S)-1-tert-butoxycarbonyl-4-phthalimido-2-pyrrolidinylcarbonyl)-1,3-thiazolidine (1.21 g) as a white solid.

(2) The above-mentioned compound (362 mg) was dissolved in dichloromethane (4 mL) and trifluoroacetic acid (2 mL) was added thereto. The mixture was stirred at room temperature for 20 hr. The solvent was evaporated under reduced pressure to give the title compound (374 mg) as a pale-yellow solid.

$^1$H-NMR(500 MHz,DMSO-$d_6$)δ2.38–2.44(1H,m), 2.80–2.84(1H,m), 3.07–3.13(2H,m), 3.50–3.54(1H,m), 3.60–3.89(3H,m), 4.46–4.50(1H,m), 4.62–4.78(2H,m), 4.97–5.00(1H,m), 7.86–7.90(4H,m), 8.74(1H,brs), 9.90(1H, brs).

Example 119

Synthesis of 3-[(2S,4S)-4-(4-nitrophthalimido)-2-pyrrolidinylcarbonyl]-1,3-thiazolidine trifluoroacetate (1) Using the title compound (2.31 g) of Reference Example 10 and 4-nitrophthalic anhydride (1.16 g), and in the same manner as in Example 118 (1), 3-[(2S,4S)-1-tert-butoxycarbonyl-4-(4-nitrophthalimido)-2-pyrrolidinylcarbonyl]-1,3-thiazolidine (1.42 g) was obtained as a white solid.

(2) Using the above-mentioned compound (355 mg), and in the same manner as in Example 118 (2), the title compound (298 mg) was obtained as a white powder.

$^1$H-NMR(500 MHz,DMSO-$d_6$)δ2.40–2.45(1H,m), 2.82–2.88(1H,m), 3.06–3.14(2H,m), 3.52–3.56(1H,m), 3.62–3.89(3H,m), 4.47–4.50(1H,m), 4.62–4.78(2H,m), 5.01–5.07(1H,m), 8.15(1H,d,J=8.2 Hz), 8.51(1H,d,J=1.9 Hz), 8.65(1H,dd,J=8.2,1.9 Hz), 9.24(2H,brs).

Example 120

Synthesis of 3-[(2S,4S)-4-(3-phenylureido)-2-pyrrolidinylcarbonyl]-1,3-thiazolidine trifluoroacetate (1) The title compound (401 mg) of Reference Example 10 was dissolved in tetrahydrofuran (10 mL), and phenyl isocyanate (167 mg) was added thereto at room temperature. The mixture was stirred for 18 hr. To the reaction mixture was added 10% citric acid solution and the mixture was extracted with ethyl acetate. The extract was washed successively with saturated aqueous sodium hydrogencarbonate solution and brine, and dried. The solvent was evaporated under reduced pressure to give 3-[(2S,4S)-1-tert-butoxycarbonyl-4-(3-phenylureido)-2-pyrrolidinylcarbonyl]-1,3-thiazolidine (560 mg) as a white solid.

(2) The above-mentioned compound (532 mg) was dissolved in trifluoroacetic acid (2 mL) and the mixture was stirred at room temperature for 3 hr. The solvent was evaporated under reduced pressure to give the title compound (363 mg) as a brown powder.

$^1$H-NMR(500 MHz,DMSO-$d_6$)δ1.75–1.80(1H,m), 2.75–2.80(1H,m), 3.04–3.20(3H,m), 3.43–3.47(1H,m), 3.68–3.89(2H,m), 4.40–4.71(4H,m), 6.72–6.75(1H,m), 6.91 (1H,t,J=7.4 Hz), 7.21–7.24(2H,m), 7.39(2H,d,J=7.8 Hz), 8.85(1H,brs), 8.89–8.90(1H,m), 9.60(1H,brs).

Example 121

Synthesis of 3-{(2S,4S)-4-[3-(4-cyanophenyl)ureido]-2-pyrrolidinylcarbonyl}-1,3-thiazolidine (1) Using the title compound (640 mg) of Reference Example 10 and 4-cyanophenyl isocyanate (321 mg), and in the same manner as in Example 120 (1), 3-{(2S,4S)-1-tert-butoxycarbonyl-4-[3-(4-cyanophenyl)ureido]-2-pyrrolidinylcarbonyl}-1,3-thiazolidine (992 mg) was obtained as a white powder.

(2) The above-mentioned compound (978 mg) was dissolved in chloroform (5 mL), and then dissolved in trifluoroacetic acid (3 mL), and the mixture was stirred at room temperature for 8 hr. The solvent was evaporated under reduced pressure and saturated aqueous sodium hydrogencarbonate solution was added to the residue. The mixture was extracted with chloroform. The extract was concentrated under reduced pressure to give the title compound (140 mg) as a white powder.

$^1$H-NMR(DMSO-$d_6$)δ1.60–1.68(1H,m), 2.22–2.32(1H, m), 2.67–2.72(1H,m), 2.91–3.11(4H,m), 3.65–3.93(3H,m), 4.13–4.16(1H,m), 4.43–4.72(2H,m), 6.47(1H,d,J=7.2 Hz), 7.56(2H,d,J=8.7 Hz), 7.65(2H,d,J=8.7 Hz), 9.11(1H,s).

Example 122

Synthesis of 3-((2S,4S)-4-phenylsulfonylamino-2-pyrrolidinylcarbonyl)-1,3-thiazolidine hydrochloride (1) The title compound (543 mg) of Reference Example 10 was dissolved in dichloromethane (10 mL), and 4-methylmorpholine (240 μL) and benzenesulfonyl chloride (240 μL) were added thereto at room temperature. The mixture was stirred for 17 hr. To the reaction mixture was added 10% citric acid solution, and the mixture was extracted with ethyl acetate. The extract was washed successively with saturated aqueous sodium hydrogencarbonate solution and brine, and dried. The solvent was evaporated under reduced pressure to give 3-((2S,4S)-1-tert-butoxycarbonyl-4-phenylsulfonylamino-2-pyrrolidinylcarbonyl)-1,3-thiazolidine (644 mg) as a white powder.

(2) The above-mentioned compound (634 mg) was dissolved in ethyl acetate (4 mL) and 4 mol/L hydrochloric acid-ethyl acetate (1.8 mL) was added thereto. The mixture was stirred at room temperature for 67 hr. The precipitate was collected by filtration to give the title compound (437 mg) as a pale-yellow powder.

$^1$H-NMR(500 MHz,DMSO-$d_6$)δ1.68–1.74(1H,m), 2.50–2.58(1H,m), 3.00–3.08(3H,m), 3.17–3.20(1H,m), 3.53–3.87(3H,m), 4.38–4.63(3H,m), 7.62–7.71(3H,m), 7.84–7.85(2H,m), 8.24–8.27(1H,m), 9.50(2H,brs).

Example 123

Synthesis of 3-[(2S,4S)-4-(4-cyanophenylsulfonyl)amino-2-pyrrolidinylcarbonyl]-1,3-thiazolidine hydrochloride (1) Using the title compound (1.09 g) of Reference Example 10 and 4-cyanobenzenesulfonyl chloride (0.780 g), and in the same manner as in Example 122 (1), 3-[(2S,4S)-1-tert-butoxycarbonyl-4-(4-cyanophenylsulfonyl)amino-2-pyrrolidinylcarbonyl]-1,3-thiazolidine (1.67 g) was obtained as a white powder.

(2) Using the above-mentioned compound (798 mg), and in the same manner as in Example 122 (2), the title compound (544 mg) was obtained as a pale-yellow powder.

$^1$H-NMR(500 MHz,DMSO-$d_6$)δ1.68–1.75(1H,m), 2.53–2.59(1H,m), 3.02–3.09(3H,m), 3.23–3.28(1H,m), 3.54–3.90(3H,m), 4.40–4.64(3H,m), 8.01(2H,d,J=8.4 Hz), 8.13(2H,d,J=8.4 Hz), 8.62–8.65(1H,m), 9.93(2H,brs).

Example 124

Synthesis of 3-{(2S,4S)-4-[N-(4-cyanophenylmethyl)-N-(4-cyanophenylsulfonyl)amino]-2-pyrrolidinylcarbonyl}-1,3-thiazolidine hydrochloride (1) 3-[(2S,4S)-1-tert-Butoxycarbonyl-4-(4-cyanophenylsulfonyl)amino-2-pyrrolidinylcarbonyl]-1,3- thiazolidine [product of Example 123 (1), 856 mg] was dissolved in DMF (20 mL), and potassium carbonate (380 mg) and 4-cyanobenzyl bromide (400 mg) were added thereto at room temperature. The mixture was stirred for 4 hr. To the reaction mixture was added 10% citric acid solution, and the precipitate was collected by filtration to give 3-{(2S,4S)-1-tert-butoxycarbonyl-4-[N-(4-cyanophenylmethyl)-N-(4-cyanophenylsulfonyl)amino]-2-pyrrolidinylcarbonyl}-1,3-thiazolidine (900 mg) as a pale-yellow solid.

(2) Using the above-mentioned compound (900 mg), and in the same manner as in Example 122 (2), the title compound (800 mg) was obtained as a pale-yellow powder.

$^1$H-NMR(500 MHz,DMSO-$d_6$)δ1.54–1.60(1H,m), 2.45–2.50(1H,m), 2.79(1H,dd,J=8.7,1.6 Hz), 3.00–3.20(3H, m), 3.55–3.58(1H,m), 3.68–3.82(1H,m), 4.34–4.63(3H,m), 4.65(2H,s), 4.87–4.93(1H,m), 7.51(2H,d,J=8.2 Hz), 7.86 (2H,d,J=8.2 Hz), 8.11(2H,d,J=8.4 Hz), 8.16(2H,d,J=8.4 Hz), 8.85(1H,brs), 9.91(1H,brs).

Example 125

Synthesis of 3-[(2S,4S)-4-(1-pyrrolidinyl)-2-pyrrolidinylcarbonyl]-1,3-thiazolidine dihydrochloride (1) Using the title compound (1.00 g) of Reference Example 12 and pyrrolidine (0.274 g), and in the same manner as in Example 70 (1), 3-[(2S,4S)-1-tert-butoxycarbonyl-4-(1-pyrrolidinyl)-2-pyrrolidinylcarbonyl]-1,3-thiazolidine (0.793 g) was obtained as a white solid.

(2) Using the above-mentioned compound (791 mg), and in the same manner as in Example 70 (2), the title compound (626 mg) was obtained as a white powder.

$^1$H-NMR(DMSO-$d_6$)δ1.80–2.15(6H,m), 2.16–2.28(2H, m), 2.95–3.25(3H,m), 3.50–3.95(3H,m), 4.02–4.15(2H,m), 4.45–4.75(4H,m).

Example 126

Synthesis of 3-((2S,4S)-4-morpholino-2-pyrrolidinylcarbonyl)-1,3-thiazolidine dihydrochloride (1) Using the title compound (1.00 g) of Reference Example 12 and morpholine (0.319 g), and in the same manner as in Example 70 (1), 3-((2S,4S)-1-tert-butoxycarbonyl-4-morpholino-2-pyrrolidinylcarbonyl)-1,3-thiazolidine (0.987 g) was obtained as a white solid.

(2) Using the above-mentioned compound (985 mg), and in the same manner as in Example 70 (2), the title compound (746 mg) was obtained as a white powder.

$^1$H-NMR(DMSO-$d_6$)δ2.22–2.35(2H,m), 2.90–3.50(7H, m), 3.70–4.20(5H,m), 4.46–4.83(6H,m), 9.30(1H,brs).

Example 127

Synthesis of 3-((2S,4S)-4-piperidino-2-pyrrolidinylcarbonyl)-1,3-thiazolidine dihydrochloride (1) Using the title compound (1.00 g) of Reference Example 12 and piperidine (0.318 g), and in the same manner as in Example 70 (1), 3-((2S,4S)-1-tert-butoxycarbonyl-4-piperidino-2-pyrrolidinylcarbonyl)-1,3-thiazolidine (0.908 g) was obtained as a white solid.

(2) Using the above-mentioned compound (906 mg), and in the same manner as in Example 70 (2), the title compound (705 mg) was obtained as a white powder.

$^1$H-NMR(DMSO-$d_6$)δ1.65–1.90(6H,m), 2.18–2.34(2H, m), 2.85–3.20(4H,m), 3.30–3.50(2H,m), 3.55–4.05(2H,m), 4.50–4.82(6H,m).

Example 128

Synthesis of 3-[(2S,4S)-4-(4-hydroxypiperidino)-2-pyrrolidinylcarbonyl]-1,3-thiazolidine trihydrochloride (1) Using the title compound (988 mg) of Reference Example 12 and 4-hydroxypiperidine (867 mg), and in the same manner as in Example 70 (1), 3-[(2S,4S)-1-tert-butoxycarbonyl-4-(4-hydroxypiperidino)-2-pyrrolidinylcarbonyl]-1,3-thiazolidine (408 mg) was obtained as a white solid.

(2) Using the above-mentioned compound (408 mg), and in the same manner as in Example 70 (2), the title compound (250 mg) was obtained as a white powder.

$^1$H-NMR(DMSO-$d_6$)δ1.60–1.82(2H,m),δ1.84–2.05(2H, m), 2.12–2.33(2H,m), 2.85–3.55(6H,m), 3.59–4.10(6H,m), 4.45–4.78(3H,m).

Example 129

Synthesis of 3-[(2S,4S)-4-(3-azaspiro[5.5]undec-3-yl)-2-pyrrolidinylcarbonyl]-1,3-thiazolidine 2 trifluoroacetate (1) The title compound (340 mg) of Reference Example 12, 3-azaspiro[5.5]undecene (210 mg) and acetic acid (0.066 mL) were dissolved in 1,2-dichloroethane (10 mL), and sodium triacetoxyborohydride (485 mg) was added thereto. The mixture was stirred at room temperature for 17 hr. The reaction mixture was added to saturated aqueous sodium hydrogencarbonate solution and the mixture was extracted with chloroform. The extract was washed with brine and dried. The solvent was evaporated under reduced pressure. Ethyl acetate was added to the residue, and the precipitate was collected by filtration to give 3-[(2S,4S)-4-(3-azaspiro[5.5]undec-3-yl)-1-tert-butoxycarbonyl-2-pyrrolidinylcarbonyl]-1,3-thiazolidine (141 mg) as a white solid.

(2) The above-mentioned compound (140 mg) was dissolved in methanol (3 mL) and chloroform (3 mL) and 4 mol/L hydrochloric acid-1,4-dioxane (1 mL) were added thereto. The mixture was stirred at room temperature for 18 hr. The solvent was evaporated under reduced pressure and the residue was purified by HPLC to give the title compound (52 mg) as a white solid.

$^1$H-NMR(500 MHz,DMSO-$d_6$)δ1.39–1.75(14H,m), 2.08–2.14(1H,m), 2.96–3.30(8H,m), 3.64–3.89(3H,m), 4.05–4.10(1H,m), 4.44–4.69(3H,m), 9.84(2H,brs).

Example 130

Synthesis of 3-[(2S,4S)-4-(4-oxo-1-phenyl-1,3,8-triazaspiro[4.5]dec-8-yl)-2-pyrrolidinylcarbonyl]-1,3-thiazolidine dihydrochloride (1) Using the title compound (1.00 g) of Reference Example 12 and 4-oxo-1-phenyl-1,3,8-triazaspiro[4.5]decane (0.81 g), and in the same manner as in Example 70 (1), 3-[(2S,4S)-1-tert-butoxycarbonyl-4-(4-oxo-1-phenyl-1,3,8-triazaspiro[4.5]dec-8-yl)-2-pyrrolidinylcarbonyl]-1,3-thiazolidine (1.64 g) was obtained as a white solid powder.

(2) Using the above-mentioned compound (1.64 g), and in the same manner as in Example 70 (2), the title compound (0.900 g) was obtained as a white powder.

$^1$H-NMR(DMSO-$d_6$)δ1.50–2.16(6H,m), 2.80–3.30(5H,m), 3.40–3.95(6H,m), 4.45–4.80(5H,m), 6.75–6.85(1H,m), 6.90–7.05(2H,m), 7.21–7.30(2H,m).

Example 131

Synthesis of 3-[(2S,4S)-4-(4-phenylpiperidino)-2-pyrrolidinylcarbonyl]-1,3-thiazolidine dihydrochloride (1) Using the title compound (461 mg) of Reference Example 12 and 4-phenylpiperidine (300 mg), and in the same manner as in Example 129 (1), 3-[(2S,4S)-1-tert-butoxycarbonyl-4-(4-phenylpiperidino)-2-pyrrolidinylcarbonyl]-1,3-thiazolidine (118 mg) was obtained as a white solid.

(2) Using the above-mentioned compound (116 mg), and in the same manner as in Example 129 (2), the title compound (78 mg) was obtained as a white powder.

$^1$H-NMR(DMSO-$d_6$)δ1.98–2.06(4H,m), 2.22–2.33(1H,m), 2.84–2.90(1H,m), 3.00–3.20(5H,m), 3.53–4.04(7H,m), 4.47–4.74(3H,m), 7.23–7.38(5H,m).

Example 132

Synthesis of 3-[(2S,4S)-4-(1,2,3,6-tetrahydro-4-phenyl-1-pyridyl)-2-pyrrolidinylcarbonyl]-1,3-thiazolidine dihydrochloride (1) Using the title compound (236 mg) of Reference Example 12 and 1,2,3,6-tetrahydro-4-phenyl-1-pyridine (150 mg), and in the same manner as in Example 70 (1), 3-[(2S,4S)-1-tert-butoxycarbonyl-4-(1,2,3,6-tetrahydro-4-phenyl-1-pyridyl)-2-pyrrolidinylcarbonyl]-1,3-thiazolidine (227 mg) was obtained as a white solid.

(2) The above-mentioned compound (225 mg) was dissolved in dichloromethane (4 mL), and trifluoroacetic acid (1 mL) was added thereto at room temperature. The mixture was stirred for 16 hr. The solvent was evaporated under reduced pressure, and saturated aqueous sodium hydrogencarbonate solution was added to the residue. The mixture was extracted with chloroform. The extract was washed with brine and dried. The solvent was evaporated under reduced pressure. The residue was dissolved in ethyl acetate and 4 mol/L hydrochloric acid-ethyl acetate was added and the precipitate was collected by filtration to give the title compound (158 mg) as a white powder.

$^1$H-NMR(500 MHz,DMSO-$d_6$)δ2.27–2.32(1H,m), 2.83(2H,brs), 3.03–3.16(4H,m), 3.68–4.15(8H,m), 4.48–4.75(3H,m), 6.19(1H,s), 7.32–7.41(3H,m), 7.49–7.51(2H,m).

Example 133

Synthesis of 3-{(2S,4S)-4-[4-(p-tolyl)piperidino]-2-pyrrolidinylcarbonyl}-1,3-thiazolidine dihydrochloride (1) The title compound (504 mg) of Reference Example 12, 4-(p-tolyl)piperidine (353 mg) and acetic acid (0.096 mL) were dissolved in 1,2-dichloroethane (10 mL), and sodium triacetoxyborohydride (710 mg) was added thereto. The mixture was stirred at room temperature for 18 hr. The reaction mixture was added to water and the mixture was extracted with chloroform. The extract was washed with brine and dried. The solvent was evaporated under reduced pressure to give 3-{(2S,4S)-1-tert-butoxycarbonyl-4-[4-(p-tolyl)piperidino]-2-pyrrolidinylcarbonyl}-1,3-thiazolidine (115 mg) as a white solid.

(2) The above-mentioned compound (114 mg) was dissolved in methanol (3 mL), and chloroform (3 mL) and 4 mol/L hydrochloric acid-1,4-dioxane (1 mL) were added thereto. The mixture was stirred at room temperature for 18 hr. The solvent was evaporated under reduced pressure to give the title compound (84 mg) as a white powder.

$^1$H-NMR(DMSO-$d_6$)δ1.97–2.06(4H,m), 2.25–2.35(1H,m), 2.27(3H,s), 2.78–2.85(1H,m), 3.00–3.17(5H,m), 3.50–4.05(7H,m), 4.47–4.74(3H,m), 7.10–7.17(4H,m).

Example 134

Synthesis of 3-{(2S,4S)-4-[4-(3,4-xylyl)piperidino]-2-pyrrolidinylcarbonyl}-1,3-thiazolidine dihydrochloride (1) Using the title compound (450 mg) of Reference Example 12 and 4-(3,4-xylyl)piperidine (312 mg), and in the same manner as in Example 70 (1), 3-{(2S,4S)-1-tert-butoxycarbonyl-4-[4-(3,4-xylyl)piperidino]-2-pyrrolidinylcarbonyl}-1,3-thiazolidine 618 mg) was obtained as a white solid.

(2) Using the above-mentioned compound (613 mg), and in the same manner as in Example 70 (2), the title compound (374 mg) was obtained as a white powder.

$^1$H-NMR(DMSO-$d_6$)δ1.86–2.15(4H,m), 2.18(3H,s), 2.20(3H,s), 2.22–2.37(1H,m), 2.68–2.74(1H,m), 2.93–3.25(5H,m), 3.42–4.07(7H,m), 4.44–4.77(3H,m), 6.88–7.04(2H,m), 7.09(1H,d,J=7.8 Hz), 10.1(1H,brs), 11.91(1H,brs).

Example 135

Synthesis of 3-{(2S,4S)-4-[4-(2,4-dimethoxyphenyl)piperidino]-2-pyrrolidinylcarbonyl}-1,3-thiazolidine dihydrochloride (1) Using the title compound (487 mg) of Reference Example 12 and 4-(2,4-dimethoxyphenyl)piperidine (430 mg), and in the same manner as in Example 133 (1), 3-{(2S,4S)-1-tert-butoxycarbonyl-4-[4-(2,4-dimethoxyphenyl)piperidino]-2-pyrrolidinylcarbonyl}-1,3-thiazolidine (82 mg) was obtained as a pale-brown solid.

(2) Using the above-mentioned compound (82 mg), and in the same manner as in Example 133 (2), the title compound (61 mg) was obtained as a brown powder.

$^1$H-NMR(DMSO-$d_6$)δ1.99–2.08(4H,m), 2.25–2.35(1H,m), 2.78–3.17(6H,m), 3.53–4.06(7H,m), 3.72(3H,s), 3.75(3H,s), 4.47–4.75(3H,m), 6.74(1H,d,J=8.1 Hz), 6.83(1H,s), 6.91(1H,d,J=8.1 Hz).

Example 136

Synthesis of 3-{(2S,4S)-4-[4-(2,3-dihydrobenzo[b]furan-5-yl)piperidino]-2-pyrrolidinylcarbonyl}-1,3-thiazolidine dihydrochloride (1) Using the title compound (450 mg) of Reference Example 12 and 4-(2,3-dihydrobenzo[b]furan-5-yl)piperidine (335 mg), and in the same manner as in Example 70 (1), 3-{(2S,4S)-1-tert-butoxycarbonyl-4-[4-(2,3-dihydrobenzo[b]furan-5-yl)piperidino]-2-pyrrolidinylcarbonyl}-1,3-thiazolidine (494 mg) was obtained as a white solid.

(2) Using the above-mentioned compound (489 mg), and in the same manner as in Example 70 (2), the title compound (330 mg) was obtained as-a white powder.

$^1$H-NMR(DMSO-$d_6$)δ1.84–2.14(4H,m), 2.21–2.37(1H,m), 2.72–2.86(1H,m), 2.96–3.26(7H,m), 3.47–4.07(7H,m), 4.44–4.77(5H,m), 6.71(1H,d,J=8.1 Hz), 6.94(1H,d,J=8.1 Hz), 7.09(1H,s), 9.9(1H,brs), 11.89(1H,brs).

Example 137

Synthesis of 3-{(2S,4S)-4-[4-(3,4-methylenedioxyphenyl)piperidino]-2-pyrrolidinylcarbonyl}-1,3-thiazolidine dihydrochloride (1) Using the title compound (505 mg) of Reference Example 12 and 4-(3,4-methylenedioxyphenyl)piperidine (414 mg), and in the same manner as in Example 133 (1), 3-{(2S,4S)-1-tert-butoxycarbonyl-4-[4-(3,4-methylenedioxyphenyl)piperidino]-2-pyrrolidinylcarbonyl}-1,3-thiazolidine (105 mg) was obtained as a white solid.

(2) Using the above-mentioned compound (105 mg), and in the same manner as in Example 133 (2), the title compound (61 mg) was obtained as a white powder.

$^1$H-NMR(DMSO-$d_6$)δ1.97–2.04(4H,m), 2.25–2.35(1H, m), 2.78–2.82(1H,m), 3.00–3.17(5H,m), 3.50–4.03(7H,m), 4.47–4.76(3H,m), 5.98(2H,s), 6.70(1H,d,J=8.1 Hz), 6.82 (1H,s), 6.87(1H,d,J=8.1 Hz).

Example 138

Synthesis of 3-{(2S,4S)-4-[4-(4-fluoro-3-methylphenyl)piperidino]-2-pyrrolidinylcarbonyl}-1,3-thiazolidine dihydrochloride (1) Using the title compound (450 mg) of Reference Example 12 and 4-(4-fluoro-3-methylphenyl)piperidine (326 mg), and in the same manner as in Example 70 (1), 3-{(2S,4S)-1-tert-butoxycarbonyl-4-[4-(4-fluoro-3-methylphenyl)piperidino]-2-pyrrolidinylcarbonyl}-1,3-thiazolidine (603 mg) was obtained as a white solid.

(2) Using the above-mentioned compound (597 mg), and in the same manner as in Example 70 (2), the title compound (441 mg) was obtained as a white powder.

$^1$H-NMR(DMSO-$d_6$)δ1.90–2.16(4H,m), 2.23(3H,s), 2.25–2.38(1H,m), 2.77–2.92(1H,m), 2.96–3.26(5H,m), 3.48–4.07(7H,m), 4.46–4.78(3H,m), 7.04–7.19(3H,m), 10.5 (1H,brs), 11.94(1H,brs).

Example 139

Synthesis of 3-{(2S,4S)-4-[4-(3,4-dichlorophenyl)piperidino]-2-pyrrolidinylcarbonyl}-1,3-thiazolidine dihydrochloride (1) Using the title compound (480 mg) of Reference Example 12 and 4-(3,4-dichlorophenyl)piperidine (442 mg), and in the same manner as in Example 133 (1), 3-{(2S,4S)-1-tert-butoxycarbonyl-4-[4-(3,4-dichlorophenyl)piperidino]-2-pyrrolidinylcarbonyl}-1,3-thiazolidine (820 mg) was obtained as a white powder.

(2) Using the above-mentioned compound (820 mg), and in the same manner as in Example 133 (2), the title compound (654 mg) was obtained as a white powder.

$^1$H-NMR(DMSO-$d_6$)δ1.99–2.10(4H,m), 2.25–2.35(1H, m), 2.89–3.20(6H,m), 3.53–4.06(7H,m), 4.47–4.77(3H,m), 7.26(1H,d,J=8.1 Hz), 7.50(1H,d,J=3.3 Hz), 7.61(1H,dd,J=8.1,3.3 Hz).

Example 140

Synthesis of 3-{(2S,4S)-4-[4-(4-chloro-3-trifluoromethylphenyl)piperidino]-2-pyrrolidinylcarbonyl}-1,3-thiazolidine dihydrochloride (1) Using the title compound (503 mg) of Reference Example 12 and 4-(4-chloro-3-trifluoromethylphenyl)piperidine (530 mg), and in the same manner as in Example 133 (1), 3-{(2S,4S)-1-tert-butoxycarbonyl-4-[4-(4-chloro-3-trifluoromethylphenyl)piperidino]-2-pyrrolidinylcarbonyl}-1,3-thiazolidine (189 mg) was obtained as a white solid.

(2) Using the above-mentioned compound (189 mg), and in the same manner as in Example 133 (2), the title compound (116 mg) was obtained as a white powder.

$^1$H-NMR(DMSO-$d_6$)δ2.07–2.12(4H,m), 2.25–2.35(1H, m), 3.00–3.17(6H,m), 3.59–4.10(7H,m), 4.47–4.76(3H,m), 7.57–7.74(3H,m).

Example 141

Synthesis of 3-{(2S,4S)-4-[4-(1-naphthyl)piperidino]-2-pyrrolidinylcarbonyl}-1,3-thiazolidine dihydrochloride (1) Using the title compound (601 mg) of Reference Example 12 and 4-(1-naphthyl)piperidine (630 mg), and in the same manner as in Example 133 (1), 3-{(2S,4S)-1-tert-butoxycarbonyl-4-[4-(1-naphthyl)piperidino]-2-pyrrolidinylcarbonyl}-1,3-thiazolidine (130 mg) as a pale-brown solid.

(2) Using the above-mentioned compound (129 mg), and in the same manner as in Example 133 (2), the title compound (72 mg) was obtained as a brown powder.

$^1$H-NMR(500 MHz,DMSO-$d_6$)δ1.99–2.35(5H,m), 3.05–3.41(5H,m), 3.63–4.06(8H,m), 4.49–4.75(3H,m), 7.38–7.39(1H,m), 7.45–7.61(3H,m), 7.83–7.84(1H,m), 7.95–7.97(1H,m), 8.21–8.23(1H,m).

Example 142

Synthesis of 3-{(2S,4S)-4-[4-(2-naphthyl)piperidino]-2-pyrrolidinylcarbonyl}-1,3-thiazolidine dihydrochloride (1) Using the title compound (450 mg) of Reference Example 12 and 4-(2-naphthyl)piperidine (349 mg), and in the same manner as in Example 70 (1), 3-{(2S,4S)-1-tert-butoxycarbonyl-4-[4-(2-naphthyl)piperidino]-2-pyrrolidinylcarbonyl}-1,3-thiazolidine (721 mg) was obtained as a white solid.

(2) Using the above-mentioned compound (616 mg), and in the same manner as in Example 70 (2), the title compound (206 mg) was obtained as a white powder.

$^1$H-NMR(DMSO-$d_6$)δ2.03–2.40(5H,m), 2.97–3.35(6H, m), 3.54–4.15(7H,m), 4.47–4.80(3H,m), 7.40–7.57(3H,m), 7.73(1H,s), 7.86–7.97(3H,m), 10.1(1H,brs), 11.95(1H,brs).

Example 143

Synthesis of 3-{(2S,4S)-4-[4-(2-benzo[b]thienyl)piperidino]-2-pyrrolidinylcarbonyl}-1,3-thiazolidine dihydrochloride (1) Using the title compound (450 mg) of Reference Example 12 and 4-(2-benzo[b]thienyl)piperidine (330 mg), and in the same manner as in Example 70 (1), 3-{(2S,4S)-1-tert-butoxycarbonyl-4-[4-(2-benzo[b]thienyl)piperidino]-2-pyrrolidinylcarbonyl}-1,3-thiazolidine (531 mg) was obtained as a white solid.

(2) Using the above-mentioned compound (447 mg), and in the same manner as in Example 70 (2), the title compound (258 mg) was obtained as a white powder.

$^1$H-NMR(DMSO-$d_6$)δ2.03–2.40(5H,m), 2.96–4.10(13H, m), 4.46–4.77(3H,m), 7.23–7.42(3H,m), 7.78(1H,d,J=7.2 Hz), 7.92(1H,d,J=7.5 Hz), 10.3(1H,brs), 11.95(1H,brs).

Example 144

Synthesis of 3-{(2S,4S)-4-[4-(1-indolinyl)piperidino]-2-pyrrolidinylcarbonyl}-1,3-thiazolidine trihydrochloride (1) 1-tert-Butoxycarbonylpiperidin-4-one (2.50 g), indoline (1.50 g) and acetic acid (0.73 mL) were dissolved in 1,2-dichloroethane (75 mL), and sodium triacetoxyborohydride (5.32 g) was added thereto. The mixture was stirred at room temperature for 12 hr. The reaction mixture was added to iced water and the mixture was extracted with chloroform. The extract was dried and the solvent was evaporated under reduced pressure. The residue was purified by silica gel chromatography to give 1-tert-butoxycarbonyl-4-(1-indolinyl)piperidine (2.82 g).

(2) The above-mentioned compound (2.82 g) was dissolved in methanol (20 mL) and 4 mol/L hydrochloric acid-1,4-dioxane (20 mL) was added thereto. The mixture was stirred at room temperature for 12 hr. The reaction mixture was added to aqueous sodium hydrogencarbonate solution, and the mixture was extracted with chloroform. The extract was dried and the solvent was evaporated under reduced pressure to give 4-(1-indolinyl)piperidine (0.60 g).

(3) Using the above-mentioned compound (470 mg) and the title compound (700 mg) of Reference Example 12, and in the same manner as in Example 70 (1), 3-{(2S,4S)-1-tert-butoxycarbonyl-4-[4-(1-indolinyl)piperidino]-2-pyrrolidinylcarbonyl}-1,3-thiazolidine (449 mg) was obtained as a white solid.

(4) Using the above-mentioned compound (448 mg), and in the same manner as in Example 70 (2), the title compound (350 mg) was obtained as a white powder.

$^1$H-NMR(DMSO-$d_6$)δ1.85–2.30(5H,m), 2.85–3.25(9H, m), 3.50–4.02(8H,m), 4.52–4.81(3H,m), 6.51–6.60(2H,m), 6.98–7.05(2H,m).

Example 145

Synthesis of 3-{(2S,4S)-4-[4-(1-indolyl)piperidino]-2-pyrrolidinylcarbonyl}-1,3-thiazolidine dihydrochloride (1) Using the title compound (604 mg) of Reference Example 12 and 4-(1-indolyl)piperidine (403 mg), and in the same manner as in Example 70 (1), 3-{(2S,4S)-1-tert-butoxycarbonyl-4-[4-(1-indolyl)piperidino]-2-pyrrolidinylcarbonyl}-1,3-thiazolidine (868 mg) was obtained as a white solid.

(2) Using the above-mentioned compound (868 mg), and in the same manner as in Example 70 (2), the title compound (642 mg) was obtained as a white powder.

$^1$H-NMR(DMSO-$d_6$)δ2.05–2.60(6H,m), 2.99–3.18(4H, m), 3.55–4.20(6H,m), 4.30–4.90(5H,m), 6.50(1H,d,J=3.0 Hz), 7.05(1H, dd,J=8.2,3.0 Hz), 7.16(1H,dd,J=8.1,3.0 Hz), 7.35(1H,d,J=3.0 Hz), 7.57(1H,d,J=8.1 Hz), 7.61(1H,d,J=8.1 Hz), 9.30(1H,brs), 10.00(1H,brs).

Example 146

Synthesis of 3-{(2S,4S)-4-[4-(5-bromo-1-indolinyl)piperidino]-2-pyrrolidinylcarbonyl}-1,3-thiazolidine trihydrochloride (1) Using 1-tert-butoxycarbonylpiperidin-4-one (2.81 g) and 5-bromo-1-indoline (3.00 g), and in the same manner as in Example 144 (1), 1-tert-butoxycarbonyl-4-(5-bromo-1-indolinyl)piperidine (3.34 g) was obtained.

(2) Using the above-mentioned compound (3.34 g), and in the same manner as in Example 144 (2), 4-(5-bromo-1-indolinyl)piperidine (1.79 g) was obtained.

(3) Using the above-mentioned compound (1.12 g) and the title compound (1.20 g) of Reference Example 12, and in the same manner as in Example 70 (1), 3-{(2S,4S)-4-[4-(5-bromo-1-indolinyl)piperidino]-1-tert-butoxycarbonyl-2-pyrrolidinylcarbonyl}-1,3-thiazolidine (1.27 g) was obtained as a white powder.

(4) Using the above-mentioned compound (1.27 g), and in the same manner as in Example 70 (2), the title compound (0.850 g) was obtained as a white powder.

$^1$H-NMR(DMSO-$d_6$)δ1.76–1.98(2H,m), 2.01–2.20(2H, m), 2.21–2.35(2H,m), 2.85–3.30(9H,m), 3.11–3.45(2H,m), 3.55–4.10(5H,m), 4.55–4.85(3H,m), 6.49(1H,d,J=8.4 Hz), 7.13(1H,d,J=1.8 Hz), 7.15(1H,dd,J=8.4,1.8 Hz), 9.25(1H, brs).

Example 147

Synthesis of 3-{(2S,4S)-4-[4-(2-oxo-1-benzimidazolinyl)piperidino]-2-pyrrolidinylcarbonyl}-1,3-thiazolidine dihydrochloride (1) Using the title compound (450 mg) of Reference Example 12 and 4-(2-oxo-1-benzimidazolinyl)piperidine (358 mg), and in the same manner as in Example 70 (1), 3-{(2S,4S)-1-tert-butoxycarbonyl-4-[4-(2-oxo-1-benzimidazolinyl)piperidino]-2-pyrrolidinylcarbonyl}-1,3-thiazolidine (752 mg) was obtained as a white solid.

(2) The above-mentioned compound (635 mg) was dissolved in 1.5 mol/L hydrochloric acid-methanol (5 mL), and the mixture was stirred at room temperature for 36 hr. The reaction mixture was concentrated under reduced pressure and ethanol (10 mL) was added to the residue. The precipitate was collected by filtration to give the title compound (352 mg) as a pale-brown powder.

$^1$H-NMR(DMSO-$d_6$)δ1.83–1.98(2H,m), 2.20–2.37(1H, m), 2.72–2.93(2H,m), 2.96–3.45(5H,m), 3.52–4.10(7H,m), 4.46–4.77(4H,m), 7.00(3H,brs), 7.58(1H,brs), 10.97(1H, brs), 12.23(1H,brs).

Example 148

Synthesis of 3-[(2S,4S)-4-(4-anilinopiperidino)-2-pyrrolidinylcarbonyl]-1,3-thiazolidine trihydrochloride (1) Using 1-tert-butoxycarbonylpiperidin-4-one (2.50 g) and aniline (1.24 g), and in the same manner as in Example 144 (1), 4-anilino-1-tert-butoxycarbonylpiperidine (2.35 g) was obtained.

(2) Using the above-mentioned compound (2.34 g), and in the same manner as in Example 144 (2), 4-anilinopiperidine (0.88 g) as obtained.

(3) Using the above-mentioned compound (320 mg) and the title compound (500 mg) of Reference Example 12, and in the same manner as in Example 70 (1), 3-[(2S,4S)-4-(4-anilinopiperidino)-1-tert-butoxycarbonyl-2-pyrrolidinylcarbonyl]-1,3-thiazolidine (679 mg) was obtained as a white solid.

(4) Using the above-mentioned compound (678 mg), and in the same manner as in Example 70 (2), the title compound (469 mg) was obtained as a white powder.

$^1$H-NMR(DMSO-$d_6$)δ1.98–2.45(6H,m), 2.90–3.25(6H, m), 3.30–4.25(5H,m), 4.50–4.85(4H,m), 6.95–7.50(5H,m), 9.22(1H,brs).

Example 149

Synthesis of 3-{(2S,4S)-4-[4-(4-nitrophenyl)aminopiperidino]-2-pyrrolidinylcarbonyl}-1,3-thiazolidine trihydrochloride (1) 4-Amino-1-tert-butoxycarbonylpiperazine (3.00 g), 4-fluoronitrobenzene (2.54 g) and N,N-diisopropylethylamine (8.82 g) were dissolved in N-methyl-2-pyrrolidone (30 mL), and the mixture was stirred at 80° C. for 18 hr. The reaction mixture was added to water and the mixture was extracted with ethyl acetate. The extract was washed with brine and dried. The solvent was evaporated under reduced pressure. The residue was purified by silica gel column chromatography to give 1-tert-butoxycarbonyl-4-(4-nitrophenyl)aminopiperidine (2.55 g) as a white solid.

(2) Using the above-mentioned compound (1.00 g), and in the same manner as in Example 144 (2), 4-(4-nitrophenyl)aminopiperidine (0.563 g) was obtained.

(3) Using the above-mentioned compound (562 mg) and the title compound (761 mg) of Reference Example 12, and in the same manner as in Example 70 (1), 3-{(2S,4S)-1-tert-butoxycarbonyl-4-[4-(4-nitrophenyl)aminopiperidino]-2-pyrrolidinylcarbonyl}-1,3-thiazolidine (780 mg) was obtained as a yellow solid.

(4) Using the above-mentioned compound (778 mg), and in the same manner as in Example 70 (2), the title compound (575 mg) was obtained as a yellow powder.

$^1$H-NMR(DMSO-$d_6$)δ1.85–2.01(2H,m), 2.05–2.24(2H, m), 2.25–2.45(2H,m), 3.00–3.21(5H,m), 3.50–4.20(7H,m), 4.48–4.85(3H,m), 6.72(2H,d,J=9.3 Hz), 8.00(2H,d,J=9.3 Hz), 9.21(1H,brs).

Example 150

Synthesis of 3-{(2S,4S)-4-[4-(4-trifluoromethylphenyl)aminopiperidino]-2-pyrrolidinylcarbonyl}-1,3-thiazolidine trihydrochloride (1) Using 1-tert-butoxycarbonylpiperidin-4-one (2.50 g) and 4-trifluoromethylaniline (2.12 g), and in the same manner as in Example 144 (1), 1-tert-butoxycarbonyl-4-(4-trifluoromethylphenyl)aminopiperidine (2.23 g) was obtained.

(2) Using the above-mentioned compound (2.23 g), and in the same manner as in Example 144 (2), 4-(4-trifluoromethylphenyl)aminopiperidine (1.36 g) was obtained.

(3) Using the above-mentioned compound (447 mg) and the title compound (500 mg) of Reference Example 12, and in the same manner as in Example 70 (1), 3-{(2S,4S)-1-tert-butoxycarbonyl-4-[4-(4-trifluoromethylphenyl)aminopiperidino]-2-pyrrolidinylcarbonyl}-1,3-thiazolidine (775 mg) was obtained as a white solid.

(4) Using the above-mentioned compound (774 mg), and in the same manner as in Example 70 (2), the title compound (514 mg) was obtained as a white powder.

$^1$H-NMR(DMSO-$d_6$)δ1.75–1.95(2H,m), 2.05–2.30(2H, m), 2.25–2.55(2H,m), 2.95–3.30(6H,m), 3.40–4.15(5H,m), 4.50–4.80(4H,m), 6.72(2H,d,J=8.7 Hz), 7.38(2H,d,J=8.7 Hz), 9.21(1H,brs).

Example 151

Synthesis of 3-{(2S,4S)-4-[4-(4-chlorophenyl)aminopiperidino]-2-pyrrolidinylcarbonyl}-1,3-thiazolidine trihydrochloride (1) Using 1-tert-butoxycarbonylpiperidin-4-one (3.00 g) and 4-chloroaniline (1.92 g), and in the same manner as in Example 144 (1), 1-tert-butoxycarbonyl-4-(4-chlorophenyl)aminopiperidine (2.77 g) was obtained.

(2) Using the above-mentioned compound (2.76 g), and in the same manner as in Example 144 (2), 4-(4-chlorophenyl)aminopiperidine (1.07 g) was obtained.

(3) Using the above-mentioned compound (725 mg) and the title compound (500 mg) of Reference Example 12, and in the same manner as in Example 70 (1), 3-{(2S,4S)-1-tert-butoxycarbonyl-4-[4-(4-chlorophenyl)aminopiperidino]-2-pyrrolidinylcarbonyl}-1,3-thiazolidine (553 mg) was obtained as an oil.

(4) Using the above-mentioned compound (550 mg), and in the same manner as in Example 70 (2), the title compound (416 mg) was obtained as a white powder.

$^1$H-NMR(DMSO-$d_6$)δ1.65–1.99(2H,m), 2.05–2.35(3H, m), 2.95–3.25(5H,m), 3.26–4.15(8H,m), 4.48–4.82(3H,m), 6.58–6.85(2H,m), 7.08–7.20(2H,m), 9.22(1H,brs).

Example 152

Synthesis of 3-{(2S,4S)-4-[4-(5-cyano-2-pyridyl)aminopiperidino]-2-pyrrolidinylcarbonyl}-1,3-thiazolidine trihydrochloride (1) Using the title compound (254 mg) of Reference Example 12 and 4-(5-cyano-2-pyridyl)aminopiperidine (155 mg), and in the same manner as in Example 70 (1), 3-{(2S,4S)-1-tert-butoxycarbonyl-4-[4-(5-cyano-2-pyridyl)aminopiperidino]-2-pyrrolidinylcarbonyl}-1,3-thiazolidine (225 mg) was obtained as a white solid.

(2) Using the above-mentioned compound (224 mg), and in the same manner as in Example 70 (2), the title compound (219 mg) was obtained as a white powder.

$^1$H-NMR(DMSO-$d_6$)δ1.80–1.99(2H,m), 2.02–2.20(2H, m), 2.21–2.45(2H,m), 2.98–3.23(5H,m), 3.75–4.20(7H,m), 4.55–4.86(3H,m), 6.55–6.62(1H,m), 7.72(1H,d,J=9.0 Hz), 8.42(1H,s), 9.22(1H,brs).

Example 153

Synthesis of 3-{(2S,4S)-4-[4-(N-methylanilino)piperidino]-2-pyrrolidinylcarbonyl}-1,3-thiazolidine trihydrochloride (1) 3-[(2S,4S)-4-(4-Anilinopiperidino)-1-tert-butoxycarbonyl-2-pyrrolidinylcarbonyl]-1,3-thiazolidine [product of Example 148 (3), 1.18 g] was dissolved in 1,2-dichloroethane (75 mL), and sodium triacetoxyborohydride (5.32 g), acetic acid (0.73 mL) and 37% formaldehyde solution (5.0 mL) were added thereto. The mixture was stirred at room temperature for 12 hr. The reaction mixture was added to water, and the mixture was extracted with chloroform. The extract was dried and the solvent was evaporated under reduced pressure. The residue was purified by silica gel column chromatography to give 3-{(2S,4S)-1-tert-butoxycarbonyl-4-[4-(N-methylanilino)piperidino]-2-pyrrolidinylcarbonyl}-1,3-thiazolidine (967 mg).

(2) Using the above-mentioned compound (965 mg), and in the same manner as in Example 70 (2), the title compound (618 mg) was obtained as a white powder.

$^1$H-NMR(DMSO-$d_6$)δ1.75–2.35(6H,m), 2.78–3.28(9H, m), 3.40–4.15(6H,m), 4.48–4.85(3H,m), 7.20–7.75(5H,m), 9.22(1H,brs), 9.22(1H,brs).

Example 154

Synthesis of 3-{(2S,4S)-4-[4-(4-chlorophenyl)-4-hydroxypiperidino]-2-pyrrolidinylcarbonyl}-1,3-thiazolidine 2 trifluoroacetate (1) The title compound (593 mg) of Reference Example 12 was dissolved in methanol (10 mL), and 4-(4- chlorophenyl)-4-hydroxypiperidine (500 mg), acetic acid (113 μL) and sodium cyanoborohydride (124 mg) were added thereto at room temperature. The mixture was stirred for 21 hr. Water was added to the reaction mixture, and the mixture was extracted with chloroform. The extract was washed with brine and dried. The solvent was evaporated under reduced pressure to give 3-{(2S,4S)-1-tert-butoxycarbonyl-4-[4-(4-chlorophenyl)-4-hydroxypiperidino]-2-pyrrolidinylcarbonyl}-1,3-thiazolidine (428 mg) as a white solid.

(2) Formic acid (10 mL) was added to the above-mentioned compound (427 mg). The mixture was stirred at room temperature for 21 hr. The solvent was evaporated under reduced pressure and the residue was purified by HPLC to give the title compound (78 mg) as a white powder.

$^1$H-NMR(DMSO-$d_6$)δ1.81–1.85(2H,m), 2.05–2.19(3H, m), 3.00–4.06(12H,m), 4.45–4.71(3H,m), 5.60(1H,brs), 7.42–7.50(4H,m).

Example 155

Synthesis of 3-{(2S,4S)-4-[4-ethoxycarbonyl-4-(4-fluorophenyl)piperidino]-2-pyrrolidinylcarbonyl}-1,3-thiazolidine dihydrochloride (1) Using the title compound (450 mg) of Reference Example 12 and 4-ethoxycarbonyl-4-(4-fluorophenyl) piperidine (414 mg), and in the same manner as in Example 70 (1), 3-{(2S,4S)-1-tert-butoxycarbonyl-4-[4-ethoxycarbonyl-4-(4-fluorophenyl)piperidino]-2-pyrrolidinylcarbonyl}-1,3-thiazolidine (742 mg) was obtained as a white solid.

(2) The above-mentioned compound (321 mg) was dissolved in ethanol (4 mL), and 4.6 mol/L hydrochloric acid-ethanol (1 mL) was added thereto. The mixture was stirred at room temperature for 18 hr. The precipitate was collected by filtration to give the title compound (218 mg) as a white powder.

$^1$H-NMR(DMSO-$d_6$)δ1.14(3H,t,J=6.8 Hz), 2.05–2.28 (2H,m), 2.58–2.67(2H,m), 2.83–3.16(5H,m), 3.5–4.15(10H, m), 4.42–4.73(3H,m), 7.24(2H,t,J=8.8 Hz), 7.34(2H,brs), 9.1(1H,brs), 10.35(1H,brs), 11.95(1H,brs).

Example 156

Synthesis of 3-{(2S,4S)-4-[1-(4-nitrophenyl)-4-piperidinyl]amino-2-pyrrolidinylcarbonyl}-1,3-thiazolidine trihydrochloride (1) 1,4-Dioxa-8-azaspiro[4,5]decane (7.88 g) was dissolved in N-methyl-2-pyrrolidine (50 mL), and diisopropylethylamine (9.5.8 mL) and 4-fluoronitrobenzene (7.06 g) were successively added. The mixture was stirred at room temperature for 2 hr. The reaction mixture was added to iced water, and the precipitated solid was collected by filtration to give N-(4-nitrophenyl)-4-piperidone ethylene ketal (10.6 g) as a yellow powder.

(2) The above-mentioned compound (9.25 g) was suspended in acetone (100 mL), and p-toluenesulfonic acid monohydrate (7.32 g) and hydrochloric acid (20 mL) were successively added. The mixture was stirred at room temperature for 18 hr. Aqueous sodium hydroxide solution was added to the reaction mixture and the precipitate was collected by filtration to give [1-(4-nitrophenyl)-4-piperidinyl] amine (6.48 g) as a yellow powder.

(3) Using the above-mentioned compound (6.17 g) and the title compound (4.22 g) of Reference Example 10, and in the same manner as in Example 70 (1), 3-{(2S,4S)-1-tert-butoxycarbonyl-4-[1-(4-nitrophenyl)-4-piperidinyl]amino-2-pyrrolidinylcarbonyl}-1,3-thiazolidine (7.26 g) was obtained.

(4) The above-mentioned compound (524 mg) was dissolved in ethyl acetate (2.07 mL), and 4 mol/L hydrochloric acid-ethyl acetate (1.04 mL) was added thereto. The mixture was stirred at room temperature for 18 hr. The precipitate was collected by filtration to give the title compound (406 mg) as a yellow powder.

$^1$H-NMR(DMSO-$d_6$)δ1.53–1.79(2H,m), 2.02–2.25(3H, m), 2.88–3.01(5H,m), 3.35–3.96(5H,m), 3.96–4.28(3H,m), 4.39–4.78(3H,m), 7.08(2H,d,J=9.6 Hz), 8.07(2H,d,J=9.3 Hz).

Example 157

Synthesis of 3-{(2S,4S)-4-{N-methyl-N-[1-(4-nitrophenyl)-4-piperidinyl]amino}-2-pyrrolidinylcarbonyl}-1,3-thiazolidine dihydrochloride (1) Using 3-{(2S,4S)-1-tert-butoxycarbonyl-4-[1-(4-nitrophenyl)-4-piperidinyl]amino-2-pyrrolidinylcarbonyl}-1,3-thiazolidine [product of Example 156 (3), 1.01 g], and in the same manner as in Example 64 (1), 3-{(2S,4S)-1-tert-butoxycarbonyl-4-{N-methyl-N-[1-(4-nitrophenyl)-4-piperidinyl]amino}-2-pyrrolidinylcarbonyl}-1,3-thiazolidine (1.04 g) was obtained.

(2) The above-mentioned compound (1.04 g) was dissolved in methanol (4 ML), and 4 mol/L hydrochloric acid-1,4-dioxane (2 mL) was added thereto. The mixture was stirred at room temperature for 18 hr. The reaction mixture was concentrated under reduced pressure and the obtained solid was washed with ethanol to give the title compound (0.555 g) as a yellow powder.

$^1$H-NMR(DMSO-$d_6$)δ1.50–1.90(2H,m), 1.95–2.40(3H, m), 2.68(3H,s), 2.80–3.25(5H,m), 3.25–3.98(5H,m), 4.02–4.37(3H,m), 4.40–4.75(3H,m), 7.09(2H,d,J=9.6 Hz), 8.07(2H,d,J=9.3 Hz).

Example 158

Synthesis of 3-{(2s,4s)-4-{N-(4-cyanophenylmethyl)-N-[1-(4-nitrophenyl)-4-piperidinyl]amino}-2-pyrrolidinylcarbonyl}-1,3-thiazolidine dihydrochloride (1) The product (1.01 g) of Example 156 (3) was dissolved in N-methyl-2-pyrrolidone (6 mL), and 4-cyanobenzyl bromide (0.392 g) and diisopropylethylamine (1.05 mL) were added thereto. The mixture was stirred at 80° C. for 8 hr with heating. The reaction mixture was added to saturated aqueous sodium hydrogencarbonate solution and the mixture was extracted with ethyl acetate. The extract was dried and the solvent was evaporated under reduced pressure. The residue was purified by silica gel chromatography to give 3-{(2S,4S)-1-tert-butoxycarbonyl-4-{N-(4-cyanophenylmethyl)-N-[1-(4-nitrophenyl)-4-piperidinyl]amino}-2-pyrrolidinylcarbonyl}-1,3-thiazolidine (0.685 g) as a yellow oil.

(2) The above-mentioned compound (1.04 g) was dissolved in ethyl acetate (4.41 mL), and 4 mol/L hydrochloric acid-ethyl acetate (2.20 mL) was added thereto. The mixture was stirred at room temperature for 18 hr. The reaction mixture was added to saturated aqueous sodium hydrogencarbonate solution and the mixture was extracted with chloroform. The extract was dried and concentrated under reduced pressure. The residue was purified by silica gel chromatography and was dissolved in chloroform. 4 mol/L Hydrochloric acid-ethyl acetate (0.309 mL) was added and the precipitate was collected by filtration to give the title compound (0.249 g) as a yellow powder.

$^1$H-NMR(DMSO-$d_6$)δ1.34–2.35(5H,m), 2.45–3.20(7H, m), 3.20–4.25(8H,m), 4.35–4.80(3H,m), 7.01(2H,d,J=9.6 Hz), 7.50–7.90(4H,m), 8.03(2H,d,J=9.3 Hz), 8.87(1H,brs), 10.24(1H,brs).

Example 159

Synthesis of 3-[(2S,4S)-4-(4-methyl-1-piperazinyl)-2-pyrrolidinylcarbonyl]-1,3-thiazolidine trihydrochloride The title compound (450 mg) of Reference Example 12, 1-methylpiperazine (0.20 mL) and acetic acid (0.09 mL) were dissolved in 1,2-dichloroethane (8 mL), and sodium triacetoxyborohydride (636 mg) was added thereto. The mixture was stirred at room temperature for 30 hr. Saturated aqueous sodium hydrogencarbonate solution was added to the reaction mixture and the mixture was extracted with ethyl acetate. The extract was washed with brine and dried. The solvent was evaporated under reduced pressure and the residue was purified by silica gel chromatography to give 3-[(2S,4S)-1-tert-butoxycarbonyl-4-(4-methyl-1-piperazinyl)-2-pyrrolidinylcarbonyl]-1,3-thiazolidine (526 mg) as a white solid.

(2) The above-mentioned compound (522 mg) was dissolved in methanol (25 mL), and 1.5 mol/L hydrochloric acid-methanol (25 mL) was added thereto. The mixture was stirred at room temperature for 38 hr. The reaction mixture was concentrated under reduced pressure and ethyl acetate was added to the residue. The precipitate was collected by filtration to give the title compound (355 mg) as a white powder.

$^1$H-NMR(DMSO-$d_6$)δ1.88–2.03(1H,m), 2.79(3H,s), 2.80–2.94(1H,m), 2.98–3.93(15H,m), 4.43–4.77(3H,m), 9.10(1H,brs), 10.78(1H,brs), 11.5(1H,brs).

Example 160

Synthesis of 3-[(2S,4S)-4-(4-phenyl-1-piperazinyl)-2-pyrrolidinylcarbonyl]-1,3-thiazolidine trihydrochloride (1) Using the title compound (450 mg) and 1-phenylpiperazine (0.27 mL), and in the same manner as in Example 70 (1), 3-[(2S,4S)-1-tert-butoxycarbonyl-4-(4-phenyl-1-piperazinyl)-2-pyrrolidinylcarbonyl]-1,3-thiazolidine (566 mg) was obtained as a white solid.

(2) The above-mentioned compound (442 mg) was dissolved in 1.5 mol/L hydrochloric acid-methanol (10 mL), and the mixture was stirred at room temperature for 20 hr. the reaction mixture was concentrated under reduced pressure and ethyl acetate was added to the residue. The precipitate was collected by filtration to give the title compound (418 mg) as a white powder.

$^1$H-NMR(DMSO-$d_6$)δ2.35(1H,q,J=11.2 Hz), 2.94–3.95 (15H,m), 4.03–4.18(1H,m), 4.44–4.77(3H,m), 6.89(1H,t,J=7.3 Hz), 7.03(2H,d,J=8.0 Hz), 7.28(2H,dd,J=8.0,7.3 Hz), 9.23(1H,brs), 10.94(1H,brs).

Example 161

Synthesis of 1-[(2S,4S)-4-(4-phenyl-1-piperazinyl)-2-pyrrolidinylcarbonyl]pyrrolidine trihydrochloride (1) Using the title compound (565 mg) of Reference Example 14 and 1-phenylpiperazine (0.37 mL), and in the same manner as in Example 70 (1), 1-[(2S,4S)-1-tert-butoxycarbonyl-4-(4-phenyl-1-piperazinyl)-2-pyrrolidinylcarbonyl]pyrrolidine (832 mg) was obtained as a white solid.

(2) The above-mentioned compound (700 mg) was dissolved in methanol (50 mL) and chloroform (50 mL), and 1.5 mol/L hydrochloric acid-methanol (50 mL) was added thereto. The mixture was stirred at room temperature for 5 days. The reaction mixture was concentrated under reduced pressure and methanol was added to the residue. The precipitated solid was collected by filtration to give the title compound (632 mg) as a white powder.

$^1$H-NMR(DMSO-$d_6$)δ1.73–1.98(4H,m), 2.29(1H,q,J=11.6 Hz), 2.93–4.18(16H,m), 4.45–4.57(1H,m), 6.89(1H,t, J=8.0 Hz), 7.03(2H,d,J=8.0 Hz), 7.28(2H,t,J=8.0 Hz), 9.13 (1H,brs), 10.89(1H,brs).

Example 162

Synthesis of 3-[(2S,4S)-4-(4-benzyl-1-piperazinyl)-2-pyrrolidinylcarbonyl]-1,3-thiazolidine trihydrochloride (1) The title compound (437 mg) of Reference Example 12, 1-benzylpiperazine (303 mg) and acetic acid (0.085 mL) were dissolved in 1,2-dichloroethane (6 mL), and sodium triacetoxyborohydride (650 mg) was added thereto. The mixture was stirred at room temperature for 5 hr. Saturated aqueous sodium hydrogencarbonate solution was added to the reaction mixture and the mixture was extracted with ethyl acetate. The extract was washed with brine and dried. The solvent was evaporated under reduced pressure and the residue was purified by silica gel chromatography to give 3-[(2S,4S)-4-(4-benzyl-1-piperazinyl)-1-tert-butoxycarbonyl-2-pyrrolidinylcarbonyl]-1,3-thiazolidine (556 mg) as a white solid.

(2) The above-mentioned compound (546 mg) was dissolved in methanol (16 mL), and 4 mol/L hydrochloric acid-1,4-dioxane (8 mL) was added thereto. The mixture was stirred at room temperature for 15 hr. The precipitate was collected by filtration to give the title compound (412 mg) as a white powder.

$^1$H-NMR(DMSO-$d_6$)δ1.79–1.89(1H,m), 2.76–2.84(1H, m), 2.90–3.90(15H,m), 4.35(2H,s), 4.45–4.73(3H,m), 7.45–7.47(3H,m), 7.62–7.65(2H,m), 8.99(1H,brs), 10.45 (1H,brs).

Example 163

Synthesis of 3-{(2s,4S)-4-[4-(diphenylmethyl)-1-piperazinyl)-2-pyrrolidinylcarbonyl]-1,3-thiazolidine trihydrochloride (1) Using the title compound (402 mg) of Reference Example 12 and 1-diphenylmethylpiperazine (405 mg), and in the same manner as in Example 162 (1), 3-{(2S,4S)-1-tert-butoxycarbonyl-4-[4-(diphenylmethyl)-1-piperazinyl]-2-pyrrolidinylcarbonyl}-1,3-thiazolidine (470 mg) was obtained as a white powder.

(2) Using the above-mentioned compound (470 mg), and in the same manner as in Example 162 (2), the title compound (449 mg) was obtained as a white powder.

$^1$H-NMR(DMSO-$d_6$)δ1.94–2.01(1H,m), 2.79–2.85(1H, m), 3.03–3.92(15H,m), 4.43–4.73(3H,m), 4.48(1H,brs), 7.30–7.44(6H,m), 7.88(4H,brs), 9.09(1H,brs), 10.50(1H, brs).

Example 164

Synthesis of 3-{(2S,4S)-4-[4-(4-cyanophenyl)-1-piperazinyl]-2-pyrrolidinylcarbonyl}-1,3-thiazolidine trihydrochloride (1) Using the title compound (485 mg) of Reference Example 12 and 1-(4-cyanophenyl)piperazine (335 mg), and in the same manner as in Example 70 (1), 3-{(2S,4S)-1-tert-butoxycarbonyl-4-[4-(4-cyanophenyl)-1-piperazinyl]-2-pyrrolidinylcarbonyl)-1,3-thiazolidine (492 mg) was obtained as a white powder.

(2) Formic acid (8 mL) was added to the above-mentioned compound (492 mg). The mixture was stirred at room temperature for 2 days. The solvent was evaporated under reduced pressure, and saturated aqueous sodium hydrogencarbonate solution was added to the residue. The mixture was extracted with chloroform. The extract was washed with brine and dried. The solvent was evaporated under reduced pressure, and the residue was purified by silica gel chromatography. 4 mol/L Hydrochloric acid-ethyl acetate was added and the precipitate was collected by filtration to give the title compound (78 mg) as a white powder.

$^1$H-NMR(500 MHz,DMSO-$d_6$)δ2.20–2.27(1H,m), 2.95–3.16(3H,m), 3.10–4.05(13H,m), 4.47–4.74(3H,m), 7.13(1H,d,J=8.8 Hz), 7.65(1H,d,J=8.8 Hz), 9.13(1H,brs), 10.61(1H,brs).

Example 165

Synthesis of 3-{(2S,4S)-4-[4-(3-trifluoromethylphenyl)-1-piperazinyl]-2-pyrrolidinylcarbonyl}-1,3-thiazolidine trihydrochloride (1) Using the title compound (411 mg) of Reference Example 12 and 1-(3-trifluoromethylphenyl)piperazine (378 mg), and in the same manner as in Example 162 (1), 3-{(2S,4S)-1-tert-butoxycarbonyl-4-[4-(3-trifluoromethylphenyl)-1-piperazinyl]-2-pyrrolidinylcarbonyl}-1,3-thiazolidine (700 mg) was obtained as a white powder.

(2) Using the above-mentioned compound (700 mg), and in the same manner as in Example 162 (2), the title compound (553 mg) was obtained as a white powder.

$^1$H-NMR(DMSO-$d_6$)δ2.25–2.36(1H,m), 3.00–4.10(16H, m), 4.47–4.77(3H,m), 7.17(1H,d,J=7.8 Hz), 7.26–7.33(2H, m), 7.48(1H,t,J=7.8 Hz), 9.25(1H,brs), 10.82(1H,brs).

Example 166

Synthesis of 3-{(2S,4S)-4-[4-(4-methoxyphenyl)-1-piperazinyl]-2-pyrrolidinylcarbonyl}-1,3-thiazolidine trihydrochloride (1) Using the title compound (513 mg) of Reference Example 12 and 1-(4-methoxyphenyl)piperazine (394 mg), and in the same manner as in Example 162 (1), 3-{(2S,4S)-1-tert-butoxycarbonyl-4-[4-(4-methoxyphenyl)-1-piperazinyl]-2-pyrrolidinylcarbonyl}-1,3-thiazolidine (536 mg) was obtained as a white powder.

(2) Using the above-mentioned compound (530 mg), and in the same manner as in Example 162 (2), the title compound (567 mg) was obtained as a white powder.

$^1$H-NMR(DMSO-$d_6$)δ2.28–2.39(1H,m), 3.00–3.17(3H, m), 3.68–4.12(13H,m), 3.71(3H,s), 4.47–4.77(3H,m), 6.89 (2H,d,J=9.0 Hz), 7.05(2H,d,J=9.0 Hz), 9.22(1H,brs), 11.00 (1H,brs).

Example 167

Synthesis of 3-{(2S,4S)-4-[4-(4-hydroxyphenyl)-1-piperazinyl]-2-pyrrolidinylcarbonyl}-1,3-thiazolidine trihydrochloride (1) Using the title compound (515 mg) of Reference Example 12 and 1-(4-hydroxyphenyl)piperazine (366 mg) and in the same manner as in Example 70 (1), 3-{(2S,4S)-1-tert-butoxycarbonyl-4-[4-(4-hydroxyphenyl)-1-piperazinyl]-2-pyrrolidinylcarbonyl}-1,3-thiazolidine (260 mg) was obtained as a pale-brown solid.

(2) The above-mentioned compound (259 mg) was dissolved in dichloromethane (10 mL), and trifluoroacetic acid (3 mL) was added thereto. The mixture was stirred at room temperature for 16 hr. The reaction mixture was added to saturated aqueous sodium hydrogencarbonate solution, and the mixture was extracted with chloroform. The extract was washed with brine and dried. The solvent was evaporated under reduced pressure, and the residue was purified by silica gel column chromatography. Thereto was added 4 mol/L hydrochloric acid-ethyl acetate and the precipitate was collected by filtration to give the title compound (15 mg) as a brown powder.

$^1$H-NMR(DMSO-$d_6$)δ2.18–2.28(1H,m), 2.97–4.00(16H, m), 4.46–4.75(3H,m), 6.73(2H,d,J=8.7 Hz), 6.96–6.99(2H, m), 9.18(1H,brs), 10.51(1H,brs).

Example 168

Synthesis of 3-{(2S,4S)-4-[4-(2-nitrophenyl)-1-piperazinyl]-2-pyrrolidinylcarbonyl}-1,3-thiazolidine dihydrochloride (1) Piperazine (12.9 g) was dissolved in DMF (100 mL), and a solution of 2-fluoronitrobenzene (7.06 g) in DMF (30 mL) was added dropwise. The mixture was stirred at room temperature for 3 hr. The reaction mixture was added to water and the mixture was extracted with ethyl acetate. The extract was washed with water and dried. The solvent was evaporated to give 1-(2-nitrophenyl)piperazine (7.7 g) as a red oil.

(2) Using the above-mentioned compound (414 mg) and the title compound (601 mg) of Reference Example 12, and in the same manner as in Example 70 (1), 3-{(2S,4S)-1-tert-butoxycarbonyl-4-[4-(2-nitrophenyl)-1-piperazinyl]-2-pyrrolidinylcarbonyl}-1,3-thiazolidine (690 mg) was obtained as a red oil.

(3) Using the above-mentioned compound (690 mg) and in the same manner as in Example 161 (2), the title compound (433 mg) was obtained as a yellow powder.

$^1$H-NMR(DMSO-$d_6$)δ2.19–2.40(1H,m), 2.90–4.24(16H, m), 4.44–4.80(3H,m), 7.27(1H,t,J=7.5 Hz), 7.41(1H,d,J=7.8 Hz), 7.68(1H,t,J=7.2 Hz), 7.92(1H,d,J=8.1 Hz).

Example 169

Synthesis of 3-{(2S,4S)-4-[4-(4-nitrophenyl)-1-piperazinyl]-2-pyrrolidinylcarbonyl}-1,3-thiazolidine trihydrochloride (1) Using the title compound (465 mg) of Reference Example 12 and 1-(4-nitrophenyl)piperazine (385 mg), and in the same manner as in Example 162 (1), 3-{(2S,4S)-1-tert-butoxycarbonyl-4-[4-(4-nitrophenyl)-1-piperazinyl]-2-pyrrolidinylcarbonyl}-1,3-thiazolidine (688 mg) was obtained as a yellow powder: $^1$H-NMR($CDCl_3$)δ1.41(4.5H, s), 1.46(4.5H,s), 1.79–1.99(1H,m), 2.38–2.52(1H,m), 2.52–2.74(4H,m), 2.75–3.22(3H,m), 3.25–3.50(5H,m), 3.60–4.20(3H,m), 4.36–4.82(3H,m), 6.82(2H,d,J=9.4 Hz), 8.12(2H,d,J=9.4 Hz).

(2) Using the above-mentioned compound (560 mg), and in the same manner as in Example 162 (2), the title compound (511 mg) was obtained as a yellow powder.

$^1$H-NMR(DMSO-$d_6$)δ2.23–2.32(1H,m), 2.95–3.17(3H, m), 3.57–4.04(13H,m), 4.47–4.76(3H,m), 7.15(2H,d,J=9.3

Hz), 8.12(2H,d,J=9.3 Hz), 9.19(1H,brs), 10.68(1H,brs);[.]$_D^{24}$-35(c1.0,$H_2O$).

Example 170

Synthesis of 3-{(2S,4S)-4-[4-(4-fluorophenyl)-1-piperazinyl]-2-pyrrolidinylcarbonyl}-1,3-thiazolidine trihydrochloride (1) Using the title compound (409 mg) of Reference Example 12 and 1-(4-fluorophenyl)piperazine (300 mg), and in the same manner as in Example 162 (1), 3-{(2S,4S)-1-tert-butoxycarbonyl-4-[4-(4-fluorophenyl)-1-piperazinyl]-2-pyrrolidinylcarbonyl}-1,3-thiazolidine (404 mg) was obtained as a white solid.

(2) Using the above-mentioned compound (402 mg), and in the same manner as in Example 162 (2), the title compound (371 mg) was obtained as a white powder.

$^1$H-NMR(DMSO-$d_6$)δ2.28–2.39(1H,m), 3.00–4.10(16H, m), 4.47–4.76(3H,m), 7.02–7.14(4H,m), 9.20(1H,brs), 10.79(1H,brs).

Example 171

Synthesis of 3-{(2S,4S)-4-[4-(2-chlorophenyl)-1-piperazinyl]-2-pyrrolidinylcarbonyl}-1,3-thiazolidine dihydrochloride (1) Using the title compound (430 mg) of Reference Example 12 and 1-(2-chlorophenyl)piperazine (338 mg), and in the same manner as in Example 162 (1), 3-{(2S,4S)-1-tert-butoxycarbonyl-4-[4-(2-chlorophenyl)-1-piperazinyl]-2-pyrrolidinylcarbonyl}-1,3-thiazolidine (687 mg) was obtained as a white powder.

(2) Using the above-mentioned compound (687 mg), and in the same manner as in Example 162 (2), the title compound (531 mg) was obtained as a white powder.

$^1$H-NMR(DMSO-$d_6$)δ2.28–2.38(1H,m), 2.97–4.15(16H, m), 4.47–4.77(3H,m), 7.12(1H,td,J=4.8,1.5 Hz), 7.21(1H, dd,J=4.8,1.5 Hz), 7.35(1H,td,J=8.1,1.5 Hz), 7.46(1H,dd,J=8.1,1.5 Hz), 9.30(1H,brs), 10.15(1H,brs).

Example 172

Synthesis of 3-{(2S,4S)-4-[4-(3-chlorophenyl)-1-piperazinyl]-2-pyrrolidinylcarbonyl}-1,3-thiazolidine trihydrochloride (1) Using the title compound (476 mg) of Reference Example 12 and 1-(3-chlorophenyl)piperazine (374 mg), and in the same manner as in Example 162 (1), 3-{(2S,4S)-1-tert-butoxycarbonyl-4-[4-(3-chlorophenyl)-1-piperazinyl]-2-pyrrolidinylcarbonyl}-1,3-thiazolidine (495 mg) was obtained as a white solid.

(2) Using the above-mentioned compound (494 mg), and in the same manner as in Example 162 (2), the title compound (426 mg) was obtained as a white powder.

$^1$H-NMR(DMSO-$d_6$)δ2.22–2.32(1H,m), 2.97–4.06(16H, m), 4.47–4.76(3H,m), 6.88(1H,dd,J=8.1,1.8 Hz), 6.98(1H, dd,J=8.1,1.8 Hz), 7.07(1H,d,J=1.8 Hz), 7.27(1H,t,J=8.1 Hz), 9.24(2H,brs);

Example 173

Synthesis of 3-{(2S,4S)-4-[4-(4-chlorophenyl)-1-piperazinyl]-2-pyrrolidinylcarbonyl}-1,3-thiazolidine trihydrochloride (1) Using the title compound (473 mg) of Reference Example 12 and 1-(4-chlorophenyl)piperazine (372 mg), and in the same manner as in Example 162 (1), 3-{(2S,4S)-1-tert-butoxycarbonyl-4-[4-(4-chlorophenyl)-1-piperazinyl]-2-pyrrolidinylcarbonyl}-1,3-thiazolidine (564 mg) was obtained as a white solid.

(2) Using the above-mentioned compound (554 mg), and in the same manner as in Example 162 (2), the title compound (533 mg) was obtained as a white powder.

$^1$H-NMR(DMSO-$d_6$)δ2.25–2.35(1H,m), 2.98–3.94(15H, m), 4.04–4.10(1H,m), 4.45–4.75(3H,m), 7.05(2H,d,J=9.0 Hz), 7.30(2H,d,J=9.0 Hz), 9.19(1H,brs), 10.63(1H,brs).

Example 174

Synthesis of 3-{(2S,4S)-4-[4-(4-bromophenyl)-1-piperazinyl]-2-pyrrolidinylcarbonyl}-1,3-thiazolidine trihydrochloride (1) Using the title compound (332 mg) of Reference Example 12 and 1-(4-bromophenyl)piperazine (300 mg), and in the same manner as in Example 162 (1), 3-{(2S,4S)-1-tert-butoxycarbonyl-4-[4-(4-bromophenyl)-1-piperazinyl]-2-pyrrolidinylcarbonyl}-1,3-thiazolidine (390 mg) was obtained as a white solid.

(2) Using the above-mentioned compound (388 mg), and in the same manner as in Example 162 (2), the title compound (341 mg) was obtained as a white powder.

$^1$H-NMR(500 MHz,DMSO-$d_6$)δ2.18–2.27(1H,m), 2.95–4.06(16H,m), 4.47–4.74(3H,m), 6.98(2H,d,J=8.8 Hz), 7.40(2H,d,J=8.8 Hz), 9.15(1H,brs), 10.50(1H,brs).

Example 175

Synthesis of 3-{(2S,4s)-4-[4-(3,4-dicyanophenyl)-1-piperazinyl]-2-pyrrolidinylcarbonyl}-1,3-thiazolidine trihydrochloride (1) Using the title compound (561 mg) of Reference Example 12 and 1-(3,4-dicyanophenyl)piperazine (475 mg), and in the same manner as in Example 70 (1), 3-{(2S,4S)-1-tert-butoxycarbonyl-4-[4-(3,4-dicyanophenyl)-1-piperazinyl]-2-pyrrolidinylcarbonyl}-1,3-thiazolidine (945 mg) was obtained as a pale-yellow powder.

(2) Using the above-mentioned compound (935 mg), and in the same manner as in Example 167 (2), the title compound (508 mg) was obtained as a pale-yellow powder.

$^1$H-NMR(DMSO-$d_6$)δ2.18–2.28(1H,m), 2.93–3.90(16H, m), 4.46–4.75(3H,m), 7.41(1H,dd,J=9.0,2.7 Hz), 7.72(1H, d,J=2.7 Hz), 7.90(1H,d,J=9.0 Hz), 9.19(1H,brs), 10.63(1H, brs).

Example 176

Synthesis of 3-{(2S,4S)-4-[4-(3,4-dichlorophenyl)-1-piperazinyl]-2-pyrrolidinylcarbonyl}-1,3-thiazolidine trihydrochloride (1) Using the title compound (540 mg) of Reference Example 12 and 1-(3,4-dichlorophenyl)piperazine (500 mg), and in the same manner as in Example 162 (1), 3-3-{(2S, 4S)-1-tert-butoxycarbonyl-4-[4-(3,4-dichlorophenyl)-1-piperazinyl]-2-pyrrolidinylcarbonyl}-1,3-thiazolidine (540 mg) was obtained as a white solid.

(2) Using the above-mentioned compound (540 mg), and in the same manner as in Example 162 (2), the title compound (503 mg) was obtained as a white solid.

$^1$H-NMR(DMSO-$d_6$)δ2.22–2.32(1H,m), 2.97–4.06(16H, m), 4.47–4.76(3H,m), 7.03(1H,dd,J=9.0,2.7 Hz), 7.27(1H, d,J=2.7 Hz), 7.46(1H,d,J=9.0 Hz), 9.20(1H,brs), 10.70(1H, brs).

Example 177

Synthesis of 3-{(2S,4S)-4-[4-(3,5-dichlorophenyl)-1-piperazinyl]-2-pyrrolidinylcarbonyl}-1,3-thiazolidine trihydrochloride (1) Using the title compound (481 mg) of Reference Example 12 and 1-(3,5-dichlorophenyl)piperazine (444 mg), and in the same manner as in Example 162 (1), 3-{(2S,4S)-1-tert-butoxycarbonyl-4-[4-(3,5-dichlorophenyl)-1-piperazinyl]-2-pyrrolidinylcarbonyl}-1,3-thiazolidine (523 mg) was obtained as a white solid.

(2) Using the above-mentioned compound (520 mg), and in the same manner as in Example 162 (2), the title compound (442 mg) was obtained as a white powder.

$^1$H-NMR(DMSO-$d_6$)δ2.20–2.30(1H,m), 2.97–4.06(16H, m), 4.47–4.75(3H,m), 6.97(1H,s), 7.07(2H,s), 9.20(1H,brs), 10.60(1H,brs).

Example 178

Synthesis of 3-{(2S,4S)-4-[4-(4-nitro-1-naphthyl)-1-piperazinyl]-2-pyrrolidinylcarbonyl}-1,3-thiazolidine dihydrochloride (1) Using the title compound (400 mg) of Reference Example 12 and 1-(4-nitro-1-naphthyl)piperazine (414 mg), and in the same manner as in Example 162 (1), 3-{(2S,4S)-1-tert-butoxycarbonyl-4-[4-(4-nitro-1-naphthyl)-1-piperazinyl]-2-pyrrolidinylcarbonyl}-1,3-thiazolidine (600 mg) was obtained as a yellow powder.

(2) Using the above-mentioned compound (596 mg), and in the same manner as in Example 162 (2), the title compound (449 mg) was obtained as a pale-yellow powder.

$^1$H-NMR(DMSO-$d_6$)δ2.29–2.39(1H,m), 3.00–3.18(3H, m), 3.57–4.17(13H,m), 4.48–4.78(3H,m), 7.29(1H,d,J=8.7 Hz), 7.73(1H,t,J=7.8 Hz), 7.83(1H,t,J=7.8 Hz), 8.27(1H,d, J=8.4 Hz), 8.36(1H,d,J=8.4 Hz), 8.52(1H,d,J=8.7 Hz), 9.20 (1H,brs), 10.60(1H,brs).

Example 179

Synthesis of 3-{(2S,4S)-4-[4-(2-pyridyl)-1-piperazinyl]-2-pyrrolidinylcarbonyl}-1,3-thiazolidine trihydrochloride (1) Using the title compound (426 mg) of Reference Example 12 and 1-(2-pyridyl)piperazine (0.26 mL), and in the same manner as in Example 162 (1), 3-{(2S,4S)-1-tert-butoxycarbonyl-4-[4-(2-pyridyl)-1-piperazinyl]-2-pyrrolidinylcarbonyl}-1,3-thiazolidine (375 mg) was obtained as a white solid.

(2) Using the above-mentioned compound (374 mg), and in the same manner as in Example 162 (2), the title compound (466 mg) was obtained as a white powder.

$^1$H-NMR(DMSO-$d_6$)δ2.26–2.37(1H,m), 3.00–3.16(3H, m), 3.43–4.06(13H,m), 4.47–4.78(3H,m), 6.98(1H,t,J=6.0 Hz), 7.35(1H,d,J=9.0 Hz), 7.96(1H,td,J=9.0,1.5 Hz), 8.13 (1H,dd,J=6.0,1.5 Hz), 9.23(1H,brs), 10.98(1H,brs).

Example 180

Synthesis of 3-{(2S,4S)-4-[4-(4-pyridyl)-1-piperazinyl]-2-pyrrolidinylcarbonyl}-1,3-thiazolidine trihydrochloride (1) Using the title compound (601 mg) of Reference Example 12 and 1-(4-pyridyl)piperazine (326 mg), and in the same manner as in Example 70 (1), 3-{(2S,4S)-1-tert-butoxycarbonyl-4-[4-(4-pyridyl)-1-piperazinyl]-2-pyrrolidinylcarbonyl}-1,3-thiazolidine (366 mg) was obtained.

(2) Using the above-mentioned compound (366 mg), and in the same manner as in Example 161 (2), the title compound (133 mg) was obtained as a white powder.

$^1$H-NMR(DMSO-$d_6$)δ2.03–2.30(1H,m), 2.79–4.30(16H, m), 4.40–4.80(3H,m), 7.32(2H,d,J=7.5 Hz), 8.34(2H,d,J=7.2 Hz), 9.15(1H,brs), 10.80(1H,brs), 14.00(1H,brs).

Example 181

Synthesis of 3-{(2S,4S)-4-[4-(4-cyano-2-pyridyl)-1-piperazinyl]-2-pyrrolidinylcarbonyl}-1,3-thiazolidine trihydrochloride (1) Using the title compound (494 mg) of Reference Example 12 and 1-(4-cyano-2-pyridyl)piperazine (371 mg), and in the same manner as in Example 154 (1), 3-{(2S,4S)-1-tert-butoxycarbonyl-4-[4-(4-cyano-2-pyridyl)-1-piperazinyl]-2-pyrrolidinylcarbonyl}-1,3-thiazolidine (431 mg) was obtained as a white solid.

(2) Using the above-mentioned compound (424 mg), and in the same manner as in Example 167 (2), the title compound (194 mg) was obtained as a pale-yellow powder.

$^1$H-NMR(500 MHz,DMSO-$d_6$)δ2.32–2.39(1H,m), 3.00–3.16(3H,m), 3.25–4.07(13H,m), 4.48–4.75(3H,m), 7.10(1H,dd,J=5.1,0.8 Hz), 7.50(1H,d,J=0.8 Hz), 8.36(1H,d, J=5.1 Hz), 9.22(1H,brs), 10.91(1H,brs).

Example 182

Synthesis of 1-{(2S,4S)-4-[4-(4-cyano-2-pyridyl)-1-piperazinyl]-2-pyrrolidinylcarbonyl}pyrrolidine trihydrochloride (1) Using the title compound (527 mg) of Reference Example 14 and 1-(4-cyano-2-pyridyl)piperazine (422 mg), and in the same manner as in Example 70 (1), 1-{(2S,4S)-1-tert-butoxycarbonyl-4-[4-(4-cyano-2-pyridyl)-1-piperazinyl]-2-pyrrolidinylcarbonyl}pyrrolidine (502 mg) was obtained as a pale-yellow solid.

(2) Using the above-mentioned compound (491 mg), and in the same manner as in Example 167 (2), the title compound (134 mg) was obtained as a pale-yellow powder.

$^1$H-NMR(500 MHz,DMSO-$d_6$)δ1.83–1.96(4H,m), 2.25–2.30(1H,m), 2.98–3.02(1H,m), 3.20–3.56(10H,m), 3.70–3.72(2H,m), 4.04–4.08(1H,m), 4.30–4.54(2H,m), 4.50–4.54(1H,m), 7.10(1H,dd,J=5.1,0.8 Hz), 7.50(1H,d,J=0.8 Hz), 8.36(1H,d,J=5.1 Hz), 9.12(1H,brs), 10.73(1H,brs).

Example 183

Synthesis of 3-{(2S,4S)-4-[4-(5-cyano-2-pyridyl)-1-piperazinyl]-2-pyrrolidinylcarbonyl}-1,3-thiazolidine trihydrochloride (1) Using the title compound (740 mg) of Reference Example 12 and 1-(5-cyano-2-pyridyl)piperazine (516 mg), and in the same manner as in Example 154 (1), 3-{(2S,4S)-1-tert-butoxycarbonyl-4-[4-(5-cyano-2-pyridyl)-1-piperazinyl]-2-pyrrolidinylcarbonyl}-1,3-thiazolidine (772 mg) was obtained as a white powder.

$^1$H-NMR($CDCl_3$)δ1.41(4.5H,s), 1.46(4.5H,s), 1.86–1.98 (1H,m), 2.45–2.60(5H,m), 2.83–3.25(3H,m), 3.31–3.39(1H, m), 3.60–3.79(5H,m), 3.81–3.99(2H,m), 4.40–4.85(3H,m), 6.58(1H,d,J=9.0 Hz), 7.61(1H,dd,J=9.0,2.1 Hz), 8.40(1H,d, J=2.1 Hz).

(2) Using the above-mentioned compound (744 mg), and in the same manner as in Example 167 (2), the title compound (202 mg) was obtained as a pale-yellow powder.

$^1$H-NMR(DMSO-$d_6$)δ2.28–2.39(1H,m), 2.97–3.16(3H, m), 3.35–4.10(13H,m), 4.47–4.76(3H,m), 7.11(1H,d,J=9.3 Hz), 7.98(1H,dd,J=9.3,2.1 Hz), 8.57(1H,d,J=2.1 Hz), 9.25 (1H,brs), 10.91(1H,brs);$[.]_D^{23}$-32(c1.0,$H_2O$).

Example 184

Synthesis of 3-{(2S,4S)-4-[4-(5-trifluoromethyl-2-pyridyl)-1-piperazinyl]-2-pyrrolidinylcarbonyl}-1,3-thiazolidine dihydrochloride (1) Piperazine (12.9 g) was suspended in N-methyl-2-pyrrolidone (130 mL), and a solution of 2-chloro-5-trifluoromethylpyridine (9.08 g) in N-methyl-2-pyrrolidone (30 mL) was added dropwise. The mixture was stirred at room temperature for 18 hr. The reaction mixture was added to water and the mixture was extracted with ethyl acetate. The extract was washed with water and dried. The solvent was evaporated under reduced pressure to give 1-(5-trifluoromethyl-2-pyridyl)piperazine (11.5 g) as a white solid.

(2) Using the above-mentioned compound (462 mg) and the title compound (601 mg) of Reference Example 12, and in the same manner as in Example 70 (1), 3-{(2S,4S)-1-tert-butoxycarbonyl-4-[4-(5-trifluoromethyl-2-pyridyl)-1-piperazinyl]-2-pyrrolidinylcarbonyl}-1,3-thiazolidine (379 mg) as an oil.

(3) Using the above-mentioned compound (368 mg), and in the same manner as in Example 161 (2), the title compound (276 mg) was obtained as a white powder.

$^1$H-NMR(DMSO-$d_6$)δ2.20–2.48(1H,m), 2.87–5.00(19H, m), 7.14(1H,d,J=9.0 Hz), 7.92(1H,dd,J=9.3,2.4 Hz), 8.49 (1H,d,J=0.6 Hz).

Example 185

Synthesis of 3-{(2S,4S)-4-[4-(5-nitro-2-pyridyl)-1-piperazinyl]-2-pyrrolidinylcarbonyl}-1,3-thiazolidine dihydrochloride (1) Using 2-chloro-5-nitropyridine (7.93 g), and in the same manner as in Example 184 (1), 1-(5-nitro-2-pyridyl) piperazine (9.3 g) was obtained as a yellow powder.

(2) Using the above-mentioned compound (416 mg) and the title compound (601 mg) of Reference Example 12, and in the same manner as in Example 70 (1), 3-{(2S,4S)-1-tert-butoxycarbonyl-4-[4-(5-nitro-2-pyridyl)-1-piperazinyl]-2-pyrrolidinylcarbonyl}-1,3-thiazolidine (754 mg) was obtained as a yellow powder.

(3) Using the above-mentioned compound (693 mg), and in the same manner as in Example 161 (2), the title compound (475 mg) was obtained as a yellow powder.

$^1$H-NMR(DMSO-$d_6$)δ2.00–2.34(1H,m), 2.75–4.10(16H, m), 4.40–4.80(3H,m), 7.09(1H,d,J=9.6 Hz), 8.32(1H,dd,J=9.6,3.0 Hz), 9.01(1H,d,J=3.0 Hz), 9.18(1H,brs), 10.50(1H, brs).

Example 186

Synthesis of 1-{(2S,4S)-4-[4-(5-nitro-2-pyridyl)-1-piperazinyl]-2-pyrrolidinylcarbonyl}pyrrolidine trihydrochloride (1) Using 1-(5-nitro-2-pyridyl)piperazine [product of Example 185 (1), 625 mg] and the title compound (565 mg) of Reference Example 14, and in the same manner as in Example 70 (1), 1-{(2S,4S)-1-tert-butoxycarbonyl-4-[4-(5-nitro-2-pyridyl)-1-piperazinyl]-2-pyrrolidinylcarbonyl}pyrrolidine (632 mg) was obtained as a yellow powder.

(2) The above-mentioned compound (522 mg) was dissolved in methanol (10 mL) and chloroform (2.5 mL), and 4 mol/L hydrochloric acid-ethyl acetate (5 mL) was added thereto. The mixture was stirred at room temperature for 18 hr. The reaction mixture was concentrated under reduced pressure, and the residue was washed with ethanol to give the title compound (395 mg) as a yellow powder.

$^1$H-NMR(DMSO-$d_6$)δ1.70–2.04(4H,m), 2.09–2.36(1H, m), 2.86–3.07(1H,m), 3.20–5.00(14H,m), 7.11(1H,d,J=9.6 Hz), 8.33(1H,dd,J=9.6,3.0 Hz), 9.02(1H,d,J=2.7 Hz), 9.11 (1H,brs), 10.80(1H,brs).

Example 187

Synthesis of 3-{(2S,4S)-4-[4-(5-chloro-2-pyridyl)-1-piperazinyl]-2-pyrrolidinylcarbonyl}-1,3-thiazolidine trihydrochloride (1) Using the title compound (340 mg) of Reference Example 12 and 1-(5-chloro-2-pyridyl)piperazine (268 mg), and in the same manner as in Example 162 (1), 3-{(2s,4s)-1-tert-butoxycarbonyl-4-[4-(5-chloro-2-pyridyl)-1-piperazinyl]-2-pyrrolidinylcarbonyl}-1,3-thiazolidine (421 mg) was obtained as a white solid.

(2) Using the above-mentioned compound (418 mg), and in the same manner as in Example 162 (2), the title compound (262 mg) was obtained as a white powder.

$^1$H-NMR(500 MHz,DMSO-$d_6$)δ2.26–2.31(1H,m), 2.97–4.40(16H,m), 4.47–4.73(3H,m), 7.03(1H,d,J=9.1 Hz), 7.71(1H,dd,J=9.1,2.5 Hz), 8.18(1H,d,J=2.5 Hz), 9.18(1H, brs), 10.57(1H,brs).

Example 188

Synthesis of 3-{(2S,4S)-4-[4-(2-quinolyl)-1-piperazinyl]-2-pyrrolidinylcarbonyl}-1,3-thiazolidine trihydrochloride (1) Using the title compound (488 mg) of Reference Example 12 and 1-(2-quinolyl)piperazine (416 mg), and in the same manner as in Example 162 (1), 3-{(2S,4S)-1-tert-butoxycarbonyl-4-[4-(2-quinolyl)-1-piperazinyl]-2-pyrrolidinylcarbonyl}-1,3-thiazolidine (724 mg) was obtained as a white solid.

(2) Using the above-mentioned compound (720 mg), and in the same manner as in Example 162 (2), the title compound (560 mg) was obtained as a white powder.

$^1$H-NMR(DMSO-$d_6$)δ2.20–2.30(1H,m), 2.96–3.17(3H, m), 3.64–4.40(13H,m), 4.47–4.76(3H,m), 7.50(1H,t,J=7.5 Hz), 7.60(1H,d,J=9.6 Hz), 7.77(1H,t,J=7.8 Hz), 7.93(1H,d, J=7.5 Hz), 8.15–8.20(1H,m), 8.44(1H,d,J=9.6 Hz), 9.21(1H, brs), 10.68(1H,brs).

Example 189

Synthesis of 3-{(2S,4S)-4-[4-(4-quinolyl)-1-piperazinyl]-2-pyrrolidinylcarbonyl}-1,3-thiazolidine trihydrochloride (1) Piperazine (13.2 g) was melted by heating at 140° C., and 4-chloroquinoline (2.5 g) was added thereto. The mixture was stirred at 140° C. for 30 min. The reaction mixture was added to iced water, and the mixture was extracted with chloroform to give 1-(4-quinolyl)piperazine (3.45 g) as a pale-yellow oil.

(2) Using the above-mentioned compound (469 mg) and the title compound (601 mg) of Reference Example 12, and in the same manner as in Example 70 (1), 3-{(2S,4S)-1-tert-butoxycarbonyl-4-[4-(4-quinolyl)-1-piperazinyl]-2-pyrrolidinylcarbonyl}-1,3-thiazolidine (995 mg) was obtained.

(3) Using the above-mentioned compound (995 mg), and in the same manner as in Example 186 (2), the title compound (392 mg) as obtained as a white powder.

$^1$H-NMR(DMSO-$d_6$)δ2.16–2.40(1H,m), 2.70–4.30(16H, m), 4.40–4.80(3H,m), 7.37(1H,d,J=6.9 Hz), 7.77(1H,t,J=8.1 Hz), 8.04(1H,t,J=8.4 Hz), 8.21(1H,d,J=8.7 Hz), 8.85(1H,d, J=6.9 Hz).

Example 190

Synthesis of 3-{(2S,4S)-4-[4-(1-isoquinolyl)-1-piperazinyl]-2-pyrrolidinylcarbonyl}-1,3-thiazolidine trihydrochloride (1) Using the title compound (606 mg) of Reference Example 12 and 1-(1-isoquinolyl)piperazine (692 mg), and in the same manner as in Example 162 (1), 3-{(2S,4S)-1-tert-butoxycarbonyl-4-[4-(1-isoquinolyl)-1-piperazinyl]-2-pyrrolidinylcarbonyl}-1,3-thiazolidine (216 mg) was obtained as a white solid.

(2) Using the above-mentioned compound (215 mg), and in the same manner as in Example 162 (2), the title compound (99 mg) was obtained as a pale-yellow powder.

$^1$H-NMR(500 MHz,DMSO-$d_6$)δ2.25–2.30(1H,m), 3.00–3.17(3H,m), 3.59–3.95(12H,m), 4.13–4.18(1H,m), 4.49–4.77(3H,m), 7.59(1H,d,J=6.1 Hz), 7.71–7.74(1H,m), 7.86–7.89(1H,m), 8.02(1H,d,J=8.2 Hz), 8.08(1H,d,J=6.1 Hz), 8.21(1H,d,J=8.5 Hz), 9.25(1H,brs), 10.89(1H,brs).

Example 191

Synthesis of 3-{(2S,4S)-4-[4-(2-trifluoromethyl-4-quinolyl)-1-piperazinyl]-2-pyrrolidinylcarbonyl}-1,3-thiazolidine dihydrochloride (1) Using the title compound (0.655 g) of Reference Example 12 and 1-(2-trifluoromethyl-4-quinolyl)piperazine (0.735 g), and in the same manner as in Example 162 (1), 3-{(2S,4S)-1-tert-butoxycarbonyl-4-[4-(2-trifluoromethyl-4-quinolyl)-1-piperazinyl]-2-pyrrolidinylcarbonyl}-1,3-thiazolidine (1.23 g) was obtained as a pale-yellow powder: $^1$H-NMR(DMSO-$d_6$)δ1.33(4.5H,s), 1.41(4.5H,s), 1.55–1.64 (1H,m), 2.60–2.78(5H,m), 2.90–3.15(4H,m), 3.33–3.38(4H, m), 3.67–3.85(3H,m), 4.04–4.69(3H,m), 7.25(1H,s), 7.70 (1H,t,J=8.1 Hz), 7.81–7.87(1H,m), 8.07(2H,d,J=8.4 Hz).

(2) Using the above-mentioned compound (1.23 g), and in the same manner as in Example 162 (2), the title compound (1.06 g) was obtained as a pale-yellow powder.

$^1$H-NMR(DMSO-$d_6$)δ2.28–2.38(1H,m), 3.00–3.18(3H, m), 3.48–4.15(13H,m), 4.48–4.78(3H,m), 7.39(1H,s), 7.75 (1H,t,J=7.5 Hz), 7.89(1H,t,J=7.5 Hz), 8.11–8.16(2H,m), 9.23(1H,brs), 10.68(1H,brs);$[\cdot]_D^{24-32}$(c1.0,$H_2O$).

Example 192

Synthesis of 3-((2S,4S)-4-[4-(2-benzoxazolyl)-1-piperazinyl]-2-pyrrolidinylcarbonyl}-1,3-thiazolidine trihydrochloride (1) Using 2-chlorobenzoxazole (7.68 g) and piperazine (12.9 g), and in the same manner as in Example 168 (1), 1-(2-benzoxazolyl)piperazine (2.4 g) was obtained as a white solid.

(2) Using the above-mentioned compound (610 mg) and the title compound (601 mg) of Reference Example 12, and in the same manner as in Example 70 (1), 3-{(2S,4S)-4-[4-(2-benzoxazolyl)-1-tert-butoxycarbonyl-1-piperazinyl]-2-pyrrolidinylcarbonyl}-1,3-thiazolidine (526 mg) was obtained as a white powder.

(3) Using the above-mentioned compound (416 mg), and in the same manner as in Example 186 (2), the title compound (286 mg) was obtained as a white powder.

$^1$H-NMR(DMSO-$d_6$)δ2.20–2.42(1H,m), 2.89–3.20(3H, m), 3.25–4.35(13H,m), 4.40–4.80(3H,m), 7.10(1H,td,J=7.5, 1.2 Hz), 7.22(1H,td,J=7.8,1.2 Hz), 7.37(1H,dd,J=7.8,0.6 Hz), 7.47(1H,d,J=7.8 Hz), 9.25(1H,brs), 11.00(1H,brs).

Example 193

Synthesis of 3-{(2S,4S)-4-[4-(2-benzothiazolyl)-1-piperazinyl]-2-pyrrolidinylcarbonyl}-1,3-thiazolidine trihydrochloride (1) Using 2-chlorobenzothiazole (8.48 g) and piperazine (43.1 g), and in the same manner as in Example 189 (1), 1-(2-benzothiazolyl)piperazine (10.9 g) was obtained.

(2) Using the above-mentioned compound (482 mg) and the title compound (601 mg) of Reference Example 12, and in the same manner as in Example 70 (1), 3-{(2S,4S)-4-[4-(2-benzothiazolyl)-1-piperazinyl]-1-tert-butoxycarbonyl-2-pyrrolidinylcarbonyl}-1,3-thiazolidine (798 mg) was obtained as a white powder.

(3) Using the above-mentioned compound (606 mg), and in the same manner as in Example 186 (2), the title compound (591 mg) was obtained as a white powder.

$^1$H-NMR(DMSO-$d_6$)δ2.20–2.44(1H,m), 2.90–3.20(3H, m), 3.35–4.30(13H,m), 4.42–4.82(3H,m), 7.16(1H,t,J=7.2 Hz), 7.35(1H,t,J=7.2 Hz), 7.55(1H,d,J=7.8 Hz), 7.86(1H,d, J=7.5 Hz), 9.25(1H,brs), 10.90(1H,brs).

Example 194

Synthesis of 3-{(2S,4S)-4-[4-(benz-2-oxa-1,3-diazol-5-yl)-1-piperazinyl]-2-pyrrolidinylcarbonyl}-1,3-thiazolidine dihydrochloride (1) Using 5-chlorobenzofurazan (0.500 g) and piperazine (2.79 g), and in the same manner as in Example 189 (1), 1-(benz-2-oxa-1,3-diazol-5-yl)piperazine (0.433 g) was obtained.

(2) Using the above-mentioned compound (433 mg) and the title compound (601 mg) of Reference Example 12, and in the same manner as in Example 70 (1), 3-{(2S,4S)-4-[4-(benz-2-oxa-1,3-diazol-5-yl)-1-tert-butoxycarbonyl-1-piperazinyl]-2-pyrrolidinylcarbonyl}-1,3-thiazolidine (500 mg) was obtained as a yellow powder.

(3) Using the above-mentioned compound (438 mg), and in the same manner as in Example 186 (2), the title compound (409 mg) was obtained as a yellow powder.

$^1$H-NMR(DMSO-$d_6$)δ2.10–2.40(1H,m), 2.80–4.30(16H, m), 4.40–4.80(3H,m), 7.02(1H,s), 7.72(1H,dd,J=9.9,1.5 Hz), 7.94(1H,d,J=9.9 Hz).

Example 195

Synthesis of 3-{(2S,4S)-4-[4-(4-nitrobenzoyl)-1-piperazinyl]-2-pyrrolidinylcarbonyl}-1,3-thiazolidine dihydrochloride (1) Using the title compound (454 mg) of Reference Example 12 and 1-(4-nitrobenzoyl)piperazine (426 mg), and in the same manner as in Example 162 (1), 3-{(2S,4S)-1-tert-butoxycarbonyl-4-[4-(4-nitrobenzoyl)-1-piperazinyl]-2-pyrrolidinylcarbonyl}-1,3-thiazolidine (500 mg) was obtained as a white solid.

(2) Using the above-mentioned compound (496 mg), and in the same manner as in Example 162 (2), the title compound (242 mg) was obtained as a white powder.

$^1$H-NMR(DMSO-d$_6$)δ2.15–2.22(1H,m), 2.90–2.94(1H, m), 3.07–3.93(15H,m), 4.46–4.73(3H,m), 7.75(2H,d,J=8.6 Hz), 8.32(2H,d,J=8.6 Hz), 9.15(1H,brs), 10.63(1H,brs).

Example 196

Synthesis of 3-{(2S,4S)-4-[4-(4-nitrophenyl)-1,4-diazepam-1-yl]-2-pyrrolidinylcarbonyl}-1,3-thiazolidine dihydrochloride (1) Homopiperazine (15.0 g) was dissolved in N-methyl-2-pyrrolidine (50 mL), and 4-fluoronitrobenzene (7.06 g) was added thereto. The mixture was stirred at room temperature for 30 min. The reaction mixture was added to iced water, and the precipitate was collected by filtration to give N-(4-nitrophenyl)-1,4-diazepam (10.9 g) as a yellow powder.

(2) Using the above-mentioned compound (443 mg) and the title compound (601 mg) of Reference Example 12, and in the same manner as in Example 70 (1), 3-{(2S,4S)-1-tert.butoxycarbonyl-4-[4-(4-nitrophenyl)-1,4-diazepam-1-yl]-2-pyrrolidinylcarbonyl}-1,3-thiazolidine (429 mg) was obtained as a yellow powder.

(3) Using the above-mentioned compound (398 mg), and in the same manner as in Example 161 (2), the title compound (118 mg) was obtained as a yellow powder.

$^1$H-NMR(DMSO-d$_6$)δ1.80–2.60(3H,m), 2.70–4.20(12H, m), 4.38–4.78(3H,m), 6.89(2H,d,J=9.3 Hz), 8.09(2H,d,J=9.3 Hz).

Example 197

Synthesis of 3-{(2S,4S)-4-[4-(2-trifluoromethyl-4-quinolyl)-1,4-diazepam-1-yl]-2-pyrrolidinylcarbonyl}-1,3-thiazolidine trihydrochloride (1) Using 4-chloro-2-trifluoromethylquinoline (5.00 g) and homopiperazine (20.7 g), and by reaction in the same manner as in Example 196 (1) at 60° C., N-(2-trifluoromethyl-4-quinolyl)-1,4-diazepam (6.11 g) was obtained as a yellow solid.

(2) Using the above-mentioned compound (0.83 g) and the title compound (0.703 g) of Reference Example 12, and in the same manner as in Example 70 (1), 3-{(2S,4S)-1-tert-butoxycarbonyl-4-[4-(2-trifluoromethyl-4-quinolyl)-1,4-diazepam-1-yl]-2-pyrrolidinylcarbonyl}-1,3-thiazolidine (1.35 g) was obtained as a white powder.

(3) Using the above-mentioned compound (1.35 g), and in the same manner as in Example 133 (2), the title compound (1.21 g) was obtained as a pale-yellow powder.

$^1$H-NMR(500 MHz,DMSO-d$_6$)δ2.19–2.49(3H,m), 2.96–3.19(3H,m), 3.30–4.28(13H,m), 4.48–4.76(3H,m), 7.17(1H,s), 7.67(1H,t,J=7.6 Hz), 7.83(1H,t,J=7.6 Hz), 8.05–8.10(2H,m), 9.14(1H,brs), 10.91(1H,brs), 12.51(1H, brs)

Example 198

Synthesis of 3-{(2S,4S)-4-[4-(2-hydroxyethyl)-1-piperazinyl]-2-pyrrolidinylcarbonyl}-1,3-thiazolidine trihydrochloride (1) Using 1-piperazineethanol (147 mg) and the title compound (307 mg) of Reference Example 12, and in the same manner as in Example 70 (1), 3-{(2S,4S)-1-tert-butoxycarbonyl-4-[4-(2-hydroxyethyl)-1-piperazinyl]-2-pyrrolidinylcarbonyl}-1,3-thiazolidine (354 mg) was obtained as an oil.

(2) Using the above-mentioned compound (350 mg), and in the same manner as in Example 132 (2), deprotection was conducted. The solvent was evaporated under reduced pressure, and the residue was dissolved in ethyl acetate (5 mL). 4 mol/L Hydrochloric acid-ethyl acetate (1.0 mL) was added thereto, and the precipitated solid was collected by filtration to give the title compound (158 mg) as a white powder.

$^1$H-NMR(500 MHz,DMSO-d$_6$)δ1.91(1H,m), 2.78–3.93 (20H,m), 4.46–4.74(3H,m), 8.97(1H,brs), 10.80(1H,brs), 11.97(1H,brs).

Example 199

Synthesis of 3-[(2S,4S)-4-(4-pivaloyl-1-piperazinyl)-2-pyrrolidinylcarbonyl]-1,3-thiazolidine dihydrochloride (1) Using N-benzyloxycarbonyl-L-trans-4-hydroxyproline (25.0 g), and in the same manner as in Reference Examples 9 and 12, 3-((2S)-1-benzyloxycarbonyl-4-oxo-2-pyrrolidinylcarbonyl)-1,3-thiazolidine (10.9 g) was obtained as white crystals.

(2) Using the above-mentioned compound (4.05 g) and 1-tert-butoxycarbonylpiperazine (2.48 g), and in the same manner as in Example 70 (1), 3-[(2S,4S)-1-benzyloxycarbonyl-4-(4-tert-butoxycarbonyl-1-piperazinyl)-2-pyrrolidinylcarbonyl]-1,3-thiazolidine (4.64 g) was obtained as a white powder.

(3) The above-mentioned compound (4.04 g) was deprotected in the same manner as in Example 132 (2). The solvent was evaporated under reduced pressure, and saturated aqueous sodium hydrogencarbonate solution was added to the residue. The mixture was extracted with chloroform, and the extract was dried and concentrated under reduced pressure to give 3-[(2S,4S)-1-benzyloxycarbonyl-4-(1-piperazinyl)-2-pyrrolidinylcarbonyl]-1,3-thiazolidine (3.10 g) as a white powder.

(4) The above-mentioned compound (405 mg) and triethylamine (170 μL) were dissolved in chloroform (4 mL), and pivaloyl chloride (126 μL) was added thereto at room temperature. The mixture was stirred for 3 hr. Water was added to the reaction mixture and the mixture was extracted with chloroform. The extract was dried and the mixture was concentrated under reduced pressure to give 3-[(2S,4S)-1-benzyloxycarbonyl-4-(4-pivaloyl-1-piperazinyl)-2-pyrrolidinylcarbonyl]-1,3-thiazolidine (430 mg) as a white solid.

(5) The above-mentioned compound (423 mg) was dissolved in trifluoroacetic acid, and thioanisole (0.6 mL) was added thereto. The mixture was stirred at room temperature for 21 hr. Diethyl ether was added to the reaction mixture, and the precipitated solid was collected by filtration and purified by HPLC. This was converted to hydrochloride with 4 mol/L hydrochloric acid-ethyl acetate to give the title compound (95 mg) as a white powder.

$^1$H-NMR(500 MHz,DMSO-d$_6$)δ1.20(9H,s), 2.12–2.33 (1H,m), 2.85–4.05(16H,m), 4.48–4.73(3H,m), 9.08(1H,brs), 10.73(1H,brs).

Example 200

Synthesis of 3-[(2S,4S)-4-(4-methoxycarbonyl-1-piperazinyl)-2-pyrrolidinylcarbonyl]-1,3-thiazolidine dihydrochloride (1) Using 3-[(2S,4S)-1-benzyloxycarbonyl-4-(I-piperazinyl)-2-pyrrolidinylcarbonyl]-1,3-thiazolidine

[product of Example 199 (3), 405 mg] and methyl chlorocarbonate (79 μL), and in the same manner as in Example 199 (4), 3-[(2S,4S)-1-benzyloxycarbonyl-4-(4-methoxycarbonyl-1-piperazinyl)-2-pyrrolidinylcarbonyl]-1,3-thiazolidine (413 mg) was obtained as a white solid.

(2) Using the above-mentioned compound (407 mg), and in the same manner as in Example 199 (5), the title compound (43 mg) was obtained as a brown powder.

$^1$H-NMR(500 MHz,DMSO-$d_6$)δ2.13–2.43(1H,m), 2.85–4.05(16H,m), 3.63(3H,s), 4.47–4.74(3H,m), 9.08(1H,brs), 10.73(1H,brs).

Example 201

Synthesis of 3-[(2S,4S)-4-(4-isobutyloxycarbonyl-1-piperazinyl)-2-pyrrolidinylcarbonyl]-1,3-thiazolidine dihydrochloride (1) Using the product (405 mg) of Example 199 (3) and isobutyl chlorocarbonate (133 μL), and in the same manner as in Example 199 (4), 3-[(2S,4S)-1-benzyloxycarbonyl-4-(4-isobutyloxycarbonyl-1-piperazinyl)-2-pyrrolidinylcarbonyl]-1,3-thiazolidine (421 mg) was obtained as a white solid.

(2) Using the above-mentioned compound (416 mg), and in the same manner as in Example 199 (5), the title compound (59 mg) was obtained as a white powder.

$^1$H-NMR(500 MHz,DMSO-$d_6$)δ0.90(6H,d,J=6.8 Hz), 1.81–1.97(1H,m), 2.19–2.39(1H,m), 2.90–4.20(16H,m), 3.83(2H,d,J=6.5 Hz), 4.47–4.74(3H,m), 9.12(1H,brs), 11.07 (1H,brs).

Example 202

Synthesis of 3-[(2S,4S)-4-(4-benzyloxycarbonyl-1-piperazinyl)-2-pyrrolidinylcarbonyl]-1,3-thiazolidine dihydrochloride (1) Using 1-benzyloxycarbonylpiperazine (217 mg) and the title compound (307 mg) of Reference Example 12, and in the same manner as in Example 70 (1), 3-[(2S,4S)-4-(4-benzyloxycarbonyl-1-piperazinyl)-1-tert-butoxycarbonyl-2-pyrrolidinylcarbonyl]-1,3-thiazolidine (500 mg) was obtained as a white powder.

(2) Using the above-mentioned compound (490 mg), and in the same manner as in Example 133 (2), the title compound (399 mg) was obtained as a white powder.

$^1$H-NMR(500 MHz,DMSO-$d_6$)δ2.10–2.30(1H,m), 1.70–4.20(16H,m), 4.46–4.73(3H,m), 5.11(2H,s), 7.31–7.42 (5H,m), 9.06(1H,brs), 10.67(1H,brs), 12.50(1H,brs).

Example 203

Synthesis of 3-[(2S,4S)-4-(4-cyclohexylaminocarbonyl-1-piperazinyl)-2-pyrrolidinylcarbonyl]-1,3-thiazolidine dihydrochloride (1) Using the product (405 mg) of Example 199 (3) and cyclohexyl isocyanate (127 μL), and in the same manner as in Example 199 (4), 3-[(2S,4S)-1-benzyloxycarbonyl-4-(4-cyclohexylaminocarbonyl-1-piperazinyl)-2-pyrrolidinylcarbonyl]-1,3-thiazolidine (296 mg) was obtained as a white solid.

(2) Using the above-mentioned compound (296 mg), and in the same manner as in Example 199 (5), the title compound (85 mg) was obtained as a white powder.

$^1$H-NMR(500 MHz,DMSO-$d_6$)δ1.00–1.29(5H,m), 1.53–1.80(5H,m), 2.12–2.32(1H,m), 2.80–4.20(17H,m), 4.47–4.73(3H,m), 6.48(1H,brs), 9.09(1H,brs), 10.65(1H,brs), 12.18(1H,brs).

Example 204

Synthesis of 3-{(2S,4S)-4-[4-(2,6-dimethylphenyl)aminocarbonyl-1-piperazinyl]-2-pyrrolidinylcarbonyl}-1,3-thiazolidine dihydrochloride (1) Using the product (405 mg) of Example 199 (3) and 2,6-dimethylphenyl isocyanate (142 μL), and in the same manner as in Example 199 (4), 3-{(2S,4S)-1-benzyloxycarbonyl-4-[4-(2,6-dimethylphenyl)aminocarbonyl-1-piperazinyl]-2-pyrrolidinylcarbonyl}-1,3-thiazolidine (517 mg) was obtained as a white powder.

(2) Using the above-mentioned compound (503 mg), and in the same manner as in Example 199 (5), the title compound (166 mg) was obtained as a white powder.

$^1$H-NMR(500 MHz,DMSO-$d_6$)δ2.15(6H,s), 2.09–2.29 (1H,m), 2.85–4.20(16H,m), 4.48–4.73(3H,m), 7.04(3H,m), 8.16(1H,s), 9.07(1H,brs), 10.61(1H,brs).

Example 205

Synthesis of 3-{(2S,4S)-4-[4-(8-quinolinesulfonyl)-1-piperazinyl]-2-pyrrolidinylcarbonyl}-1,3-thiazolidine trihydrochloride (1) 1-tert-Butoxycarbonylpiperazine (2.22 g) and triethylamine (2.0 mL) were dissolved in dichloromethane (100 mL), and 8-quinolinesulfonyl chloride (2.71 g) was added thereto. The mixture was stirred at room temperature for 14 hr. 10% citric acid solution was added to the reaction mixture and the mixture was extracted with chloroform. The extract was washed with brine, dried and concentrated under reduced pressure. The residue was dissolved in dichloromethane (20 mL), and trifluoroacetic acid (5 mL) was added thereto. The mixture was stirred at room temperature for 1.5 hr. The reaction mixture was concentrated under reduced pressure, and saturated aqueous sodium hydrogencarbonate solution was added to the residue. The mixture was extracted with chloroform, and the extract was dried and concentrated under reduced pressure to give 1-(8-quinolinesulfonyl)piperazine (0.73 g) as a white solid.

(2) using the above-mentioned compound (0.725 g) and the title compound (0.714 g) of Reference Example 12, and in the same manner as in Example 70 (1), 3-{(2S,4S)-1-tert-butoxycarbonyl-4-[4-(8-quinolinesulfonyl)-1-piperazinyl]-2-pyrrolidinylcarbonyl}-1,3-thiazolidine (1.34 g) was obtained as a white powder.

(3) Using the above-mentioned compound (1.34 g), and in the same manner as in Example 133 (2), the title compound (0.56 g) was obtained as a pale-yellow powder.

$^1$H-NMR(500 MHz,DMSO-$d_6$)δ2.01–2.21(1H,m), 2.80–3.95(16H,m), 4.43–4.72(3H,m), 7.74(1H,dd,J=8.3,4.2 Hz), 7.79(1H,t,J=7.9 Hz), 8.35–8.40(2H,m), 8.58(1H,dd,J=8.3,1.7 Hz), 9.00(1H,brs), 9.06(1H,dd,J=4.2,1.7 Hz), 10.60 (1H,brs).

Example 206

Synthesis of 3-{(2S,4S)-4-[4-(1-ethoxycarbonyl-4-piperidinyl)-1-piperazinyl]-2-pyrrolidinylcarbonyl}-1,3-thiazolidine tetrahydrochloride (1) Using 1-(9-fluorenylmethoxycarbonyl)piperazine (1.47 g) and the title compound (1.30 g) of Reference Example 12, and in the same manner as in Example 70 (1), 3-{(2S,4S)-1-tert-butoxycarbonyl-4-[4-(9-fluorenylmethoxycarbonyl)-1-piperazinyl]-2-pyrrolidinylcarbonyl}-1,3-thiazolidine (1.68 g) was obtained as a white powder.

(2) The above-mentioned compound (1.68 g) was dissolved in dichloromethane (30 mL), and piperidine (1.5 mL) was added thereto at room temperature. The mixture was stirred for 4 hr. The solvent was evaporated under reduced pressure, and the residue was purified by silica gel chromatography to give 3-[(2S,4S)-1-tert-butoxycarbonyl-4-(1-piperazinyl)-2-pyrrolidinylcarbonyl]-1,3-thiazolidine (206 mg) as a white solid.

(3) Using the above-mentioned compound (202 mg) and 1-ethoxycarbonyl-4-piperidone (90 μL), and in the same manner as in Example 70 (1), 3-{(2S,4S)-1-tert-butoxycarbonyl-4-[4-(1-ethoxycarbonyl-4-piperidinyl)-1-piperazinyl]-2-pyrrolidinylcarbonyl}-1,3-thiazolidine (168 mg) was obtained as a white powder.

(4) Using the above-mentioned compound (168 mg), and in the same manner as in Example 133 (2), the title compound (113 mg) was obtained as a white powder.

$^1$H-NMR(500 MHz,DMSO-$d_6$)δ1.18(3H,t,J=7.1 Hz), 1.53–1.65(2H,m), 1.81–1.95(1H,m), 2.01–2.21(2H,m), 2.70–4.20(21H,m), 4.04(2H,q,J=7.1 Hz), 4.47–4.73(3H,m), 8.89(1H,brs), 10.39(1H,brs), 11.46(1H,brs).

Example 207

Synthesis of 3-{(2S,4R)-4-[4-(4-nitrophenyl)-1-piperazinyl]-2-pyrrolidinylcarbonyl}-1,3-thiazolidine dihydrochloride (1) 3-((2S,4R)-4-Amino-1-tert-butoxycarbonyl-2-pyrrolidinylcarbonyl)-1,3-thiazolidine (title compound of Reference Example 15, 1 g) was dissolved in N-methyl-2-pyrrolidone (20 mL), and N,N-bis{2-[(methylsulfonyl)oxy]ethyl}-4-nitroaniline (1.27 g) and N,N-diisopropylethylamine (1.73 mL) were added thereto. The mixture was stirred at 80° C. for 24 hr with heating. The reaction mixture was added to saturated aqueous sodium hydrogencarbonate solution, and the mixture was extracted with ethyl acetate. The extract was washed with brine and the solvent was evaporated under reduced pressure. The residue was purified by silica gel chromatography to give 3-{(2S,4R)-1-tert-butoxycarbonyl-4-[4-(4-nitrophenyl)-1-piperazinyl]-2-pyrrolidinylcarbonyl}-1,3-thiazolidine.

(2) This was dissolved in methanol (20 mL) and chloroform (10 mL), and 4 mol/L hydrochloric acid-ethyl acetate (10 mL) was added thereto. The mixture was stirred for 2 hr. The reaction mixture was concentrated under reduced pressure, and saturated aqueous sodium hydrogencarbonate solution was added to the residue. The mixture was extracted with chloroform and the extract was concentrated under reduced pressure. The residue was purified by silica gel chromatography to give a free base (161 mg) of the title compound. This was dissolved in ethanol (5 mL), and 4 mol/L hydrochloric acid-ethyl acetate (0.21 mL) was added thereto. The solvent was evaporated under reduced pressure to give the title compound (128 mg) as a yellow powder.

$^1$H-NMR(DMSO-$d_6$)δ2.22–2.46(1H,m), 2.75–2.99(1H, m), 3.00–3.20(2H,m), 3.20–4.30(13H,m), 4.40–5.07(3H,m), 7.16(2H,d,J=9.3 Hz), 8.12(2H,d,J=9.3 Hz).

Example 208

Synthesis of 3-{(2S,4S)-4-[4-(4-trifluoromethylphenyl)-1-piperazinyl]-2-pyrrolidinylcarbonyl}-1,3-thiazolidine trihydrochloride (1) Using the title compound (450 mg) of Reference Example 12 and 1-(4-trifluoromethylphenyl)piperazine (414 mg), and in the same manner as in Example 70 (1), 3-{(2S,4S)-1-tert-butoxycarbonyl-4-[4-(4-trifluoromethylphenyl)-1-piperazinyl]-2-pyrrolidinylcarbonyl}-1,3-thiazolidine (772 mg) was obtained as a white solid.

(2) The above-mentioned compound (766 mg) was dissolved in methanol (5 mL), and 1.1 mol/L hydrochloric acid-methanol (14 mL) was added thereto. The mixture was stirred at room temperature for 4 days. The reaction mixture was concentrated under reduced pressure, and ethyl acetate was added to the residue. The precipitated solid was collected by filtration to give the title compound (680 mg) as a pale-brown powder.

$^1$H-NMR(DMSO-$d_6$)δ2.27–2.40(1H,m), 2.96–4.16(16H, m), 4.46–4.77(3H,m), 7.18(2H,d,J=8.8), 7.58(2H,d,J=8.8), 9.22(1H,brs), 10.73(1H,brs).

Example 209

Synthesis of 3-{(2S,4S)-4-[4-(3-cyano-2-pyridyl)-1-piperazinyl]-2-pyrrolidinylcarbonyl}-1,3-thiazolidine trihydrochloride (1) Piperazine (125 g) was melted by heating at 150° C. and 2-chloro-3-cyanopyridine (20.0 g) was added thereto. The mixture was stirred at 110° C. for 2 hr. Water was added to the reaction mixture and the mixture was extracted with chloroform. The extract was washed with brine, dried and concentrated under reduced pressure to give 1-(3-cyano-2-pyridyl)piperazine (24.2 g) as a brown solid.

(2) Using the above-mentioned compound (0.621 g) and the title compound (0.901 g) of Reference Example 12, and in the same manner as in Example 70 (1), 3-{(2S,4S)-1-tert-butoxycarbonyl-4-[4-(3-cyano-2-pyridyl)-1-piperazinyl]-2-pyrrolidinylcarbonyl}-1,3-thiazolidine (1.42 g) was obtained as a white solid.

$^1$H-NMR($CDCl_3$)δ1.41(4.5H,s), 1.46(4.5H,s), 1.83–1.97 (1H,m), 2.40–2.51(1H,m), 2.53–2.72(4H,m), 2.82–3.22(3H, m), 3.33(1H,t,J=9.9 Hz), 3.35–4.14(7H,m), 4.38–4.79(3H, m), 6.76(1H,dd,J=7.6,4.7 Hz), 7.77(1H,dd,J=7.6,1.7 Hz), 8.34(1H,dd,J=4.7,1.7 Hz).

(3) The above-mentioned compound (1.42 g) was dissolved in ethyl acetate (7.5 mL), and 4 mol/L hydrochloric acid-ethyl acetate (7.5 mL) was added thereto. The mixture was stirred at room temperature for 12 hr. The precipitated solid was collected by filtration to give the title compound (1.00 g) as a white powder.

$^1$H-NMR(DMSO-$d_6$)δ2.26–2.40(1H,m), 2.93–3.18(3H, m), 3.2–4.8(16H,m), 7.09(1H,dd,J=7.7,4.8), 8.19(1H,dd,J=7.7,1.9), 8.49(1H,dd,J=4.8,1.9), 9.16(1H,brs), 11.02(1H, brs), 12.7(1H,brs).

Example 210

Synthesis of 3-{(2S,4S)-4-[4-(3-chloro-2-pyridyl)-1-piperazinyl]-2-pyrrolidinylcarbonyl}-1,3-thiazolidine trihydrochloride (1) Piperazine (20.0 g) was melted by heating at 140° C. and 2,3-dichloropyridine (3.42 g) was added thereto. The mixture was stirred at 120° C. for 2 hr. Water was added to the reaction mixture and the mixture was extracted with chloroform. The extract was washed with brine, dried and concentrated under reduced pressure to give 1-(3-chloro-2-pyridyl)piperazine (4.68 g) as a dark-brown oil.

(2) Using the above-mentioned compound (0.712 g) and the title compound (0.901 g) of Reference Example 12, and in the same manner as in Example 70 (1), 3-{(2S,4S)-1-tertbutoxycarbonyl-4-[4-(3-chloro-2-pyridyl)-1-piperazinyl]-2-pyrrolidinylcarbonyl}-1,3-thiazolidine (1.41 g) was obtained as a white solid.

$^1$H-NMR($CDCl_3$)δ1.41(4.5H,s), 1.46(4.5H,s), 1.84–1.99 (1H,m), 2.40–2.51(1H,m), 2.53–2.73(4H,m), 2.79–3.18(3H, m), 3.28–3.45(5H,m), 3.58–4.12(3H,m), 4.38–4.78(3H,m), 6.84(1H,dd,J=7.7,4.7 Hz), 7.58(1H,dd,J=7.7,1.5 Hz), 8.18 (1H,dd,J=4.7,1.5 Hz).

(3) The above-mentioned compound (1.40 g) was dissolved in ethanol (4 mL), and 4.1 mol/L hydrochloric acid-ethanol (4 mL) was added thereto. The mixture was stirred at room temperature for 14 hr. The precipitated solid was collected by filtration to give the title compound (1.14 g) as a white powder.

$^1$H-NMR(DMSO-$d_6$)δ2.30–2.43(1H,m), 2.95–3.18(3H, m), 3.2–4.2(13H,m), 4.45–4.80(3H,m), 7.12(1H,dd,J=7.8, 4.7 Hz), 7.89(1H,dd,J=7.8,1.5 Hz), 8.28(1H,dd,J=4.7,1.5 Hz), 9.16(1H,brs), 10.96(1H,brs), 12.55(1H,brs).

Example 211

Synthesis of 3-{(2S,4S)-4-[4-(5-ethoxycarbonyl-2-pyridyl)-1-piperazinyl]-2-pyrrolidinylcarbonyl}-1,3-thiazolidine trihydrochloride (1) Ethyl 6-chloronicotinate (1.12 g) was dissolved in DMF (30 mL), and 1-tert-butoxycarbonylpiperazine (1.24 g) and potassium carbonate (1.00 g) were added thereto. The mixture was stirred at 80° C. for 18 hr. Water (100 mL) was added to the reaction mixture and the mixture was extracted with ethyl acetate. The extract was washed successively with saturated aqueous sodium hydrogencarbonate solution and brine and dried. The solvent was evaporated under reduced pressure. The residue was dissolved in dichloromethane (10 mL), and trifluoroacetic acid (5 mL) was added thereto at room temperature. The mixture was stirred for 2 hr and the reaction mixture was concentrated under reduced pressure. Water (50 mL) was added to the residue, and the mixture was washed with diethyl ether. The aqueous layer was basified with aqueous sodium hydrogen carbonate solution. The mixture was extracted with chloroform. The extract was dried and the mixture was concentrated under reduced pressure to give 1-(5-ethoxycarbonyl-2-pyridyl)piperazine (1.17 g) as an oil.

(2) Using the above-mentioned compound (1.17 g) and the title compound (1.47 g) of Reference Example 12, and in the same manner as in Example 70 (1), 3-{(2S,4S)-1-tert-butoxycarbonyl-4-[4-(5-ethoxycarbonyl-2-pyridyl)-1-piperazinyl]-2-pyrrolidinylcarbonyl}-1,3-thiazolidine (2.07 g) as a white solid.

(3) Using the above-mentioned compound (1.06 g), and in the same manner as in Example 133 (2), the title compound (1.06 g) was obtained as a white powder.

$^1$H-NMR(500 MHz,DMSO-$d_6$)δ1.30(3H,t,J=7.1 Hz), 2.23–2.43(1H,m), 2.92–4.90(19H,m), 4.28(2H,q,J=7.1 Hz), 7.05(1H,d,J=9.1 Hz), 8.04(1H,dd,J=9.1,2.3 Hz), 8.69(1H,d, J=2.3 Hz), 9.13(1H,brs), 10.91(1H,brs), 12.58(1H,brs).

Example 212

Synthesis of 3-{(2S,4S)-4-[4-(5-carboxy-2-pyridyl)-1-piperazinyl]-2-pyrrolidinylcarbonyl}-1,3-thiazolidine trihydrochloride 6 mol/L Hydrochloric acid was added to 3-{(2S,4S)-1-tert-butoxycarbonyl-4-[4-(5-ethoxycarbonyl-2-pyridyl)-1-piperazinyl]-2-pyrrolidinylcarbonyl}-1,3-thiazolidine trihydrochloride [product of Example 211 (2), 1.00 g] and the mixture was refluxed for 2 hr. The solvent was evaporated under reduced pressure, and the residue was purified by HPLC. This was converted to hydrochloride with 4 mol/L hydrochloric acid-1,4-dioxane to give the title compound (158 mg) as a white powder.

$^1$H-NMR(500 MHz,DMSO-$d_6$)δ2.21–2.41(1H,m), 2.90–4.90(19H,m), 7.04(1H,d,J=9.0 Hz), 8.03(1H,dd,J=9.0, 2.2 Hz), 8.67(1H,d,J=2.2 Hz), 9.12(1H,brs), 10.80(1H,brs), 12.50(1H,brs).

Example 213

Synthesis of 3-{(2S,4S)-4-[4-(5-carbamoyl-2-pyridyl)-1-piperazinyl]-2-pyrrolidinylcarbonyl}-1,3-thiazolidine trihydrochloride (1) Using 6-chloronicotinamide (5.00 g) and piperazine (27.6 g), and by reaction in the same manner as in Example 196 (1) at 100° C., 1-(5-carbamoyl-2-pyridyl)piperazine (0.41 g) was obtained as a yellow powder.

(2) Using the above-mentioned compound (370 mg) and the title compound (450 mg) of Reference Example 12, and in the same manner as in Example 70 (1), 3-{(2S,4S)-1-tert-butoxycarbonyl-4-[4-(5-carbamoyl-2-pyridyl)-1-piperazinyl]-2-pyrrolidinylcarbonyl}-1,3-thiazolidine (350 mg) was obtained as a white solid.

(3) Using the above-mentioned compound (347 mg), and in the same manner as in Example 133 (2), the title compound (332 mg) was obtained as a white powder.

$^1$H-NMR(500 MHz,DMSO-$d_6$)δ1.81–2.01(1H,m), 2.93–4.10(14H,m), 4.28–4.75(5H,m), 7.08(1H,d,J=9.0 Hz), 7.26(1H,brs), 7.91(1H,brs), 8.10(1H,dd,J=9.0,2.3 Hz), 8.66 (1H,d,J=2.3 Hz), 9.12(1H,brs), 10.87(1H,brs), 12.51(1H, brs).

Example 214

Synthesis of 3-{(2S,4R)-4-[4-(5-cyano-2-pyridyl)-1-piperazinyl]-2-pyrrolidinylcarbonyl}-1,3-thiazolidine trihydrochloride (1) The title compound (1.74 g) of Reference Example 11 and triethylamine (1.0 mL) were dissolved in dichloromethane (35 mL), and methanesulfonyl chloride (0.49 mL) was added dropwise under ice-cooling. The mixture was stirred for 3 hr. Iced water was added to the reaction mixture and the mixture was extracted with dichloromethane. The extract was washed with brine, dried and concentrated under reduced pressure to give 3-{(2S,4S)-1-tert-butoxycarbonyl-4-methanesulfonyloxy-2-pyrrolidinylcarbonyl}-1,3-thiazolidine (2.03 g) as a pale-brown solid.

(2) The-above-mentioned compound (1.10 g) and 1-(5-cyano-2-pyridyl)piperazine (1.12 g) were dissolved in 1-methyl-2-pyrrolidone (20 mL), and the mixture was stirred at 90° C. for 12 hr. The reaction mixture was added to water and the mixture was extracted with ethyl acetate. The extract was concentrated under reduced pressure and the residue was purified by column chromatography to give 3-{(2S,4R)-1-tert-butoxycarbonyl-4-[4-(5-cyano-2-pyridyl)-1-piperazinyl]-2-pyrrolidinylcarbonyl}-1,3-thiazolidine (170 mg).

$^1$H-NMR($CDCl_3$)δ1.41(4.5H,s), 1.46(4.5H,s), 2.07–2.20 (2H,m), 2.45–2.65(4H,m), 3.00–3.40(4H,m), 3.57–3.79(5H, m), 3.81–4.00(2H,m), 4.45–4.83(3H,m), 6.59(1H,d,J=9.3 Hz), 7.61(1H,dd,J=9.3,1.9 Hz), 8.40(1H,d,J=1.9 Hz).

(3) The above-mentioned compound (150 mg) was suspended in tetrahydrofuran (40 mL), and 4 mol/L hydrochloric acid-ethyl acetate (40 mL) was added thereto. The mixture was stirred at 55° C. for 5 hr. After allowing to cool, the precipitated solid was collected by filtration to give the title compound (130 mg) as a white powder.

$^1$H-NMR(DMSO-d$_6$)δ2.26–2.45(1H,m), 2.80–3.00(1H, m), 3.01–3.27(3H,m), 3.28–3.94(8H,m), 3.95–4.15(3H,m), 4.38–4.77(3H,m), 4.84–5.01(1H,m), 7.12(1H,d,J=9.3 Hz), 8.00(1H,dd,J=9.3,2.1 Hz), 8.58(1H,d,J=2.1 Hz), 9.22(1H, brs).

Example 215

Synthesis of 3-{(2S,4S)-4-[4-(3-chloro-5-trifluoromethyl-2-pyridyl)-1-piperazinyl]-2-pyrrolidinylcarbonyl}-1,3-thiazolidine trihydrochloride (1) Piperazine (40 g) was melted by heating at 140° C. and 2,3-dichloro-5-trifluoromethylpyridine (10 g) was added thereto. The mixture was stirred at 120° C. for 2 hr. Water was added to the reaction mixture and the mixture was extracted with chloroform. The extract was washed with brine, dried and concentrated under reduced pressure to give 1-(3-chloro-5-trifluoromethyl-2-pyridyl)piperazine (12.8 g) as a brown solid.

(2) Using the above-mentioned compound (0.956 g) and the title compound (0.901 g) of Reference Example 12, and in the same manner as in Example 70 (1), 3-{(2S,4S)-1-tert-butoxycarbonyl-4-[4-(3-chloro-5-trifluoromethyl-2-pyridyl)-1-piperazinyl]-2-pyrrolidinylcarbonyl}-1,3-thiazolidine (1.64 g) was obtained as a white solid.

$^1$H-NMR(CDCl$_3$)δ1.41(4.5H,s), 1.46(4.5H,s), 1.83–1.98 (1H,m), 2.38–2.50(1H,m), 2.52–2.70(4H,m), 2.78–3.19(3H, m), 3.33(1H,t,J=10.1 Hz), 3.47–4.13(7H,m), 4.37–4.81(3H, m), 7.75(1H,s), 8.38(1H,s).

(3) The above-mentioned compound (1.64 g) was dissolved in ethanol (4 mL), and 4.1 mol/L hydrochloric acid-ethanol (4 mL) was added thereto. The mixture was stirred at room temperature for 5 days. The precipitated solid was collected by filtration to give the title compound (1.20 g) as a white powder.

$^1$H-NMR(DMSO-d$_6$)δ2.30–2.47(1H,m), 2.92–4.2(16H, m), 4.45–4.78(3H,m), 8.31(1H,d,J=1.9 Hz), 8.63(1H,d,J=1.9 Hz), 9.15(1H,brs), 10.77(1H,brs), 12.6(1H,brs).

Example 216

Synthesis of 3-{(2S,4S)-4-[4-(3-chloro-5-ethoxycarbonyl-2-pyridyl)-1-piperazinyl]-2-pyrrolidinylcarbonyl}-1,3-thiazolidine trihydrochloride (1) 5,6-Dichloronicotinic acid (4.90 g) was dissolved in ethanol (40 mL), and thionyl chloride (2.0 mL) was added thereto under ice-cooling. The mixture was refluxed for 1.5 hr. The reaction mixture was concentrated under reduced pressure, and saturated aqueous sodium hydrogencarbonate solution was added to the residue. The mixture was extracted with ethyl acetate. The extract was dried and the solvent was evaporated under reduced pressure. The residue was purified by silica gel chromatography to give ethyl 5,6-dichloronicotinate (4.85 g) as a white solid.

(2) Piperazine (19.0 g) was melted by heating at 140° C. and the above-mentioned compound (4.80 g) was added thereto. The mixture was stirred at 120° C. for 2 hr. Water was added to the reaction mixture and the mixture was extracted with chloroform. The extract was washed with brine, dried and concentrated under reduced pressure to give 1-(3-chloro-5-ethoxycarbonyl-2-pyridyl)piperazine (5.64 g) as a dark brown solid.

(3) Using the above-mentioned compound (5.12 g) and the title compound (4.75 g) of Reference Example 12, and in the same manner as in Example 70 (1), 3-{(2S,4S)-1-tert-butoxycarbonyl-4-[4-(3-chloro-5-ethoxycarbonyl-2-pyridyl)-1-piperazinyl]-2-pyrrolidinylcarbonyl}-1,3-thiazolidine (7.53 g) was obtained as a white solid.

$^1$H-NMR(CDCl$_3$)δ1.38(3H,t,J=7.1 Hz), 1.41(4.5H,s), 1.46(4.5H,s), 1.83–1.98(1H,m), 2.38–2.50(1H,m), 2.53–2.73(4H,m), 2.78–3.20(3H,m), 3.33(1H,t,J=10.3 Hz), 3.45–4.13(7H,m), 4.36(2H,q,J=7.1 Hz), 4.32–4.78(3H,m), 8.11(1H,d,J=1.8 Hz), 8.74(1H,d,J=1.8 Hz).

(4) The above-mentioned compound (1.00 g) was dissolved in dichloroethane (10 mL) and trifluoroacetic acid (5 mL) was added thereto. The mixture was stirred at room temperature for 3 hr. The reaction mixture was concentrated under reduced pressure, and the residue was dissolved in ethyl acetate (10 mL). 4 mol/L Hydrochloric acid-ethyl acetate (2.25 mL) was added thereto, and the mixture was stirred at room temperature for 1 hr. The precipitated solid was collected by filtration to give the title compound (0.82 g) as a white powder.

$^1$H-NMR(DMSO-d$_6$)δ1.32(3H,t,J=7.1 Hz), 2.26–2.40 (1H,m), 2.93–3.18(3H,m), 3.25–4.15(13H,m), 4.32(2H,q,J=7.1 Hz), 4.4–4.78(3H,m), 8.19(1H,d,J=2.0 Hz), 8.73(1H,d, J=2.0 Hz), 9.16(1H,brs), 10.78(1H,brs), 12.5(1H,brs).

Example 217

Synthesis of 3-{(2S,4S)-4-[4-(5-carboxy-3-chloro-2-pyridyl)-1-piperazinyl]-2-pyrrolidinylcarbonyl}-1,3-thiazolidine trihydrochloride (1) 3-{(2S,4S)-1-tert-Butoxycarbonyl-4-[4-(3-chloro-5-ethoxycarbonyl-2-pyridyl)-1-piperazinyl]-2-pyrrolidinylcarbonyl}-1,3-thiazolidine [product of Example 216 (3), 6.49 g] was dissolved in ethanol (30 mL), and aqueous solution (30 mL) of lithium hydroxide (0.59 g) was added thereto. The mixture was stirred at room temperature for 19 hr and ethanol was evaporated under reduced pressure. The concentrate was washed with ethyl acetate, and 1 mol/L hydrochloric acid was added thereto. The precipitated solid was collected by filtration to give 3-{(2S,4S)-1-tert-butoxycarbonyl-4-[4-(5-carboxy-3-chloro-2-pyridyl)-1-piperazinyl]-2-pyrrolidinylcarbonyl}-1,3-thiazolidine (2.64 g) as a white solid.

$^1$H-NMR(DMSO-d$_6$)δ1.33(4.5H,s), 1.41(4.5H,s), 1.97–2.15(1H,m), 2.77–2.87(1H,m), 2.95–4.25(15H,m), 4.40–4.76(3H,m), 8.16(1H,d,J=2.0 Hz), 8.71(1H,d,J=2.0 Hz), 11.40(1H,brs).

(2) Using the above-mentioned compound (500 mg), and in the same manner as in Example 216 (4), the title compound (437 mg) was obtained as a white powder.

$^1$H-NMR(DMSO-d$_6$)δ2.27–2.42(1H,m), 2.94–3.18(3H, m), 3.2–4.8(16H,m), 8.17(1H,d,J=2.0 Hz), 8.71(1H,d,J=2.0 Hz), 9.16(1H,brs), 10.95(1H,brs), 12.60(1H,brs)

Example 218

Synthesis of 3-{(2S,4S)-4-[4-(5-carbamoyl-3-chloro-2-pyridyl)-1-piperazinyl]-2-pyrrolidinylcarbonyl}-1,3-thiazolidine trihydrochloride (1) 3-{(2S,4S)-1-tert-Butoxycarbonyl-4-[4-(5-carboxy-3-chloro-2-pyridyl)-1-piperazinyl]-2-pyrrolidinylcarbonyl}-1, 3-thiazolidine [product of Example 217 (1), 2.63 g] and ammonium chloride (0.54 g) were dissolved in DMF (30 mL), and N-methylmorpholine (1.1 mL), HOBT (1.53 g) and EDC hydrochloride (1.15 g) were successively added thereto. The mixture was stirred at room temperature for 4 hr. The reaction mixture was concentrated under reduced pressure, and saturated aqueous sodium hydrogencarbonate solution was added to the residue. The mixture was extracted with ethyl acetate. The extract washed with brine and dried. The solvent was evaporated under reduced pressure to give 3-{(2S,4S)-1-tert-butoxycarbonyl-4-[4-(5-carbamoyl-3-chloro-2-pyridyl)-1-piperazinyl]-2-pyrrolidinylcarbonyl}-1,3-thiazolidine (2.50 g) as a white solid.

$^1$H-NMR($CDCl_3$)δ1.41(4.5H,s), 1.45(4.5H,s), 1.84–1.98 (1H,m), 2.39–2.52(1H,m), 2.53–2.73(4H,m), 2.78–3.18(3H, m), 3.34(1H,t,J=10.0 Hz), 3.45–4.13(7H,m), 4.38–4.78(3H, m), 5.87(1H,brs), 6.17(1H,brs), 8.07(1H,d,J=2.0 Hz), 8.56 (1H,d,J=2.0 Hz).

(2) The above-mentioned compound (683 mg) was dissolved in ethanol (2 mL), and 4.1 mol/L hydrochloric acid-ethanol (2 mL) as added thereto. The mixture was stirred at room temperature for 22 hr. The precipitated solid was collected by filtration to give the title compound (616 mg) as a white powder.

$^1$H-NMR(DMSO-$d_6$)δ2.26–2.42(1H,m), 2.92–4.3(16H, m), 4.46–4.78(3H,m), 7.56(1H,brs), 8.12(1H,brs), 8.26(1H, s), 8.73(1H,s), 9.15(1H,brs), 10.83(1H,brs), 12.52(1H,brs).

Example 219

Synthesis of 3-{(2S,4S)-4-[4-(3-chloro-5-cyano-2-pyridyl)-1-piperazinyl]-2-pyrrolidinylcarbonyl}-1,3-thiazolidine trihydrochloride (1) 3-{(2S,4S)-1-tert-Butoxycarbonyl-4-[4-(5-carbamoyl-3-chloro-2-pyridyl)-1-piperazinyl]-2-pyrrolidinylcarbonyl}-1,3-thiazolidine [product of Example 218 (1), 1000 mg] and imidazole (195 mg) were dissolved in pyridine (10 mL), and phosphorus oxychloride (0.35 mL) was added thereto under ice-cooling. The mixture was stirred at room temperature for 13 hr and saturated aqueous sodium hydrogencarbonate solution was added to the reaction mixture. The mixture was extracted with chloroform. The extract was washed with brine, dried and concentrated under reduced pressure. The residue was purified by silica gel chromatography to give 3-{(2S,4S)-1-tert-butoxycarbonyl-4-[4-(3-chloro-5-cyano-2-2-pyridyl)-1-piperazinyl]-2-pyrrolidinylcarbonyl}-1,3-thiazolidine (628 mg) as a white solid.

$^1$H-NMR($CDCl_3$)δ1.41(4.5H,s), 1.45(4.5H,s), 1.83–1.98 (1H,m), 2.38–2.70(5H,m), 2.80–3.20(3H,m), 3.33(1H,t,J= 10.0 Hz), 3.53–4.13(7H,m), 4.37–4.82(3H,m), 7.73(1H,d,J= 1.9 Hz), 8.37(1H,d,J=1.9 Hz).

(2) The above-mentioned compound (622 mg) was dissolved in ethyl acetate (1.5 mL), and 4 mol/L hydrochloric acid-ethyl acetate (1.5 mL) was added thereto. The mixture was stirred at room temperature for 14 hr. The reaction mixture was concentrated under reduced pressure, and saturated aqueous sodium hydrogencarbonate solution was added to the residue. The mixture was extracted with chloroform. The extract was dried and concentrated under reduced pressure. The residue was purified by silica gel chromatography to give a white solid. This was dissolved in ethyl acetate (6 mL) and 4 mol/L hydrochloric acid-ethyl acetate (0.9 mL) was added thereto. The mixture was stirred at room temperature for 1 hr. The precipitated solid was collected by filtration to give the title compound (388 mg) as a white powder.

$^1$H-NMR(DMSO-$d_6$)δ2.10–2.26(1H,m), 2.90–4.2(16H, m), 4.47–4.78(3H,m), 8.41(1H,d,J=1.9 Hz), 8.69(1H,d,J= 1.9 Hz), 9.13(1H,brs), 10.81(1H,brs), 12.57(1H,brs).

Example 220

Synthesis of 3-{(2S,4S)-4-[4-(3,5-dichloro-2-pyridyl)-1-piperazinyl]-2-pyrrolidinylcarbonyl}-1,3-thiazolidine trihydrochloride (1) Piperazine (24.0 g) was melted by heating at 140° C. and 2,3,5-trichloropyridine (5.00 g) was added thereto. The mixture was stirred at 120° C. for 2 hr. Water was added to the reaction mixture and the mixture was extracted with chloroform. The extract was washed with brine, dried and concentrated under reduced pressure to give 1-(3,5-dichloro-2-pyridyl)piperazine (6.43 g) as a brown solid.

(2) Using the above-mentioned compound (0.832 g) and the title compound (0.901 g) of Reference Example 12, and in the same manner as in Example 70 (1), 3-{(2S,4S)-1-tert-butoxycarbonyl-4-[4-(3,5-dichloro-2-pyridyl)-1-piperazinyl]-2-pyrrolidinylcarbonyl}-1,3-thiazolidine (1.35 g) was obtained as a white solid.

$^1$H-NMR($CDCl_3$)δ1.41(4.5H,s), 1.46(4.5H,s), 1.82–1.98 (1H,m), 2.38–2.50(1H,m), 2.53–2.73(4H,m), 2.78–3.22(3H, m), 3.28–3.44(5H,m), 3.62–4.14(3H,m), 4.38–4.80(3H,m), 7.59(1H,d,J=2.2 Hz), 8.12(1H,d,J=2.2 Hz).

(3) The above-mentioned compound (1.34 g) was dissolved in ethanol (3.5 mL), and 4.1 mol/L hydrochloric acid-ethanol (3.5 mL) was added thereto. The mixture was stirred at room temperature for 15 hr. The precipitated solid was collected by filtration to give the title compound (1.10 g) as a white powder.

$^1$H-NMR(DMSO-$d_6$)δ2.20–2.38(1H,m), 2.90–4.15(16H, m), 4.46–4.78(3H,m), 8.15(1H,d,J=2.3 Hz), 8.73(1H,d,J= 2.3 Hz), 9.13(1H,brs), 10.84(1H,brs), 12.55(1H,brs).

Example 221

Synthesis of 3-{(2S,4S)-4-[4-(3,5-dichloro-4-pyridyl)-1-piperazinyl]-2-pyrrolidinylcarbonyl}-1,3-thiazolidine trihydrochloride (1) Using 1-(3,5-dichloro-4-pyridyl)piperazine (0.766 g) and the title compound (0.901 g) of Reference Example 12, and in the same manner as in Example 70 (1), 3-{(2S,4S)-1-tert-butoxycarbonyl-4-[4-(3,5-dichloro-4-pyridyl)-1-piperazinyl]-2-pyrrolidinylcarbonyl}-1,3-thiazolidine (1.53 g) was obtained as a white solid.

$^1$H-NMR($CDCl_3$)δ1.41(4.5H,s), 1.46(4.5H,s), 1.82–1.98 (1H,m), 2.40–2.52(1H,m), 2.55–2.72(4H,m), 2.83–3.21(3H, m), 3.28–3.45(5H,m), 3.62–4.14(3H,m), 4.38–4.81(3H,m), 8.33(2H,s).

(2) The above-mentioned compound (1.53 g) was dissolved in ethyl acetate (7.5 mL), and 4 mol/L hydrochloric acid-ethyl acetate (7.5 mL) was added thereto. The mixture was stirred at room temperature for 13 hr. The precipitated solid was collected by filtration to give the title compound (1.64 g) as a white powder.

$^1$H-NMR(DMSO-$d_6$)δ2.27–2.43(1H,m), 2.95–4.2(16H, m), 4.45–4.78(3H,m), 8.52(2H,s), 9.14(1H,brs), 10.97(1H, brs), 12.6(1H,brs).

Example 222

Synthesis of 3-{(2S,4S)-4-[4-(3-methyl-1-phenyl-5-pyrazolyl)-1-piperazinyl]-2-pyrrolidinylcarbonyl}-1,3-thiazolidine trihydrochloride (1) 1-tert-Butoxycarbonylpiperazine (5.02 g) was dissolved in DMF (90 mL), and diketene (2.50 mL) was added thereto at room temperature. The mixture was stirred for 1.5 hr and the solvent was evaporated under reduced pressure. Water was added to the residue, and the mixture was extracted with ethyl acetate. The extract was washed with brine and dried. The solvent was evaporated under reduced pressure to give 1-acetoacetyl-4-tert-butoxycarbonylpiperazine (6.26 g) as a pale-brown powder.

(2) The above-mentioned compound (6.24 g) was dissolved in ethanol (500 mL), and phenylhydrazine (2.27 mL) and methanesulfonic acid (350 μL) were added at room temperature. The mixture was stirred for 14 hr and pyridine (6 mL) was added to the reaction mixture. The solvent was evaporated under reduced pressure and the residue was dissolved in pyridine (250 mL). Phosphorus oxychloride (5.0 mL) was added thereto at room temperature and the mixture was stirred for 20 hr. The solvent was evaporated under reduced pressure, the residue was acidified with dilute hydrochloric acid to pH 3. The mixture was extracted with ethyl acetate. The extract was washed successively with saturated aqueous sodium hydrogencarbonate solution and brine and dried. The solvent was evaporated under reduced pressure and the residue was purified by silica gel chromatography to give 1-tert-butoxycarbonyl-4-(3-methyl-1-phenyl-5-pyrazolyl)piperazine (935 mg) as an oil.

(3) The above-mentioned compound (935 mg) was dissolved in dichloromethane (10 mL), and trifluoroacetic acid (5 mL) was added thereto at room temperature. The mixture was stirred for 1.5 hr. The solvent was evaporated under reduced pressure, and water (50 mL) was added to the residue. The mixture was washed with diethyl ether. The aqueous layer was basified with aqueous sodium hydrogen carbonate solution, and the mixture was extracted with chloroform. The extract was dried, and evaporated under reduced pressure to give 1-(3-methyl-1-phenyl-5-pyrazolyl) piperazine (584 mg) as a brown powder.

(4) Using the above-mentioned compound (584 mg) and the title compound (604 mg) of Reference Example 12, and in the same manner as in Example 70 (1), 3-{(2S,4S)-1-tert-butoxycarbonyl-4-[4-(3-methyl-1-phenyl-5-pyrazolyl)-1-piperazinyl]-2-pyrrolidinylcarbonyl}-1,3-thiazolidine (846 mg) was obtained as a pale-yellow powder.

(5) Using the above-mentioned compound (844 mg), and in the same manner as in Example 133 (2), the title compound (751 mg) was obtained as a white solid.

$^1$H-NMR(500 MHz,DMSO-$d_6$)δ2.17(3H,s), 2.18–2.38 (1H,m), 2.90–4.10(16H,m), 4.46–4.74(3H,m), 5.93(1H,s), 7.31(1H,m), 7.47(2H,m), 7.79(2H,m), 9.09(1H,brs), 10.91 (1H,brs), 12.40(1H,brs).

Example 223

Synthesis of 3-{(2S,4S)-4-[4-(1-tert-butyl-3-methyl-5-pyrazolyl)-1-piperazinyl]-2-pyrrolidinylcarbonyl}-1,3-thiazolidine trihydrochloride (1) 1-Acetoacetyl-4-tert-butoxycarbonylpiperazine [product of Example 222 (1), 3.92 g] was dissolved in ethanol (300 mL), and tert-butylhydrazine hydrochloride (1.81 g) and molecular sieves 3A (10 g) were added thereto at room temperature. The mixture was stirred for 15 hr. The reaction mixture was filtrated and the filtrate was concentrated under reduced pressure. The residue was dissolved in pyridine (200 mL), and phosphorus oxychloride (3.0 mL) was added thereto at room temperature. The mixture was stirred for 24 hr. The reaction mixture was concentrated under reduced pressure, the residue was acidified with dilute hydrochloric acid to pH 3. The mixture was extracted with ethyl acetate. The extract was washed successively with saturated aqueous sodium hydrogencarbonate solution and brine and dried. The solvent was evaporated under reduced pressure and the residue was purified by silica gel chromatography to give 1-tert-butoxycarbonyl-4-(1-tert-butyl-3-methyl-5-pyrazolyl)piperazine (886 mg) as an oil.

(2) Using the above-mentioned compound (880 mg), and in the same manner as in Example 222 (3), 1-(3-methyl-1-tert-butyl-5-pyrazolyl)piperazine (607 mg) was obtained as a pale-yellow powder.

(3) Using the above-mentioned compound (0.607 g) and the title compound (0.781 g) of Reference Example 12, and in the same manner as in Example 70 (1), 3-{(2S,4S)-1-tert-butoxycarbonyl-4-[4-(3-methyl-1-tert-butyl-5-pyrazolyl)-1-piperazinyl]-2-pyrrolidinylcarbonyl}-1,3-thiazolidine (1.17 g) was obtained as a white powder.

(4) Using the above-mentioned compound (1.17 g), and in the same manner as in Example 133 (2), the title compound (0.902 g) was obtained as a white solid.

$^1$H-NMR(500 MHz,DMSO-$d_6$)δ1.56(9H,s), 2.09(3H,s), 2.27–2.47(1H,m), 2.90–4.20(16H,m), 4.48–4.78(3H,m), 6.00(1H,s), 9.12(1H,brs), 11.12(1H,brs), 12.49(1H,brs).

Example 224

Synthesis of 3-{(2S,4S)-4-[4-(1-phenyl-2-imidazolyl)-1-piperazinyl]-2-pyrrolidinylcarbonyl}-1,3-thiazolidine trihydrochloride (1) 1-Benzyloxycarbonylpiperazine (5.00 g) was dissolved in acetone (50 mL), and phenyl isothiocyanate (2.9 mL) was added thereto under ice-cooling. The mixture was stirred at room temperature for 1 hr. The precipitated solid was collected by filtration to give 1-(anilinocarbothioyl)-4-(benzyloxycarbonyl)piperazine (5.08 g) as a white powder.

(2) The above-mentioned compound (5.07 g) was dissolved in methanol (100 mL) and dichloromethane (20 mL), methyl iodide (1.4 mL) were added thereto. The mixture was stirred at room temperature for 17 hr. The reaction mixture was concentrated under reduced pressure, and saturated aqueous sodium hydrogencarbonate solution was added to the residue. The mixture was extracted with dichloromethane, and the extract was washed with brine, dried and concentrated under reduced pressure to give 1-benzyloxycarbonyl-4-[(methylthio)phenyliminomethyl] piperazine (5.71 g) as a slightly yellow oil.

(3) The above-mentioned compound (3.00 g) and aminoacetaldehyde dimethyl acetal (1.8 mL) were dissolved in pyridine (15 mL), and the mixture was stirred at 100° C. for 2 days with heating. The reaction mixture was concentrated under reduced pressure, and saturated aqueous sodium hydrogencarbonate solution was added to the residue. The mixture was extracted with chloroform and the extract was washed with brine, dried and concentrated under reduced pressure. The residue was dissolved in 2 mol/L hydrochloric acid (30 mL), and heated at 100° C. for 2 hr. Saturated aqueous sodium hydrogencarbonate solution was added to the reaction mixture, and the mixture was extracted with chloroform. The extract was washed with brine, dried and concentrated under reduced pressure. The residue was purified by silica gel chromatography to give 1-benzyloxycarbonyl-4-(1-phenyl-2-imidazolyl)piperazine (1.16 g) as a brown oil.

(4) The above-mentioned compound (1.16 g) was dissolved in methanol (30 mL). The solution was stirred in the presence of 10% palladium/carbon (232 mg) under a hydrogen atomosphere (1 atm) at room temperature for 20 hr. The reaction mixture was filtrated and the filtrate was concentrated under reduced pressure to give 1-(1-phenyl-2-imidazolyl)piperazine (0.742 g) as a white solid.

(5) Using the above-mentioned compound (0.740 g) and the title compound (0.901 g) of Reference Example 12, and in the same manner as in Example 70 (1), 3-{(2S,4S)-1-tert-butoxycarbonyl-4-[4-(1-phenyl-2-imidazolyl)-1-piperazinyl]-2-pyrrolidinylcarbonyl}-1,3-thiazolidine (1.30 g) was obtained as a white solid.

$^1$H-NMR($CDCl_3$)δ1.39(4.5H,s), 1.44(4.5H,s), 1.75–1.92 (1H,m), 2.36–2.57(5H,m), 2.74–2.89(1H,m), 2.93–3.17(6H, m), 3.25(1H,t,J=10.0 Hz), 3.60–4.08(3H,m), 4.34–4.77(3H, m), 6.83–6.88(2H,m), 7.34(1H,t,J=7.1 Hz), 7.43–7.54(4H, m).

(6) The above-mentioned compound (1.30 g) was dissolved in ethanol (3 mL), and 4.1 mol/L hydrochloric acid-ethanol (3 mL) was added thereto. The mixture was stirred at room temperature for 18 hr. The precipitated solid was collected by filtration to give the title compound (1.15 g) as a white powder.

$^1$H-NMR(DMSO-$d_6$)δ2.10–2.26(1H,m), 2.83–4.05(16H, m), 4.43–4.77(3H,m), 7.48(1H,d,J=2.3 Hz), 7.53(1H,d,J=2.3 Hz), 7.54–7.72(5H,m), 9.07(1H,brs), 10.98(1H,brs).

Example 225

Synthesis of 3-{(2S,4S)-4-[4-(5-methyl-1-phenyl-2-imidazolyl)-1-piperazinyl]-2-pyrrolidinylcarbonyl}-1,3-thiazolidine trihydrochloride (1) 1-Benzyloxycarbonyl-4-[(methylthio)phenyliminomethyl]piperazine [product of Example 224 (2), 2.70 g] and propargylamine (2.3 mL) were dissolved in 1-butanol (25 mL), and p-toluenesulfonic acid monohydrate (156 mg) was added thereto. The mixture was refluxed for 20 hr. The reaction mixture was concentrated under reduced pressure, and saturated aqueous sodium hydrogencarbonate solution was added to the residue. The mixture was extracted with chloroform, and the extract was washed with brine, dried and concentrated under reduced pressure. The residue was purified by silica gel chromatography to give 1-benzyloxycarbonyl-4-(5-methyl-1-phenyl-2-imidazolyl)piperazine (1.82 g) as a brown oil.

(2) Using the above-mentioned compound (1.16 g), and in the same manner as in Example 224 (4), 1-(5-methyl-1-phenyl-2-imidazolyl)piperazine (1.23 g) was obtained as a brown solid.

(3) Using the above-mentioned compound (0.800 g) and the title compound (0.901 g) of Reference Example 12, and in the same manner as in Example 70 (1), 3-{(2S,4S)-1-tert-butoxycarbonyl-4-[4-(5-methyl-1-phenyl-2-imidazolyl)-1-piperazinyl]-2-pyrrolidinylcarbonyl}-1,3-thiazolidine (1.20 g) was obtained as a white solid.

$^1$H-NMR($CDCl_3$)δ1.38(4.5H,s), 1.43(4.5H,s), 1.75–1.88 (1H,m), 1.99(3H,s), 2.28–2.46(5H,m), 2.68–2.83(1H,m), 2.90–3.16(6H,m), 3.22(1H,t,J=10.1 Hz), 3.57–4.07(3H,m), 4.32–4.75(3H,m), 6.57(1H,s), 7.27–7.53(5H,m).

(4) The above-mentioned compound (1.19 g) was dissolved in ethanol (3 mL), and 4.1 mol/L hydrochloric acid-ethanol (3 mL) as added thereto. The mixture was stirred at room temperature or 13 hr. The precipitated solid was collected by filtration to give the title compound (0.913 g) as a white powder.

$^1$H-NMR(DMSO-$d_6$)δ2.00–2.18(1H,m), 2.79–3.93(16H, m), 4.42–4.76(3H,m), 7.23(1H,s), 7.58–7.72(5H,m), 9.02 (1H,brs), 10.86(1H,brs), 14.01(1H,brs).

Example 226

Synthesis of 3-{(2S,4S)-4-[4-(4-phenyl-2-thiazolyl)-1-piperazinyl]-2-pyrrolidinylcarbonyl}-1,3-thiazolidine trihydrochloride (1) Phenacyl bromide (4 g) was dissolved in acetonitrile (30 mL), and sodium thiocyanate (1.8 g) was added at room temperature with stirring. The reaction mixture was concentrated under reduced pressure, and brine was added to the residue. The mixture was extracted with ethyl acetate. The extract was dried, and the solvent was evaporated under reduced pressure to give 2-isocyanatoacetophenone (3.53 g) as white crystals.

(2) Piperazine (3.8 g) was dissolved in ethanol (40 mL), and a solution of the above-mentioned compound (3.53 g) in ethyl acetate (10 mL) was added thereto. The mixture was heated at 70° C. for 1 hr. The reaction mixture was concentrated under reduced pressure, and brine was added to the residue. The mixture was extracted with ethyl acetate, and the extract was dried and concentrated under reduced pressure. The residue was purified by silica gel chromatography to give 4-phenyl-2-(1-piperazinyl)thiazole (2.38 g) as a yellow oil.

(3) Using the above-mentioned compound (0.810 g) and the title compound (0.901 g) of Reference Example 12, and in the same manner as in Example 70 (1), 3-{(2S,4S)-1-tert-butoxycarbonyl-4-[4-(4-phenyl-2-thiazolyl)-1-piperazinyl]-2-pyrrolidinylcarbonyl}-1,3-thiazolidine (1.59 g) was obtained as a pale-yellow solid.

$^1$H-NMR($CDCl_3$)δ1.41(4.5H,s), 1.46(4.5H,s), 1.84–1.98 (1H,m), 2.40–2.72(5H,m), 2.80–3.18(3H,m), 3.34(1H,t,J=9.9 Hz), 3.49–4.15(7H,m), 4.38–4.80(3H,m), 6.78(1H,s), 7.26–7.46(13H,m), 7.83(2H,d,J=7.1 Hz).

(4) The above-mentioned compound (1.59 g) was dissolved in ethanol (6 mL), and 4.1 mol/L hydrochloric acid-ethanol (6 mL) was added thereto. The mixture was stirred at room temperature for 12 hr. The precipitated solid was collected by filtration to give the title compound (1.41 g) as a pale-brown powder.

$^1$H-NMR(DMSO-$d_6$)δ2.27–2.42(1H,m), 2.95–3.18(3H, m), 3.37–4.18(16H,m), 4.47–4.78(3H,m), 7.30(1H,t,J=7.3 Hz), 7.37–7.45(3H,s), 7.87(2H,d,J=7.1 Hz), 9.17(1H,brs), 10.93(1H,brs).

Example 227

Synthesis of 3-((2S,4S)-4-{4-[4-(4-cyanophenyl)-2-thiazolyl]-1-piperazinyl}-2-pyrrolidinylcarbonyl)-1,3-thiazolidine trihydrochloride (1) 4-Acetylbenzonitrile (4.35 g) was dissolved in chloroform (40 mL), and a solution of bromine (1.7 mL) in chloroform (10 mL) was added dropwise. The mixture was stirred at room temperature. The reaction mixture was washed with saturated aqueous sodium hydrogencarbonate solution, dried and concentrated under reduced pressure. The residue was dissolved in acetonitrile (40 mL), and sodium thiocyanate (2.4 g) was added thereto. The mixture was stirred at room temperature and concentrated under reduced pressure. Brine was added to the residue, and the mixture was extracted with ethyl acetate. The extract was dried and the solvent was evaporated under reduced pressure. The residue was purified by silica gel chromatography to give 4-(2-isocyanatoacetyl)benzonitrile (4.39 g) as yellow crystals.

(2) The above-mentioned compound (4.39 g) and piperazine (4.15 g) were dissolved in ethanol (70 mL), and the mixture was stirred at 80° C. for 1 hr with heating. The reaction mixture as concentrated under reduced pressure, and brine was added to the residue. The mixture was extracted with ethyl acetate. The extract was dried and concentrated under reduced pressure. The residue was purified by silica gel chromatography to give 1-[4-(4-cyanophenyl)-2-thiazolyl]piperazine (1.83 g) as a yellow solid.

(3) Using the above-mentioned compound (0.892 g) and the title compound (0.901 g) of Reference Example 12, and in the same manner as in Example 70 (1), 3-((2S,4S)-1-tert-butoxycarbonyl-4-{4-[4-(4-cyanophenyl)-2-thiazolyl]-1-piperazinyl}-2-pyrrolidinylcarbonyl)-1,3-thiazolidine (1.40 g) was obtained as a brown solid.

$^1$H-NMR($CDCl_3$)δ1.41(4.5H,s), 1.46(4.5H,s), 1.83–1.98 (1H,m), 2.38–2.75(5H,m), 2.82–3.22(3H,m), 3.34(1H,t,J=9.9 Hz), 3.48–4.15(7H,m), 4.38–4.81(3H,m), 6.93(1H,s), 7.65(2H,d,J=8.3 Hz), 8.34(2H,d,J=8.3 Hz).

(4) The above-mentioned compound (1.39 g) was dissolved in ethyl acetate (3 mL), and 4 mol/L hydrochloric acid-ethyl acetate (6 mL) was added thereto. The mixture was stirred at room temperature for 4 days. The precipitated solid was collected by filtration to give the title compound (1.23 g) as a pale-yellow powder.

$^1$H-NMR(DMSO-$d_6$)δ2.24–2.38(1H,m), 2.94–3.18(3H, m), 3.35–4.14(16H,m), 4.46–4.78(3H,m), 7.73(1H,s), 7.87 (2H,d,J=8.5 Hz), 8.07(2H,d,J=8.5 Hz), 9.16(1H,brs), 10.83 (1H,brs).

Example 228

Synthesis of 3-{(2S,4S)-4-[4-(1-phenyl-1H-tetrazol-5-yl)-1-piperazinyl]-2-pyrrolidinylcarbonyl}-1,3-thiazolidine trihydrochloride (1) Using 5-chloro-1-phenyl-1H-tetrazol (2.10 g) and piperazine (10.0 g), and reaction at 100° C. in the same manner as in Example 196 (1), 1-(1-phenyl-1H-tetrazol-5-yl)piperazine (2.67 g) was obtained as a pale-yellow powder.

(2) Using the above-mentioned compound (0.59 g) and the title compound (0.696 g) of Reference Example 12, and in the same manner as in Example 70 (1), 3-{(2S,4S)-1-tert-butoxycarbonyl-4-[4-(1-phenyl-1H-tetrazol-5-yl)-1-piperazinyl]-2-pyrrolidinylcarbonyl}-1,3-thiazolidine (1.19 g) was obtained as a white powder.

(3) Using the above-mentioned compound (1.19 g), and in the same manner as in Example 133 (2), the title compound (0.863 g) was obtained as a white powder.

$^1$H-NMR(500 MHz,DMSO-$d_6$)δ2.02–2.22(1H,m), 2.80–3.95(16H,m), 4.45–4.73(3H,m), 7.57–7.73(5H,m), 9.04(1H,brs), 10.61(1H,brs).

Example 229

Synthesis of 3-{(2S,4S)-4-[4-(1-cyclohexyl-1H-tetrazol-5-yl)-1-piperazinyl]-2-pyrrolidinylcarbonyl}-1,3-thiazolidine trihydrochloride (1) 1-Benzyloxycarbonylpiperazine (2.07 g) was dissolved in dichloromethane (50 mL), and cyclohexyl isocyanate (1.20 mL) was added thereto at room temperature. The mixture was stirred for 1 hr. The solvent was evaporated under reduced pressure, and the residue was dissolved in tetrahydrofuran (100 mL). Phosphorus oxychloride (8.8 mL) was added thereto, and the mixture was refluxed for 18 hr. The reaction mixture was concentrated under reduced pressure, and a 0.5 mol/L solution of triazole in acetonitrile (100 mL) was added to the residue. The mixture was stirred at room temperature for 3 hr. The solvent was evaporated under reduced pressure, and saturated aqueous sodium hydrogencarbonate solution was added to the residue. The mixture was extracted with ethyl acetate, and the extract was washed with brine and dried. The solvent was distilled away under reduced pressure, and the residue was dissolved in methanol (100 mL). An aqueous solution (20 mL) of sodium azide (6.50 g) was added thereto. The mixture was stirred at 70° C. for 3 hr and the reaction mixture was concentrated under reduced pressure. Water was added to the residue, and the mixture was extracted with ethyl acetate. The extract was washed with brine and dried. The solvent was evaporated under reduced pressure and the residue was purified by silica gel chromatography to give 1-benzyloxycarbonyl-4-(1-cyclohexyl-1H-tetrazol-5-yl)piperazine (390 mg) as a white powder.

(2) The above-mentioned compound (388 mg) was dissolved in ethanol (10 mL) and ethyl acetate (10 mL). The mixture was stirred in the presence of 10% palladium/carbon (140 mg) under a hydrogen atomosphere (1 atm) for 2 hr. The reaction mixture was filtrated and the filtrate was concentrated under reduced pressure to give 1-(1-cyclohexyl-1H-tetrazol-5-yl)piperazine (248 mg) as a white powder.

(3) Using the above-mentioned compound (248 mg) and the title compound (290 mg) of Reference Example 12, and in the same manner as in Example 70 (1), 3-{(2S,4S)-1-tert-butoxycarbonyl-4-[4-(1-cyclohexyl-1H-tetrazol-5-yl)-1-piperazinyl]-2-pyrrolidinylcarbonyl}-1,3-thiazolidine (502 mg) was obtained as a white powder.

(4) Using the above-mentioned compound (502 mg), and in the same manner as in Example 133 (2), the title compound (302 mg) was obtained as a white powder.

$^1$H-NMR(500 MHz,DMSO-$d_6$)δ1.20–1.34(1H,m), 1.40–1.50(2H,m), 1.64–1.88(5H,m), 1.97–2.03(2H,m), 2.12–2.32(1H,m), 2.90–4.05(16H,m), 4.25(1H,m), 4.48–4.75(3H,m), 9.10(1H,brs), 10.67(1H,brs).

Example 230

Synthesis of 3-{(2S,4S)-4-[4-(2-benzimidazolyl)-1-piperazinyl]-2-pyrrolidinylcarbonyl}-1,3-thiazolidine dihydrochloride (1) Using 2-chlorobenzimidazole (0.500 g) and piperazine (8.47 g), and in the same manner as in Example 189 (1), 1-(2-benzimidazolyl)piperazine (0.086 g) was obtained as a white powder.

(2) Using the above-mentioned compound (86 mg) of Reference Example 12 and the title compound (128 mg), and in the same manner as in Example 70 (1), 3-{(2S,4S)-4-[4-(2-benzimidazolyl)-1-piperazinyl]-1-tert-butoxycarbonyl-2-pyrrolidinylcarbonyl}-1,3-thiazolidine (203 mg) was obtained as a white solid.

(3) Using the above-mentioned compound (203 mg), and in the same manner as in Example 186 (2), the title compound (94 mg) was obtained as a white powder.

$^1$H-NMR(DMSO-$d_6$)δ1.72–2.16(1H,m), 2.65–4.30(16H, m), 4.40–4.80(3H,m), 7.18–7.33(2H,m), 7.36–7.51(2H,m), 8.95(1H,brs), 9.70(1H,brs), 10.50(1H,brs), 13.71(2H,brs).

Example 231

Synthesis of 3-{(2S,4S)-4-[4-(5-cyano-2-benzimidazolyl)-1-piperazinyl]-2-pyrrolidinylcarbonyl}-1,3-thiazolidine trihydrochloride (1) 4-Amino-3-nitrobenzonitrile (25 g) was dissolved in methanol (200 mL) and tetrahydrofuran (200 mL). The mixture was stirred in the presence of 10% palladium/carbon (3.0 g) under a hydrogen atomosphere (1 atm) for 20 hr. The reaction mixture was filtrated and the filtrate was concentrated under reduced pressure to give 3,4-diaminobenzonitrile (20 g) as a charcoal brown solid.

(2) The above-mentioned compound (2.60 g) was dissolved in DMF (20 mL) and pyridine (2 mL), and a solution of triphosgene (2.12 g) in tetrahydrofuran (20 mL) was added dropwise under ice-cooling. The mixture was stirred at room temperature for 18 hr. Dilute hydrochloric acid was added to the reaction mixture, and the mixture was extracted with ethyl acetate. The extract was washed with brine and dried. The solvent was evaporated under reduced pressure and ethyl acetate was added to the residue. The precipitated solid was collected by filtration to give 2-hydroxybenzimidazole-5-carbonitrile (896 g) as a purple solid.

(3) The above-mentioned compound (894 mg) was dissolved in phosphorus oxychloride (12 mL), and the solution was refluxed for 3 hr. The reaction mixture was added to ice, and extracted with ethyl acetate. The extract was washed with brine, dried and concentrated under reduced pressure. The residue was purified by silica gel chromatography to give 2-chlorobenzimidazole-5-carbonitrile (322 mg) as a white powder.

(4) The product (345 mg) of Example 199 (3) was dissolved in N-methyl-2-pyrrolidone (6 mL), and the above-mentioned compound (182 mg) and N,N-diisopropylethylamine (180 μL) were added thereto. The mixture was stirred at 100° C. for 17 hr. The reaction mixture was added to water, and the mixture was extracted with ethyl acetate. The extract was washed with brine, dried and concentrated under reduced pressure. The residue was purified by HPLC to give 3-{(2S,4S)-1-benzyloxycarbonyl-4-[4-(5-cyano-2-benzimidazolyl)-1-piperazinyl]-2-pyrrolidinylcarbonyl}-1,3-thiazolidine (250 mg) as a white solid.

(5) Using the above-mentioned compound (200 mg), and in the same manner as in Example 199 (5), the title compound (50 mg) was obtained as a white powder.

$^1$H-NMR(500 MHz,DMSO-$d_6$)δ1.89–2.09(1H,m), 2.78–4.20(16H,m), 4.47–4.82(3H,m), 7.51(1H,d,J=8.2 Hz), 7.61(1H,d,J=8.2 Hz), 7.81(1H,s), 8.97(1H,brs), 10.28(1H, brs).

Example 232

Synthesis of 3-{(2s,4s)-4-[4-(5-trifluoromethyl-2-benzimidazolyl)-1-piperazinyl]-2-pyrrolidinylcarbonyl}-1,3-thiazolidine trihydrobromide (1) Using 4-trifluoromethyl-2-nitroaniline (25.0 g), and in the same manner as in Example 231 (1), 4-trifluoromethyl-1,2-phenylenediamine (21.3 g) was obtained as a white solid.

(2) Using the above-mentioned compound (10.2 g) and in the same manner as in Example 231 (2), the reaction mixture was added to water. The precipitated solid was collected by filtration to give 5-trifluoromethyl-2-hydroxybenzimidazole (3.28 g) as a white solid.

(3) Using the above-mentioned compound (3.27 g), and in the same manner as in Example 231 (3), 2-chloro-5-trifluoromethylbenzimidazole (2.48 g) was obtained as a white powder.

(4) Using the above-mentioned compound (226 mg) and the product (345 mg) of Example 199 (3), and in the same manner as in Example 231 (4), 3-{(2S,4S)-1-benzyloxycarbonyl-4-[4-(5-trifluoromethyl-2-benzimidazolyl)-1-piperazinyl]-2-pyrrolidinylcarbonyl}-1,3-thiazolidine (192 mg) was obtained as a white solid.

(5) 30% Hydrogen bromide-acetic acid solution (10 mL) was added to the above-mentioned compound (190 mg), and the mixture was stirred at room temperature for 6 hr. Diethyl ether was added to the reaction mixture, and the precipitated solid was collected by filtration and washed with ethanol. The title compound (101 mg) was obtained as a white powder.

$^1$H-NMR(500 MHz,DMSO-$d_6$)δ1.761.96(1H,m), 2.75–4.80(16H,m), 4.46–4.74(3H,m), 7.60(2H,s), 7.67(1H, s), 8.96(1H,brs), 9.59(1H,brs), 13.02(1H,brs).

Example 233

Synthesis of 3-{(2S,4S)-4-[4-(5-fluoro-2-benzimidazolyl)-1-piperazinyl]-2-pyrrolidinylcarbonyl}-1,3-thiazolidine trihydrobromide (1) Using 4-fluoro-2-nitroaniline (25.0 g), and in the same manner as in Example 231 (1), 4-fluoro-1,2-phenylenediamine (20.1 g) was obtained as a charcoal brown solid.

(2) Using the above-mentioned compound (10.0 g), and in the same manner as in Example 231 (2), the reaction mixture was added to water. The precipitated solid was collected by filtration to give 5-fluoro-2-hydroxybenzimidazole (2.14 g) as a brown solid.

(3) Using the above-mentioned compound (2.13 g), and in the same manner as in Example 231 (3), 2-chloro-5-fluorobenzimidazole (1.44 g) was obtained as a brown solid.

(4) Using the above-mentioned compound (174 mg) and the product (345 mg) of Example 199 (3), and in the same manner as in Example 231 (4), 3-{(2S,4S)-1-benzyloxycarbonyl-4-[4-(5-fluoro-2-benzimidazolyl)-1-piperazinyl]-2-pyrrolidinylcarbonyl}-1,3-thiazolidine (66 mg) was obtained as a white solid.

(5) Using the above-mentioned compound (66 mg), and in the same manner as in Example 232 (5), the title compound (20 mg) was obtained as a white powder.

$^1$H-NMR(500 MHz,DMSO-$d_6$)δ1.77–1.97(1H,m), 2.88–4.20(16H,m), 4.46–4.76(3H,m), 7.12–7.16(1H,m), 7.32(1H,dd,J=8.5,2.2 Hz), 7.44(1H,dd,J=8.7,4.5 Hz), 8.97 (1H,brs), 9.61(1H,brs), 13.16(1H,brs).

Example 234

Synthesis of 3-{(2S,4S)-4-[4-(5-chloro-2-benzimidazolyl)-1-piperazinyl]-2-pyrrolidinylcarbonyl}-1,3-thiazolidine trihydrobromide (1) 2-Chlorobenzimidazole (1.05 g) was dissolved in DMF (10 mL), and N-chlorosuccinimide (1.01 g) was added thereto. The mixture was stirred at 60° C. for 30 min and the reaction mixture was added to water. The precipitated solid was collected by filtration to give 2,5-dichlorobenzimidazole (0.480 g) as a white solid.

(2) Using the above-mentioned compound (191 mg) and the product (345 mg) of Example 199 (3), and in the same manner as in Example 231 (4), 3-{(2S,4S)-1-benzyloxycarbonyl-4-[4-(5-chloro-2-benzimidazolyl)-1-piperazinyl]-2-pyrrolidinylcarbonyl}-1,3-thiazolidine (122 mg) was obtained as a pale-yellow solid.

(3) Using the above-mentioned compound (110 mg), and in the same manner as in Example 232 (5), the title compound (56 mg) was obtained as a white powder.

$^1$H-NMR(500 MHz,DMSO-$d_6$)δ1.76–1.96(1H,m), 2.70–4.87(16H,m), 4.46–4.74(3H,m), 7.32(1H,dd,J=8.5,1.7 Hz), 7.44(1H,d,J=8.5 Hz), 7.48(1H,d,J=1.7 Hz), 8.96(1H, brs), 9.59(1H,brs), 13.15(1H,brs).

Example 235

Synthesis of 3-{(2S,4S)-4-[4-(5-nitro-2-benzimidazolyl)-1-piperazinyl]-2-pyrrolidinylcarbonyl}-1,3-thiazolidine trihydrochloride (1) Using 4-nitro-1,2-phenylenediamine (9.12 g), and in the same manner as in Example 231 (2), the reaction mixture was added to water. The precipitated solid was collected by filtration to give 5-nitro-2-hydroxyxisobenzimidazole (5.69 g) as an yellow solid.

(2) Using the above-mentioned compound (5.69 g), and in the same manner as in Example 231 (3), 2-chloro-5-nitrobenzimidazole (2.41 g) was obtained as a yellow solid.

(3) Using the above-mentioned compound (1.00 g) and piperazine (4.70 g), and by a reaction at 100° C. in the same manner as in Example 196 (1), 1-(5-nitro-2-benzimidazolyl) piperazine (0.16 g) was obtained as an orange solid.

(4) Using the above-mentioned compound (160 mg) and the title compound (162 mg) of Reference Example 12, and in the same manner as in Example 70 (1), 3-{(2S,4S)-1-tert-butoxycarbonyl-4-[4-(5-nitro-2-benzimidazolyl)-1-piperazinyl]-2-pyrrolidinylcarbonyl}-1,3-thiazolidine (172 mg) was obtained as a yellow solid.

(5) Using the above-mentioned compound (172 mg), and in the same manner as in Example 133 (2), the title compound (138 mg) was obtained as a yellow powder.

$^1$H-NMR(500 MHz,DMSO-$d_6$)δ2.08–2.24(1H,m), 2.78–4.03(16H,m), 4.48–4.75(3H,m), 7.52(2H,d,J=8.6 Hz), 8.11(2H,dd,J=8.6,2.0 Hz), 8.12(1H,d,J=2.0 Hz), 9.06(1H, brs), 10.59(1H,brs).

Example 236

Synthesis of 3-{(2S,4S)-4-[4-(1-methyl-2-benzimidazolyl)-1-piperazinyl]-2-pyrrolidinylcarbonyl}-1,3-thiazolidine trihydrochloride (1) Sodium hydride (contained by 60%, 0.288 g) was suspended in DMF (10 mL), and 2-chlorobenzimidazole (1 g) was added thereto. The mixture was stirred at room temperature for 30 min and methyl iodide (0.61 mL) was added thereto. After stirring at room temperature for 1 hr, water was added to the reaction mixture. The mixture was extracted with ethyl acetate, and the extract was washed with brine and concentrated under reduced pressure to give 2-chloro-1-methylbenzimidazole (0.928 g) as a white powder.

(2) Using the above-mentioned compound (0.928 g) and piperazine (9.60 g), and in the same manner as in Example 189 (1), 1-(1-methyl-2-benzimidazolyl)piperazine (1.18 g) was obtained as a pale-yellow solid.

(3) Using the above-mentioned compound (476 mg) and the title compound (601 mg) of Reference Example 12, and in the same manner as in Example 70 (1), 3-{(2S,4S)-1-tert-butoxycarbonyl-4-[4-(1-methyl-2-benzimidazolyl)-1-piperazinyl]-2-pyrrolidinylcarbonyl}-1,3-thiazolidine (947 mg) was obtained as a white solid.

(4) Using the above-mentioned compound (857 mg), and in the same manner as in Example 186 (2), the title compound (532 mg) was obtained as a white powder.

$^1$H-NMR(DMSO-$d_6$)δ2.19–2.38(1H,m), 2.89–3.20(3H, m), 3.30–4.30(13H,m), 3.79(3H,s), 4.42–4.85(3H,m), 7.34–7.47(2H,m), 7.53–7.63(1H,m), 7.64–7.76(1H,m), 9.15 (1H,brs), 11.08(1H,brs).

Example 237

Synthesis of 3-{(2S,4S)-4-[4-(5-trifluoromethyl-1-methyl-2-benzimidazolyl)-1-piperazinyl]-2-pyrrolidinylcarbonyl}-1,3-thiazolidine trihydrochloride (1) 4-Fluoro-3-nitrobenzotrifluoride (25 g) was dissolved in ethanol (50 mL), and 30% methylamine-ethanol solution (97.9 g) was gradually added dropwise under ice-cooling, and the mixture was stirred at room temperature for 40 min. The reaction mixture was added to water, and the precipitated solid was collected by filtration to give 4-methylamino-3-nitrobenzotrifluoride (25.5 g) as yellow crystals.

(2) Using the above-mentioned compound (25.3 g), and in the same manner as in Example 231 (1), 4-trifluoromethyl-N1-methyl-1,2-phenylenediamine (21.9 g) was obtained as a pale-yellow solid.

(3) The above-mentioned compound (21.9 g) was subjected to the reaction in the same manner as in Example 231 (2), and water was added to the reaction mixture. The precipitated solid was collected by filtration to give 5-trifluoromethyl-2-hydroxy-1-methylbenzimidazole (23.8 g) as a white solid.

(4) Using the above-mentioned compound (10.1 g), and in the same manner as in Example 231 (3), 2-chloro-5-trifluoromethyl-1-methylbenzimidazole (10.5 g) was obtained as a white solid.

(5) Using the above-mentioned compound (5.07 g) and piperazine (18.6 g), and by a reaction at 100° C. in the same manner as in Example 196 (1), 1-(5-trifluoromethyl-1-methyl-2-benzimidazolyl)piperazine (4.87 g) was obtained as a white solid.

(6) Using the above-mentioned compound (485 mg) and the title compound (518 mg) of Reference Example 12, and in the same manner as in Example 70 (1), 3-{(2S,4S)-1-tert-butoxycarbonyl-4-[4-(5-trifluoromethyl-1-methyl-2-benzimidazolyl)-1-piperazinyl]-2-pyrrolidinylcarbonyl}-1,3-thiazolidine (978 mg) was obtained as a white powder.

(7) Using the above-mentioned compound (978 mg), and in the same manner as in Example 133 (2), the title compound (483 mg) was obtained as a white powder.

$^1$H-NMR(500 MHz,DMSO-$d_6$)δ2.23–2.43(1H,m), 2.97–4.15(16H,m), 3.76(3H,s), 4.49–4.77(3H,m), 7.61(1H, d,J=8.4 Hz), 7.74(1H,d,J=8.4 Hz), 7.80(1H,s), 9.14(1H,brs), 10.94(1H,brs).

Example 238

Synthesis of 3-{(2S,4S)-4-[4-(5-fluoro-1-methyl-2-benzimidazolyl)-1-piperazinyl]-2-pyrrolidinylcarbonyl}-1,3-thiazolidine trihydrochloride (1) Using 2,5-difluoronitrobenzene (25.4 g), and in the same manner as in Example 237 (1), 5-fluoro-2-(methylamino)nitrobenzene (27.2 g) was obtained as an orange solid.

(2) Using the above-mentioned compound (27.2 g), and in the same manner as in Example 231 (1), 4-fluoro-N1-methyl-1,2-phenylenediamine (20.9 g) was obtained as an orange solid.

(3) Using the above-mentioned compound (18.1 g), and in the same manner as in Example 231 (2), 5-fluoro-2-hydroxy-1-methylbenzimidazole (0.682 g) was obtained as a pale-yellow solid.

(4) Using the above-mentioned compound (675 mg), and in the same manner as in Example 231 (3), 2-chloro-5-fluoro-1-methylbenzimidazole (647 mg) was obtained as a white solid.

(5) Using the above-mentioned compound (0.633 g) and piperazine (3.2 g), and by a reaction at 100° C. in the same manner as in Example 196 (1), 1-(5-fluoro-1-methyl-2-benzimidazolyl)piperazine (0.77 g) was obtained as a pale-yellow solid.

(6) Using the above-mentioned compound (0.76 g) and the title compound (0.80 g) of Reference Example 12, and in the same manner as in Example 70 (1), 3-{(2S,4S)-1-tert-butoxycarbonyl-4-[4-(5-fluoro-1-methyl-2-benzimidazolyl)-1-piperazinyl]-2-pyrrolidinylcarbonyl}-1,3-thiazolidine (1.40 g) was obtained as a white powder.

(7) Using the above-mentioned compound (1.40 g), and in the same manner as in Example 133 (2), the title compound (0.676 g) was obtained as a white powder.

$^1$H-NMR(500 MHz,DMSO-$d_6$)δ2.20–2.40(1H,m), 2.85–4.14(16H,m), 3.76(3H,s), 4.49–4.76(3H,m), 7.23(1H, m), 7.38(1H,dd,J=8.6,2.1 Hz), 7.65(1H,dd,J=8.7,4.3 Hz), 9.13(1H,brs), 11.03(1H,brs).

Example 239

Synthesis of 3-{(2S,4S)-4-[4-(5-cyano-2-benzoxazolyl)-1-piperazinyl]-2-pyrrolidinylcarbonyl}-1,3-thiazolidine dihydrochloride (1) 3-Amino-4-cyanophenol (6.71 g) was dissolved in pyridine (100 mL), and potassium ethylxanthate (8.82 g) was added thereto. The mixture was refluxed for 2 hr. After allowing to cool, iced water (200 mL) was added to the reaction mixture, and conc. hydrochloric acid (40 mL) was added thereto. The precipitated solid was collected by filtration to give 5-cyano-2-mescaptobenzoxazole (5.62 g) as a gray powder.

(2) The above-mentioned compound (5 g) and two drops of DMF were added to thionyl chloride (20 mL), and the mixture was refluxed for 1 hr. The reaction mixture was concentrated under reduced pressure to give 2-chloro-5-cyanobenzoxazole (5.06 g).

(3) Piperazine (4.29 g) was dissolved in DMF (40 mL), and the above-mentioned compound (2.96 g) was added thereto. The mixture was stirred at room temperature for 3 hr. The reaction mixture was added to water, and the mixture was extracted with chloroform. 1 mol/L Hydrochloric acid was added to the extract, and the aqueous layer was separated. Aqueous sodium hydroxide solution was added thereto, and the mixture was extracted with chloroform. The extract was concentrated under reduced pressure to give 1-(5-cyano-2-benzoxazolyl)piperazine (0.933 g) as a pale-yellow powder.

(4) Using the above-mentioned compound (502 mg) and the title compound (601 mg) of Reference Example 12, and in the same manner as in Example 70 (1), 3-{(2S,4S)-1-tert-butoxycarbonyl-4-[4-(5-cyano-2-benzoxazolyl)-1-piperazinyl]-2-pyrrolidinylcarbonyl}-1,3-thiazolidine (428 mg) was obtained as a white powder.

(5) The above-mentioned compound (424 mg) was dissolved in chloroform (10 mL), and 5 mol/L hydrochloric acid-ethyl acetate (5 mL) was added thereto. The mixture was stirred at room temperature for 18 hr and the reaction mixture was concentrated under reduced pressure. The residue was washed with ethanol to give the title compound (302 mg) as a white powder.

$^1$H-NMR(DMSO-$d_6$)δ1.94–2.26(1H,m), 2.80–3.00(1H, m), 3.00–4.30(15H,m), 4.45–4.78(3H,m), 7.56(1H,dd,J= 8.4,1.8 Hz), 7.66(1H,d,J=8.4 Hz), 7.83(1H,d,J=1.5 Hz), 9.05 (1H,brs), 10.43(1H,brs).

Example 240

Synthesis of 3-{(2S,4S)-4-[4-(5-cyano-2-benzothiazolyl)-1-piperazinyl]-2-pyrrolidinylcarbonyl}-1,3-thiazolidine dihydrochloride (1) 2-Bromo-5-nitroaniline (10 g) was dissolved in N-methyl-2-pyrrolidone (50 mL), and potassium ethylxanthate (14.8 g) was added thereto. The mixture was stirred at 140° C. with heating. The reaction mixture was concentrated under reduced pressure, and water (300 mL) and conc. hydrochloric acid (10 mL) were added to the residue. The precipitated solid was collected by filtration, which was then dissolved in 1 mol/L aqueous sodium hydroxide solution (80 mL). After washing with chloroform, 1 mol/L hydrochloric acid was added thereto, and the precipitated solid was collected by filtration to give 2-mercapto-5-nitrobenzothiazole (8.43 g) as an orange powder.

(2) Sodium hydride (contained by 60%, 1.05 g) was suspended in DMF (50 mL) and the above-mentioned compound (8.43 g) was added thereto under ice-cooling. After the mixture was stirred for 30 min, methyl iodide (2.72 mL) was added thereto under ice-cooling. The mixture was stirred at room temperature for 2 hr. The reaction mixture was added to water, and the mixture was extracted with ethyl acetate (insoluble material was removed by filtration). The extract was washed successively with water and brine and concentrated under reduced pressure to give 2-methylthio-5-nitrobenzothiazole (4.82 g) as a pale-brown powder.

(3) The above-mentioned compound (3.33 g) was dissolved in ethanol (70 mL), and chloride dihydrate (II) (14.0 g) was added thereto. The mixture was refluxed for 1 hr. The reaction mixture was concentrated under reduced pressure, and saturated aqueous sodium hydrogencarbonate solution was added to the residue. The mixture was extracted with chloroform (insoluble material was filtered off). The extract was washed with brine and concentrated under reduced pressure to give 5-amino-2-methylthiobenzothiazole (2.54 g) as a red-orange solid.

(4) The above-mentioned compound (2.54 g) was suspended in water (40 mL) and conc. hydrochloric acid (3.75 mL) was added thereto under ice-cooling. Thereto was added dropwise a solution of sodium nitrite (1.00 g) in water (10 mL) under ice-cooling. After stirring the reaction mixture for 20 min, 5% aqueous potassium carbonate solution (20 mL) was added dropwise under ice-cooling. This reaction mixture was added dropwise under ice-cooling to a solution of copper cyanide (2.35 g) and potassium cyanide (3.44 g) in water (40 mL) prepared separately. After stirring under ice-cooling for 1 hr, the mixture was stirred at 50° C. for 10 min with heating. The reaction mixture was added to water (50 mL), and the mixture was extracted with ethyl acetate (insoluble material was filtered off). The extract was washed with brine, and concentrated under reduced pressure to give 5-cyano-2-methylthiobenzothiazole (1.96 g).

(5) Using the above-mentioned compound (0.645 g) and piperazine (8.08 g), and in the same manner as in Example 189 (1), 1-(5-cyano-2-benzothiazolyl)piperazine (0.601 g) was obtained as a brown solid.

(6) Using the above-mentioned compound (601 mg) and the title compound (601 mg) of Reference Example 12, and in the same manner as in Example 70 (1), 3-{(2S,4S)-1-tert-butoxycarbonyl-4-[4-(5-cyano-2-benzothiazolyl)-1-piperazinyl]-2-pyrrolidinylcarbonyl}-1,3-thiazolidine (649 mg) was obtained as a pale-orange powder.

(7) Using the above-mentioned compound (649 mg), and in the same manner as in Example 239 (5), the title compound (500 mg) was obtained as a white powder.

$^1$H-NMR(DMSO-$d_6$)δ2.04–2.28(1H,m), 2.82–3.00(1H, m), 3.00–4.30(15H,m), 4.43–4.80(3H,m), 7.53(1H,dd,J=8.2,1.5 Hz), 7.93(1H,d,J=1.5 Hz), 8.07(1H,d,J=8.2 Hz), 9.08 (1H,brs), 10.51(1H,brs).

Example 241

Synthesis of 3-{(2S,4S)-4-[4-(6-cyano-2-benzothiazolyl)-1-piperazinyl]-2-pyrrolidinylcarbonyl}-1,3-thiazolidine dihydrochloride (1) Sodium hydride (containing by 60%, 6.15 g) was suspended in DMF (120 mL) and 2-mercapto-6-nitrobenzothiazole (20 g) was added thereto under ice-cooling. After completion of bubbling, methyl iodide (26.4 mL) was added thereto. The mixture was stirred at room temperature for 18 hr. Water (800 mL) was added to the reaction mixture, and the precipitated solid was collected by filtration to give 2-methylthio-6-nitrobenzothiazole (21.2 g) as a pale-yellow powder.

(2) Using the above-mentioned compound (10 g) and tin(II) chloride (41.9 g), and in the same manner as in Example 240 (3), 6-amino-2-methylthiobenzothiazole (7.75 g) was obtained as a white solid.

(3) Using the above-mentioned compound (2.59 g), sodium nitrite (1.00 g), copper cyanide (2.35 g) and potassium cyanide (3.44 g), and in the same manner as in Example 240 (4), 6-cyano-2-mercaptobenzothiazole (2.22 g) was obtained as a brown solid.

(4) Using the above-mentioned compound (2.04 g) and piperazine (8.82 g), and in the same manner as in Example 189 (1), 1-(6-cyano-2-benzothiazolyl)piperazine (2.02 mg) was obtained as a brown-reddish solid.

(5) Using the above-mentioned compound (538 mg) and the title compound (601 mg) of Reference Example 12, and in the same manner as in Example 70 (1), 3-{(2S,4S)-1-tert-butoxycarbonyl-4-[4-(6-cyano-2-benzothiazolyl)-1-piperazinyl]-2-pyrrolidinylcarbonyl}-1,3-thiazolidine (526 mg) was obtained as an orange powder.

(6) Using the above-mentioned compound (526 mg), and in the same manner as in Example 239 (5), the title compound (394 mg) was obtained as a white powder.

$^1$H-NMR(DMSO-$d_6$)δ2.00–2.30(1H,m), 2.80–3.00(1H, m), 3.00–4.30(15H,m), 4.42–4.80(3H,m), 7.59(1H,d,J=8.4 Hz), 7.72(1H,dd,J=8.1,1.5 Hz), 8.39(1H,d,J=1.5 Hz), 9.06 (1H,brs), 10.58(1H,brs).

Example 242

Synthesis of 3-{(2S,4S)-4-[4-(6-trofluoromethyl-2-benzothiazolyl)-1-piperazinyl]-2-pyrrolidinylcarbonyl}-1,3-thiazolidine dihydrochloride (1) 4-Amino-3-bromobenzotrifluoride (2.40 g) was dissolved in N-methyl-2-pyrrolidone (10 mL), and potassium ethylxanthate (3.52 g) was added thereto. The mixture was stirred at 160° C. for 3 hr with heating. Water (300 mL) was added to the reaction mixture, and the mixture was extracted with ethyl acetate. The extract was washed successively with water and brine, and concentrated under reduced pressure to give 6-trifluoromethyl-2-mercaptobenzothiazole (607 mg) as an orange powder.

(2) Using the above-mentioned compound (607 mg), sodium hydride (containing by 60%, 155 mg) and methyl iodide (241 mL), and in the same manner as in Example 236 (1), 6-trifluoromethyl-2-methylthiobenzothiazole (665 mg) was obtained as a brown solid.

(3) Using the above-mentioned compound (0.665 g) and piperazine (11.5 g), and in the same manner as in Example 189 (1), 1-(6-trifluoromethylbenzothiazolyl)piperazine (0.56 g) was obtained as a white powder.

(4) Using the above-mentioned compound (560 mg) and the title compound (532 mg) of Reference Example 12, and in the same manner as in Example 70 (1), 3-{(2S,4S)-1-tert-butoxycarbonyl-4-[4-(6-trifluoromethyl-2-benzothiazolyl)-1-piperazinyl]-2-pyrrolidinylcarbonyl}-1,3-thiazolidine (477 mg) was obtained as a white powder.

(5) Using the above-mentioned compound (477 mg), and in the same manner as in Example 186 (2), the title compound (403 mg) was obtained as a white powder.

$^1$H-NMR(DMSO-$d_6$)δ2.05–2.33(1H,m), 2.79–3.00(1H, m), 3.00–3.29(2H,m), 3.29–4.30(13H,m), 4.45–4.80(3H,m), 7.58–7.70(2H,m), 8.34(1H,s), 9.10(1H,brs), 10.72(1H,brs).

Example 243

Synthesis of 3-{(2S,4S)-4-[4-(6-methoxy-2-benzothiazolyl)-1-piperazinyl]-2-pyrrolidinylcarbonyl}-1,3-thiazolidine trihydrochloride (1) Using 2-chloro-6-methoxybenzothiazole (1 g) and piperazine (8.63 g), and in the same manner as in Example 189 (1), 1-(6-methoxybenzothiazolyl)piperazine (1.22 g) was obtained as a pale-brown powder.

(5) Using the above-mentioned compound (549 mg) and the title compound (601 mg) of Reference Example 12, and in the same manner as in Example 70 (1), 3-{(2S,4S)-1-tert-butoxycarbonyl-4-[4-(6-methoxy-2-benzothiazolyl)-1-piperazinyl]-2-pyrrolidinylcarbonyl}-1,3-thiazolidine (420 mg) was obtained as a white powder.

(6) Using the above-mentioned compound (420 mg), and in the same manner as in Example 186 (2), the title compound (393 mg) was obtained as a white powder.

$^1$H-NMR(DMSO-$d_6$)δ2.22–2.41(1H,m), 2.90–3.20(3H, m), 3.25–4.20(13H,m), 3.77(3H,s), 4.42–4.81(3H,m), 6.96 (1H,dd,J=8.9,2.6 Hz), 7.47(1H,d,J=8.8 Hz), 7.50(1H,d,J=2.6 Hz).

Example 244

Synthesis of 3-{(2S,4S)-4-[4-(6-isopropoxy-2-benzothiazolyl)-1-piperazinyl]-2-pyrrolidinylcarbonyl}-1,3-thiazolidine trihydrochloride (1) 4-Isopropoxyaniline (24.2 g) was dissolved in acetic acid (300 mL), and a mixture of bromine (8.25 mL) and acetic acid (80 mL) was added dropwise. After stirring at room temperature for 2 hr, the reaction mixture was concentrated under reduced pressure. Water was added to residue, and the mixture was extracted with diethylether.

The extract was washed successively with aqueous sodium thiosulfate solution and brine, and concentrated under reduced pressure. The residue was purified by silica gel chromatography to give 2-bromo-4-isopropoxyaniline (10.2 g) as a black brown oil.

(2) The above-mentioned compound (10.2 g) was dissolved in N-methyl-2-pyrrolidone (50 mL), and potassium ethylxanthate (14.2 g) was added thereto. The mixture was stirred at 140° C. for 6 hr with heating. The reaction mixture was concentrated under reduced pressure, and 1 mol/L aqueous sodium hydroxide solution (50 mL) was added to the residue. The mixture was washed with chloroform, and conc. hydrochloric acid (30 mL) was added thereto. The mixture was extracted with chloroform. The extract was concentrated under reduced pressure to give 6-isopropoxy-2-mercaptobenzothiazole (12.6 g) as a black brown oil.

(3) The above-mentioned compound (11.6 g) and 2 drops of DMF were added to thionyl chloride (30 mL), and the mixture was stirred at room temperature for 18 hr. The reaction mixture was concentrated under reduced pressure, and saturated aqueous sodium hydrogencarbonate solution was added to the residue. The mixture was extracted with chloroform. The extract was concentrated under reduced pressure and the residue was purified by silica gel chromatography to give 2-chloro-6-isopropoxybenzothiazole (9.37 g) as a black oil.

(4) Using the above-mentioned compound (9.37 g) and piperazine (35.4 g), and in the same manner as in Example 189 (1), 1-(6-isopropoxy-2-benzothiazolyl)piperazine (2.8 g) was obtained as a black powder.

(5) Using the above-mentioned compound (1.25 g) and the title compound (0.901 g) of Reference Example 12, and in the same manner as in Example 70 (1), 3-{(2S,4S)-1-tert-butoxycarbonyl-4-[4-(6-isopropoxy-2-benzothiazolyl)-1-piperazinyl]-2-pyrrolidinylcarbonyl}-1,3-thiazolidine (0.993 g) was obtained as a pale-brown powder.

(6) Using the above-mentioned compound (933 mg), and in the same manner as in Example 186 (2), the title compound (749 mg) was obtained as a white powder.

$^1$H-NMR(DMSO-d$_6$)δ1.26(6H,d,J=6.0 Hz), 2.20–2.40 (1H,m), 2.90–3.20(3H,m), 3.28–4.12(14H,m), 4.39–4.80 (3H,m), 6.92(1H,dd,J=8.8,2.6 Hz), 7.44(1H,d,J=8.8 Hz), 7.48(1H,d,J=2.6 Hz), 9.18(1H,brs), 10.90(1H,brs).

Example 245

Synthesis of 3-{(2S,4S)-4-[4-(5-nitro-2-benzothiazolyl)-1-piperazinyl]-2-pyrrolidinylcarbonyl}-1,3-thiazolidine dihydrochloride (1) Using 2-methylthio-5-nitrobenzothiazole [product of Example 240 (2), 1.5 g] and piperazine (11.4 g), and in the same manner as in Example 189 (1), 1-(5-nitro-2-benzothiazolyl)piperazine (1.55 g) was obtained as a yellow powder.

(2) Using the above-mentioned compound (581 mg) and the title compound (601 mg) of Reference Example 12, and in the same manner as in Example 70 (1), 3-{(2S,4S)-1-tert-butoxycarbonyl-4-[4-(5-nitro-2-benzothiazolyl)-1-piperazinyl]-2-pyrrolidinylcarbonyl}-1,3-thiazolidine (507 mg) was obtained as a yellow powder.

(3) Using the above-mentioned compound (507 mg), and in the same manner as in Example 186 (2), the title compound (243 mg) was obtained as a yellow powder.

$^1$H-NMR(DMSO-d$_6$)δ2.00–2.22(1H,m), 2.79–3.00(1H, m), 3.00–4.30(15H,m), 4.42–4.80(3H,m), 7.98(1H,dd,J=8.7,2.2 Hz), 8.13(1H,d,J=8.7 Hz), 8.21(1H,d,J=2.2 Hz), 9.05 (1H,brs), 10.40(1H,brs).

Example 246

Synthesis of 3-{(2S,4S)-4-[4-(6-nitro-2-benzothiazolyl)-1-piperazinyl]-2-pyrrolidinylcarbonyl}-1,3-thiazolidine dihydrochloride (1) Conc. sulfuric acid (50 mL) was added to 2-chlorobenzothiazole (10 g) under ice-cooling, and conc. nitric acid (5 mL) was added dropwise under ice-cooling. The mixture was stirred under ice-cooling for 1 hr, and iced water (600 mL) was added to the reaction mixture. The precipitated solid was collected by filtration, which was then recrystallized from acetone to give 2-chloro-6-nitrobenzothiazole (6.36 g) as a pale-yellow powder.

(2) Using the above-mentioned compound (6.36 g) and piperazine (25.8 g), and in the same manner as in Example 189 (1), 1-(6-nitro-2-benzothiazolyl)piperazine (1.84 g) was obtained as a yellow powder.

(3) Using the above-mentioned compound (581 mg) and the title compound (601 mg) of Reference Example 12, and in the same manner as in Example 70 (1), 3-{(2S,4S)-1-tert-butoxycarbonyl-4-[4-(6-nitro-2-benzothiazolyl)-1-piperazinyl]-2-pyrrolidinylcarbonyl}-1,3-thiazolidine (664 mg) was obtained as a yellow powder.

(4) Using the above-mentioned compound (588 mg), and in the same manner as in Example 186 (2), the title compound (495 mg) was obtained as a yellow powder.

$^1$H-NMR(DMSO-d$_6$)δ2.00–2.26(1H,m), 2.83–3.00(1H, m), 3.01–4.30(15H,m), 4.43–4.80(3H,m), 7.60(1H,d,J=9.0 Hz), 8.19(1H,dd,J=9.0,2.4 Hz), 8.89(1H,d,J=2.4 Hz), 9.16 (1H,brs), 10.45(1H,brs).

Example 247

Synthesis of 3-{(2S,4S)-4-[4-(6-fluoro-2-benzothiazolyl)-1-piperazinyl]-2-pyrrolidinylcarbonyl}-1,3-thiazolidine dihydrochloride (1) Using 2-bromo-4-fluoroaniline (25 g) and potassium ethylxanthate (42.2 g), and in the same manner as in Example 244 (2), 6-fluoro-2-mercaptobenzothiazole (1.01 g) was obtained as a white powder.

(2) Using the above-mentioned compound (1.01 g), sodium hydride (containing by 60%, 0.24 g), and methyl iodide (373 mL), and in the same manner as in Example 236 (1), 6-fluoro-2-methylthiobenzothiazole (0.928 g) was obtained as a pale-yellow solid.

(3) Using the above-mentioned compound (0.928 g) and piperazine (8.02 g), and in the same manner as in Example 189 (1), 1-(6-fluoro-2-benzothiazolyl)piperazine (0.627 g) was obtained as a pale-yellow oil.

(4) Using the above-mentioned compound (627 mg) and the title compound (601 mg) of Reference Example 12, and in the same manner as in Example 70 (1), 3-{(2S,4S)-1-tert-butoxycarbonyl-4-[4-(6-fluoro-2-benzothiazolyl)-1-piperazinyl]-2-pyrrolidinylcarbonyl}-1,3-thiazolidine (535 mg) was obtained as a white powder.

(5) Using the above-mentioned compound (535 mg), and in the same manner as in Example 186 (2), the title compound (441 mg) was obtained as a white powder.

$^1$H-NMR(DMSO-d$_6$)δ2.05–2.38(1H,m), 2.82–4.30(16H, m), 4.42–4.80(3H,m), 7.17(1H,td,J=9.0,2.7 Hz), 7.52(1H, dd,J=9.0,4.8 Hz), 7.79(1H,dd,J=8.7,2.7 Hz), 9.09(1H,brs), 10.72(1H,brs).

Example 248

Synthesis of 3-{(2S,4S)-4-[4-(5-chloro-2-benzothiazolyl)-1-piperazinyl]-2-pyrrolidinylcarbonyl}-1,3-thiazolidine trihydrochloride (1) Using 5-chloro-2-mercaptobenzothiazole (25 g), sodium hydride (containing by 60%, 5.45 g) and methyl iodide (8.49 mL), and in the same manner as in Example 241 (1), 5-chloro-2-methylthiobenzothiazole (26.7 g) was obtained as a white powder.

(2) Using the above-mentioned compound (10.8 g) and piperazine (43.1 g), and in the same manner as in Example 189 (1), 1-(6-chloro-2-benzothiazolyl)piperazine (10.9 g) was obtained as a white powder.

(3) Using the above-mentioned compound (558 mg) and the title compound (601 mg) of Reference Example 12, and in the same manner as in Example 70 (1), 3-{(2S,4S)-1-tert-butoxycarbonyl-4-[4-(5-chloro-2-benzothiazolyl)-1-piperazinyl]-2-pyrrolidinylcarbonyl}-1,3-thiazolidine (834 mg) was obtained as a white powder.

(4) Using the above-mentioned compound (834 mg), and in the same manner as in Example 186 (2), the title compound (735 mg) was obtained as a white powder.

$^1$H-NMR(DMSO-$d_6$)δ2.20–2.40(1H,m), 2.89–3.20(3H, m), 3.23–3.60(4H,m), 3.60–4.85(12H,m), 7.18(1H,dd,J=8.4,2.1 Hz), 7.56(1H,d,J=2.1 Hz), 7.88(1H,d,J=8.4 Hz), 9.15 (1H,brs), 10.86(1H,brs).

Example 249

Synthesis of 3-{(2S,4S)-4-[4-(6-chloro-2-benzothiazolyl)-1-piperazinyl]-2-pyrrolidinylcarbonyl}-1,3-thiazolidine trihydrochloride (1) Using 2,6-dichlorobenzothiazole (1 g) and piperazine (8.44 g), and in the same manner as in Example 189 (1), 1-(6-chloro-2-benzothiazolyl)piperazine (1.24 g) was obtained as a pale-brown solid (2) Using the above-mentioned compound (558 mg) and the title compound (601 mg) of Reference Example 12, and in the same manner as in Example 70 (1), 3-{(2S,4S)-1-tert-butoxycarbonyl-4-[4-(6-chloro-2-benzothiazolyl)-1-piperazinyl]-2-pyrrolidinylcarbonyl}-1,3-thiazolidine (740 mg) was obtained as a white powder.

(3) Using the above-mentioned compound (647 mg), and in the same manner as in Example 186 (2), the title compound (603 mg) was obtained as a white powder.

$^1$H-NMR(DMSO-$d_6$)δ2.22–2.42(1H,m), 2.90–3.21(3H, m), 3.30–4.20(13H,m), 4.43–4.81(3H,m), 7.36(1H,dd,J=8.5,2.2 Hz), 7.52(1H,d,J=8.5 Hz), 8.01(1H,d,J=2.2 Hz), 9.25 (1H,brs), 11.10(1H,brs).

Example 250

Synthesis of 3-{(2S,4S)-4-[4-(1-methyl-1H-indazol-3-yl)-1-piperazinyl]-2-pyrrolidinylcarbonyl}-1,3-thiazolidine trihydrochloride (1) Using 1-(1-methyl-1H-indazol-3-yl)piperazine (0.714 g) and the title compound (0.901 g) of Reference Example 12, and in the same manner as in Example 70 (1), 3-{(2S, 4S)-1-tert-butoxycarbonyl-4-[4-(1-methyl-1H-indazol-3-yl)-1-piperazinyl]-2-pyrrolidinylcarbonyl}-1,3-thiazolidine (1.37 g) was obtained as a pale-yellow solid.

$^1$H-NMR($CDCl_3$)δ1.41(4.5H,s), 1.46(4.5H,s), 1.85–2.00 (1H,m), 2.42–2.55(1H,m), 2.62–2.80(4H,m), 2.83–3.22(3H, m), 3.35(1H,t,J=10.1 Hz), 3.40–3.52(4H,m), 3.63–4.14(6H, m), 4.39–4.81(3H,m), 7.01(1H,t,J=7.6 Hz), 7.23–7.38(2H, m), 7.67(1H,d,J=8.2 Hz).

(2) The above-mentioned compound (1.36 g) was dissolved in ethanol (3.5 mL), and 4.1 mol/L hydrochloric acid-ethanol (3.5 mL) was added thereto. The mixture was stirred at room temperature for 15 hr. The reaction mixture was concentrated under reduced pressure, and the obtained crystal was recrystallized from ethanol to give the title compound (0.985 g) as a white powder.

$^1$H-NMR(DMSO-$d_6$)δ2.30–2.42(1H,m), 2.95–3.17(3H, m), 3.2–4.2(16H,m), 4.46–4.78(3H,m), 7.02–7.08(1H,m), 7.35–7.42(1H,m), 7.51(1H,d,J=8.6 Hz), 7.81(1H,d,J=8.2 Hz), 9.17(1H,brs), 10.86(1H,brs), 12.40(1H,brs).

Example 251

Synthesis of 3-{(2S,4S)-4-[4-(1-phenyl-1H-indazol-3-yl)-1-piperazinyl]-2-pyrrolidinylcarbonyl}-1,3-thiazolidine trihydrochloride (1) Using 1-(1-phenyl-1H-indazol-3-yl)piperazine (0.918 g) and the title compound (0.901 g) of Reference Example 12, and in the same manner as in Example 70 (1), 3-{(2S, 4S)-1-tert-butoxycarbonyl-4-[4-(1-phenyl-1H-indazol-3-yl)-1-piperazinyl]-2-pyrrolidinylcarbonyl}-1,3-thiazolidine (1.23 g) was obtained as a white solid.

$^1$H-NMR($CDCl_3$)δ1.41(4.5H,s), 1.47(4.5H,s), 1.88–2.04 (1H,m), 2.45–2.57(1H,m), 2.66–3.18(7H,m), 3.38(1H,t,J=9.9 Hz), 3.50–4.15(7H,m), 4.39–4.80(3H,m), 7.11(1H,t,J=7.5 Hz), 7.24–7.32(1H,m), 7.40(1H,t,J=7.6 Hz), 7.49(2H,t, J=7.5 Hz), 7.66–7.78(4H,m).

(2) The above-mentioned compound (1.22 g) was dissolved in ethanol (3 mL), and 4.1 mol/L hydrochloric acid-ethanol (6 mL) was added thereto. The mixture was stirred at room temperature for 14 hr. The precipitated solid was collected by filtration to give the title compound (0.823 g) as a white powder.

$^1$H-NMR(DMSO-$d_6$)δ2.30–2.46(1H,m), 2.96–3.18(3H, m), 3.3–4.2(13H,m), 4.46–4.79(3H,m), 7.17–7.25(1H,m), 7.33(1H,t,J=7.4 Hz), 7.46–7.58(3H,m), 7.74(2H,d,J=7.6 Hz), 7.81(1H,d,J=8.6 Hz), 7.98(1H,d,J=8.2 Hz), 9.18(1H, brs), 10.94(1H,brs), 12.50(1H,brs).

Example 252

Synthesis of 3-{(2S,4S)-4-[4-(3-benz[d]isoxazolyl)-1-piperazinyl]-2-pyrrolidinylcarbonyl}-1,3-thiazolidine trihydrochloride (1) Hydroxylammonium hydrochloride (15 g) was dissolved in 10% aqueous sodium hydroxide solution (220 mL), and a solution of ethyl salicylate (24 g) in 1,4-dioxane (70 mL) was gradually added, and the mixture was stirred at room temperature for 5 hr. The reaction mixture was concentrated until the amount thereof became almost the half, and acidified with conc. hydrochloric acid. The precipitated solid was collected by filtration, which was then recrystallized from methanol to give salicylhydroxamic acid (12 g) as white crystals.

(2) The above-mentioned compound (12 g) was suspended in tetrahydrofuran (30 mL) and thionyl chloride (13 mL) was added thereto. The mixture was stirred at room temperature for 1 hr. The reaction mixture was concentrated under reduced pressure, and the residue was dissolved in 1,4-dioxane (30 mL). To this solution was gradually added triethylamine (33 mL), and the mixture was stirred at room temperature for 2 hr. The reaction mixture was acidified with conc. hydrochloric acid, extracted with toluene. The extract was washed successively with water and brine, dried and concentrated under reduced pressure. The residue was washed with diisopropyl ether to give 3-hydroxybenz[d]isoxazole (3.7 g) as a pale-brown powder.

(3) Pyridine (1.2 mL) and phosphorus oxychloride (2.1 mL) were added to the above-mentioned compound (2.0 g), and the mixture was stirred at 125° C. for 5 hr. Ice was added to the reaction mixture, and the mixture was extracted with chloroform. The extract was washed with water, dried and concentrated under reduced pressure to give 3-chlorobenz[d]isoxazole (1.7 g) as a brown solid.

(4) Using the above-mentioned compound (1.7 g) and piperazine (7.6 g), and in the same manner as in Example 189 (1), 4-(3-benz[d]isoxazolyl)piperazine (0.944 g) was obtained as a gray powder.

(5) Using the title compound (0.900 g) of Reference Example 12 and the above-mentioned compound (0.734 g), and in the same manner as in Example 70 (1), 3-{(2S,4S)-4-[4-(3-benz[d]isoxazolyl)-1-piperazinyl]-1-tert-butoxycarbonyl-2-pyrrolidinylcarbonyl}-1,3-thiazolidine (1.5 g) was obtained as a white solid.

(6) Using the above-mentioned compound (1.0 g), and in the same manner as in Example 70 (2), the title compound (0.978 g) was obtained as a white powder.

$^1$H-NMR(DMSO-$d_6$)δ2.19–2.35(1H,m), 2.90–3.16(3H,m), 3.25–3.55(4H,m), 3.60–4.15(10H,m), 4.47–4.75(4H,m), 7.06–7.12(1H,m), 7.18–7.23(1H,m), 7.36(1H,d,J=7.5 Hz), 7.46(1H,d,J=7.8 Hz), 9.13(1H,brs), 10.86(1H,brs)

Example 253

Synthesis of 3-{(2S,4S)-4-[4-(5-cyano-3-benz[d]isoxazolyl)-1-piperazinyl]-2-pyrrolidinylcarbonyl}-1,3-thiazolidine trihydrochloride (1) Methyl salicylate (149 g) was dissolved in acetic acid (900 mL), and bromine (50 mL) was added thereto. The mixture was stirred at room temperature for 21 hr. Water (10 L) was added to the reaction mixture, and the precipitated solid was collected by filtration, which was then recrystallized from methanol to give methyl 5-bromosalicylate (175 g) as white crystals.

(2) Using the above-mentioned compound (30 g), and in the same manner as in Example 252 (1), 5-bromosalicylhydroxamic acid (24 g) was obtained as white crystals.

(3) Using the above-mentioned compound (10 g), and in the same manner as in Example 252 (2), 5-bromo-3-hydroxybenz[d]isoxazole (8.6 g) was obtained as a white powder.

(4) Using the above-mentioned compound (8.6 g), and in the same manner as in Example 252 (3), 5-bromo-3-chlorobenz[d]isoxazole (7.4 g) was obtained as a white powder.

(5) Using the above-mentioned compound (7.4 g) and piperazine (21 g), and in the same manner as in Example 189 (1), 4-(5-bromo-3-benz[d]isoxazolyl)piperazine (6.5 g) was obtained as a gray powder.

(6) The above-mentioned compound (6.5 g) was dissolved in a solution of tetrahydrofuran (100 mL) and sodium hydroxide (1.0 g) in water (125 mL) and benzyl chloroformate (3.9 mL) was gradually added under ice-cooling. The mixture was stirred at room temperature for 2 hr. The precipitated solid was collected by filtration, and washed with diisopropyl ether to give 1-benzyloxycarbonyl-4-(5-bromo-3-benz[d]isoxazolyl)piperazine (8.3 g) as a pale-brown powder.

(7) The above-mentioned compound (3.0 g) and zinc cyanide (1.1 g) was dissolved in DMF (15 mL), and tetrakistriphenylphosphinepalladium (0.633 g) was added thereto. The mixture was stirred at 85° C. for 18 hr under a nitrogen atmosphere. The reaction mixture was added to 2 mol/L aqueous ammonia and extracted with ethyl acetate. The extract was washed successively with water and brine, dried and concentrated under reduced pressure. The residue was purified by silica gel chromatography to give 1-benzyloxycarbonyl-4-(5-cyano-3-benz[d]isoxazolyl)piperazine (2.1 g) as a white solid.

(8) The above-mentioned compound (1.5 g) was suspended in methanol (60 mL), and ammonium formate (1.8 g) and 5% palladium carbon (0.230 g) were added thereto. The mixture was refluxed for 0.5 hr. The reaction mixture was filtrated and the filtrate was concentrated under reduced pressure. Saturated aqueous sodium hydrogencarbonate solution was added to the residue, and the mixture was extracted with chloroform. The extract was dried and concentrated under reduced pressure to give a mixture (1.1 g) containing 4-(5-cyano-3-benz[d]isoxazolyl)piperazine as a white solid.

(9) Using the title compound (904 mg) and the above-mentioned compound (681 mg), and in the same manner as in Example 70 (1), 3-{(2S,4S)-1-tert-butoxycarbonyl-4-[4-(5-cyano-3-benz[d]isoxazolyl)-1-piperazinyl]-2-pyrrolidinylcarbonyl}-1,3-thiazolidine (778 mg) was obtained as a white solid.

(10) Using the above-mentioned compound (778 mg), and in the same manner as in Example 70 (2), the title compound (349 mg) was obtained as a white powder.

$^1$H-NMR(DMSO-$d_6$)δ2.15–2.40(1H,m), 2.90–3.20(3H,m), 3.25–4.20(14H,m), 4.47–4.77(4H,m), 7.86(1H,d,J=8.7 Hz), 8.06(1H,dd,J=8.7,1.2 Hz), 8.81(1H,brs), 9.11(1H,brs), 10.65(1H,brs).

Example 254

Synthesis of 3-{(2S,4S)-4-[4-(5-methoxy-3-benz[d]isoxazolyl)-1-piperazinyl]-2-pyrrolidinylcarbonyl}-1,3-thiazolidine trihydrochloride (1) 5-Methoxysalicylic acid (41 g) was dissolved in acetonitrile (500 mL), and ethyl iodide (20 mL) and DBU (38 mL) were added thereto. The mixture was refluxed for 6 hr. The reaction mixture was concentrated under reduced pressure, and 1 mol/L hydrochloric acid was added to the residue. The mixture was extracted with ethyl acetate. The extract was washed successively with saturated aqueous sodium hydrogencarbonate solution and brine, dried and concentrated under reduced pressure to give a mixture (44 g) containing ethyl 5-methoxysalicylate as a brown oil.

(2) Using the above-mentioned compound (44 g), and in the same manner as in Example 252 (1), 5-methoxysalicylhydroxamic acid (33 g) was obtained as white crystals.

(3) Using the above-mentioned compound (33 g), and in the same manner as in Example 252 (2), 3-hydroxy-5-methoxybenz[d]isoxazole (5.9 g) was obtained as a pale-brown powder.

(4) Using the above-mentioned compound (5.9 g), and in the same manner as in Example 252 (3), a mixture (4.2 g) containing 3-chloro-5-hydroxybenz[d]isoxazole was obtained as a black oil.

(5) Piperazine (19 g) was melted by heating at 140° C., and the above-mentioned title compound (4.2 g) was added thereto. After stirring at 140° C. for 1 hr, the mixture was poured into iced water and extracted with chloroform. After drying, the solvent was evaporated under reduced pressure, and the residue was diluted with ethyl acetate and extracted with 1 mol/L hydrochloric acid. The aqueous layer was basified with 2 mol/L aqueous sodium hydroxide solution and extracted with chloroform. After drying, the solvent was evaporated under reduced pressure to give 4-(5-methoxy-3-benz[d]isoxazolyl)piperazine (804 mg) as a black solid.

(6) Using the title compound (0.900 g) of Reference Example 12 and the above-mentioned compound (0.804 g), and in the same manner as in Example 70 (1), 3-{(2S,4S)-1-tert-butoxycarbonyl-4-[4-(5-methoxy-3-benz[d]isoxazolyl)-1-piperazinyl]-2-pyrrolidinylcarbonyl}-1,3-thiazolidine (1.0 g) was obtained as white amorphous.

(7) Using the above-mentioned compound (1.0 g), and in the same manner as in Example 70 (2), the title compound (0.693 g) was obtained as a white powder.

$^1$H-NMR(DMSO-$d_6$)δ2.20–2.40(1H,m), 2.90–3.19(3H,m), 3.30–3.60(4H,m), 3.65–4.15(13H,m), 4.30–4.76(4H,m), 6.65(1H,dd,J=8.7,2.4 Hz), 6.97(1H,d,J=2.4 Hz), 7.35(1H,d,J=8.7 Hz), 10.15(1H,brs), 10.95(1H,brs).

Example 255

Synthesis of 3-{(2S,4S)-4-[4-(3-benz[d]isothiazolyl)-1-piperazinyl]-2-pyrrolidinylcarbonyl}-1,3-thiazolidine 1.5 oxalate (1) Using 1-(3-benz[d]isothiazolyl)piperazine (385 mg) and the title compound (500 mg) of Reference Example 12, and in the same manner as in Example 70 (1), 3-{(2S,4S)-4-[4-(3-benz[d]isothiazolyl)-1-piperazinyl]-1-tert-butoxycarbonyl-2-pyrrolidinylcarbonyl}-1,3-thiazolidine (716 mg) was obtained as a white powder.

(2) The above-mentioned compound (709 mg) was dissolved in methanol (10 mL), and 4 mol/L hydrochloric acid-ethyl acetate (10 mL) was added thereto. The mixture was stirred at room temperature for 19 hr. The precipitated solid was collected by filtration, and saturated aqueous sodium hydrogencarbonate solution was added thereto. The mixture was extracted with chloroform. The extract was concentrated under reduced pressure, and the residue was dissolved in ethanol (10 mL), and oxalic acid (130 mg) was added thereto. The precipitated solid was collected by filtration to give the title compound (150 mg) as a white powder.

$^1$H-NMR(DMSO-$d_6$)δ1.60–1.81(1H,m), 2.78–2.85(4H,m), 2.89–3.24(4H,m), 3.52–3.99(7H,m), 4.43–4.74(4H,m), 7.39–7.48(1H,m), 7.53–7.60(1H,m), 8.01–8.09(2H,m).

Example 256

Synthesis of 3-{(2S,4S)-4-[4-(2-oxazolo[4,5-b]pyridyl)-1-piperazinyl]-2-pyrrolidinylcarbonyl}-1,3-thiazolidine trihydrochloride (1) 2-Amino-3-hydroxypyridine (5.51 g) was dissolved in pyridine (100 mL), and potassium ethylxanthate (8.82 g) was added thereto. The mixture was refluxed for 2 hr. Iced water (400 mL) was added to the reaction mixture, and concentrated hydrochloric acid (40 mL) was added thereto. The mixture was extracted with chloroform and the extract was washed with brine and concentrated under reduced pressure to give 1,3-oxazolo[4,5-b]pyridine-2-thiol (5.13 g) as a pale-brown powder.

(2) The above-mentioned compound (5 g) and 2 drops of DMF were added to thionyl chloride (20 mL). The mixture was refluxed for 1 hr. The reaction mixture was concentrated under reduced pressure to give 2-chloro-1,3-oxazolo[4,5-b]pyridine (5.08 g) as a pale-brown powder.

(3) Using the above-mentioned compound (3.09 g) and piperazine (5.17 g), and in the same manner as in Example 239 (3), 1-(2-oxazolo[4,5-b]pyridyl)piperazine (1.15 g) was obtained as a yellowish brown powder.

(4) Using the above-mentioned compound (1.15 g) and the title compound (0.601 g) of Reference Example 12, and in the same manner as in Example 70 (1), 3-{(2S,4S)-1-tert-butoxycarbonyl-4-[4-(2-oxazolo[4,5-b]pyridyl)-1-piperazinyl]-2-pyrrolidinylcarbonyl}-1,3-thiazolidine (0.635 g) was obtained as a white solid.

(5) Using the above-mentioned compound (635 mg), and in the same manner as in Example 186 (2), the title compound (293 mg) was obtained as a white powder.

$^1$H-NMR(DMSO-$d_6$)δ2.02–2.30(1H,m), 2.83–3.00(1H,m), 3.00–3.20(2H,m), 3.20–3.48(4H,m), 3.48–4.30(9H,m), 4.40–4.80(3H,m), 7.16(1H,dd,J=7.8,5.4 Hz), 7.95(1H,d,J=7.8 Hz), 8.22(1H,d,J=5.4 Hz), 9.09(1H,brs), 10.59(1H,brs)

Example 257

Synthesis of 3-((2S,4S)-4-{4-[2-(1-ethoxycarbonyl-1-methylethyl)-6-imidazo[1,2-b]pyridazinyl]-1-piperazinyl}-2-pyrrolidinylcarbonyl)-1,3-thiazolidine trihydrochloride (1) Using ethyl 2-(6-chloroimidazo[1,2-b]pyridazin-2-yl)-2-methylpropionate (2.00 g) and piperazine (19.7 g), and by a reaction at 100° C. in the same manner as in Example 196 (1), 1-[2-(1-ethoxycarbonyl-1-methylethyl)-6-imidazo[1,2-b]pyridazinyl]piperazine (2.37 g) was obtained as an oil.

(2) Using the above-mentioned compound (2.37 g) and the title compound (1.87 g) of Reference Example 12, and in the same manner as in Example 70 (1), 3-((2S,4S)-1-tert-butoxycarbonyl-4-{4-[2-(1-ethoxycarbonyl-1-methylethyl)-6-imidazo[1,2-b]pyridazinyl]-1-piperazinyl}-2-pyrrolidinylcarbonyl)-1,3-thiazolidine (3.29 g) was obtained as a pale-yellow solid.

(3) The above-mentioned compound (1.10 g) was dissolved in dichloromethane (10 mL), and trifluoroacetic acid (5 mL) was added thereto. The mixture was stirred at room temperature for 1.5 hr. The solvent was evaporated under reduced pressure, and the residue was dissolved in ethyl acetate. 4 mol/L Hydrochloric acid-ethyl acetate solution (1 mL) was added thereto, and the precipitated solid was collected by filtration to give the title compound (1.05 g) as a white powder.

$^1$H-NMR(500 MHz,DMSO-$d_6$)δ1.15(3H,t,J=7.1 Hz), 1.61(6H,s), 2.16–2.36(1H,m), 2.90–4.80(19H,m), 4.10(2H,q,J=7.1 Hz), 7.64(1H,d,J=10Hz), 8.10(1H,d,J=10Hz), 8.22(1H,s), 9.11(1H,brs), 10.85(1H,brs).

Example 258

Synthesis of 3-((2S,4S)-4-{4-[2-(1-carboxy-1-methylethyl)-6-imidazo[1,2-b]pyridazinyl]-1-piperazinyl}-2-pyrrolidinylcarbonyl)-1,3-thiazolidine trihydrochloride (1) 3-((2S,4S)-1-tert-Butoxycarbonyl-4-{4-[2-(1-ethoxycarbonyl-1-methylethyl)-6-imidazo[1,2-b]pyridazinyl]-1-piperazinyl}-2-pyrrolidinylcarbonyl)-1,3- thiazolidine [product of Example 257 (2), 608 mg] was dissolved in ethanol (2 mL). A solution of lithium hydroxide monohydrate (85 mg) in water (1 mL) was added, and the mixture was stirred at 60° C. for 2 hr. Dilute hydrochloric acid was added to the reaction mixture to make the pH 6. The mixture was extracted with chloroform. The extract was dried and concentrated under reduced pressure to give 3-((2S,4S)-1-tert-butoxycarbonyl-4-{4-[2-(1-carboxy-1-methylethyl)-6-imidazo[1,2-b]pyridazinyl]-1-piperazinyl}-2-pyrrolidinylcarbonyl)-1,3-thiazolidine (580 mg) as a pale-yellow powder.

(2) Using the above-mentioned compound (579 mg), and in the same manner as in Example 257 (3), the title compound (477 mg) was obtained as a white powder.

$^1$H-NMR(500 MHz,DMSO-$d_6$)δ1.59(6H,s), 2.11–2.31 (1H,m), 2.82–4.20(16H,m), 4.47–4.74(3H,m), 7.64(1H,d,J=10 Hz), 8.09(1H,d,J=10 Hz), 8.22(1H,s), 9.07(1H,brs), 10.68(1H,brs), 12.85(1H,brs).

Example 259

Synthesis of 3-{(2S,4S)-4-[4-(2-methyl-4-quinolyl)-1-piperazinyl]-2-pyrrolidinylcarbonyl}-1,3-thiazolidine trihydrochloride (1) Phosphorus oxychloride (30 mL) was added to 4-hydroxy-2-methylquinoline (10 g), and the mixture was stirred at room temperature for 30 min. The reaction mixture was concentrated under reduced pressure, and saturated aqueous sodium carbonate solution was added to the residue under ice-cooling. The mixture was extracted with ethyl acetate. The extract was washed with brine, and concentrated under reduced pressure to give 4-chloro-2-methylquinoline (11.2 g) as a black oil.

(2) Using the above-mentioned compound (5.33 g) and piperazine (25.8 g), and in the same manner as in Example 189 (1), 1-(2-methyl-4-quinolyl)piperazine (4.19 g).

(3) Using the above-mentioned compound (500 mg) and the title compound (601 mg) of Reference Example 12, and in the same manner as in Example 70 (1), 3-{(2S,4S)-1-tert-butoxycarbonyl-4-[4-(2-methyl-4-quinolyl)-1-piperazinyl]-2-pyrrolidinylcarbonyl}-1,3-thiazolidine (1.15 g) was obtained as a pale-yellow oil.

(4) Using the above-mentioned compound (1.15 g), and in the same manner as in Example 186 (2), the title compound (0.863 g) was obtained as a pale-brown powder.

$^1$H-NMR(DMSO-$d_6$)δ2.20–2.42(1H,m), 2.81(3H,s), 2.91–3.20(3H,m), 3.30–4.26(13H,m), 4.44–4.87(3H,m), 7.35(1H,s), 7.73(1H,t,J=7.6 Hz), 8.00(1H,t,J=7.6 Hz), 8.16 (1H,d,J=8.4 Hz), 8.24(1H,d,J=8.4 Hz)

Example 260

Synthesis of 3-{(2S,4R)-4-[4-(2-trifluoromethyl-4-quinolyl)-1-piperazinyl]-2-pyrrolidinylcarbonyl}-1,3-thiazolidine dihydrochloride (1) Diethanolamine (20 mL) was added to 4-chloro-2-trifluoromethylquinoline (5.04 g), and the mixture was stirred at 80° C. for 19 hr. Brine was added to the reaction mixture, and the mixture was extracted with ethyl acetate. The extract was dried and concentrated under reduced pressure. The residue was purified by silica gel chromatography to give 4-[N,N-bis(2-hydroxyethyl)amino]-2-trifluoromethylquinoline (3.40 g) as a white powder.

(2) The above-mentioned compound (1.77 g) and triethylamine (2.63 mL) were dissolved in ethyl acetate (100 mL), and methanesulfonyl chloride (1.28 mL) was added under ice-cooling. The mixture was stirred at room temperature for 30 min. The precipitated solid was collected by filtration, and the filtrate was concentrated under reduced pressure to give dimesylate as an oil. This was dissolved in N-methyl-2-pyrrolidone (100 mL), and the title compound (2.02 g) of Reference Example 15 and N,N-diisopropylethylamine (3.10 mL) were added thereto. The mixture was stirred at 100° C. for 15 hr. 10% Aqueous citric acid solution was added to the reaction mixture, and the mixture was extracted with ethyl acetate. The extract was washed successively with saturated aqueous sodium hydrogencarbonate solution and brine, dried and concentrated under reduced pressure. The residue was purified by silica gel chromatography to give 3-{(2S,4R)-1-tert-butoxycarbonyl-4-[4-(2-trifluoromethyl-4-quinolyl)-1-piperazinyl]-2-pyrrolidinylcarbonyl}-1,3-thiazolidine (0.248 g) as a pale-brown powder.

(3) Using the above-mentioned compound (246 mg), and in the same manner as in Example 133 (2), the title compound (101 mg) was obtained as a white powder.

$^1$H-NMR(500 MHz,DMSO-$d_6$)δ2.40–2.50(1H,m), 3.00–3.18(3H,m), 3.59–3.95(12H,m), 4.12–4.22(1H,m), 4.47–5.03(3H,m), 7.39(1H,s), 7.75(1H,t,J=7.9 Hz), 7.88–7.91(1H,m), 8.12–8.14(2H,m), 9.30(1H,brs), 10.75 (1H,brs).

Example 261

Synthesis of 3-{(2S,4S)-4-[4-(7-trifluoromethyl-4-quinolyl)-1-piperazinyl]-2-pyrrolidinylcarbonyl}-1,3-thiazolidine trihydrochloride (1) Using 4-chloro-7-(trifluoromethyl)quinoline (2.5 g) and piperazine (9.30 g), and in the same manner as in Example 189 (1), 1-(7-trifluoromethyl-4-quinolyl) piperazine (3.04 g) was obtained as a pale-brown solid.

(2) Using the above-mentioned compound (619 mg) and the title compound (601 mg) of Reference Example 12, and in the same manner as in Example 70 (1), 3-{(2S,4S)-1-tert-butoxycarbonyl-4-[4-(7-trifluoromethyl-4-quinolyl)-1-piperazinyl]-2-pyrrolidinylcarbonyl}-1,3-thiazolidine (458 mg) was obtained as a pale-yellow oil.

(3) Using the above-mentioned compound (458 mg), and in the same manner as in Example 186 (2), the title compound (282 mg) was obtained as a brown powder.

$^1$H-NMR(DMSO-$d_6$)δ2.20–2.47(1H,m), 2.90–3.20(3H, m), 3.30–4.30(13H,m), 4.45–4.85(3H,m), 7.46(1H,d,J=6.7 Hz), 7.98(1H,dd,J=9.0,1.5 Hz), 8.43(1H,d,J=8.9 Hz), 8.62 (1H,s), 8.96(1H,d,J=6.7 Hz).

Example 262

Synthesis of 3-{(2S,4S)-4-[4-(2-methoxycarbonyl-4-quinolyl)-1-piperazinyl]-2-pyrrolidinylcarbonyl}-1,3-thiazolidine trihydrochloride (1) Phosphorus oxychloride (100 mL) was added to kynurenic acid (25 g). The mixture was refluxed for 6 hr. The reaction mixture was concentrated under reduced pressure, and the residue was dissolved in 1,4-dioxane (100 mL). Aqueous ammonia (400 mL) was dropwise added thereto under ice-cooling. Water (500 mL) was added thereto, and the mixture was extracted with chloroform. The extract was washed with brine and concentrated under reduced pressure to give 4-chloroquinoline-2-carboxamide (27.3 g) as a black purple solid.

(2) Piperazine (12.9 g) was suspended in N-methyl-2-pyrrolidone (170 mL) and the above-mentioned compound (10.3 g) was added thereto. The mixture was stirred at 80° C. with heating. The reaction mixture was concentrated under reduced pressure, and the residue was added to 1 mol/L hydrochloric acid (150 mL), and the mixture was washed with chloroform. The mixture was basified with aqueous sodium hydroxide solution, and the mixture was extracted with chloroform. The extract was concentrated under reduced pressure to give 1-(2-carbamoyl-4-quinolyl) piperazine (35.18 g) as a pale-yellow powder.

(3) Using the above-mentioned compound (2.54 g) and the title compound (1.26 g) of Reference Example 12, and in the same manner as in Example 70 (1), 3-{(2S,4S)-1-tert-butoxycarbonyl-4-[4-(2-carbamoyl-4-quinolyl)-1-piperazinyl]-2-pyrrolidinylcarbonyl}-1,3-thiazolidine (2.19 g).

(4) The above-mentioned compound (2.19 g) and imidazole (0.551 g) were dissolved in pyridine (20 mL), and phosphorus oxychloride (1.51 mL) was dropwise added to the reaction mixture under ice-cooling. The mixture was stirred under ice-cooling for 1 hr. Saturated aqueous sodium hydrogencarbonate solution was added to the reaction mixture, and the mixture was extracted with chloroform. The extract was concentrated under reduced pressure and the residue was purified by silica gel chromatography to give 3-{(2S,4S)-1-tert-butoxycarbonyl-4-[4-(2-cyano-4-quinolyl)-1-piperazinyl]-2-pyrrolidinylcarbonyl}-1,3-thiazolidine (0.658 g) as a red orange solid.

(5) 5.6 mol/L Hydrochloric acid-methanol (30 mL) was added to the above-mentioned compound (992 mg), and the mixture was stirred at room temperature for 24 hr. The reaction mixture was concentrated under reduced pressure, and saturated aqueous sodium hydrogencarbonate solution was added to the residue. The mixture was extracted with chloroform and the extract was concentrated under reduced pressure. The residue was purified by silica gel chromatography to give a free base (670 mg) of the title compound as a pale-yellow oil. This was dissolved in methanol (10 mL), and 5.6 mol/L hydrochloric acid-methanol (0.79 mL) was added thereto. The mixture was concentrated under reduced pressure to give the title compound (615 mg) as a pale-yellow powder.

$^1$H-NMR(DMSO-$d_6$)δ2.20–2.56(1H,m), 2.82–3.20(3H, m), 3.40–4.30(13H,m), 4.00(3H,s), 4.41–4.82(3H,m), 7.63 (1H,s), 7.75(1H,t,J=7.8 Hz), 7.93(1H,t,J=7.8 Hz), 8.17(1H, d,J=7.8 Hz), 8.24(1H,d,J=7.8 Hz), 9.20(1H,brs), 11.05(1H, brs).

Example 263

Synthesis of 3-{(2S,4S)-4-[4-(2-carbamoyl-4-quinolyl)-1-piperazinyl]-2-pyrrolidinylcarbonyl}-1,3-thiazolidine trihydrochloride Using 3-{(2S,4S)-1-tert-butoxycarbonyl-4-[4-(2-carbamoyl-4-quinolyl)-1-piperazinyl]-2-pyrrolidinylcarbonyl}-1,3-thiazolidine [product of Example 262 (3), 1.05 g], and in the same manner as in Example 186 (2), the title compound (696 mg) was obtained as a brown powder.

$^1$H-NMR(DMSO-$d_6$)δ2.20–2.42(1H,m), 2.89–3.20(3H, m), 3.30–4.30(13H,m), 4.44–4.83(3H,m), 7.73(1H,t,J=8.0 Hz), 7.87(1H,s), 7.95(1H,t,J=8.0 Hz), 8.17(1H,d,J=8.0 Hz), 8.24(1H,brs), 8.28(1H,d,J=8.0 Hz), 8.86(1H,brs), 9.18(1H, brs), 10.89(1H,brs).

Example 264

Synthesis of 3-{(2S,4S)-4-[4-(3-exycarbonyl-4-quinolyl)-1-piperazinyl]-2-pyrrolidinylcarbonyl}-1,3-thiazolidine trihydrochloride (1) Diethyl ethoxymethylenemalonate (115 g) was dropwise added to aniline (50 g), and the mixture was refluxed for 1 hr. The resulting ethanol was evaporated under atmospheric pressure, and the residue was heated at 200° C. and poured into diphenyl ether (750 mL). The mixture was stirred at 220–250° C. for 2 hr with heating. The resulting ethanol was again evaporated under atmospheric pressure, and the reaction mixture was allowed to cool to room temperature. The precipitated solid was collected by filtration and washed with hexane to give ethyl 4-hydroxyquinoline-3-carboxylate (51.0 g) as a white powder.

(2) The above-mentioned compound (51.0 g) was added to phosphorus oxychloride (121 mL), and the mixture was stirred at 60–70° C. for 2 hr with heating. The reaction mixture was concentrated under reduced pressure, and the residue was added to iced water (1 L). The mixture was basified with 1 mol/L aqueous sodium hydroxide solution (500 mL) and sodium hydrogencarbonate. The mixture was extracted with ethyl acetate, washed with brine and concentrated under reduced pressure to give ethyl 4-chloroquinoline-3-carboxylate (54.2 g) as a pale-brown solid.

(3) Piperazine (12.9 g) was dissolved in DMF (100 mL), and a solution of the above-mentioned compound (11.8 g) in DMF (100 mL) was added thereto. The mixture was stirred at room temperature for 1 hr. The reaction mixture was added to iced water (500 mL), and the mixture was extracted with ethyl acetate. The extract was washed successively with water and brine, and concentrated under reduced pressure to give 1-(2-ethoxycarbonyl-4-quinolyl)piperazine (7.92 g) as a pale-yellow solid.

(4) Using the above-mentioned compound (3.42 g) and the title compound (2.70 g) of Reference Example 12, and in the same manner as in Example 70 (1), 3-{(2S,4S)-1-tert-butoxycarbonyl-4-[4-(3-ethoxycarbonyl-4-quinolyl)-1-piperazinyl]-2-pyrrolidinylcarbonyl}-1,3-thiazolidine (4.57 g) was obtained as a pale-yellow powder.

(5) The above-mentioned compound (600 mg) was dissolved in ethanol (20 mL), and 4.1 mol/L hydrochloric acid-ethanol (10 mL) was added thereto. The mixture was stirred at room temperature for 24 hr. The reaction mixture was concentrated under reduced pressure, and saturated aqueous sodium hydrogencarbonate solution was added to the residue. The mixture was extracted with chloroform and the extract was concentrated under reduced pressure. The residue was purified by silica gel chromatography to give a free base (269 mg) of the title compound. This was dissolved in ethanol (5 mL) and 4.1 mol/L hydrochloric acid-ethanol (0.42 mL) was added thereto. The mixture was concentrated under reduced pressure to give the title compound (253 mg) as a pale-yellow powder.

$^1$H-NMR(DMSO-$d_6$)δ1.41(3H,t,J=6.9 Hz), 2.22–2.46 (1H,m), 2.90–3.20(3H,m), 3.30–4.30(13H,m), 4.33–4.82 (5H,m), 7.80(1H,t,J=7.8 Hz), 8.02(1H,t,J=7.8 Hz), 8.19(1H, d,J=7.8 Hz), 8.27(1H,d,J=7.8 Hz), 9.02(1H,s), 9.15(1H,brs), 10.88(1H,brs).

Example 265

Synthesis of 3-{(2S,4S)-4-[4-(2-cyano-4-quinolyl)-1-piperazinyl]-2-pyrrolidinylcarbonyl}-1,3-thiazolidine trihydrochloride 3-{(2S,4S)-1-tert-Butoxycarbonyl-4-[4-(2-cyano-4-quinolyl)-1-piperazinyl]-2-pyrrolidinylcarbonyl}-1,3-thiazolidine [product of Example 262(4), 658 mg] was dissolved in chloroform (10 mL), and 4 mol/L hydrochloric acid-ethyl acetate (5 mL) was added thereto. The mixture was stirred at room temperature for 24 hr. The solvent was evaporated under reduced pressure, and saturated aqueous sodium hydrogencarbonate solution was added to the residue. The mixture was extracted with chloroform and the extract was concentrated under reduced pressure. The residue was purified by silica gel chromatography to give a free base (435 mg) of the title compound. This was dissolved in ethanol (20 mL), and 4.1 mol/L hydrochloric acid-ethanol (0.75 mL) was added thereto. The mixture was concentrated under reduced pressure to give the title compound (353 mg) as a pale-yellow powder.

$^1$H-NMR(DMSO-d$_6$)δ2.20–2.45(1H,m), 2.90–3.20(3H, m), 3.30–4.22(13H,m), 4.43–4.80(3H,m), 7.63(1H,s), 7.75 (1H,t,J=7.8 Hz), 7.89(1H,t,J=7.8 Hz), 8.01–8.19(2H,m), 9.17(1H,brs), 10.71(1H,brs).

Example 266

Synthesis of 3-{(2S,4S)-4-[4-(2-phenyl-4-quinolyl)-1-piperazinyl]-2-pyrrolidinylcarbonyl}-1,3-thiazolidine trihydrochloride (1) Using 4-chloro-2-phenylquinoline (2.50 g) and piperazine (8.98 g), and in the same manner as in Example 268 (1), 1-(2-phenyl-4-quinolyl)piperazine (2.72 g) was obtained.

(2) Using the above-mentioned compound (1.01 g) and the title compound (1.00 g) of Reference Example 12, and in the same manner as in Example 70 (1), 3-{(2S,4S)-1-tert-butoxycarbonyl-4-[4-(2-phenyl-4-quinolyl)-1-piperazinyl]-2-pyrrolidinylcarbonyl}-1,3-thiazolidine (1.77 g) was obtained as a white powder.

(3) The above-mentioned compound (1.75 g) was dissolved in methanol (10 mL), and 4 mol/L hydrochloric acid-ethyl acetate (10 mL) was added thereto. The mixture was stirred at room temperature for 14 hr. The precipitated solid was collected by filtration to give the title compound (0.970 g) as a white powder.

$^1$H-NMR(DMSO-d$_6$)δ2.20–2.45(1H,m), 2.90–3.17(3H, m), 3.28–4.00(13H,m), 4.42–4.80(3H,m), 7.57(1H,s), 7.61–7.82(4H,m), 7.95–8.08(1H,m), 8.16–8.31(3H,m), 8.50 (1H,d,J=8.7 Hz), 9.15(1H,brs), 11.06(1H,brs).

Example 267

Synthesis of 3-{(2S,4S)-4-[4-(2-amino-4-quinolyl)-1-piperazinyl]-2-pyrrolidinylcarbonyl}-1,3-thiazolidine trihydrochloride (1) Bromine (2.32 mL) was dissolved in 5% aqueous potassium hydroxide solution (190 mL), and a solution of 4-chloroquinoline-2-carboxamide [product of Example 262 (1), 9.80 g] in tetrahydrofuran (190 mL) was dropwise added thereto. The mixture was stirred at room temperature for 30 min, and the mixture was stirred at 80° C. for 1 hr with heating. The reaction mixture was filtrated and the filtrate was added to water. The mixture was extracted with chloroform, and the extract was washed with brine and concentrated under reduced pressure. The residue was purified by silica gel chromatography to give 2-amino-4-chloroquinoline (1.98 g) as a pale-yellow solid.

(2) Using the above-mentioned compound (1.98 g) and piperazine (19.1 g), and in the same manner as in Example 189 (1), 1-(2-amino-4-quinolyl)piperazine (1.85 g) was obtained as a pale-brown powder.

(3) Using the above-mentioned compound (913 mg) and the title compound (901 mg) of Reference Example 12, and in the same manner as in Example 70 (1), 3-{(2S,4S)-1-tert-butoxycarbonyl-4-[4-(2-amino-4-quinolyl)-1-piperazinyl]-2-pyrrolidinylcarbonyl}-1,3-thiazolidine (465 mg) was obtained as a white solid.

(4) Using the above-mentioned compound (465 mg), and in the same manner as in Example 186 (2), the title compound (439 mg) was obtained as a white powder.

$^1$H-NMR(DMSO-d$_6$)δ2.20–2.42(1H,m), 2.86–3.20(3H, m), 3.30–4.30(13H,m), 4.41–4.84(3H,s), 6.52(1H,s), 7.46 (1H,t,J=8.1 Hz), 7.59–7.82(2H,m), 7.91(1H,d,J=8.1 Hz), 8.33(2H,brs), 9.14(1H,brs), 10.85(1H,brs), 13.79(1H,brs)

Example 268

Synthesis of 3-{(2S,4S)-4-[4-(7-chloro-4-quinolyl)-1-piperazinyl]-2-pyrrolidinylcarbonyl}-1,3-thiazolidine trihydrochloride (1) Piperazine (65.2 g) was melted by heating at 120° C., and 4,7-dichloroquinoline (15.0 g) was added thereto. The mixture was stirred at 120° C. for 2.5 hr and the reaction mixture was added to water. The mixture was extracted with chloroform and concentrated under reduced pressure to give 1-(7-chloro-4-quinolyl)piperazine (7.72 g).

(2) Using the above-mentioned compound (0.87 g) and the title compound (1.00 g) of Reference Example 12, and in the same manner as in Example 70 (1), 3-{(2S,4S)-1-tert-butoxycarbonyl-4-[4-(7-chloro-4-quinolyl)-1-piperazinyl]-2-pyrrolidinylcarbonyl}-1,3-thiazolidine (1.65 g) was obtained as a white powder.

(3) The above-mentioned compound (1.64 g) was suspended in methanol (10 mL), and 4 mol/L hydrochloric acid-ethyl acetate (8.0 mL) was added thereto. The mixture was stirred at room temperature for 13 hr. The precipitated solid was collected by filtration to give the title compound (1.04 g) as a white powder.

$^1$H-NMR(DMSO-d$_6$)δ2.10–2.37(1H,m), 2.84–4.00(16H, m), 4.41–4.82(3H,m), 7.36(1H,d,J=6.9 Hz), 7.77(1H,dd,J=9.0,1.8 Hz), 8.22(1H,d,J=9.0 Hz), 8.27(1H,d,J=1.8 Hz), 8.85 (1H,d,J=6.9 Hz), 9.18(1H,brs), 10.82(1H,brs).

Example 269

Synthesis of 3-{(2S,4S)-4-[4-(2-trifluoromethyl-8-methyl-4-quinolyl)-1-piperazinyl]-2-pyrrolidinylcarbonyl}-1,3-thiazolidine dihydrochloride (1) 2-Methylaniline (5.00 g) was dissolved in 75% phosphoric acid (20 mL), and ethyl trifluoroacetoacetate (8.60 g) was dropwise added thereto at 105° C. The mixture was stirred at 105° C. for 5.5 hr. After allowing to cool, the reaction mixture was added to water. The precipitated solid was collected by filtration to give 2-trifluoromethyl-4-hydroxy-8-methylquinoline (1.84 g).

(2) The above-mentioned compound (1.82 g) was dissolved in phosphorus oxychloride (8.00 mL), and the mixture was stirred at 70° C. for 2.5 hr. The reaction mixture was concentrated under reduced pressure, and saturated aqueous sodium hydrogencarbonate solution was added to the residue. The mixture was extracted with chloroform and the extract was concentrated under reduced pressure to give 4-chloro-2-trifluoromethyl-8-methylquinoline (1.66 g).

(3) Using the above-mentioned compound (1.65 g) and piperazine (4.00 g), and in the same manner as in Example 268 (1), 1-(2-trifluoromethyl-8-methyl-4-quinolyl) piperazine (1.57 g) was obtained.

(4) Using the above-mentioned compound (1.03 g) and the title compound (1.00 g) of Reference Example 12, and in the same manner as in Example 70 (1), 3-{(2S,4S)-1-tert-butoxycarbonyl-4-[4-(2-trifluoromethyl-8-methyl-4-quinolyl)-1-piperazinyl]-2-pyrrolidinylcarbonyl}-1,3-thiazolidine (1.81 g) was obtained as a white powder.

(5) Using the above-mentioned compound (1.80 g), and in the same manner as in Example 268 (3), the title compound (1.30 g) was obtained as a white powder.

$^1$H-NMR(DMSO-$d_6$)δ2.20–2.45(1H,m), 2.72(3H,s), 2.90–3.20(3H,m), 3.25–4.25(13H,m), 4.44–4.82(3H,m), 7.40(1H,s), 7.63(1H,dd,J=8.3,6.9 Hz), 7.75(1H,d,J=6.9 Hz), 7.93(1H,d,J=8.3 Hz), 9.12(1H,brs), 10.85(1H,brs), 12.65 (1H,brs).

Example 270

Synthesis of 3-((2S,4S)-4-{4-[2,6-bis(trifluoromethyl)-4-quinolyl]-1-piperazinyl}-2-pyrrolidinylcarbonyl)-1,3-thiazolidine dihydrochloride (1) 4-Hydroxy-2,6-bis(trifluoromethyl)quinoline (1.28 g) was dissolved in phosphorus oxychloride (5.0 mL), and the mixture was stirred at room temperature for 17 hr. The reaction mixture was concentrated under reduced pressure, and saturated aqueous sodium hydrogencarbonate solution was added to the residue. The mixture was extracted with chloroform and concentrated under reduced pressure to give 4-chloro-2,6-bis(trifluoromethyl)quinoline (1.17 g).

(2) Using the above-mentioned compound (1.14 g) and piperazine (3.29 g), and in the same manner as in Example 189 (1), 1-[2,6-bis(trifluoromethyl)-4-quinolyl]piperazine (870 mg) was obtained.

(3) Using the above-mentioned compound (0.860 g) and the title compound (0.86 g) of Reference Example 12, and in the same manner as in Example 70 (1), 3-((2S,4S)-1-tert-butoxycarbonyl-4-{4-[2,6-bis(trifluoromethyl)-4-quinolyl]-1-piperazinyl}-2-pyrrolidinylcarbonyl)-1,3-thiazolidine (1.55 g) was obtained as a white powder.

(3) Using the above-mentioned compound (1.54 g), and in the same manner as in Example 268 (3), the title compound (860 mg) was obtained as a white powder.

$^1$H-NMR(DMSO-$d_6$)δ2.11–2.46(1H,m), 2.72–4.20(16H, m), 4.35–4.89(3H,m), 7.54(1H,s), 8.14(1H,dd,J=9.0,1.2 Hz), 8.33(1H,d,J=9.0 Hz), 8.38(1H,d,J=1.2 Hz), 9.24(1H, brs), 10.88(1H,brs).

Example 271

Synthesis of 3-((2S,4S)-4-{4-[2,8-bis(trifluoromethyl)-4-quinolyl]-1-piperazinyl}-2-pyrrolidinylcarbonyl)-1,3-thiazolidine dihydrochloride (1) Using 4-chloro-2,8-bis(trifluoromethyl)quinoline (0.500 g) and piperazine (7.19 g), and in the same manner as in Example 189 (1), 1-[2,8-bis(trifluoromethyl)-4-quinolyl]piperazine (0.519 g) was obtained as a pale-brown solid.

(2) Using the above-mentioned compound (519 mg) and the title compound (406 mg) of Reference Example 12, and in the same manner as in Example 70 (1), 3-{(2S,4S)-1-tert-butoxycarbonyl-4-{4-[2,8-bis(trifluoromethyl)-4-quinolyl]-1-piperazinyl}-2-pyrrolidinylcarbonyl}-1,3-thiazolidine (631 mg) was obtained as a white powder.

(3) Using the above-mentioned compound (547 mg), and in the same manner as in Example 186 (2), the title compound (362 mg) was obtained as a white powder.

$^1$H-NMR(DMSO-$d_6$)δ2.11–2.45(1H,m), 2.86–3.20(3H, m), 3.30–4.30(13H,m), 4.45–4.86(3H,m), 7.52(1H,s), 7.85 (1H,t,J=8.4 Hz), 8.31(1H,d,J=8.4 Hz), 8.42(1H,d,J=8.4 Hz).

Example 272

Synthesis of 3-{(2S,4S)-4-[4-(2-trifluoromethyl-6-methoxy-4-quinolyl)-1-piperazinyl]-2-pyrrolidinylcarbonyl}-1,3-thiazolidine trihydrochloride (1) 4-Methoxyaniline (5.00 g) was dissolved in 75% phosphoric acid (20 mL) and ethyl trifluoroacetoacetate (7.48 g) was dropwise added thereto at 110° C. The mixture was stirred at 110° C. for 4 hr with heating. After allowing to cool, the reaction mixture was added to saturated aqueous sodium hydrogencarbonate solution, and the mixture was extracted with ethyl acetate. The extract was dried and the solvent was evaporated under reduced pressure. The residue was purified by silica gel chromatography to give 2-trifluoromethyl-4-hydroxy-6-methoxyquinoline (0.450 g).

(2) Using the above-mentioned compound (450 mg), and in the same manner as in Example 270 (1), 4-chloro-2-trifluoromethyl-6-methoxyquinoline (410 mg) was obtained as a white powder.

(3) Using the above-mentioned compound (0.410 g) and piperazine (1.32 g), and in the same manner as in Example 189 (1), 1-(2-trifluoromethyl-6-methoxy-4-quinolyl) piperazine (0.450 g) was obtained.

(4) Using the above-mentioned compound (450 mg) and the title compound (430 mg) of Reference Example 12, and in the same manner as in Example 70 (1), 3-{(2S,4S)-1-tert-butoxycarbonyl-4-[4-(2-trifluoromethyl-6-methoxy-4-quinolyl)-1-piperazinyl]-2-pyrrolidinylcarbonyl}-1,3-thiazolidine (660 mg) was obtained as a white powder.

(5) Using the above-mentioned compound (660 mg), and in the same manner as in Example 268 (3), the title compound (290 mg) was obtained as a white powder.

$^1$H-NMR(DMSO-$d_6$)δ2.34–2.54(1H,m), 2.93–3.21(3H, m), 3.31–4.30(13H,m), 3.97(3H,s), 4.45–4.85(3H,m), 7.31 (1H,d,J=2.7 Hz), 7.38(1H,s), 7.55(1H,dd,J=9.3,2.7 Hz), 8.06(1H,d,J=9.3 Hz), 9.18(1H,brs), 11.84(1H,brs), 12.78 (1H,brs).

Example 273

Synthesis of 3-{(2S,4S)-4-[4-(2-trifluoromethyl-7-methoxy-4-quinolyl)-1-piperazinyl]-2-pyrrolidinylcarbonyl}-1,3-thiazolidine dihydrochloride (1) Using 3-methoxyaniline (20.0 g) and ethyl trifluoroacetoacetate (29.9 g), and in the same manner as in Example 269 (1), 2-trifluoromethyl-4-hydroxy-7-methoxyquinoline (860 mg) was obtained.

(2) Using the above-mentioned compound (850 mg), and in the same manner as in Example 269 (2), 4-chloro-2-trifluoromethyl-7-methoxyquinoline (820 mg) was obtained as a white powder.

(3) Using the above-mentioned compound (0.820 g) and piperazine (4.00 g), and in the same manner as in Example 189 (1), 1-(2-trifluoromethyl-7-methoxy-4-quinolyl) piperazine (0.840 g) was obtained.

(4) Using the above-mentioned compound (0.830 g) and the title compound (0.800 g) of Reference Example 12, and in the same manner as in Example 70 (1), 3-{(2S,4S)-1-tert-butoxycarbonyl-4-[4-(2-trifluoromethyl-7-methoxy-4- quinolyl)-1-piperazinyl]-2-pyrrolidinylcarbonyl}-1,3-thiazolidine (1.25 g) was obtained as a white powder.

(5) Using the above-mentioned compound (1.24 g), and in the same manner as in Example 268 (3), the title compound (0.900 g) was obtained as a white powder.

$^1$H-NMR(DMSO-$d_6$)δ2.28–2.48(1H,m), 2.95–3.20(3H, m), 3.21–3.97(12H,m), 3.95(3H,s), 4.03–4.24(1H,m), 4.44–4.83(3H,m), 7.25(1H,s), 7.36(1H,dd,J=9.9,2.6 Hz), 7.51(1H,d,J=2.6 Hz), 8.04(1H,d,J=9.9 Hz), 9.16(1H,brs), 11.69(1H,brs).

Example 274

Synthesis of 3-{(2S,4S)-4-[4-(2-trifluoromethyl-8-methoxy-4-quinolyl)-1-piperazinyl]-2-pyrrolidinylcarbonyl}-1,3-thiazolidine dihydrochloride (1) Using 2-methoxyaniline (10.0 g) and ethyl trifluoroacetoacetate (14.5 g), and in the same manner as in Example 269 (1), 2-trifluoromethyl-4-hydroxy-8-methoxyquinoline (2.03 g) was obtained.

(2) Using the above-mentioned compound (2.00 g), and in the same manner as in Example 269 (2), 4-chloro-2-trifluoromethyl-8-methoxyquinoline (1.95 g) was obtained as a white powder.

Using the above-mentioned compound (1.95 g) and piperazine (8.00 g), and in the same manner as in Example 189 (1), 1-(2-trifluoromethyl-8-methoxy-4-quinolyl)piperazine (2.14 g) was obtained.

(4) Using the above-mentioned compound (1.60 g) and the title compound (1.01 g) of Reference Example 12, and in the same manner as in Example 70 (1), 3-{(2S,4S)-1-tert-butoxycarbonyl-4-[4-(2-trifluoromethyl-8-methoxy-4-quinolyl)-1-piperazinyl]-2-pyrrolidinylcarbonyl}-1,3-thiazolidine (1.01 g) was obtained as a white powder.

(5) Using the above-mentioned compound (1.01 g), and in the same manner as in Example 268 (3), the title compound (0.640 g) was obtained as a white powder.

$^1$H-NMR(DMSO-$d_6$)δ2.15–2.39(1H,m), 2.80–3.19(3H, m), 3.20–4.18(13H,m), 3.99(3H,s), 4.40–4.78(3H,m), 7.29–7.33(1H,m), 7.35(1H,s), 7.60–7.69(2H,m), 9.14(1H, brs), 10.71(1H,brs), 12.61(1H,brs).

Example 275

Synthesis of 3-{(2S,4S)-4-[4-(8-fluoro-2-trifluoromethyl-4-quinolyl)-1-piperazinyl]-2-pyrrolidinylcarbonyl}-1,3-thiazolidine dihydrochloride (1) 2-Fluoroaniline (10.0 g), ethyl trifluoroacetoacetate (16.6 g) and concentrated hydrochloric acid (0.1 mL) were dissolved in benzene (40 mL), and the mixture was refluxed in a reaction vessel equipped with Dean-Stark trap for 7 hr. The reaction mixture was concentrated under reduced pressure and 75% phosphoric acid (40 mL) was added thereto. The mixture was stirred at 110° C. for 5 hr. The reaction mixture was added to water, neutralized with sodium hydrogencarbonate, and extracted with ethyl acetate. The extract was concentrated under reduced pressure to give 8-fluoro-4-hydroxy-2-trifluoromethylquinoline (1.77 g).

(2) Using the above-mentioned compound (1.77 g), and in the same manner as in Example 269 (2), 4-chloro-8-fluoro-2-trifluoromethylquinoline (1.70 g) was obtained as a white powder.

(3) The above-mentioned compound (1.45 g), piperazine (0.5 g) and N,N-diisopropylethylamine (0.751 g) were dissolved in DMF (25 mL), and the mixture was stirred at 70° C. for 6.5 hr. The reaction mixture was added to water, and the mixture was extracted with chloroform. The extract was concentrated under reduced pressure and the residue was purified by silica gel chromatography to give 1-(8-fluoro-2-trifluoromethyl-4-quinolyl)piperazine (0.187 g).

(4) Using the above-mentioned compound (186 mg) and the title compound (187 mg) of Reference Example 12, and in the same manner as in Example 70 (1), 3-{(2S,4S)-1-tert-butoxycarbonyl-4-[4-(8-fluoro-2-trifluoromethyl-4-quinolyl)-1-piperazinyl]-2-pyrrolidinylcarbonyl}-1,3-thiazolidine (302 mg) was obtained as a white powder.

(5) Using the above-mentioned compound (302 mg), and in the same manner as in Example 186 (2), the title compound (150 mg) was obtained as a white powder.

$^1$H-NMR(DMSO-$d_6$)δ2.23–2.48(1H,m), 2.91–3.20(3H, m), 3.21–3.89(11H,m), 3.90–3.99(1H,m), 4.00–4.22(1H,m), 4.45–4.85(3H,m), 7.46(1H,s), 7.65–7.78(2H,m), 7.89–8.01 (1H,m), 9.16(1H,brs), 11.02(1H,brs).

Example 276

Synthesis of 3-{(2S,4S)-4-[4-(6-chloro-2-trifluoromethyl-4-quinolyl)-1-piperazinyl]-2-pyrrolidinylcarbonyl}-1,3-thiazolidine dihydrochloride (1) 4-Chloroaniline (5.00 g) was dissolved in 75% phosphoric acid (20 mL), and ethyl trifluoroacetoacetate (8.60 g) was dropwise added thereto at 110° C. The mixture was stirred at 110° C. for 4 hr, and then at 130° C. for 7 hr. After allowing to cool, water was added thereto. The precipitated solid was collected by filtration to give 2-trifluoromethyl-4-hydroxy-6-methoxyquinoline (0.800 g).

(2) Using the above-mentioned compound (800 mg) and in the same manner as in Example 270 (1), 4,6-dichloro-2-trifluoromethylquinoline (540 mg) was obtained as a white powder.

(3) Using the above-mentioned compound (0.54 g) and piperazine (1.50 g), and in the same manner as in Example 189 (1), 1-(6-chloro-2-trifluoromethyl-4-quinolyl) piperazine (0.490 g) was obtained.

(4) Using the above-mentioned compound (480 mg) and the title compound (460 mg) of Reference Example 12, and in the same manner as in Example 70 (1), 3-{(2S,4S)-1-tert-butoxycarbonyl-4-[4-(6-chloro-2-trifluoromethyl-4-quinolyl)-1-piperazinyl]-2-pyrrolidinylcarbonyl}-1,3-thiazolidine (740 mg) was obtained as a white powder.

(5) Using the above-mentioned compound (730 mg), and in the same manner as in Example 268 (3), the title compound (550 mg) was obtained as a white powder.

$^1$H-NMR(DMSO-$d_6$)δ2.45–2.70(1H,m), 2.80–4.06(14H, m), 4.39–4.78(5H,m), 7.42(1H,s), 7.90(1H,d,J=9.0 Hz), 8.08(1H,d,J=2.7 Hz), 8.14(1H,dd,J=9.0 Hz,2.7 Hz), 9.10 (1H,brs), 10.08(1H,brs).

Example 277

Synthesis of 3-{(2S,4S)-4-[4-(8-chloro-2-trifluoromethyl-4-quinolyl)-1-piperazinyl]-2-pyrrolidinylcarbonyl}-1,3-thiazolidine dihydrochloride (1) Using 2-chloroaniline (20.0 g), and in the same manner as in Example 275 (1), 8-chloro-4-hydroxy-2-trifluoromethylquinoline (3.20 g) was obtained.

(2) Using the above-mentioned compound (3.17 g), and in the same manner as in Example 269 (2), 4,8-dichloro-2-trifluoromethylquinoline (2.30 g) was obtained as a white powder.

(3) Using the above-mentioned compound (2.30 g), and in the same manner as in Example 275 (3), 1-(8-chloro-2-trifluoromethyl-4-quinolyl)piperazine (0.950 g) was obtained.

(4) Using the above-mentioned compound (0.950 g) and the title compound (0.900 g) of Reference Example 12, and in the same manner as in Example 70 (1), 3-{(2S,4S)-1-tert-butoxycarbonyl-4-[4-(8-chloro-2-trifluoromethyl-4-quinolyl)-1-piperazinyl]-2-pyrrolidinylcarbonyl}-1,3-thiazolidine (1.20 g) was obtained as a white powder.

(5) Using the above-mentioned compound (1.18 g), and in the same manner as in Example 268 (3), the title compound (0.790 g) was obtained as a white powder.

$^1$H-NMR(DMSO-d$_6$)δ2.22–2.53(1H,m), 2.90–3.23(3H, m), 3.24–3.89(11H,m), 3.90–4.01(1H,m), 4.07–4.22(1H,m), 4.44–4.85(3H,m), 7.49(1H,s), 7.62–7.75(1H,m), 7.99–8.18 (2H,m), 9.18(1H,brs), 11.09(1H,brs).

Example 278

Synthesis of 3-{(2S,4S)-4-[4-(4-cyano-1-isoquinolyl)-1-5-piperazinyl]-2-pyrrolidinylcarbonyl}-1,3-thiazolidine trihydrochloride (1) 4-Bromo-1-hydroxyisoquinoline (1.56 g) was dissolved in N-methyl-2-pyrrolidine (25 mL), and copper cyanide (1.56 g) was added thereto. The mixture was stirred at 180° C. for 4 hr with heating. The reaction mixture was added to cool to 100° C. and added to an aqueous solution (125 mL) of sodium cyanide (31.25 g). The mixture was extracted with dichloromethane and the extract was dried and concentrated under reduced pressure. The residue was purified by silica gel chromatography to give 4-cyano-1-hydroxyisoquinoline (0.62 g) as a pale-yellow solid.

(2) The above-mentioned compound (916 mg) was dissolved in phosphorus oxychloride (10 mL), and the mixture was stirred at 70° C. for 5 hr with heating. Phosphorus oxychloride was evaporated under reduced pressure, and saturated aqueous sodium hydrogencarbonate solution was added to the residue. The mixture was extracted with ethyl acetate, and the extract was washed with brine, dried and concentrated under reduced pressure. The residue was purified by silica gel chromatography to give 1-chloro-4-cyanoisoquinoline (704 mg) as a white solid.

(3) Piperazine (4.6 g) was melted by heating at 140° C. and the above-mentioned compound (0.500 g) was added thereto. The mixture was stirred at 140° C. for 2 hr and water was added to the reaction mixture. The mixture was extracted with chloroform, and the extract was washed with brine, dried and concentrated under reduced pressure to give 1-(4-cyano-1-isoquinolyl)piperazine (0.491 g) as a dark brown solid.

(4) Using the above-mentioned compound (252 mg) and the title compound (300 mg) of Reference Example 12, and in the same manner as in Example 70 (1), 3-{(2S,4S)-1-tert-butoxycarbonyl-4-[4-(4-cyano-1-isoquinolyl)-1-piperazinyl]-2-pyrrolidinylcarbonyl}-1,3-thiazolidine (494 mg) was obtained as a pale-yellow solid.

$^1$H-NMR(CDCl$_3$)δ1.41(4.5H,s), 1.46(4.5H,s), 1.87–2.02 (1H,m), 2.41–2.55(1H,m), 2.61–2.80(4H,m), 2.84–3.32(3H, m), 3.35(1H,dt,J=2.7,10.0 Hz), 3.62–4.16(7H,m), 4.40–4.82 (3H,m), 7.59(1H,t,J=8.1 Hz), 7.77(1H,t,J=8.1 Hz), 8.01(1H, d,J=8.1 Hz), 8.07(1H,d,J=8.1 Hz), 8.46(1H,s).

(5) The above-mentioned compound (490 mg) was dissolved in tetrahydrofuran (5 mL), and 4 mol/L hydrochloric acid-ethyl acetate (2.5 mL) was added thereto. The mixture was stirred at room temperature for 14 hr. The precipitated solid was collected by filtration and recrystallized from ethanol to give the title compound (202 mg) as a pale-brown powder.

$^1$H-NMR(DMSO-d$_6$)δ2.26–2.43(1H,m), 2.93–4.20(16H, m), 4.44–4.78(3H,m), 7.74–7.82(1H,m), 7.75–8.05(2H,m), 8.22(1H,d,J=8.4 Hz), 8.69(1H,s), 9.16(1H,brs), 10.85(1H, brs), 12.65(1H,brs).

Example 279

Synthesis of 3-{(2S,4S)-4-[4-(4-chloro-1-isoquinolyl)-1-piperazinyl]-2-pyrrolidinylcarbonyl}-1,3-thiazolidine trihydrochloride (1) Using 1-chloro-1-hydroxyisoquinoline (3.63 g), and in the same manner as in Example 278 (2), 1,4-dichloroisoquinoline (3.95 g) was obtained as a gray solid.

(2) Piperazine (12.6 g) was melted by heating at 140° C., and the above-mentioned compound (2.78 g) was added thereto. The mixture was stirred at 110° C. for 1 hr. The reaction mixture was added to water and the mixture was extracted with chloroform. The extract was washed with brine, dried and concentrated under reduced pressure to give 1-(4-chloro-1-isoquinolyl)piperazine (3.86 g) as a dark brown solid.

(3) Using the above-mentioned compound (446 mg) and the title compound (450 mg) of Reference Example 12, and in the same manner as in Example 70 (1), 3-{(2S,4S)-1-tert-butoxycarbonyl-4-[4-(4-chloro-1-isoquinolyl)-1-piperazinyl]-2-pyrrolidinylcarbonyl}-1,3-thiazolidine (596 mg) was obtained as a white solid.

(4) The above-mentioned compound (592 mg) was dissolved in 1.1 mol/L hydrochloric acid-methanol (10 mL), and the mixture was stirred at room temperature for 5 days. The reaction mixture was concentrated under reduced pressure, and ethanol (5 mL) was added thereto. The precipitated solid was collected by filtration to give the title compound (318 mg) as a pale-yellow powder.

$^1$H-NMR(DMSO-d$_6$)δ2.32–2.46(1H,m), 2.95–4.20(16H, m), 4.43–4.78(3H,m), 7.74–7.82(1H,m), 7.90–7.97(1H,m), 8.14(1H,d,J=8.0 Hz), 8.23(1H,d,J=8.3 Hz), 8.30(1H,s), 9.17 (1H,brs), 10.83(1H,brs), 12.53(1H,brs).

Example 280

Synthesis of 3-{(2S,4S)-4-[4-(4-bromo-1-isoquinolyl)-1-piperazinyl]-2-pyrrolidinylcarbonyl}-1,3-thiazolidine trihydrochloride (1) Using 1-bromo-1-hydroxyisoquinoline (3.11 g), and in the same manner as in Example 278 (2), 4-bromo-1-chloroisoquinoline (3.00 g) was obtained as a pale-brown solid (2) Piperazine (6.94 g) was melted by heating at 140° C., and the above-mentioned compound (2.92 g) was added thereto. The mixture was stirred at 110° C. for 1 hr. Water was added to the reaction mixture and the mixture was extracted with chloroform. The extract was dried and concentrated under reduced pressure to give 1-(4-bromo-1-isoquinolyl)piperazine (2.52 g) as a dark brown solid.

(3) Using the above-mentioned compound (488 mg) and the title compound (450 mg) of Reference Example 12, and in the same manner as in Example 70 (1), 3-{(2S,4S)-4-[4-(4-bromo-1-isoquinolyl)-1-tert-butoxycarbonyl-1-piperazinyl]-2-pyrrolidinylcarbonyl}-1,3-thiazolidine (753 mg) was obtained as a pale-yellow solid.

(4) The above-mentioned compound (749 mg) was dissolved in 1.1 mol/L hydrochloric acid-methanol (6 mL), and the mixture was stirred at room temperature for 4 days. The precipitated solid was collected by filtration to give the title compound (135 mg) as a white powder.

$^1$H-NMR(DMSO-$d_6$)δ2.32–2.46(1H,m), 2.97–3.19(3H, m), 3.40–3.97(12H,m), 4.06–4.20(1H,m), 4.45–4.78(3H,m), 7.73–7.80(1H,m), 7.89–7.97(1H,m), 8.08(1H,d,J=8.0 Hz), 8.22(1H,d,J=8.3 Hz), 8.40(1H,s), 9.17(1H,brs), 10.94(1H, brs), 12.60(1H,brs).

Example 281

Synthesis of 3-{(2S,4S)-4-[4-(4-quinazolinyl)-1-piperazinyl]-2-pyrrolidinylcarbonyl}-1,3-thiazolidine trihydrochloride (1) 4-Hydroxyquinazoline (3.76 g) and 2 drops of DMF were added to thionyl chloride (12 mL), and the mixture was refluxed for 2 hr. The reaction mixture was concentrated under reduced pressure, and the residue was added by small portions to piperazine (10 g) melted by heating at 140° C. Water and chloroform were added to the reaction mixture and an insoluble material was filtered off. The organic layer of the filtrate was separated and extracted with 1 mol/L hydrochloric acid. The aqueous layer was basified with aqueous sodium hydroxide solution, and the mixture was extracted with chloroform and concentrated under reduced pressure to give 1-(4-quinazolinyl)piperazine (1.86 g) as a yellow oil.

(2) Using the above-mentioned compound (471 mg) and the title compound (601 mg) of Reference Example 12, and in the same manner as in Example 70 (1), 3-{(2S,4S)-1-tert-butoxycarbonyl-4-[4-(4-quinazolinyl)-1-piperazinyl]-2-pyrrolidinylcarbonyl}-1,3-thiazolidine (543 mg) was obtained as a yellow powder.

(3) Using the above-mentioned compound (543 mg), and in the same manner as in Example 186 (2), the title compound (40 mg) was obtained as a white powder.

$^1$H-NMR(DMSO-$d_6$)δ2.00–2.30(1H,m), 2.80–3.00(1H, m), 3.00–4.85(18H,m), 7.66–7.81(1H,m), 7.93–8.12(2H,m), 8.24(1H,d,J=8.4 Hz), 8.95(1H,brs), 9.09(1H,brs), 10.84(1H, brs).

Example 282

Synthesis of 3-{(2S,4S)-4-[4-(2-trifluoromethyl-4-quinazolinyl)-1-piperazinyl]-2-pyrrolidinylcarbonyl}-1,3-thiazolidine (1) 2-Amino benzamide (13.6 g) was dissolved in 1,4-dioxane (50 mL) and trifluoroacetic acid anhydride (16.8 mL) was dropwise added thereto under ice-cooling. After stirring at room temperature for 1 hr, the reaction mixture was concentrated under reduced pressure. Acetic acid (50 mL) was added to the residue and the mixture was refluxed for 2 hr. After allowing to cool, the precipitated solid was collected by filtration and washed with diethyl ether to give 4-hydroxy-2-trifluoromethylquinazoline (11.9 g) as a white powder.

(2) The above-mentioned compound (5 g) and 2 drops of DMF were added to thionyl chloride (30 mL), and the mixture was refluxed for 1 hr. The reaction mixture was concentrated under reduced pressure, and the residue was added to a solution of piperazine (6.03 g) in DMF (60 mL). The mixture was stirred at room temperature for 1 hr and then at 60° C. for 30 min. The reaction mixture was concentrated under reduced pressure, and water and chloroform were added thereto. An insoluble material was filtered off. The organic layer of the filtrate was separated and extracted with 1 mol/L hydrochloric acid. The aqueous layer was basified with aqueous sodium hydroxide solution, and the mixture was extracted with chloroform. The extract was concentrated under reduced pressure to give 1-(2-trifluoromethyl-4-quinazolinyl)piperazine (3.75 g) as a pale-yellow solid.

(3) Using the above-mentioned compound (1.13 g) and the title compound (0.901 g) of Reference Example 12, and in the same manner as in Example 70 (1), 3-{(2S,4S)-1-tert-butoxycarbonyl-4-[4-(2-trifluoromethyl-4-quinazolinyl)-1-piperazinyl]-2-pyrrolidinylcarbonyl}-1,3-thiazolidine (1.51 g) was obtained as a yellow powder.

(4) Using the above-mentioned compound (1.51 g), and in the same manner as in Example 186 (2), hydrochloride of the title compound was obtained. Aqueous sodium hydroxide solution was added thereto, and the mixture was extracted with chloroform. The extract was concentrated under reduced pressure and the residue was purified by HPLC to give the title compound (450 mg) as a yellow powder.

$^1$H-NMR($CDCl_3$)δ1.68–1.76(1H,m), 2.34–2.49(1H,m), 2.57–2.80(4H,m), 2.91–3.23(5H,m), 3.60–4.07(7H,m), 4.42–4.74(2H,m), 7.54(1H,t,J=7.8 Hz), 7.80(1H,t,J=7.8 Hz), 7.91(1H,dd,J=7.8,0.8 Hz), 8.01(1H,dd,J=7.8,0.8 Hz).

Example 283

Synthesis of 3-{(2S,4S)-4-[4-(2-phenyl-4-quinazolinyl)-1-piperazinyl]-2-pyrrolidinylcarbonyl}-1,3-thiazolidine trihydrochloride (1) Piperazine (3.22 g) was dissolved in DMF (830 mL), and 4-chloro-2-phenylquinazoline (3 g) was added thereto. The mixture was stirred at room temperature for 6 hr. The reaction mixture was concentrated under reduced pressure, water and chloroform were added to the residue and an insoluble material was filtered off. The organic layer of the filtrate was separated and extracted with 1 mol/L hydrochloric acid. The aqueous layer was basified with aqueous sodium hydroxide solution, and the mixture was extracted with chloroform. The extract was concentrated under reduced pressure to give 1-(2-phenyl-4-quinazolinyl) piperazine (2.27 g) as a white solid.

(2) Using the above-mentioned compound (1.16 g) and the title compound (0.901 g) of Reference Example 12, and in the same manner as in Example 70 (1), 3-{(2S,4S)-1-tert-butoxycarbonyl-4-[4-(2-phenyl-4-quinazolinyl)-1-piperazinyl]-2-pyrrolidinylcarbonyl}-1,3-thiazolidine (1.66 g) was obtained as a white powder.

(3) Using the above-mentioned compound (1.66 g), and in the same manner as in Example 186 (2), the title compound (1.21 g) was obtained as a white powder.

$^1$H-NMR(DMSO-$d_6$)δ2.17–2.38(1H,m), 2.85–3.18(3H, m), 3.30–4.90(16H,m), 7.56–7.80(4H,m), 8.04(1H,t,J=8.2 Hz), 8.22(1H,d,J=8.2 Hz), 8.33(1H,d,J=8.2 Hz), 8.53(2H,d, J=8.4 Hz), 9.16(1H,brs).

Example 284

Synthesis of 3-{(2S,4S)-4-[4-(5-cyano-2-pyridyl)-2-oxo-1-piperazinyl]-2-pyrrolidinylcarbonyl}-1,3-thiazolidine dihydrochloride (1) Using the title compound (2.10 g) of Reference Example 12 and 2-aminoacetaldehyde diethyl acetal 0.984, and in the same manner as in Example 70 (1), 3-{(2S,4S)-1-tert-butoxycarbonyl-4-[4-(2,2-diethoxyethyl)amino]-2-pyrrolidinylcarbonyl}-1,3-thiazolidine (3.57 g) was obtained as a pale-yellow oil.

(2) The above-mentioned compound (3.56 g) and N-benzyloxycarbonylglycine (1.54 g) were dissolved in DMF (30 mL), and HOBT (1.39 g) and EDC hydrochloride (1.61 g) were successively added thereto. The mixture was stirred at room temperature for 2 days. The reaction mixture was concentrated under reduced pressure, and 0.5 mol/L hydrochloric acid was added to the residue. The mixture was extracted with chloroform. The extract was washed with saturated aqueous sodium hydrogencarbonate solution and brine, dried and concentrated under reduced pressure. The residue was purified by silica gel chromatography to give 3-((2S,4S)-4-{N-[2-(1-benzyloxycarbonylamino)acetyl]-N-(2,2-diethoxyethyl)amino}-2-pyrrolidinylcarbonyl)-1-tert-butoxycarbonyl-1,3-thiazolidine (2.77 g) as a pale-brown oil.

(3) The above-mentioned compound (2.77 g) and p-toluenesulfonic acid monohydrate (0.164 g) were dissolved in toluene (100 mL), and the solution was heated at 70° C. for 7 hr. The reaction mixture was added to saturated aqueous sodium hydrogencarbonate solution, and the mixture was extracted with ethyl acetate. The extract was dried and concentrated under reduced pressure. The residue was dissolved in methanol (50 mL), and ammonium formate (1.44 g) and 10% palladium/carbon (1.93 g) were added thereto. The mixture was heated at 100° C. for 2 days. Furthermore, ammonium formate (1.44 g) and 10% palladium/carbon (1.93 g) were added thereto, and the mixture was stirred at 100° C. for 1 day with heating. The reaction mixture was filtrated and the filtrate was concentrated under reduced pressure. Saturated aqueous sodium hydrogencarbonate solution was added to the residue, and the mixture was extracted with chloroform. The extract was washed with brine, dried and concentrated under reduced pressure. The residue was purified by silica gel chromatography to give 3-[(2S,4S)-1-tert-butoxycarbonyl-4-(2-oxo-1-piperazinyl)-2-pyrrolidinylcarbonyl]-1,3-thiazolidine (0.237 g) as a white solid.

(4) The above-mentioned compound (237 mg) and N,N-diisopropylethylamine (0.32 mL) were dissolved in N-methyl-2-pyrrolidone (5 mL), and 2-chloro-5-cyanopyridine (145 mg) was added thereto. The mixture was heated at 80° C. for 4 hr. The reaction mixture was added to saturated aqueous sodium hydrogencarbonate solution, and the mixture was extracted with ethyl acetate. The extract was washed with brine, dried and concentrated under reduced pressure. The residue was purified by silica gel chromatography to give 3-{(2S,4S)-1-tert-butoxycarbonyl-4-[4-(5-cyano-2-pyridyl)-2-oxo-1-piperazinyl]-2-pyrrolidinylcarbonyl}-1,3-thiazolidine (425 mg) as a pale-brown oil.

$^1$H-NMR($CDCl_3$)δ1.42(4.5H,s), 1.44(4.5H,s), 1.93–2.10 (1H,m), 2.43–2.58(1H,m), 2.94–3.22(2H,m), 3.43–4.06(8H, m), 4.24(2H,s), 4.40–4.92(3H,m), 5.20–5.38(1H,m), 6.52 (1H,d,J=8.9 Hz), 7.70(1H,dd,J=8.9,2.1 Hz), 8.45(1H,d,J=2.1 Hz).

(5) The above-mentioned compound (422 mg) was dissolved in ethyl acetate (1 mL), and 4 mol/L hydrochloric acid-ethyl acetate (1.2 mL) was added thereto. The mixture was stirred at room temperature for 18 hr. The precipitated solid was collected by filtration to give the title compound (217 mg) as a white powder.

$^1$H-NMR(DMSO-$d_6$)δ1.86–1.96(1H,m), 2.14–2.23(1H, m), 2.60–2.75(1H,m), 3.12(1H,t,J=6.2 Hz), 3.25–4.32(10H, m), 4.47(1H,t,J=10.0 Hz), 4.55–4.77(2H,m), 4.95–5.10(1H, m), 7.93(1H,d,J=9.0 Hz), 7.93(1H,dd,J=9.0,2.2 Hz), 8.54 (1H,d,J=2.2 Hz), 8.79(1H,brs), 10.29(1H,brs).

Example 285

Synthesis of 3-{(2S,4S)-4-[4-(5-cyano-2-pyridyl)-3-oxo-1-piperazinyl]-2-pyrrolidinylcarbonyl}-1,3-thiazolidine dihydrochloride (1) N-(5-Cyano-2-pyridyl)ethylenediamine (10.0 g) and triethylamine (9.5 mL) were dissolved in tetrahydrofuran (300 mL), and ethyl 2-bromoacetate (6.9 mL) was added thereto under ice-cooling. The mixture was stirred at room temperature for 21 hr. Di-tert-butyl dicarbonate (14.2 mL) was added to the reaction mixture, and the mixture was further stirred at room temperature for 21 hr. The reaction mixture was filtrated and the filtrate was concentrated under reduced pressure. The residue was purified by silica gel chromatography to give N-tert-butoxycarbonyl-N'-(5-cyano-2-pyridyl)-N-(ethoxycarbonylmethyl)ethylenediamine (17.3 g) as a white solid.

(2) The above-mentioned compound (17.3 g) was dissolved in 1,4-dioxane (220 mL), and 1 mol/L aqueous sodium hydroxide solution (75 mL) was added thereto. The mixture was stirred at room temperature for 13 hr. The reaction mixture was concentrated under reduced pressure, and 10% aqueous citric acid solution was added to the residue. The mixture was extracted with ethyl acetate. The extract was washed with brine, dried, concentrated under reduced pressure and crystallized from diethyl ether-hexane to give N-tert-butoxycarbonyl-N-(carboxymethyl)-N'-(5-cyano-2-pyridyl)ethylenediamine (11.7 g) as a white solid.

(3) The above-mentioned compound (3.20 g) and triethylamine (2.8 mL) were dissolved in tetrahydrofuran (60 mL), and HOBT (1.84 g) and EDC hydrochloride (2.30 g) were successively added. The mixture was stirred at room temperature for 6 hr. The reaction mixture was concentrated under reduced pressure, and saturated aqueous sodium hydrogencarbonate solution was added to the residue. The mixture was extracted with ethyl acetate. The extract was washed with brine, dried and concentrated under reduced pressure to give 4-tert-butoxycarbonyl-1-(5-cyano-2-pyridyl)-2-oxopiperazine (2.34 g) as a white solid.

(4) The above-mentioned compound (2.34 g) was dissolved in dichloromethane (50 mL), and trifluoroacetic acid (25 mL) was added thereto under ice-cooling. The mixture was stirred for 1 hr. The reaction mixture was concentrated under reduced pressure, and saturated aqueous sodium hydrogencarbonate solution was added to the residue. The mixture was extracted with chloroform. The extract was washed with brine, dried and concentrated under reduced pressure to give 1-(5-cyano-2-pyridyl)-2-oxopiperazine (1.02 g) as a white solid.

(5) Using the above-mentioned compound (667 mg) and the title compound (901 mg) of Reference Example 12, and in the same manner as in Example 70 (1), 3-{(2S,4S)-1-tert-butoxycarbonyl-4-[4-(5-cyano-2-pyridyl)-3-oxo-1-piperazinyl]-2-pyrrolidinylcarbonyl}-1,3-thiazolidine (976 mg) was obtained as a white solid.

$^1$H-NMR($CDCl_3$)δ1.41(4.5H,s), 1.46(4.5H,s), 1.86–2.02 (1H,m), 2.42–2.55(1H,m), 2.78–4.83(16H,m), 7.91(1H,dd, J=8.8,2.1 Hz), 8.37(1H,d,J=8.8 Hz), 8.68(1H,d,J=2.1 Hz).

(6) The above-mentioned compound (972 mg) was dissolved in ethyl acetate (5 mL), and 4 mol/L hydrochloric acid-ethyl acetate (5 mL) was added thereto. The mixture was stirred at room temperature for 17 hr. The precipitated solid was collected by filtration to give the title compound (789 mg) as a white powder.

$^1$H-NMR(DMSO-$d_6$)δ1.95–2.10(1H,m), 2.80–2.94(1H, m), 3.02–3.45(5H,m), 3.50–4.15(8H,m), 4.4–4.8(3H,m), 8.21(1H,d,J=8.9 Hz), 8.32(1H,dd,J=8.9,2.3 Hz), 8.87–9.06 (2H,m), 10.61(1H,brs).

Example 286

Synthesis of 3-[(2S,4S)-4-(4-methoxycarbonylpiperidino)-2-pyrrolidinylcarbonyl]-1,3-thiazolidine dihydrochloride (1) Using methyl isonipecotinate (0.466 g) and the title compound (0.89 g) of Reference Example 12, and in the same manner as in Example 70 (1), 3-[(2S,4S)-1-tert-butoxycarbonyl-4-(4-methoxycarbonylpiperidino)-2-pyrrolidinylcarbonyl]-1,3-thiazolidine (1.19 g) was obtained as a white powder.

(2) Using the above-mentioned compound (166 mg), and in the same manner as in Example 133 (2), the title compound (132 mg) was obtained as a white powder.

$^1$H-NMR(500 MHz,DMSO-$d_6$)δ1.88–2.13(4H,m), 2.15–2.35(1H,m), 2.56–2.76(1H,m), 2.85–3.20(5H,m), 3.43–4.00(7H,m), 3.64(3H,s), 4.47–4.73(3H,m), 9.20(1H, brs), 10.70(1H,brs), 11.98(1H,brs).

Example 287

Synthesis of 3-{(2S,4S)-4-[4-(4-nitrophenyl)piperidino]-2-pyrrolidinylcarbonyl}-1,3-thiazolidine dihydrochloride (1) Using 4-(4-nitrophenyl)piperidine (625 mg) and the title compound (606 mg) of Reference Example 12, and in the same manner as in Example 70 (1), 3-{(2S,4S)-1-tert-butoxycarbonyl-4-[4-(4-nitrophenyl)piperidino]-2-pyrrolidinylcarbonyl}-1,3-thiazolidine 387 mg) was obtained as a pale-yellow solid.

(2) Using the above-mentioned compound (387 mg), and in the same manner as in Example 133 (2), the title compound (240 mg) was obtained as a white powder.

$^1$H-NMR(500 MHz,DMSO-$d_6$)δ1.95–2.38(5H,m), 2.90–3.28(6H,m), 3.51–4.08(7H,m), 4.48–4.75(3H,m), 7.54 (2H,d,J=8.1 Hz), 8.22(2H,d,J=8.1 Hz), 9.20(1H,brs), 10.60 (1H,brs), 12.07(1H,brs).

Example 288

Synthesis of 3-{(2S,4S)-4-[4-(2-pyrimidinyl)piperidino]-2-pyrrolidinylcarbonyl}-1,3-thiazolidine dihydrochloride (1) 4-Cyanopyridine (50.0 g) was suspended in methanol (50 mL), and 28% sodium methoxide-methanol solution (4.14 mL) was added thereto. After stirring at room temperature for 15 min, ammonium chloride (25.7 g) was added to the mixture. The mixture was stirred at room temperature for 24 hr. Acetone (200 mL) was added to the reaction mixture, and the precipitated solid was collected by filtration to give 4-amidinopyridine hydrochloride (62.8 g) as a white solid.

(2) The above-mentioned compound (5.00 g) and 3-dimethylamino-2-propenal (3.18 g) were suspended in methanol (30 mL), and 28% sodium methoxide-methanol solution (13.8 mL) was added thereto. The mixture was refluxed for 12 hr. The reaction mixture was filtrated and the filtrate was concentrated under reduced pressure. Water was added to the residue, and the mixture was extracted with chloroform. The extract was washed with brine and dried, and the solvent was evaporated under reduced pressure. The residue was purified by silica gel chromatography to give 4-(2-pyrimidiny)pyridine (3.45 g) as a slightly yellow solid.

(3) The above-mentioned compound (3.14 g) was dissolved in acetonitrile (50 mL), and benzyl chloride (4.60 mL) was added thereto. The mixture was refluxed for 16 hr. The reaction mixture was concentrated to about 10 mL, and diethyl ether (10 mL) was added thereto. The precipitated solid was collected by filtration to give 1-benzyl-4-(2-pyrimidinyl)pyridine hydrochloride (5.61 g) as a white solid.

(4) The above-mentioned compound (5.50 g) was suspended in ethanol (20 mL), and sodium borohydride (1.47 g) was added thereto under ice-cooling. The mixture was stirred at room temperature for 1.5 hr and water was added to the reaction mixture. The mixture was extracted with ethyl acetate, and the extract was washed successively with water and brine, and dried. The solvent was evaporated under reduced pressure. The residue was purified by silica gel chromatography to give 1-benzyl-4-(2-pyrimidinyl)-1,2,3,6-tetrahydropyridine (4.10 g) as a slightly yellow solid.

(5) The above-mentioned compound (4.10 g) was dissolved in ethanol (100 mL), and the mixture was stirred at room temperature in the presence of 10% palladium carbon (1.10 g) under a hydrogen atomosphere (1 atm). The reaction mixture was filtrated and the filtrate was concentrated under reduced pressure. The residue was purified by silica gel chromatography to give 1-benzyl-4-(2-pyrimidinyl)piperidine (3.33 g) as a colorless transparent oil.

(6) The above-mentioned compound (3.33 g) was dissolved in dichloromethane (25 mL), and a solution of 1-chloroethyl chlorocarbonate (1.70 mL) in dichloromethane (5 mL) was added under ice-cooling. The mixture was refluxed for 30 min. The reaction mixture was concentrated under reduced pressure, and the residue was dissolved in methanol (25 mL). The solution was refluxed for 1 hr and 28% sodium methoxide-methanol solution (3.40 mL) was added to the reaction mixture. After filtration, the filtrate was concentrated under reduced pressure and the residue was purified by silica gel chromatography to give 4-(2-pyrimidinyl)piperidine (1.43 g) as a brown oil.

(7) Using the above-mentioned compound (1.43 g) and the title compound (2.39 g) of Reference Example 12, and in the same manner as in Example 70 (1), 3-{(2S,4S)-1-tert-butoxycarbonyl-4-[4-(2-pyrimidinyl)piperidino]-2-pyrrolidinylcarbonyl}-1,3-thiazolidine (2.30 g) was obtained as a white solid.

(8) Using the above-mentioned compound (895 mg), and in the same manner as in Example 167 (2), the title compound (227 mg) was obtained as a slightly yellow powder.

$^1$H-NMR(DMSO-$d_6$)δ2.05–2.46(5H,m), 2.86–3.50(4H, m), 3.52–4.07(7H,m), 4.42–4.79(3H,m), 7.42(1H,t,J=5.1 Hz), 8.82(2H,d,J=5.1 Hz), 9.11(1H,brs), 11.01(1H,brs), 12.03(1H,brs).

Example 289

Synthesis of 3-{(2S,4S)-4-[4-(5-ethyl-1,3,4-oxadiazol-2-yl)piperidino]-2-pyrrolidinylcarbonyl}-1,3-thiazolidine dihydrochloride (1) Ethyl isonipecotinate (51.5 g) was dissolved in tetrahydrofuran (400 mL) and pyridine (40 mL), and a solution of benzyl chlorocarbonate (58.7 g) in tetrahydrofuran (50 mL) was dropwise added under ice-cooling. After stirring the mixture under ice-cooling for 1.5 hr, the solvent was evaporated under reduced pressure. Water was added to the residue, and the mixture was extracted with ethyl acetate. The extract was washed successively with dilute hydrochloric acid, saturated aqueous sodium hydrogencarbonate solution and brine, and dried. The solvent was evaporated under reduced pressure to give ethyl 1-benzyloxycarbonylisonipecotinate (80.4 g) as an oil.

(2) The above-mentioned compound (42.8 g) was dissolved in isopropanol (300 mL), and hydrazine monohydrate (43 mL) was added thereto. The mixture was refluxed for 10 hr. The solvent was evaporated under reduced pressure, and the residue was washed with diisopropyl ether and water to give 1-benzyloxycarbonylisonipecotic acid hydrazide (23.8 g) as a white solid.

(3) The above-mentioned compound (3.52 g) was dissolved in tetrahydrofuran (50 mL) and pyridine (5 mL), and propionyl chloride (1.21 mL) was added thereto under ice-cooling. The mixture was stirred for 4 hr. Water was added to the reaction mixture, and the precipitated solid was collected by filtration. This was suspended in 1,2-dimethoxyethane (70 mL), and phosphorus oxychloride (1.40 mL) was added thereto. The mixture was refluxed for 4 hr. The reaction mixture was concentrated under reduced pressure, and saturated aqueous sodium hydrogencarbonate solution was added to the residue. The mixture was extracted with chloroform, and the extract was dried and concentrated under reduced pressure. The residue was purified by silica gel chromatography to give 1-benzyloxycarbonyl-4-(5-ethyl-1,3,4-oxadiazol-2-yl)piperidine (2.29 g) as an oil.

(4) Using the above-mentioned compound (2.29 g), and in the same manner as in Example 232 (5), 4-(5-ethyl-1,3,4-oxadiazol-2-yl)piperidine hydrobromide (1.90 g) was obtained as a white solid.

(5) Using a free base (400 mg) of the above-mentioned compound and the title compound (553 mg) of Reference Example 12, and in the same manner as in Example 70 (1), 3-{(2S,4S)-1-tert-butoxycarbonyl-4-[4-(5-ethyl-1,3,4-oxadiazol-2-yl)piperidino]-2-pyrrolidinylcarbonyl)-1,3-thiazolidine (856 mg) was obtained as a white powder.

(6) Using the above-mentioned compound (856 mg), and in the same manner as in Example 257 (3), the title compound (307 mg) was obtained as a white powder.

$^1$H-NMR(DMSO-$d_6$)δ1.25(3H,t,J=7.5 Hz), 1.90–2.44 (5H,m), 2.84(2H,q,J=7.5 Hz), 2.89–4.20(13H,m), 4.46–4.75 (3H,m), 10.10(2H,brs), 12.15(1H,brs).

Example 290

Synthesis of 3-((2S,4S)-4-{4-[5-(4-chlorophenyl)-1,3,4-oxadiazol-2-yl]piperidino}-2-pyrrolidinylcarbonyl)-1,3-thiazolidine dihydrochloride (1) Using 4-chlorobenzoyl chloride (1.40 μL) and 1-benzyloxycarbonylisonipecotic acid hydrazide [product of Example 289 (2), 3.00 g], and in the same manner as in Example 289 (3), 1-benzyloxycarbonyl-4-[5-(4-chlorophenyl)-1,3,4-oxadiazol-2-yl]piperidine (1.26 g) was obtained as a white solid.

(2) Using the above-mentioned compound (1.26 g), and in the same manner as in Example 232 (5), 4-[5-(4-chlorophenyl)-1,3,4-oxadiazol-2-yl]piperidine hydrobromide (1.09 g) was obtained as a white solid.

(3) Using a free base (556 mg) of the above-mentioned compound and the title compound (530 mg) of Reference Example 12, and in the same manner as in Example 70 (1), 3-{(2S,4S)-1-tert-butoxycarbonyl-4-[4-(5-{4-chlorophenyl}-1,3,4-oxadiazol-2-yl)piperidino]-2-pyrrolidinylcarbonyl}-1,3-thiazolidine (922 mg) was obtained as a white powder.

(4) Using the above-mentioned compound (896 mg), and in the same manner as in Example 257 (3), the title compound (739 mg) was obtained as a white powder.

$^1$H-NMR(500 MHz,DMSO-$d_6$)δ2.06–2.48(5H,m), 2.90–4.15(13H,m), 4.48–4.98(3H,m), 7.69(2H,d,J=7.4 Hz), 8.01(2H,d,J=7.4 Hz), 9.14(1H,brs), 10.92(1H,brs), 12.25 (1H,brs).

Example 291

Synthesis of 3-((2S,4S)-4-{4-[5-(3-pyridyl)-1,3,4-oxadiazol-2-yl]piperidino}-2-pyrrolidinylcarbonyl)-1,3-thiazolidine trihydrochloride (1) Using nicotinoyl chloride (1.40 g) and the product (2.08 g) of Example 289 (2), and in the same manner as in Example 289 (3), 1-benzyloxycarbonyl-4-[5-(3-pyridyl)-1,3,4-oxadiazol-2-yl]piperidine (0.48 g) was obtained as a white solid.

(2) Using the above-mentioned compound (477 mg), and in the same manner as in Example 232 (5), 4-[5-(3-pyridyl)-1,3,4-oxadiazol-2-yl]piperidine hydrobromide (435 mg) was obtained as a white solid.

(3) Using a free base (256 mg) of the above-mentioned compound and the title compound (320 mg) of Reference Example 12, and in the same manner as in Example 70 (1), 3-{(2S,4S)-1-tert-butoxycarbonyl-4-[4-(5-{3-pyridyl}-1,3,4-oxadiazol-2-yl)piperidino]-2-pyrrolidinylcarbonyl}-1,3-thiazolidine (425 mg) was obtained as a white powder.

(4) Using the above-mentioned compound (425 mg), and in the same manner as in Example 257 (3), the title compound (430 mg) was obtained as a white powder.

$^1$H-NMR(500 MHz,DMSO-$d_6$)δ2.18–2.45(5H,m), 2.95–4.15(13H,m), 4.48–4.77(3H,m), 7.69(1H,dd,J=8.2,5.1 Hz), 8.40–8.47(1H,m), 8.82–8.85(1H,m), 9.12(1H,brs), 9.18 (1H,s), 10.88(1H,brs), 12.20(1H,brs).

Example 292

Synthesis of 3-((2S,4S)-4-{4-[5-(4-pyridyl)-1,3,4-oxadiazol-2-yl]piperidino}-2-pyrrolidinylcarbonyl)-1,3-thiazolidine trihydrochloride (1) Using isonicotinic acid chloride (1.36 g) and the product (2.02 g) of Example 289 (2), and in the same manner as in Example 289 (3), 1-benzyloxycarbonyl-4-[5-(4-pyridyl)-1,3,4-oxadiazol-2-yl]piperidine (0.287 g) was obtained as a white solid.

(2) Using the above-mentioned compound (287 mg), and in the same manner as in Example 232 (5), 4-[5-(4-pyridyl)-1,3,4-oxadiazol-2-yl]piperidine hydrobromide (211 mg) was obtained as a white solid.

(3) Using a free base (124 mg) of the above-mentioned compound and the title compound (157 mg) of Reference Example 12, and in the same manner as in Example 70 (1), 3-{(2S,4S)-1-tert-butoxycarbonyl-4-[4-(5-{4-pyridyl}-1,3,4-oxadiazol-2-yl)piperidino]-2-pyrrolidinylcarbonyl}-1,3-thiazolidine (269 mg) was obtained as a white powder.

(4) Using the above-mentioned compound (268 mg), and in the same manner as in Example 257 (3), the title compound (242 mg) was obtained as a white powder.

$^1$H-NMR(500 MHz,DMSO-$d_6$)δ2.10–2.46(5H,m), 2.92–4.08(13H,m), 4.48–4.72(3H,m), 7.97(2H,brs), 8.85–8.87(2H,m), 9.13(1H,brs), 10.55(1H,brs), 11.97(1H, brs).

Example 293

Synthesis of 3-{(2S,4S)-4-[4-(5-oxo-4,5-dihydro-1,3,4-oxadiazol-2-yl)piperidino]-2-pyrrolidinylcarbonyl}-1,3-thiazolidine dihydrochloride (1) 3-[(2S,4S)-1-tert-Butoxycarbonyl-4-(4-methoxycarbonylpiperidino)-2-pyrrolidinylcarbonyl]-1,3-thiazolidine [product of Example 286 (1), 1.01 g] was dissolved in methanol (10 mL) and water (10 mL), and 1 mol/L sodium hydroxide (3.54 mL) was added thereto under ice-cooling. The mixture was stirred at room temperature for 3 hr. Methanol was evaporated under reduced pressure and dilute hydrochloric acid was added to the residue to adjust its pH to 7. The precipitated solid was collected by filtration to give 3-[(2S,4S)-1-tert-butoxycarbonyl-4-(4-carboxylpiperidino)-2-pyrrolidinylcarbonyl]-1,3-thiazolidine (650 mg) as a white powder.

(2) The above-mentioned compound (650 mg), HOBT (290 mg) and EDC hydrochloride (362 mg) were suspended in DMF (15 mL), and. hydrazine monohydrate (114 μL) was added thereto. The mixture was stirred at room temperature for 18 hr. After DMF was evaporated under reduced pressure, saturated aqueous sodium hydrogencarbonate solution was added to the residue and the mixture was extracted with chloroform. The extract was dried and concentrated under reduced pressure. The residue was dissolved in tetrahydrofuran (50 mL) and pyridine (5 mL), and triphosgene (190 mg) was added thereto under ice-cooling. The mixture was stirred at room temperature for 2 days. Water was added to the reaction mixture, and the mixture was extracted with chloroform and dried. The solvent was evaporated under reduced pressure and the residue was purified by silica gel chromatography to give 3-{(2S,4S)-1-tert-butoxycarbonyl-4-[4-(5-oxo-4,5-dihydro-1,3,4-oxadiazol-2-yl)piperidino]-2-pyrrolidinylcarbonyl}-1,3-thiazolidine (104 mg) as a white solid.

(3) Using the above-mentioned compound (104 mg), and in the same manner as in Example 257 (3), the title compound (80 mg) was obtained as a white powder.

$^1$H-NMR(500 MHz,DMSO-$d_6$)δ1.82–2.32(5H,m), 2.80–4.10(13H,m), 4.47–4.72(3H,m), 9.10(1H,brs), 10.41 (1H,brs), 11.86(1H,brs), 12.21(1H,brs).

Example 294

Synthesis of 3-{(2S,4S)-4-[4-(4-methyl-5-oxo-4,5-dihydro-1,3,4-oxadiazol-2-yl)piperidino]-2-pyrrolidinylcarbonyl}-1,3-thiazolidine dihydrochloride (1) The product (7.46 g) of Example 289 (2) was suspended in tetrahydrofuran (200 mL) and pyridine (20 mL), and tetrahydrofuran solution (20 mL) of triphosgene (3.0 g) was added thereto under ice-cooling. The mixture was stirred at room temperature for 18 hr. The solvent was evaporated under reduced pressure, and water was added to the residue. The mixture was extracted with ethyl acetate. The extract was dried and concentrated under reduced pressure. The residue was purified by silica gel chromatography to give 1-benzyloxycarbonyl-4-(5-oxo-4,5-dihydro-1,3,4-oxadiazol-2-yl)piperidine (5.92 g) as an oil.

(2) The above-mentioned compound (1.02 g) was dissolved in DMF (15 mL), and potassium carbonate (0.700 g) and methyl iodide (320 μL) were added thereto. The mixture was stirred at room temperature for 15 hr. The reaction mixture was concentrated under reduced pressure, and water was added to the residue. The mixture was extracted with ethyl acetate. The extract was washed with brine, dried and concentrated under reduced pressure to give 1-benzyloxycarbonyl-4-(4-methyl-5-oxo-4,5-dihydro-1,3,4-oxadiazol-2-yl)piperidine (0.900 g) as an oil.

(3) Using the above-mentioned compound (894 mg), and in the same manner as in Example 232 (5), 1 mol/L aqueous sodium hydroxide solution was added to the resulting hydrobromide. The mixture was extracted with chloroform, and concentrated under reduced pressure to give 4-(4-methyl-5-oxo-4,5-dihydro-1,3,4-oxadiazol-2-yl)piperidine (352 mg) as a pale-yellow solid.

(4) Using the above-mentioned compound (352 mg) and the title compound (550 mg) of Reference Example 12, and in the same manner as in Example 70 (1), 3-{(2S,4S)-1-tert-butoxycarbonyl-4-[4-(4-methyl-5-oxo-4,5-dihydro-1,3,4-oxadiazol-2-yl)piperidino]-2-pyrrolidinylcarbonyl}-1,3-thiazolidine (402 mg) was obtained as a white solid.

(5) Using the above-mentioned compound (402 mg), and in the same manner as in Example 257 (3), the title compound (375 mg) was obtained as a white powder.

$^1$H-NMR(500 MHz,DMSO-$d_6$)δ1.90–2.32(5H,m), 2.85–4.05(13H,m), 3.29(3H,s), 4.47–4.72(3H,m), 9.10(1H, brs), 10.45(1H,brs), 11.92(1H,brs).

Example 295

Synthesis of 3-{(2S,4S)-4-[4-(4-methoxycarbonylmethyl-5-oxo-4,5-dihydro-1,3,4-oxadiazol-2-yl)piperidino]-2-pyrrolidinylcarbonyl}-1,3-thiazolidine dihydrochloride (1) Using 1-benzyloxycarbonyl-4-(5-oxo-4,5-dihydro-1,3,4-oxadiazol-2-yl)piperidine [product of Example 294 (1), 1.84 g] and methyl bromoacetate (670 μL), and in the same manner as in Example 294 (2), 1-benzyloxycarbonyl-4-(4-methoxycarbonylmethyl-5-oxo-4,5-dihydro-1,3,4-oxadiazol-2-yl)piperidine (2.28 g) was obtained as an oil.

(2) Using the above-mentioned compound (2.26 g), and in the same manner as in Example 232 (5), 1 mol/L aqueous sodium hydroxide solution was added to the resulting hydrobromide. The mixture was extracted with chloroform, and concentrated under reduced pressure to give 4-(4-methoxycarbonylmethyl-5-oxo-4,5-dihydro-1,3,4-oxadiazol-2-yl)piperidine (1.20 g) as an oil.

(3) Using the above-mentioned compound (1.20 g) and the title compound (1.24 g) of Reference Example 12, and in the same manner as in Example 70 (1), 3-{(2S,4S)-1-tert-butoxycarbonyl-4-[4-(4-methoxycarbonylmethyl-5-oxo-4,5-dihydro-1,3,4-oxadiazol-2-yl)piperidino]-2-pyrrolidinylcarbonyl}-1,3-thiazolidine (1.41 g) was obtained as a pale-yellow solid.

(4) Using the above-mentioned compound (904 mg), and in the same manner as in Example 133 (2), the title compound (877 mg) was obtained as a white powder.

$^1$H-NMR(500 MHz,DMSO-$d_6$)δ1.90–2.32(5H,m), 2.90–4.10(13H,m), 3.57(3H,s), 4.47–4.74(3H,m), 4.64(2H, s), 9.10(1H,brs), 10.73(1H,brs), 12.20(1H,brs).

Example 296

Synthesis of 3-((2S,4S)-4-{4-[4-(2-morpholinoethyl)-5-oxo-4,5-dihydro-1,3,4-oxadiazol-2-yl]piperidino}-2-pyrrolidinylcarbonyl)-1,3-thiazolidine trihydrochloride (1) Using the product (930 mg) of Example 294 (1) and 4-(2-chloroethyl)morpholine hydrochloride (685 mg), and in the same manner as in Example 294 (2), 1-benzyloxycarbonyl-4-[4-(2-morpholinoethyl)-5-oxo-4,5-dihydro-1,3,4-oxadiazol-2-yl]piperidine (720 mg) was obtained as an oil.

(2) Using the above-mentioned compound (696 mg), and in the same manner as in Example 232 (5), 1 mol/L aqueous sodium hydroxide solution was added to the resulting hydrobromide. The mixture was extracted with chloroform, and concentrated under reduced pressure to give 4-[4-(2-morpholinoethyl)-5-oxo-4,5-dihydro-1,3,4-oxadiazol-2-yl]piperidine (328 mg) as an oil.

(3) Using the above-mentioned compound (318 mg) and the title compound (322 mg) of Reference Example 12, and in the same manner as in Example 70 (1), 3-((2S,4S)-1-tert-butoxycarbonyl-4-{4-[4-(2-morpholinoethyl)-5-oxo-4,5-dihydro-1,3,4-oxadiazol-2-yl]piperidino}-2-pyrrolidinylcarbonyl)-1,3-thiazolidine (606 mg) was obtained as an oil.

(4) Using the above-mentioned compound (606 mg), and in the same manner as in Example 258 (2), the title compound (522 mg) was obtained as a white powder.

$^1$H-NMR(500 MHz,DMSO-$d_6$)δ1.95–2.36(5H,m), 2.90–4.15(25H,m), 4.47–4.74(3H,m), 9.10(1H,brs), 10.64 (1H,brs), 11.54(1H,brs), 11.83(1H,brs), 12.02(1H,brs).

Example 297

Synthesis of 3-((2S,4S)-4-{4-[5-oxo-4-(3-picolyl)-4,5-dihydro-1,3,4-oxadiazol-2-yl]piperidino}-2-pyrrolidinylcarbonyl)-1,3-thiazolidine trihydrochloride (1) Using the product (0.932 g) of Example 294 (1) and 3-picolyl chloride hydrochloride (0.605 g), and in the same manner as in Example 294 (2), 1-benzyloxycarbonyl-4-[5-oxo-4-(3-picolyl)-4,5-dihydro-1,3,4-oxadiazol-2-yl] piperidine (1.06 g) was obtained as an oil.

(2) Using the above-mentioned compound (1.01 g), and in the same manner as in Example 232 (5), 1 mol/L aqueous sodium hydroxide solution was added to the resulting hydrobromide. The mixture was extracted with chloroform, and concentrated under reduced pressure to give 4-[5-oxo-4-(3-picolyl)-4,5-dihydro-1,3,4-oxadiazol-2-yl]piperidine (0.17 g) as a pale-yellow solid.

(3) Using the above-mentioned compound (170 mg) and the title compound (187 mg) of Reference Example 12, and in the same manner as in Example 70 (1), 3-((2S,4S)-1-tert-butoxycarbonyl-4-{4-[5-oxo-4-(3-picolyl)-4,5-dihydro-1,3,4-oxadiazol-2-yl]piperidino}-2-pyrrolidinylcarbonyl)-1,3-thiazolidine (236 mg) was obtained as a white powder.

(4) Using the above-mentioned compound (236 mg), and in the same manner as in Example 257 (3), the title compound (204 mg) was obtained as a white powder.

$^1$H-NMR(500 MHz,DMSO-$d_6$)δ1.98–2.36(5H,m), 2.93–4.05(13H,m), 4.47–4.74(3H,m), 5.08(2H,s), 7.86–7.89 (1H,m), 8.30–8.32(1H,m), 8.79(1H,d,J=5.1 Hz), 8.85(1H,s), 9.10(1H,brs), 10.90(1H,brs), 12.22(1H,brs).

Example 298

Synthesis of 3-{(2S,4S)-4-[4-(2-tert-butyl-2H-tetrazol-5-yl)piperidino]-2-pyrrolidinylcarbonyl}-1,3-thiazolidine dihydrochloride (1) Isonipecotamide (19.4 g) and triethylamine (42 mL) were dissolved in dichloromethane (500 mL), and benzyloxy chlorocarbonate (24 mL) was added thereto under ice-cooling. The mixture was stirred at room temperature for 18 hr. The reaction mixture was added to saturated aqueous sodium hydrogencarbonate solution, and the mixture was extracted with chloroform. The extract was dried and concentrated under reduced pressure to give 1-benzyloxycarbonyl-4-carbamoylpiperidine (33.3 g) as a white solid.

(2) The above-mentioned compound (33.3 g) and imidazole (17.3 g) were dissolved in pyridine (350 mL), and phosphorus oxychloride (47 mL) was added thereto under ice-cooling. The mixture was stirred at room temperature for 3 hr. The saturated aqueous sodium hydrogencarbonate solution was added to the reaction mixture under ice-cooling, and the mixture was extracted with chloroform. The extract was washed with brine, dried, and the solvent was evaporated under reduced pressure. The residue was purified by silica gel chromatography to give 1-benzyloxycarbonyl-4-cyanopiperidine (20.6 g) as a slightly yellow oil.

(3) The above-mentioned compound (1.42 g) was dissolved in N-methyl-2-pyrrolidone (60 mL), and sodium azide (1.13 g) and triethylamine hydrochloride (1.24 g) were added thereto. The mixture was stirred at 150° C. for 6 hr. 1 mol/L Hydrochloric acid was added to the reaction mixture to adjust its pH to 1, and the mixture was extracted with ethyl acetate. 10% Aqueous sodium hydroxide solution was added to the extract, and the mixture was washed with diethyl ether. The aqueous layer was adjusted to pH 1 with concentrated hydrochloric acid, and the mixture was extracted with ethyl acetate. The extract was dried and concentrated under reduced pressure. Trifluoroacetic acid (6 mL), tert-butanol (0.900 g) and concentrated sulfuric acid (0.16 mL) were added to the residue, and the mixture was stirred at room temperature for 3 days. Water was added to the reaction mixture, and the mixture was extracted with ethyl acetate. The extract was washed successively with 2.5 mol/L aqueous sodium hydroxide solution and brine, dried, and concentrated under reduced pressure. The residue was purified by HPLC to give 1-benzyloxycarbonyl-4-(2-tert-butyl-2H-tetrazol-5-yl)piperidine (140 mg) as a white solid.

(4) The above-mentioned compound (140 mg) was dissolved in ethanol (10 mL), and the mixture was stirred in the presence of 10% palladium/carbon (100 mg) at room temperature under a hydrogen atomosphere (1 atm) for 4 hr. The reaction mixture was filtrated and the filtrate was concentrated under reduced pressure to give 4-(2-tert-butyl-2H-tetrazol-5-yl)piperidine (85 mg) as a white solid.

(5) Using the above-mentioned compound (85 mg) and the title compound (117 mg) of Reference Example 12, and in the same manner as in Example 70 (1), 3-{(2S,4S)-1-tert-butoxycarbonyl-4-[4-(2-tert-butyl-2H-tetrazol-5-yl) piperidino]-2-pyrrolidinylcarbonyl}-1,3-thiazolidine (192 mg) was obtained as a white powder.

(6) Using the above-mentioned compound (192 mg), and in the same manner as in Example 257 (3), the title compound (113 mg) was obtained as a white powder.

$^1$H-NMR(500 MHz,DMSO-$d_6$)δ1.67(9H,s), 1.95–2.30 (5H,m), 2.92–4.10(13H,m), 4.40–4.73(3H,m).

Example 299

Synthesis of 3-((2S,4S)-4-{4-[1-(4-methoxyphenyl)-1H-tetrazol-5-yl]piperidino}-2-pyrrolidinylcarbonyl)-1,3-thiazolidine dihydrochloride (1) Isonipecotic acid (19.0 g) was dissolved in water (150 mL) and 1,4-dioxane (300 mL), 1 mol/L aqueous sodium hydroxide solution (150 mL) and di-tert-butyl dicarbonate (35.3 g) were added thereto under ice-cooling. The mixture was stirred at room temperature for 3 days. 1,4-Dioxane was evaporated under reduced pressure, and 5% potassium hydrogen sulfate was added to the residue. The precipitated solid was collected by filtration to give 1-tert-butoxycarbonylisonipecotic acid (33.0 g) as a white solid.

(2) The above-mentioned compound (2.63 g), HOBT (2.11 g) and EDC hydrochloride (2.64 g) were dissolved in DMF (50 mL), and p-anisidine (1.41 g) was added thereto. The mixture was stirred at room temperature for 3 hr. Water was added to the reaction mixture, and the precipitated solid was collected by filtration to give 1-tert-butoxycarbonylisonipecotic acid 4-methoxyphenylamide (2.84 g) as a white solid.

(3) The above-mentioned compound (1.06 g) was dissolved in tetrahydrofuran (30 mL), and trimethylsilylazide (845 μL), triphenylphosphine (1.66 g) and 40% diisopropyl azodicarboxylate/toluene solution (3.20 g) was added thereto. The mixture was stirred at room temperature for 23 hr. Water was added to the reaction mixture, and the mixture was extracted with ethyl acetate. The extract was washed with brine, dried, and concentrated under reduced pressure. The residue was purified by HPLC to give 1-tert-butoxycarbonyl-4-[1-(4-methoxyphenyl)-1H-tetrazol-5-yl]piperidine (0.514 g) as a white solid.

(4) The above-mentioned compound (514 mg) was dissolved in dichloromethane (10 mL), and trifluoroacetic acid (3 mL) was added thereto at room temperature. The mixture was stirred for 5 hr. The solvent was evaporated under reduced pressure, and saturated aqueous sodium hydrogencarbonate solution was added to the residue. The mixture was extracted with chloroform. The extract was dried and concentrated under reduced pressure to give 4-[1-(4-methoxyphenyl)-1H-tetrazol-5-yl]piperidine (260 mg) as an oil.

(5) Using the above-mentioned compound (260 mg) and the title compound (295 mg) of Reference Example 12, and in the same manner as in Example 70 (1), 3-((2S,4S)-1-tert-butoxycarbonyl-4-{4-[1-(4-methoxyphenyl)-1H-tetrazol-5-yl]piperidino}-2-pyrrolidinylcarbonyl)-1,3-thiazolidine (427 mg) was obtained as a white powder.

(6) Using the above-mentioned compound (424 mg), and in the same manner as in Example 133 (2), the title compound (301 mg) was obtained as a white powder.

$^1$H-NMR(500 MHz,DMSO-$d_6$)δ1.95–2.35(5H,m), 2.87–3.95(13H,m), 3.87(3H,s), 4.46–4.73(3H,m), 7.19(2H, d,J=8.8 Hz), 7.61(2H,d,J=8.8 Hz), 9.10(1H,brs), 10.70(1H, brs), 12.02(1H,brs).

Example 300

Synthesis of 3-{(2S,4S)-4-[4-(5-chloro-3-benzofuranyl)piperidino]-2-pyrrolidinylcarbonyl}-1,3-thiazolidine dihydrochloride (1) Using 4-(5-chloro-3-benzofuranyl)piperidine (380 mg) and the title compound (404 mg) of Reference Example 12, and in the same manner as in Example 70 (1), 3-{(2S,4S)-1-tert-butoxycarbonyl-4-[4-(5-chloro-3-benzofuranyl)piperidino]-2-pyrrolidinylcarbonyl}-1,3-thiazolidine (697 mg) was obtained as a pale-yellow powder.

(2) Using the above-mentioned compound (697 mg), and in the same manner as in Example 133 (2), the title compound (182 mg) was obtained as a brown powder.

$^1$H-NMR(500 MHz,DMSO-$d_6$)δ2.00–2.40(5H,m), 2.90–4.14(13H,m), 4.49–4.74(3H,m), 7.35(1H,dd,J=8.7,1.8 Hz), 7.61(1H,d,J=8.7 Hz), 7.94(1H,s), 7.99(1H,s), 9.22(1H, brs), 10.71(1H,brs), 12.11(1H,brs).

Example 301

Synthesis of 3-{(2S,4S)-4-[4-(2-benzimidazolyl)piperidino]-2-pyrrolidinylcarbonyl}-1,3-thiazolidine trihydrochloride (1) Acetyl chloride (180 mL) was dropwise added to a mixture of ethanol (160 mL) and chloroform (180 mL) under ice-cooling. After the mixture was stirred for 30 min, a solution of 1-benzyloxycarbonyl-4-cyanopiperidine [product of Example 298 (2), 20.6 g] in chloroform (180 mL) was added thereto under ice-cooling. The mixture was stirred at room temperature for 18 hr. The reaction mixture was concentrated under reduced pressure to give 1-benzyloxycarbonyl-4-(ethoxycarbonimidoyl)piperidine hydrochloride (28.7 g) as a white solid.

(2) The above-mentioned compound (2.88 g) and 1,2-phenylenediamine (1.19 g) were dissolved in ethanol (50 mL), and the mixture was refluxed for 4 hr. The reaction mixture was concentrated under reduced pressure, and 0.5 mol/L aqueous sodium hydroxide solution was added to the residue. The mixture was extracted with chloroform. The extract was washed successively with 0.2 mol/L hydrochloric acid, saturated aqueous sodium hydrogencarbonate solution and brine, and dried. The solvent was evaporated under reduced pressure and the residue was purified by silica gel chromatography to give 1-benzyloxycarbonyl-4-(2-benzimidazolyl)piperidine (2.61 g) as a pale-brown solid.

(3) The above-mentioned compound (2.50 g) was dissolved in methanol (50 mL), and the mixture was stirred in the presence of 10% palladium/carbon (500 mg) at room temperature under a hydrogen atomosphere (1 atm). The reaction mixture was filtrated and the filtrate was concentrated under reduced pressure to give 4-(2-benzimidazolyl)piperidine (1.50 g) as a pale-brown solid.

(4) Using the above-mentioned compound (332 mg) and the title compound (450 mg) of Reference Example 12, and in the same manner as in Example 70 (1), 3-{(2S,4S)-4-[4-(2-benzimidazolyl)piperidino]-1-tert-butoxycarbonyl-2-pyrrolidinylcarbonyl}-1,3-thiazolidine (434 mg) was obtained as a yellow solid.

$^1$H-NMR($CDCl_3$)δ1.36(4.5H,s), 1.40(4.5H,s), 1.75–2.32 (7H,m), 2.43–2.56(1H,m), 2.75–4.15(10H,m), 4.38–4.82 (3H,m), 7.17–7.25(2H,m), 7.41(1H,brs), 7.68(1H,brs), 10.74(1H,brs).

(5) The above-mentioned compound (430 mg) was dissolved in ethanol (4 mL), and 4.1 mol/L hydrochloric acid-ethanol (2.2 mL) was added thereto. The mixture was stirred at room temperature for 13 hr. The precipitated solid was collected by filtration to give the title compound (318 mg) as a white powder.

$^1$H-NMR(DMSO-$d_6$)δ2.20–2.57(5H,m), 2.95–4.07(13H, m), 4.47–4.79(3H,m), 7.48–7.57(2H,m), 7.74–7.83(2H,m), 9.14(1H,brs), 10.91(1H,brs), 12.18(1H,brs).

Example 302

Synthesis of 3-{(2S,4S)-4-[4-(5-cyano-2-benzimidazolyl)piperidino]-2-pyrrolidinylcarbonyl}-1,3-thiazolidine trihydrochloride (1) Using 1-benzyloxycarbonyl-4-(ethoxycarbonimidoyl)piperidine hydrochloride [product of Example 301 (1), 2.87 g] and 3,4-diaminobenzonitrile [product of Example 231 (1), 1.46 g], and in the same manner as in Example 301 (2), 1-benzyloxycarbonyl-4-(5-cyano-2-benzimidazolyl) piperidine (2.11 g) was obtained as a pale-brown solid.

(2) Using the above-mentioned compound (2.11 g), and in the same manner as in Example 301 (3), 4-(5-cyano-2-benzimidazolyl)piperidine (1.44 g) was obtained as a yellow powder.

(3) Using the above-mentioned compound (498 mg) and the title compound (601 mg) of Reference Example 12, and in the same manner as in Example 70 (1), 3-{(2S,4S)-1-tert-butoxycarbonyl-4-[4-(5-cyano-2-benzimidazolyl) piperidino]-2-pyrrolidinylcarbonyl}-1,3-thiazolidine (463 mg) was obtained as a white solid.

(4) 4 mol/L Hydrochloric acid-1,4-dioxane (2.5 mL) was added to the above-mentioned compound (459 mg), and the mixture was stirred at room temperature for 10 days. The precipitated solid was collected by filtration to give the title compound (412 mg) as a white powder.

$^1$H-NMR(DMSO-$d_6$)δ2.17–2.60(5H,m), 2.95–4.10(13H, m), 4.45–4.79(3H,m), 5.7(1H,brs), 7.73(1H,d,J=8.4 Hz), 7.82(1H,d,J=8.4 Hz), 8.21(1H,s), 9.13(1H,brs), 10.97(1H, brs), 12.14(1H,brs).

Example 303

Synthesis of 3-{(2S,4S)-4-[4-(5-fluoro-2-benzimidazolyl)piperidino]-2-pyrrolidinylcarbonyl}-1,3-thiazolidine trihydrochloride (2) Using the product (2.87 g) of Example 301 (1) and 4-fluoro-1,2-phenylenediamine [product of Example 233 (1), 1.38 g], and in the same manner as in Example 301 (2), 1-benzyloxycarbonyl-4-(5-fluoro-2-benzimidazolyl) piperidine (2.72 g) was obtained as a yellow solid.

(2) Using the above-mentioned compound (2.71 g), and in the same manner as in Example 301 (3), 4-(5-fluoro-2-benzimidazolyl)piperidine (1.84 g) was obtained as a brown-dark solid.

(3) Using the above-mentioned compound (488 mg) and the title compound (601 mg) of Reference Example 12, and in the same manner as in Example 70 (1), 3-{(2S,4S)-1-tert-butoxycarbonyl-4-[4-(5-fluoro-2-benzimidazolyl )piperidino]-2-pyrrolidinylcarbonyl}-1,3-thiazolidine (505 mg) was obtained as a pale-brown solid.

(4) The above-mentioned compound (501 mg) was dissolved in ethanol (5.5 mL), and 4.1 mol/L hydrochloric acid-ethanol (3.7 mL) was added thereto. The mixture was stirred at room temperature for 3 days. The precipitated solid was collected by filtration to give the title compound (391 mg) as a white powder.

$^1$H-NMR(DMSO-$d_6$)δ2.17–2.55(5H,m), 2.93–4.10(13H, m), 4.45–4.78(3H,m), 7.30–7.41(1H,m), 7.60(1H,dd,J=8.6, 2.1 Hz), 7.79(1H,dd,J=8.9,4.5 Hz), 9.14(1H,brs), 10.96(1H, brs), 12.16(1H,brs).

Example 304

Synthesis of 3-{(2S,4S)-4-[4-(5-cyano-1-methyl-2-benzimidazolyl)piperidino]-2-pyrrolidinylcarbonyl}-1,3-thiazolidine 3 hydrochloride (1) Using the product (1.29 g) of Example 301 (1) and 3-amino-4-methylaminobenzonitrile (0.61 g), and in the same manner as in Example 301 (2), 1-benzyloxycarbonyl-4-(5-cyano-1-methyl-2-benzimidazolyl)piperidine (1.03 g) was obtained as a pale-brown solid.

(2) Using the above-mentioned compound (1.03 g), and in the same manner as in Example 301 (3), 4-(5-cyano-1-methyl-2-benzimidazolyl)piperidine (0.549 g) was obtained as a yellow solid.

(3) Using the above-mentioned compound (396 mg) and the title compound (450 mg) of Reference Example 12, and in the same manner as in Example 70 (1), 3-{(2S,4S)-1-tert-butoxycarbonyl-4-[4-(5-cyano-1-methyl-2-benzimidazolyl) piperidino]-2-pyrrolidinylcarbonyl}-1,3-thiazolidine (316 mg) was obtained as a white solid.

(4) The above-mentioned compound (313 mg) was dissolved in ethyl acetate (1 mL), and 4 mol/L hydrochloric acid-ethyl acetate (3 mL) was added thereto. The mixture was stirred at room temperature for 18 hr. The precipitated solid was collected by filtration to give the title compound (298 mg) as a white powder.

$^1$H-NMR(DMSO-$d_6$)δ2.13–2.43(5H,m), 2.97–3.35(5H, m), 3.42–4.07(13H,m), 4.47–4.90(3H,m), 7.71(1H,d,J=8.4 Hz), 7.84(1H,d,J=8.4 Hz), 8.19(1H,s), 9.14(1H,brs), 10.91 (1H,brs), 12.14(1H,brs).

Example 305

Synthesis of 3-{(2S,4S)-4-[4-(5-fluoro-1-methyl-2-benzimidazolyl)piperidino]-2-pyrrolidinylcarbonyl}-1,3-thiazolidine trihydrochloride (1) Using the product (2.87 g) of Example 301 (1) and 4-fluoro-N1-methyl-1,2-phenylenediamine [product of Example 238 (1), 1.30 g], and in the same manner as in Example 301 (2), 1-benzyloxycarbonyl-4-(5-fluoro-1-methyl-2-benzimidazolyl)piperidine (2.83 g) was obtained as a brown-dark oil.

(2) Using the above-mentioned compound (2.83 g), and in the same manner as in Example 301 (3), 4-(5-fluoro-1-methyl-2-benzimidazolyl)piperidine (1.65 g) was obtained as a brown solid.

(3) Using the above-mentioned compound (513 mg) and the title compound (601 mg) of Reference Example 12, and in the same manner as in Example 70 (1), 3-{(2S,4S)-1-tert-butoxycarbonyl-4-[4-(5-fluoro-1-methyl-2-benzimidazolyl) piperidino]-2-pyrrolidinylcarbonyl}-1,3-thiazolidine (377 mg) was obtained as a pale-brown solid.

(4) The above-mentioned compound (373 mg) was dissolved in ethyl acetate (1 mL), and 4 mol/L hydrochloric acid-ethyl acetate (3.8 mL) was added thereto. The mixture was stirred at room temperature for 12 hr. The precipitated solid was collected by filtration to give the title compound (226 mg) as a white powder.

$^1$H-NMR(DMSO-$d_6$)δ2.18–2.43(5H,m), 2.97–3.37(5H, m), 3.60–4.09(13H,m), 4.47–4.80(4H,m), 7.39(1H,t,J=8.7 Hz), 7.57(1H,dd,J=8.7,2.0 Hz), 7.83–7.92(1H,m), 9.14(1H, brs), 10.95(1H,brs), 12.14(1H,brs).

Example 306

Synthesis of 3-{(2S,4S)-4-[4-(5-methyl-2-benzoxazolyl)piperidino]-2-pyrrolidinylcarbonyl}-1,3-thiazolidine (1) Using the product (2.50 g) of Example 301 (1) and 2-amino-4-methylphenol (1.60 g), and in the same manner as in Example 301 (2), 1-benzyloxycarbonyl-4-(5-methyl-2-benzoxazolyl)piperidine (2.01 g) was obtained as a dark brown oil.

(2) Using the above-mentioned compound (2.00 g), and in the same manner as in Example 301 (3), 4-(5-methyl-2-benzoxazolyl)piperidine (1.21 g) was obtained as a green solid.

(3) Using the above-mentioned compound (0.714 g) and the title compound (0.901 g) of Reference Example 12, and in the same manner as in Example 70 (1), 3-{(2S,4S)-1-tert-butoxycarbonyl-4-[4-(5-methyl-2-benzoxazolyl)piperidino]-2-pyrrolidinylcarbonyl}-1,3-thiazolidine (1.47 g) was obtained as a pale-green solid.

(4) The above-mentioned compound (1.47 g) was dissolved in 4.1 mol/L hydrochloric acid-ethanol (7 mL), and the mixture was stirred at room temperature for 6 hr. The reaction mixture was concentrated under reduced pressure, and saturated aqueous sodium hydrogencarbonate solution was added to the residue. The mixture was extracted with chloroform. The extract was dried and concentrated under reduced pressure. The residue was purified by silica gel chromatography and recrystallized from diethyl ether to give the title compound (0.601 g) as a white powder.

$^1$H-NMR(DMSO-$d_6$)δ1.52–1.65(1H,m), 1.72–1.88(2H, m), 1.98–2.18(4H,m), 2.22–2.33(1H,m), 2.40(3H,s), 2.64–3.03(7H,m), 3.07(1H,t,J=6.2 Hz), 3.58–3.93(3H,m), 4.38–4.68(2H,m), 7.15(1H,dd,J=8.3,1.3 Hz), 7.48(1H,d,J=1.3 Hz), 7.53(1H,d,J=8.3 Hz).

Example 307

Synthesis of 3-{(2S,4S)-4-[4-(5-trifluoromethyl-2-benzoxazolyl)piperidino]-2-pyrrolidinylcarbonyl}-1,3-thiazolidine (1) Using the product (2.96 g) of Example 301 (1) and 2-amino-4-trifluoromethylphenol (2.30 g), and in the same manner as in Example 301 (2), 1-benzyloxycarbonyl-4-(5-trifluoromethyl-2-benzoxazolyl)piperidine (2.68 g) was obtained as a brown oil.

(2) Using the above-mentioned compound (2.68 g), and in the same manner as in Example 301 (3), 4-(5-trifluoromethyl-2-benzoxazolyl)piperidine (1.74 g) was obtained as a pale-green oil.

(3) Using the above-mentioned compound (0.892 g) and the title compound (0.901 g) of Reference Example 12, and in the same manner as in Example 70 (1), 3-{(2S,4S)-1-tert-butoxycarbonyl-4-[4-(5-trifluoromethyl-2-benzoxazolyl)piperidino]-2-pyrrolidinylcarbonyl}-1,3-thiazolidine (1.56 g) was obtained as a white solid.

(4) The above-mentioned compound (1.47 g) was dissolved in 4.1 mol/L hydrochloric acid-ethanol (7 mL), and the mixture was stirred at room temperature for 16 hr. The reaction mixture was concentrated under reduced pressure, and saturated aqueous sodium hydrogencarbonate solution was added to the residue. The mixture was extracted with chloroform. The extract was dried and concentrated under reduced pressure. The residue was purified by silica gel chromatography and crystallized from diethyl ether to give the title compound (0.034 g) as a white powder.

$^1$H-NMR(DMSO-$d_6$)δ1.54–1.65(1H,m), 1.74–1.89(2H, m), 2.03–2.24(4H,m), 2.27–2.38(1H,m), 2.71–3.14(8H,m), 3.58–4.03(3H,m), 4.41–4.72(2H,m), 7.74(1H,d,J=8.5 Hz), 7.92(1H,d,J=8.5 Hz), 8.14(1H,s).

Example 308

Synthesis of 3-{(2S,4S)-4-[4-(5-methoxycarbonyl-2-benzoxazolyl)piperidino]-2-pyrrolidinylcarbonyl}-1,3-thiazolidine (1) Using the product (5.92 g) of Example 301 (1) and methyl 3-amino-4-hydroxybenzoate (4.34 g), and in the same manner as in Example 301 (2), 1-benzyloxycarbonyl-4-(5-methoxycarbonyl-2-benzoxazolyl)piperidine (5.44 g) was obtained as a slightly red solid.

(2) Using the above-mentioned compound (2.02 g), and in the same manner as in Example 301 (3), 4-(5-methoxycarbonyl-2-benzoxazolyl)piperidine (1.40 g) was obtained as a pale-yellow solid.

(3) Using the above-mentioned compound (0.858 g) and the title compound (0.901 g) of Reference Example 12, and in the same manner as in Example 70 (1), 3-{(2S,4S)-1-tert-butoxycarbonyl-4-[4-(5-methoxycarbonyl-2-benzoxazolyl)piperidino]-2-pyrrolidinylcarbonyl}-1,3-thiazolidine (1.48 g) was obtained as a white solid.

(4) The above-mentioned compound (1.47 g) was dissolved in methanol (2 mL), and 5.6 mol/L hydrochloric acid-methanol (2.5 mL) was added thereto. The mixture was stirred at room temperature for 14 hr. The reaction mixture was concentrated under reduced pressure, and saturated aqueous sodium hydrogencarbonate solution was added to the residue. The mixture was extracted with chloroform. The extract was dried and concentrated under reduced pressure. The residue was purified by HPLC and crystallized from diethyl ether to give the title compound (0.080 g) as a white powder.

$^1$H-NMR(DMSO-$d_6$)δ1.56–1.67(1H,m), 1.74–1.89(2H, m), 2.03–2.24(4H,m), 2.32–2.43(1H,m), 2.72–3.12(8H,m), 3.48–3.73(1H,m), 3.48–3.73(1H,m), 3.80–3.90(1H,m), 3.88 (3H,s), 3.96–4.08(1H,m), 4.42–4.72(2H,m), 5.3(1H,brs), 7.82(1H,d,J=8.5 Hz), 8.00(1H,dd,J=8.5,1.7 Hz), 8.24(1H,d, J=1.7 Hz).

Example 309

Synthesis of 3-{(2S,4S)-4-[4-(5-ethoxycarbonyl-2-benzoxazolyl)piperidino]-2-pyrrolidinylcarbonyl}-1,3-thiazolidine (1) Using the product (25.0 g) of Example 301 (1) and ethyl 3-amino-4-hydroxybenzoate (18.8 g), and in the same manner as in Example 301 (2), 1-benzyloxycarbonyl-4-(5-ethoxycarbonyl-2-benzoxazolyl)piperidine (20.0 g) was obtained as a white solid.

(2) Using the above-mentioned compound (10.2 g), and in the same manner as in Example 301 (3), 4-(5-ethoxycarbonyl-2-benzoxazolyl)piperidine (7.05 g) was obtained as a white solid.

(3) Using the above-mentioned compound (4.04 g) and the title compound (4.03 g) of Reference Example 12, and in the same manner as in Example 70 (1), 3-{(2S,4S)-1-tert-butoxycarbonyl-4-[4-(5-ethoxycarbonyl-2-benzoxazolyl)piperidino]-2-pyrrolidinylcarbonyl}-1,3-thiazolidine (7.56 g) was obtained as a white powder.

(4) The above-mentioned compound (2.24 g) was dissolved in dichloromethane (4 mL) and trifluoroacetic acid (2 mL), and the mixture was stirred at room temperature for 15 hr. Saturated aqueous sodium hydrogencarbonate solution was added to the reaction mixture, and the mixture was extracted with chloroform. The extract was dried and the solvent was evaporated under reduced pressure. The residue was purified by silica gel chromatography and recrystallized from diethyl ether to give the title compound (1.18 g) as a white powder.

$^1$H-NMR($CDCl_3$)δ1.41(3H,t,J=7.2 Hz), 1.65–2.45(8H, m), 2.94–3.16(9H,m), 3.63–3.98(3H,m), 4.40(2H,q,J=7.2 Hz), 4.44–4.68(2H,m), 7.51(1H,d,J=8.7 Hz), 8.07(1H,dd,J=8.7,1.8 Hz), 8.39(1H,d,J=1.8 Hz).

Example 310

Synthesis of 3-{(2S,4S)-4-[4-(5-carboxy-2-benzoxazolyl)piperidino]-2-pyrrolidinylcarbonyl}-1,3-thiazolidine dihydrochloride (1) 3-{(2S,4S)-1-tert-Butoxycarbonyl-4-[4-(5-ethoxycarbonyl-2 -benzoxazolyl)piperidino]-2- pyrrolidinylcarbonyl}-1,3-thiazolidine [product of Example 309 (3), 4.51 g] was dissolved in ethanol (16 mL) and water (8 mL), and lithium hydroxide monohydrate (678 mg) was added. The mixture was stirred at room temperature for 3.5 hr. The reaction mixture was diluted with water, and 1 mol/L hydrochloric acid was added to adjust its pH to 7. The mixture was extracted with chloroform. The extract was dried and concentrated under reduced pressure to give 3-{(2S,4S)-1-tert-butoxycarbonyl-4-[4-(5-carboxy-2-benzoxazolyl)piperidino]-2-pyrrolidinylcarbonyl}-1,3-thiazolidine (3.45 g) as a white powder.

(2) Using the above-mentioned compound (786 mg), and in the same manner as in Example 167 (2), the title compound (689 mg) was obtained as a white powder.

$^1$H-NMR(DMSO-$d_6$)δ2.10–2.45(5H,m), 2.88–4.12(13H, m), 4.45–4.81(3H,m), 7.82(1H,d,J=8.7 Hz), 8.02(1H,dd,J=8.7,1.5 Hz), 8.24(1H,d,J=1.5 Hz), 9.20(1H,brs), 10.45(1H, brs), 11.90(1H,brs), 13.15(1H,brs).

Example 311

Synthesis of 3-{(2S,4S)-4-[4-(5-carbamoyl-2-benzoxazolyl)piperidino]-2-pyrrolidinylcarbonyl}-1,3-thiazolidine (1) 3-{(2S,4S)-1-tert-Butoxycarbonyl-4-[4-(5-carboxy-2-benzoxazolyl)piperidino]-2-pyrrolidinylcarbonyl}-1,3-thiazolidine [product of Example 310 (1), 1.06 g] was dissolved in tetrahydrofuran (5 mL), and triethylamine (0.279 mL) and isobutyl chlorocarbonate (0.263 mL) were added thereto under ice-cooling. The mixture was stirred at room temperature for 30 min. A solution of 7 mol/L ammonia-methanol (1 mL) was added to the reaction mixture, and the mixture was stirred at room temperature for 15 hr. Water was added to the reaction mixture, and the mixture was extracted with chloroform. The extract was dried and concentrated under reduced pressure. The residue was purified by silica gel chromatography to give 3-{(2S,4S)-1-tert-butoxycarbonyl-4-[4-(5-carbamoyl-2-benzoxazolyl)piperidino]-2-pyrrolidinylcarbonyl}-1,3-thiazolidine (345 mg) as a white powder.

(2) The above-mentioned compound (335 mg) was dissolved in dichloromethane (0.5 mL) and trifluoroacetic acid (0.5 mL), and the mixture was stirred at room temperature for 7.5 hr. Saturated aqueous sodium hydrogencarbonate solution was added to the reaction mixture, and the mixture was extracted with chloroform. The extract was dried, and concentrated under reduced pressure to give the title compound (75 mg) as a white powder.

$^1$H-NMR($CDCl_3$)δ1.65–1.78(1H,m), 1.95–2.47(8H,m), 2.85–3.19(8H,m), 3.62–3.75(1H,m), 3.77–3.98(2H,m), 4.47–4.67(2H,m), 5.88(1H,brs), 6.18(1H,brs), 7.54(1H,d,J=9.6 Hz), 7.87(1H,dd,J=9.6,1.5 Hz), 8.11(1H,d,J=1.5 Hz).

Example 312

Synthesis of 3-((2S,4S)-4-{4-[5-(N-methylcarbamoyl)-2-benzoxazolyl]piperidino}-2-pyrrolidinylcarbonyl)-1,3-thiazolidine (1) Using the product (1.06 g) of Example 310 (1) and 30% methylamine-ethanol solution (1 mL), and in the same manner as in Example 311 (1), 3-((2S,4S)-1-tert-butoxycarbonyl-4-{4-[5-(N-methylcarbamoyl)-2-benzoxazolyl]piperidino}-2-pyrrolidinylcarbonyl)-1,3-thiazolidine (0.725 g) was obtained as a white powder.

(2) Using the above-mentioned compound (669 mg), and in the same manner as in Example 311 (2), the title compound (386 mg) was obtained as a white powder.

$^1$H-NMR($CDCl_3$)δ1.62–1.78(1H,m), 1.92–2.38(8H,m), 2.87–3.20(11H,m), 3.63–3.74(1H,m), 3.75–3.97(2H,m), 4.47–4.67(2H,m), 6.35(1H,brs), 7.51(1H,d,J=8.5 Hz), 7.81 (1H,dd,J=8.5,1.7 Hz), 8.04(1H,d,J=1.7 Hz).

Example 313

Synthesis of 3-((2S,4S)-4-{4-[5-(N,N-dimethylcarbamoyl)-2-benzoxazolyl]piperidino}-2-pyrrolidinylcarbonyl)-1,3-thiazolidine dihydrochloride (1) The product (1.36 g) of Example 310 (1) and dimethylamine hydrochloride (0.244 g) were dissolved in DMF, and triethylamine (0.42 mL), HOBT (0.457 g) and EDC hydrochloride (0.572 g) were added thereto. The mixture was stirred at room temperature for 1.5 hr. The saturated aqueous sodium hydrogencarbonate solution was added to the reaction mixture, and the mixture was extracted with ethyl acetate. The extract was dried and concentrated under reduced pressure. The residue was purified by silica gel chromatography to give 3-((2S,4S)-1-tert-butoxycarbonyl-4-{4-[5-(N,N-dimethylcarbamoyl)-2-benzoxazolyl]piperidino}-2-pyrrolidinylcarbonyl)-1,3-thiazolidine (0.786 g) as a white powder.

(2) Using the above-mentioned compound (760 mg), and in the same manner as in Example 167 (2), the title compound (634 mg) was obtained as a white powder.

$^1$H-NMR(DMSO-$d_6$)δ2.13–2.46(5H,m), 2.84–4.10(19H, m), 4.41–4.79(3H,m), 7.43(1H,dd,J=1.5,8.4 Hz), 7.75–7.78 (2H,m), 9.18(1H,brs), 10.63(1H,brs), 12.05(1H,brs).

Example 314

Synthesis of 3-{(2S,4S)-4-[4-(5-cyano-2-benzoxazolyl)piperidino]-2-pyrrolidinylcarbonyl}-1,3-thiazolidine (1) Using the product (2.88 g) of Example 301 (1) and 3-amino-4-cyanophenol (1.47 g), and in the same manner as in Example 301 (2), 1-benzyloxycarbonyl-4-(5-cyano-2-benzoxazolyl)piperidine (2.43 g) was obtained as a pale-brown powder.

(2) Using the above-mentioned compound (2.43 g), and in the same manner as in Example 301 (3), 4-(5-cyano-2-benzoxazolyl)piperidine (1.33 g) was obtained as a brown-dark solid.

(3) Using the above-mentioned compound (409 mg) and the title compound (450 mg) of Reference Example 12, and in the same manner as in Example 70 (1), 3-{(2S,4S)-1-tert-butoxycarbonyl-4-[4-(5-cyano-2-benzoxazolyl)piperidino]-2-pyrrolidinylcarbonyl}-1,3-thiazolidine (230 mg) was obtained as a white solid.

(4) The above-mentioned compound (226 mg) was dissolved in ethyl acetate (1 mL), and 4 mol/L hydrochloric acid-ethyl acetate (1.1 mL) was added thereto. The mixture was stirred at room temperature for 18 hr. The reaction mixture was concentrated under reduced pressure, and saturated aqueous sodium hydrogencarbonate solution was added to the residue. The mixture was extracted with chloroform. The extract was dried, and concentrated under reduced pressure. The residue was purified by silica gel chromatography and crystallized from ethyl acetate to give the title compound (869 mg) as a white powder.

$^1$H-NMR(DMSO-$d_6$)δ1.53–1.65(1H,m), 1.73–1.90(2H, m), 2.04–2.24(4H,m), 2.27–2.37(1H,m), 2.68–3.12(8H,m), 3.60–3.98(3H,m), 4.40–4.69(2H,m), 7.84(1H,dd,J=8.4,1.4 Hz), 7.92(1H,d,J=8.4 Hz), 8.32(1H,d,J=1.4 Hz).

Example 315

Synthesis of 3-{(2S,4S)-4-[4-(5-methoxy-2-benzoxazolyl)piperidino]-2-pyrrolidinylcarbonyl}-1,3-thiazolidine dihydrochloride (1) Using the product (5.11 g) of Example 301 (1) and 3-amino-4-methoxyphenol 2.72 g, and in the same manner as in Example 301 (2), 1-benzyloxycarbonyl-4-(5-methoxy-2-benzoxazolyl)piperidine (4.35 g) was obtained as an orange oil.

(2) Using the above-mentioned compound (4.25 g), and in the same manner as in Example 301 (3), 4-(5-methoxy-2-benzoxazolyl)piperidine (2.47 g) was obtained as a red-brown solid.

(3) Using the above-mentioned compound (0.767 g) and the title compound (0.901 g) of Reference Example 12, and in the same manner as in Example 70 (1), 3-{(2S,4S)-1-tert-butoxycarbonyl-4-[4-(5-methoxy-2-benzoxazolyl)piperidino]-2-pyrrolidinylcarbonyl}-1,3-thiazolidine (1.38 g) was obtained as a white solid.

(4) The above-mentioned compound (1.37 g) was dissolved in ethanol (4 mL), and 4.1 mol/L hydrochloric acid-ethanol (6.5 mL) was added thereto. The mixture was stirred at room temperature for 16 hr. The reaction mixture was concentrated under reduced pressure and the residue was crystallized from ethanol (10 mL) to give the title compound (0.953 g) as a white powder.

$^1$H-NMR(DMSO-$d_6$)δ2.12–2.43(5H,m), 2.90–4.07(16H, m), 4.45–4.77(3H,m), 6.97(1H,dd,J=8.9,2.5 Hz), 7.28(1H, d,J=2.5 Hz), 7.60(1H,d,J=8.9 Hz), 9.14(1H,brs), 10.67(1H, brs), 12.03(1H,brs).

Example 316

Synthesis of 3-{(2S,4S)-4-[4-(2-benzothiazolyl)piperidino]-2-pyrrolidinylcarbonyl}-1,3-thiazolidine dihydrochloride (1) Using the product (5.74 g) of Example 301 (1) and 2-aminothiophenol (2.3 mL), and in the same manner as in Example 301 (2), 4-(2-benzothiazolyl)-1-benzyloxycarbonylpiperidine (3.76 g) was obtained as a yellow solid.

(2) The above-mentioned compound (986 mg) and thioanisole (1.0 mL) were dissolved in trifluoroacetic acid (10 mL), and the mixture was stirred at room temperature for 11 hr. The reaction mixture was concentrated under reduced pressure, and saturated aqueous sodium hydrogencarbonate solution was added to the residue. The mixture was extracted with chloroform. The extract was dried and concentrated under reduced pressure to give 4-(2-benzothiazolyl)piperidine (0.299 g) as a white solid.

(3) Using the above-mentioned compound (297 mg) and the title compound (409 mg) of Reference Example 12, and in the same manner as in Example 70 (1), 3-{(2S,4S)-4-[4-(2-benzothiazolyl)piperidino]-1-tert-butoxycarbonyl-2-pyrrolidinylcarbonyl}-1,3-thiazolidine (625 mg) was obtained as a white solid.

$^1$H-NMR($CDCl_3$)δ1.41(4.5H,s), 1.46(4.5H,s), 1.82–2.06 (3H,m), 2.14–2.32(4H,m), 2.39–2.52(1H,m), 2.78–3.21(6H, m), 3.32(1H,t,J=10.0 Hz), 3.63–4.12(3H,m), 4.37–4.79(3H, m), 7.35(1H,t,J=7.8 Hz), 7.46(1H,t,J=7.8 Hz), 7.86(1H,d,J=7.8 Hz), 7.97(1H,d,J=7.8 Hz).

(4) The above-mentioned compound (621 mg) was dissolved in 1.1 mol/L hydrochloric acid-methanol (6 mL), and the mixture was stirred at room temperature for 2 days. The reaction mixture was concentrated under reduced pressure and the residue was crystallized from ethanol (6 mL) to give the title compound (423 mg) as a white powder.

$^1$H-NMR(DMSO-$d_6$)δ2.16–2.46(5H,m), 2.94–3.36(5H, m), 3.40–4.08(8H,m), 4.47–4.78(3H,m), 7.44(1H,t,J=7.8 Hz), 7.52(1H,t,J=7.8 Hz), 7.99(1H,d,J=7.8 Hz), 8.11(1H,d, J=7.8 Hz), 9.13(1H,brs), 10.82(1H,brs), 12.14(1H,brs).

Example 317

Synthesis of 3-{(2S,4S)-4-[4-(5-trifluoromethyl-2-benzothiazolyl)piperidino]-2-pyrrolidinylcarbonyl}-1,3-thiazolidine (1) The product (2.96 g) of Example 301 (1), 2-amino-4-trifluoromethylthiophenol hydrochloride (2.99 g) and triethylamine (1.8 mL) were dissolved in ethanol (60 mL), and the mixture was refluxed for 4 hr. The reaction mixture was concentrated under reduced pressure, and 0.5 mol/L aqueous sodium hydroxide solution was added to the residue. The mixture was extracted with chloroform. The extract was washed successively with 0.5 mol/L hydrochloric acid, saturated aqueous sodium hydrogencarbonate solution and brine, and dried. The solvent was evaporated under reduced pressure and the residue was purified by silica gel chromatography to give 1-benzyloxycarbonyl-4-(5-trifluoromethyl-2-benzothiazolyl)piperidine (1.75 g) as a pale-yellow oil.

(2) The above-mentioned compound (1.74 g) was dissolved in 30% hydrogen bromide-acetic acid solution (8 mL), and the mixture was stirred at room temperature for 1 hr. Diethyl ether (10 mL) was added to the reaction mixture, and the precipitated solid was collected by filtration. The saturated aqueous sodium hydrogencarbonate solution was added to the precipitated solid, and the mixture was extracted with chloroform. The extract was dried and concentrated under reduced pressure to give 4-(5-trifluoromethyl-2-benzothiazolyl)piperidine (0.943 g) as a pale-yellow solid.

(3) Using the above-mentioned compound (0.923 g) and the title compound (0.901 g) of Reference Example 12, and in the same manner as in Example 70 (1), 3-{(2S,4S)-1-tert-butoxycarbonyl-4-[4-(5-trifluoromethyl-2-benzothiazolyl)piperidino]-2-pyrrolidinylcarbonyl}-1,3-thiazolidine (1.60 g) was obtained as a white solid.

(4) The above-mentioned compound (1.60 g) was dissolved in 4.1 mol/L hydrochloric acid-ethanol (7 mL), and the mixture was stirred at room temperature for 2 days. The reaction mixture was concentrated under reduced pressure, and saturated aqueous sodium hydrogencarbonate solution was added to the residue. The mixture was extracted with chloroform. The extract was dried and concentrated under reduced pressure. The residue was purified by silica gel chromatography and crystallized from diethyl ether to give the title compound (0.848 g) as a white powder.

$^1$H-NMR(DMSO-$d_6$)δ1.52–1.65(1H,m), 1.72–1.88(2H, m), 2.04–2.20(4H,m), 2.22–2.33(1H,m), 2.67–3.23(8H,m), 3.58–3.92(3H,m), 4.40–4.70(2H,m), 7.74(1H,dd,J=8.4,1.5 Hz), 8.31(1H,d,J=1.5 Hz), 8.34(1H,d,J=8.4 Hz).

Example 318

Synthesis of 3-{(2S,4S)-4-[4-(6-fluoro-3-benz[d]isoxazolyl)piperidino]-2-pyrrolidinylcarbonyl}-1,3-thiazolidine dihydrochloride (1) Using 4-(6-fluoro-3-benz[d]isoxazolyl)piperidine (0.54 g) and the title compound (0.614 g) of Reference Example 12, and in the same manner as in Example 70 (1), 3-{(2S,4S)-1-tert-butoxycarbonyl-4-[4-(6-fluoro-3-benz[d]isoxazolyl)piperidino]-2-pyrrolidinylcarbonyl}-1,3-thiazolidine (1.01 g) was obtained as a white powder.

(2) Using the above-mentioned compound (1.00 g), and in the same manner as in Example 133 (2), the title compound (0.38 g) was obtained as a white powder.

$^1$H-NMR(500 MHz,DMSO-$d_6$)δ2.05–2.46(5H,m), 2.92–4.20(13H,m), 4.49–4.73(3H,m), 7.32–7.36(1H,m), 7.72–7.74(1H,m), 8.20(1H,brs), 9.10(1H,brs), 10.60(1H, brs), 12.22(1H,brs).

Example 319

Synthesis of 3-{(2S,4S)-4-(2-[(5-cyano-2-pyridyl)amino]ethyl}amino-2-pyrrolidinylcarbonyl}-1,3-thiazolidine trihydrochloride (1) Using N-(5-cyano-2-pyridyl)ethylenediamine (0.656 g) and the title compound (1.20 g) of Reference Example 12, and in the same manner as in Example 70 (1), 3-{(2S,4S)-1-tert-butoxycarbonyl-4-{2-[(5-cyano-2-pyridyl)amino]ethyl}amino-2-pyrrolidinylcarbonyl}-1,3-thiazolidine (1.46 g) was obtained as a white solid.

(2) The above-mentioned compound (656 mg) was dissolved in ethyl acetate (4 mL), and 4 mol/L hydrochloric acid-ethyl acetate (4 mL) was added thereto. The mixture was stirred at room temperature for 12 hr. The precipitated solid was collected by filtration to give the title compound (666 mg) as a white powder.

$^1$H-NMR(DMSO-$d_6$)δ2.03–2.19(1H,m), 2.87–2.98(1H, m), 3.06(1H,t,J=6.5 Hz), 3.10–3.25(3H,m), 3.45–4.10(7H, m), 4.47–4.74(3H,m), 6.67(1H,d,J=8.9 Hz), 7.76(1H,dd,J=8.9,2.2 Hz), 8.03(1H,brs), 8.46(1H,d,J=2.2 Hz), 8.96(1H, brs), 9.96(2H,brs), 10.64(1H,brs).

Example 320

Synthesis of 3-[(2S,4S)-4-(N-acetyl-N-{2-[(5-cyano-2-pyridyl)amino]ethyl}amino)-2-pyrrolidinylcarbonyl]-1,3-thiazolidine dihydrochloride (1) 3-{(2S,4S)-1-tert-Butoxycarbonyl-4-{2-[(5-cyano-2-pyridyl)amino]ethyl}amino-2-pyrrolidinylcarbonyl}-1,3-thiazolidine [product of Example 319 (1), 800 mg] and triethylamine (0.42 mL) were dissolved in dichloromethane (20 mL), and acetyl chloride (0.18 mL) was added thereto under ice-cooling. The mixture was stirred at room temperature for 5 hr. The reaction mixture was added to saturated aqueous sodium hydrogencarbonate solution and the mixture was extracted with chloroform. The extract was washed with brine, dried, and concentrated under reduced pressure. The residue was purified by silica gel chromatography to give 3-[(2S,4S)-4-(N-acetyl-N-{2-[(5-cyano-2-pyridyl)amino]ethyl}amino)-1-tert-butoxycarbonyl-2-pyrrolidinylcarbonyl]-1,3-thiazolidine (786 mg) as a white solid.

(2) The above-mentioned compound (380 mg) was dissolved in ethyl acetate (3 mL), and 4 mol/L hydrochloric acid-ethyl acetate (1 mL) was added thereto. The mixture was stirred at room temperature for 3 hr. The precipitated solid was collected by filtration to give the title compound (314 mg) as a white powder.

$^1$H-NMR(DMSO-$d_6$)δ1.95–2.10(4H,m), 2.62–2.80(1H, m), 3.00–3.90(11H,m), 4.28–4.77(4H,m), 6.64(1H,d,J=8.8 Hz), 7.73(1H,dd,J=8.8,2.2 Hz), 7.95(1H,brs), 8.35(1H,brs), 8.42(1H,d,J=2.2 Hz), 9.96(1H,brs).

The structures of the compound obtained in the above-mentioned Examples are all shown in Tables 1–40.

TABLE 1

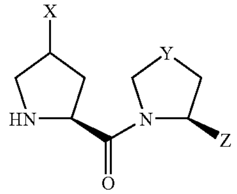

| Example No. | X | Y | Z | salt |
|---|---|---|---|---|
| 1 | 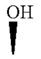 | $CH_2$ | CN | $CF_3CO_2H$ |
| 2 | 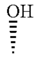 | $CH_2$ | CN | HCl |
| 3 | 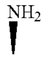 | $CH_2$ | CN | 2HCl |
| 4 | 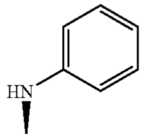 | $CH_2$ | CN | $CF_3CO_2H$ |
| 5 | 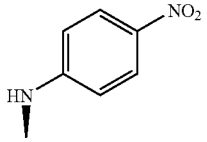 | $CH_2$ | CN | HCl |
| 6 | 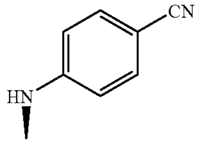 | $CH_2$ | CN | HCl |
| 7 | 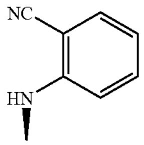 | $CH_2$ | CN | HCl |
| 8 | 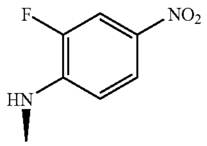 | $CH_2$ | CN | HCl |
| 9 | 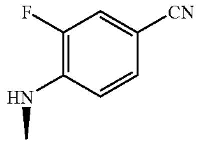 | $CH_2$ | CN | HCl |
| 10 | 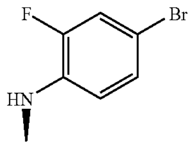 | $CH_2$ | CN | HCl |

TABLE 1-continued
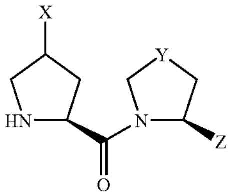
| Example No. | X | Y | Z | salt |
|---|---|---|---|---|
| 11 | 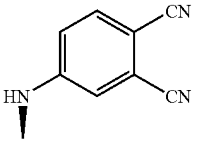 | $CH_2$ | CN | HCl |
TABLE 2
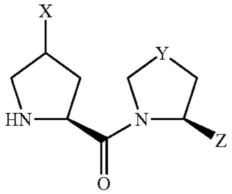
| Example No. | X | Y | Z | salt |
|---|---|---|---|---|
| 12 | 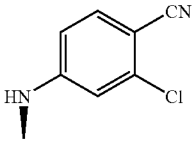 | $CH_2$ | CN | HCl |
| 13 | 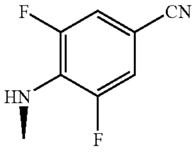 | $CH_2$ | CN | HCl |
| 14 | 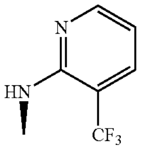 | $CH_2$ | CN | $CF_3CO_2H$ |
| 15 | 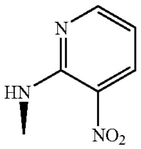 | $CH_2$ | CN | $CF_3CO_2H$ |
| 16 | 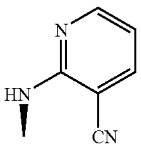 | $CH_2$ | CN | HCl |
TABLE 2-continued
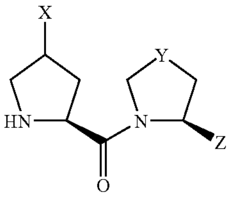
| Example No. | X | Y | Z | salt |
|---|---|---|---|---|
| 17 | 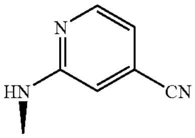 | $CH_2$ | CN | $CF_3CO_2H$ |
| 18 | 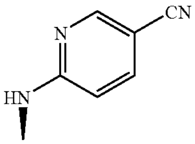 | $CH_2$ | CN | 2HCl |
| 19 | 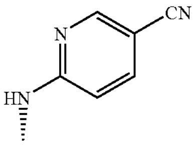 | $CH_2$ | CN | 2HCl |
| 20 | 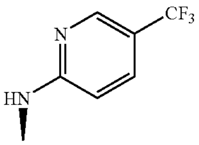 | $CH_2$ | CN | $2CF_3CO_2H$ |
| 21 | 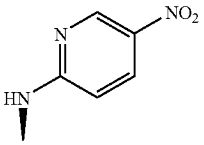 | $CH_2$ | CN | 2HCl |
TABLE 3
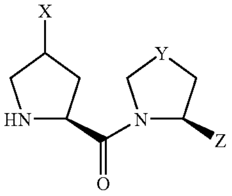
| Example No. | X | Y | Z | salt |
|---|---|---|---|---|
| 22 | 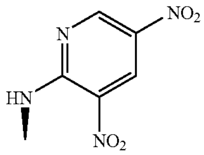 | $CH_2$ | CN | $CF_3CO_2H$ |

TABLE 3-continued
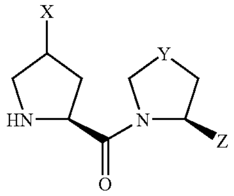
| Example No. | X | Y | Z | salt |
|---|---|---|---|---|
| 23 | 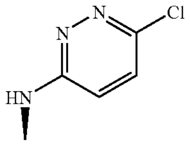 | $CH_2$ | CN | HCl |
| 24 | 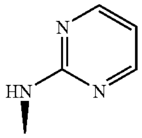 | $CH_2$ | CN | HCl |
| 25 | 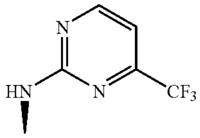 | $CH_2$ | CN | HCl |
| 26 | 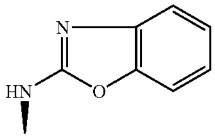 | $CH_2$ | CN | HCl |
| 27 | 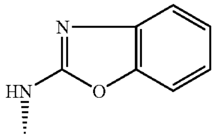 | $CH_2$ | CN | HCl |
| 28 | 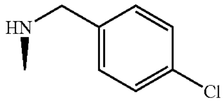 | $CH_2$ | CN | 2HCl |
| 29 | 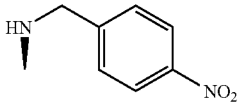 | $CH_2$ | CN | 2HCl |
| 30 | 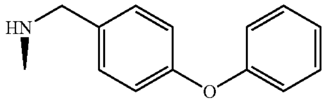 | $CH_2$ | CN | 2HCl |
| 31 | 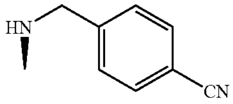 | $CH_2$ | CN | 2HCl |
TABLE 3-continued
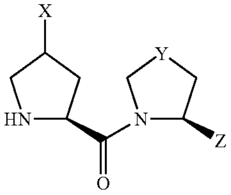
| Example No. | X | Y | Z | salt |
|---|---|---|---|---|
| 32 | 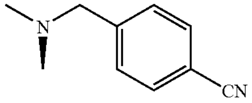 | $CH_2$ | CN | 2HCl |
TABLE 4
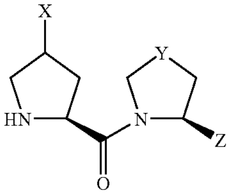
| Example No. | X | Y | Z | salt |
|---|---|---|---|---|
| 33 | 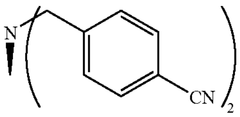 | $CH_2$ | CN | 2HCl |
| 34 | 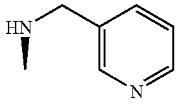 | $CH_2$ | CN | $3CF_3CO_2H$ |
| 35 | 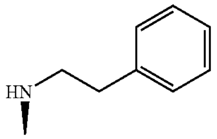 | $CH_2$ | CN | $2CF_3CO_2H$ |
| 36 | 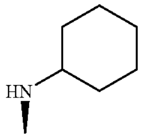 | $CH_2$ | CN | 2HCl |
| 37 | 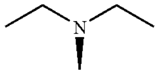 | $CH_2$ | CN | 2HCl |
| 38 | 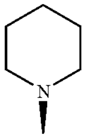 | $CH_2$ | CN | 2HCl |

TABLE 4-continued
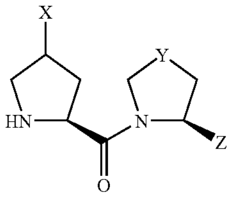
| Example No. | X | Y | Z | salt |
|---|---|---|---|---|
| 39 | 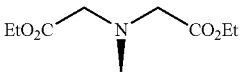 | $CH_2$ | CN | 2HCl |
| 40 | 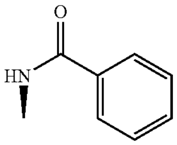 | $CH_2$ | CN | HCl |
| 41 | 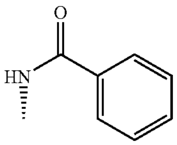 | $CH_2$ | CN | HCl |
| 42 | 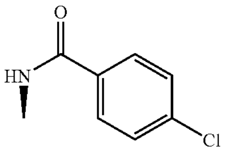 | $CH_2$ | CN | HCl |
| 43 | 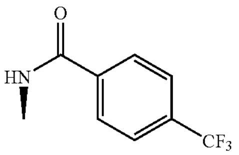 | $CH_2$ | CN | HCl |
TABLE 5
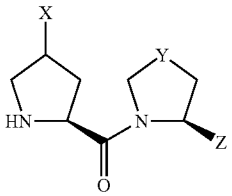
| Example No. | X | Y | Z | salt |
|---|---|---|---|---|
| 44 | 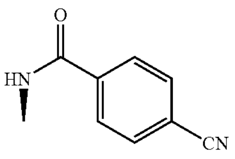 | $CH_2$ | CN | HCl |
TABLE 5-continued
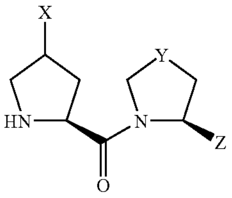
| Example No. | X | Y | Z | salt |
|---|---|---|---|---|
| 45 | 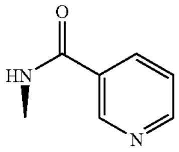 | $CH_2$ | CN | $2CF_3CO_2H$ |
| 46 | 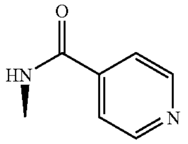 | $CH_2$ | CN | $2CF_3CO_2H$ |
| 47 | 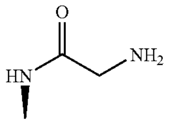 | $CH_2$ | CN | 2HCl |
| 48 | 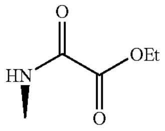 | $CH_2$ | CN | $CF_3CO_2H$ |
| 49 | 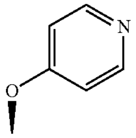 | $CH_2$ | CN | 2HCl |
| 50 | 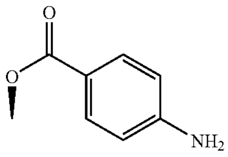 | $CH_2$ | CN | 2HCl |
| 51 | 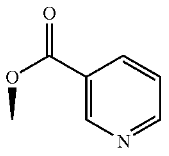 | $CH_2$ | CN | 2HCl |
| 52 | 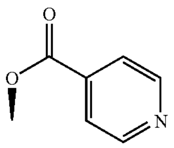 | $CH_2$ | CN | 2HCl |
| 53 | 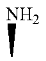 | S | H | 2HCl |

TABLE 6
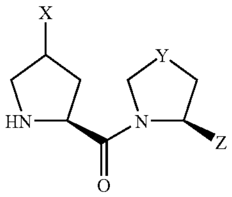
| Example No. | X | Y | Z | salt |
|---|---|---|---|---|
| 54 | 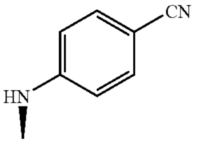 | S | H | HCl |
| 55 | 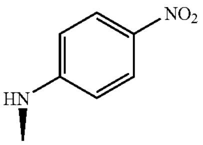 | S | H | HCl |
| 56 | 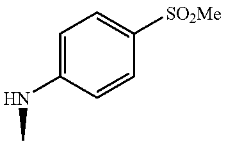 | S | H | HCl |
| 57 | 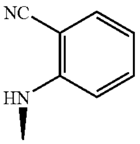 | S | H | HCl |
| 58 | 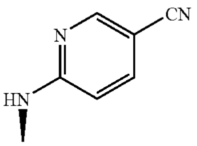 | S | H | 2HCl |
| 59 | 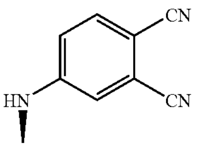 | S | H | HCl |
| 60 | 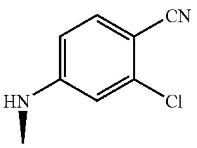 | S | H | HCl |
| 61 | 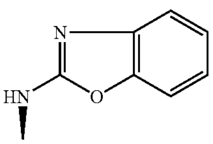 | S | H | HCl |
| 62 | 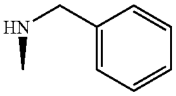 | S | H | 2HCl |
TABLE 6-continued
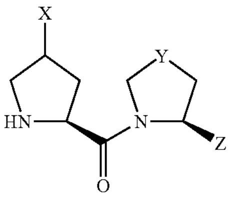
| Example No. | X | Y | Z | salt |
|---|---|---|---|---|
| 63 | 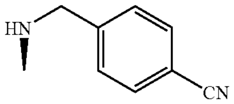 | S | H | 2HCl |
| 64 | 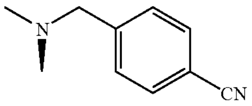 | S | H | 2HCl |
TABLE 7
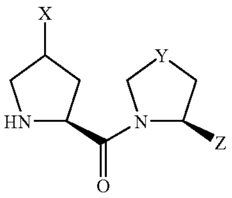
| Example No. | X | Y | Z | salt |
|---|---|---|---|---|
| 65 | 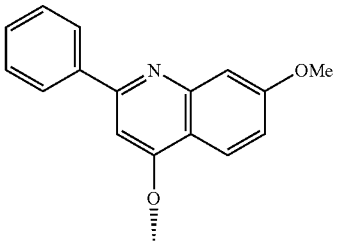 | S | H | 3HCl |
| 66 | 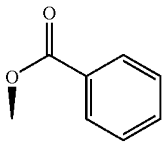 | S | H | — |
| 67 | 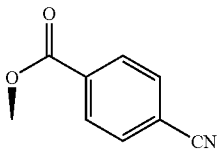 | S | H | — |
| 68 | 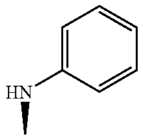 | S | H | 2HCl |

TABLE 7-continued
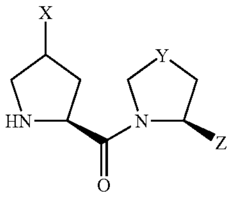
| Example No. | X | Y | Z | salt |
|---|---|---|---|---|
| 69 | 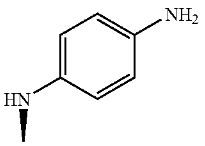 | S | H | HCl |
| 70 | 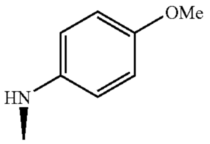 | S | H | 2HCl |
| 71 | 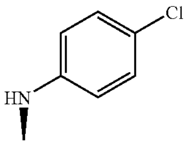 | S | H | 2HCl |
| 72 | 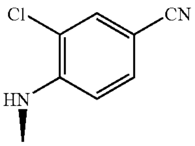 | S | H | HCl |
| 73 | 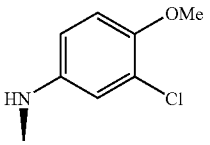 | S | H | 2HCl |
TABLE 8
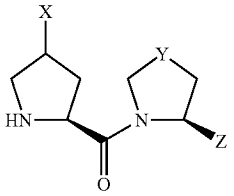
| Example No. | X | Y | Z | salt |
|---|---|---|---|---|
| 74 | 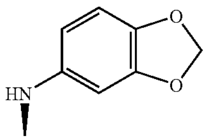 | S | H | 2HCl |
TABLE 8-continued
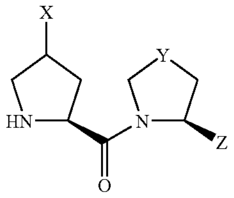
| Example No. | X | Y | Z | salt |
|---|---|---|---|---|
| 75 | 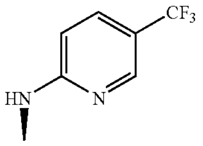 | S | H | 2HCl |
| 76 | 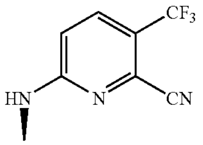 | S | H | HCl |
| 77 | 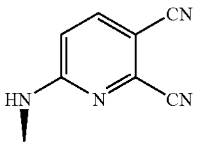 | S | H | HCl |
| 78 | 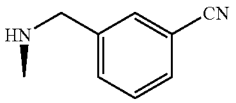 | S | H | 2HCl |
| 79 | 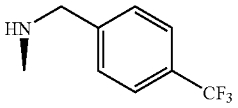 | S | H | 2HCl |
| 80 | 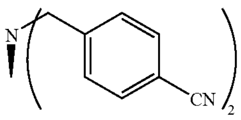 | S | H | 2HCl |
| 81 | 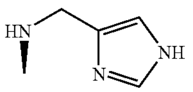 | S | H | 3HCl |
| 82 | 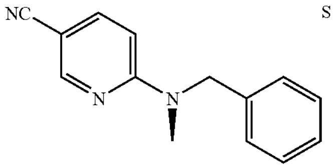 | S | H | HCl |

TABLE 8-continued
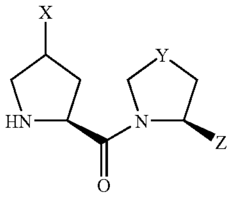
| Example No. | X | Y | Z | salt |
|---|---|---|---|---|
| 83 | 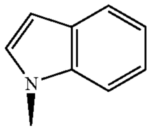 | S | H | HCl |
| 84 | 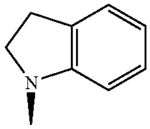 | S | H | 2HCl |
TABLE 9
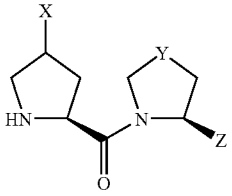
| Example No. | X | Y | Z | salt |
|---|---|---|---|---|
| 85 | 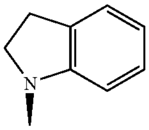 | $CH_2$ | H | 2HCl |
| 86 | 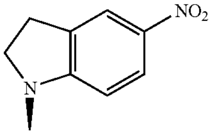 | S | H | HCl |
| 87 | 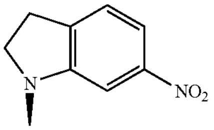 | S | H | 2HCl |
| 88 | 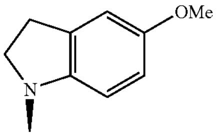 | S | H | 2HCl |
TABLE 9-continued
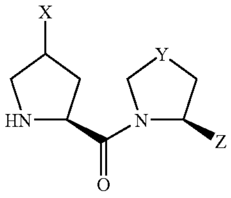
| Example No. | X | Y | Z | salt |
|---|---|---|---|---|
| 89 | 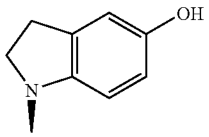 | S | H | 2HCl |
| 90 | 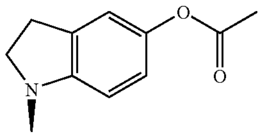 | S | H | 2HCl |
| 91 | 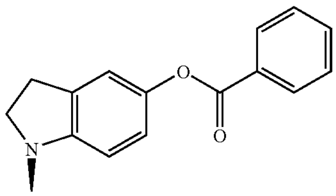 | S | H | 2HCl |
| 92 | 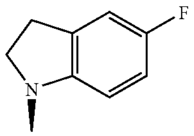 | S | H | 2HCl |
| 93 | 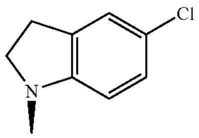 | S | H | HCl |
| 94 | 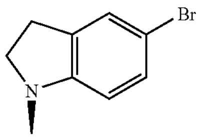 | S | H | HCl |

TABLE 10
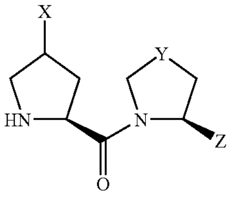
| Example No. | X | Y | Z | salt |
| --- | --- | --- | --- | --- |
| 95 | 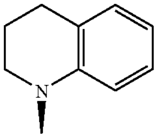 | S | H | HCl |
| 96 | 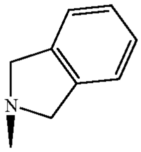 | S | H | $2CF_3CO_2H$ |
| 97 | 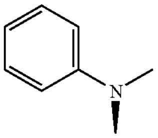 | S | H | 2HCl |
| 98 | 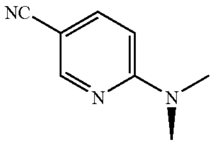 | S | H | HCl |
| 99 | 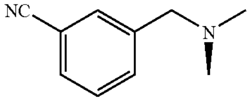 | S | H | 2HCl |
| 100 | 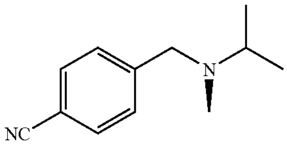 | S | H | 2HCl |
| 101 | 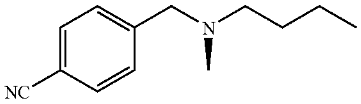 | S | H | 2HCl |
| 102 | 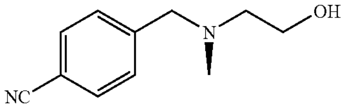 | S | H | 2HCl |
| 103 | 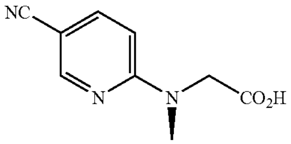 | S | H | $CF_3CO_2H$ |

TABLE 10-continued
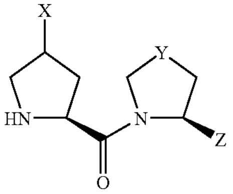
| Example No. | X | Y | Z | salt |
|---|---|---|---|---|
| 104 | 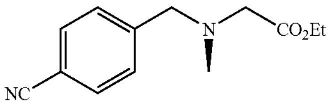 | S | H | 2HCl |
| 105 | 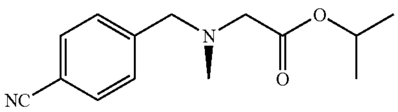 | S | H | 2HCl |
TABLE 11
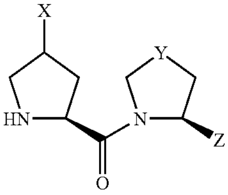
| Example No. | X | Y | Z | salt |
|---|---|---|---|---|
| 106 | 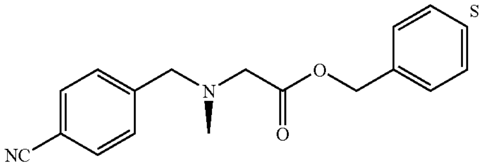 | S | H | 2HCl |
| 107 | 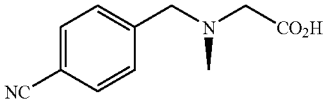 | S | H | $2CF_3CO_2H$ |
| 108 | 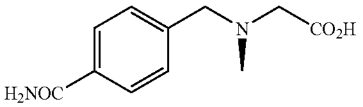 | S | H | $2CF_3CO_2H$ |
| 109 | 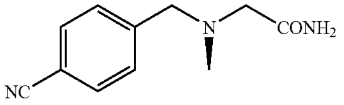 | S | H | 2HCl |
| 110 | 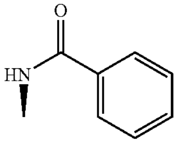 | S | H | — |

TABLE 11-continued
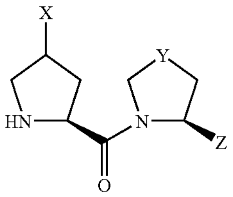
| Example No. | X | Y | Z | salt |
|---|---|---|---|---|
| 111 | 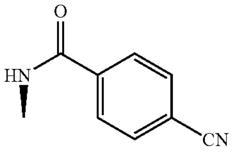 | S | H | HCl |
| 112 | 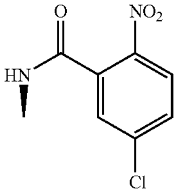 | S | H | HCl |
| 113 | 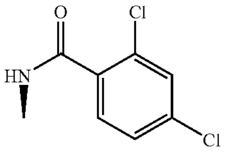 | S | H | HCl |
| 114 | 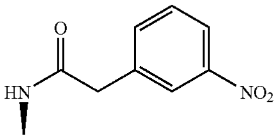 | S | H | HCl |
| 115 | 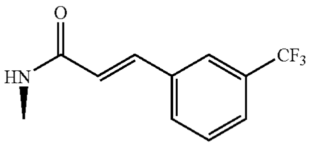 | S | H | HCl |
TABLE 12
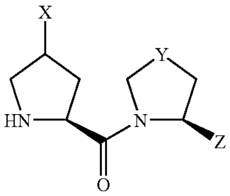
| Example No. | X | Y | Z | salt |
|---|---|---|---|---|
| 116 | 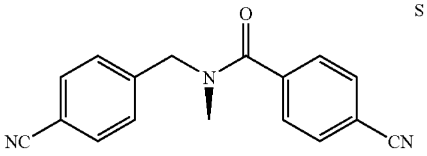 | S | H | HCl |

TABLE 12-continued
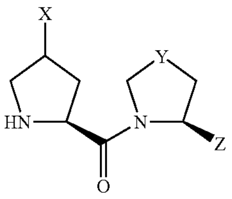
| Example No. | X | Y | Z | salt |
|---|---|---|---|---|
| 117 | 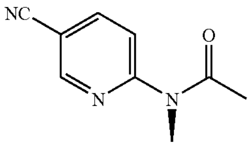 | S | H | HCl |
| 118 | 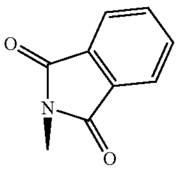 | S | H | $CF_3CO_2H$ |
| 119 | 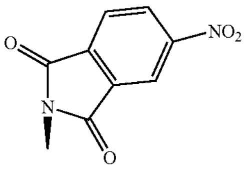 | S | H | $CF_3CO_2H$ |
| 120 | 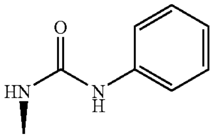 | S | H | $CF_3CO_2H$ |
| 121 | 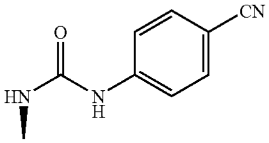 | S | H | — |
| 122 | 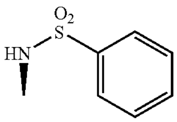 | S | H | HCl |
| 123 | 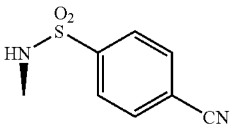 | S | H | HCl |
| 124 | 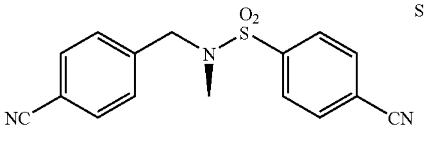 | S | H | HCl |

TABLE 12-continued
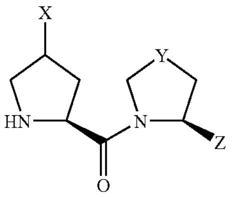
| Example No. | X | Y | Z | salt |
|---|---|---|---|---|
| 125 | 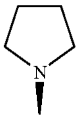 | S | H | 2HCl |
TABLE 13
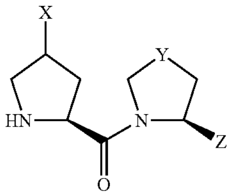
| Example No. | X | Y | Z | salt |
|---|---|---|---|---|
| 126 | 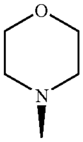 | S | H | 2HCl |
| 127 | 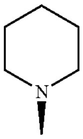 | S | H | 2HCl |
| 128 | 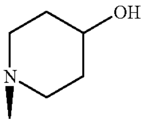 | S | H | 3HCl |
| 129 | 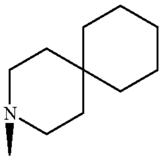 | S | H | $2CF_3CO_2H$ |
| 130 | 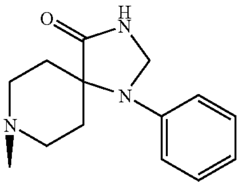 | S | H | 2HCl |
TABLE 13-continued
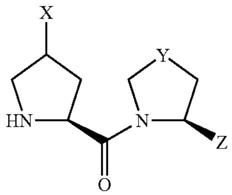
| Example No. | X | Y | Z | salt |
|---|---|---|---|---|
| 131 | 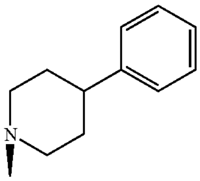 | S | H | 2HCl |
| 132 | 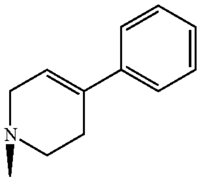 | S | H | 2HCl |
| 133 | 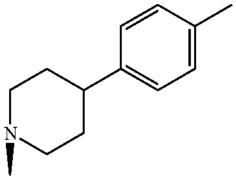 | S | H | 2HCl |
| 134 | 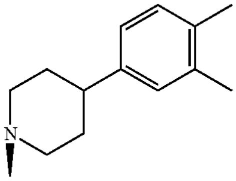 | S | H | 2HCl |

TABLE 14
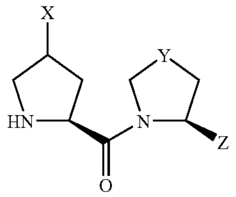
| Example No. | X | Y | Z | salt |
|---|---|---|---|---|
| 135 | 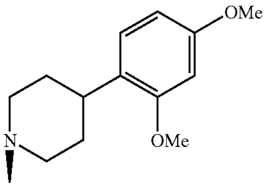 | S | H | 2HCl |
| 136 | 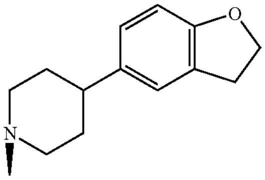 | S | H | 2HCl |
| 137 | 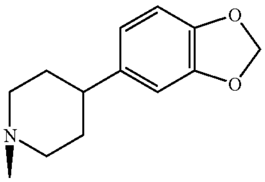 | S | H | 2HCl |
| 138 | 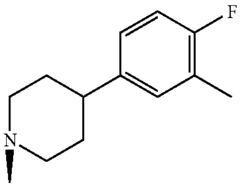 | S | H | 2HCl |
| 139 | 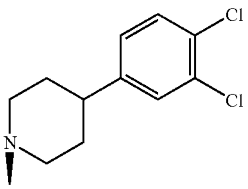 | S | H | 2HCl |
| 140 | 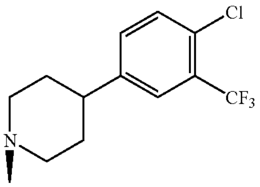 | S | H | 2HCl |
| 141 | 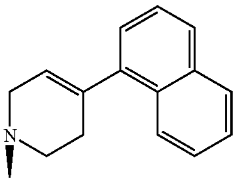 | S | H | 2HCl |
TABLE 14-continued
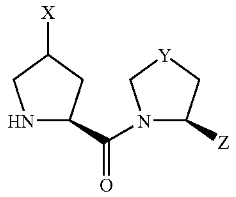
| Example No. | X | Y | Z | salt |
|---|---|---|---|---|
| 142 | 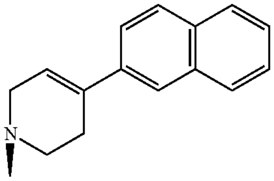 | S | H | 2HCl |
TABLE 15
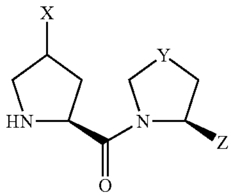
| Example No. | X | Y | Z | salt |
|---|---|---|---|---|
| 143 | 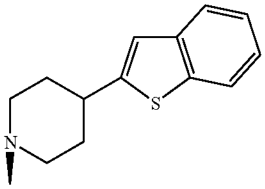 | S | H | 2HCl |
| 144 | 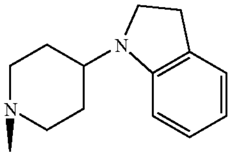 | S | H | 3HCl |
| 145 | 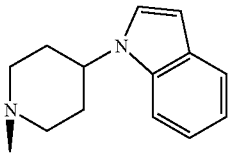 | S | H | 2HCl |

TABLE 15-continued
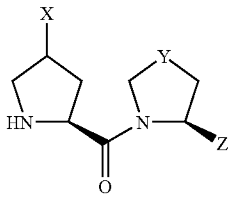
| Example No. | X | Y | Z | salt |
|---|---|---|---|---|
| 146 | 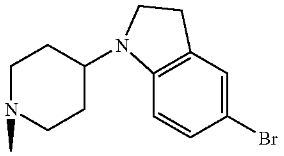 | S | H | 3HCl |
| 147 | 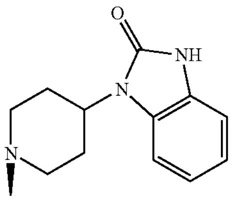 | S | H | 2HCl |
| 148 | 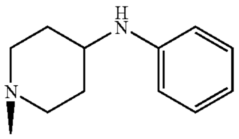 | S | H | 3HCl |
TABLE 15-continued
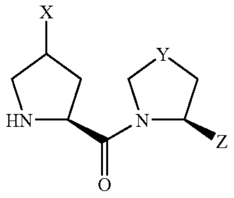
| Example No. | X | Y | Z | salt |
|---|---|---|---|---|
| 149 | 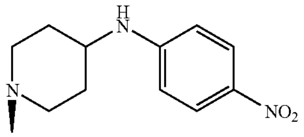 | S | H | 3HCl |
| 150 | 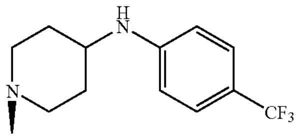 | S | H | 3HCl |
| 151 | 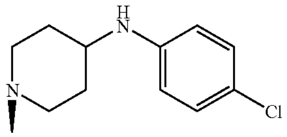 | S | H | 3HCl |
TABLE 16
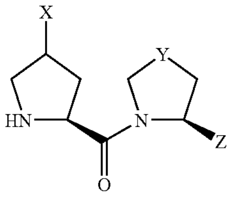
| Example No. | X | Y | Z | salt |
|---|---|---|---|---|
| 152 | 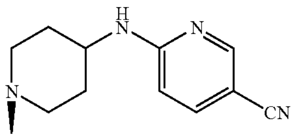 | S | H | 3HCl |
| 153 | 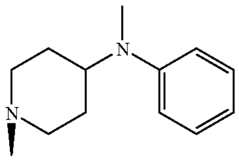 | S | H | 3HCl |

TABLE 16-continued
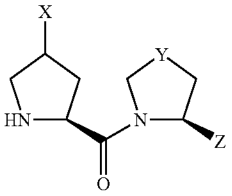
| Example No. | X | Y | Z | salt |
| --- | --- | --- | --- | --- |
| 154 | 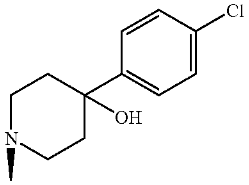 | S | H | $2CF_3CO_2H$ |
| 155 | 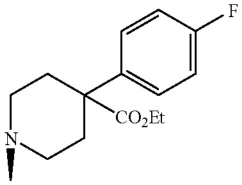 | S | H | 2HCl |
| 156 | 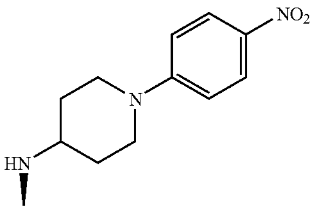 | S | H | 3HCl |
| 157 | 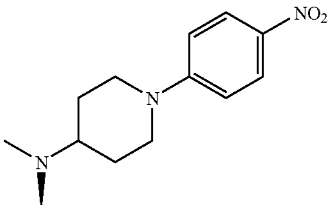 | S | H | 2HCl |
| 158 | 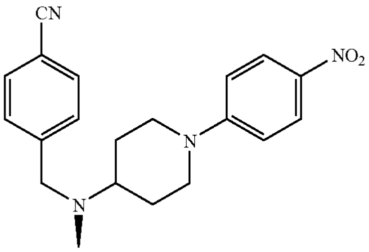 | S | H | 2HCl |
| 159 | 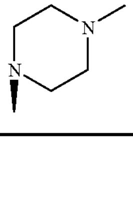 | S | H | 3HCl |

TABLE 17
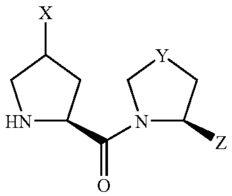
| Example No. | X | Y | Z | salt |
|---|---|---|---|---|
| 160 | 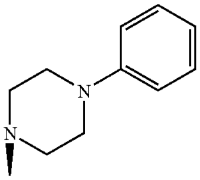 | S | H | 3HCl |
| 161 | 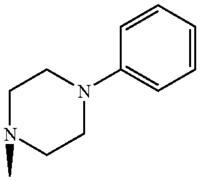 | $CH_2$ | H | 3HCl |
| 162 | 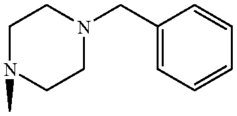 | S | H | 3HCl |
| 163 | 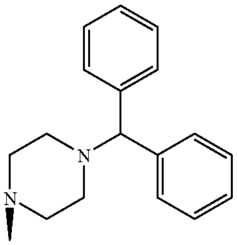 | S | H | 3HCl |
| 164 | 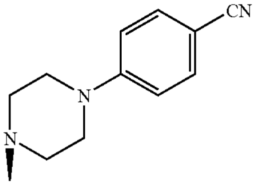 | S | H | 3HCl |
| 165 | 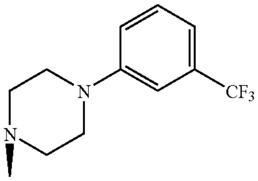 | S | H | 3HCl |
| 166 | 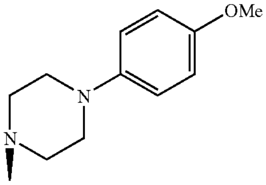 | S | H | 3HCl |
TABLE 17-continued
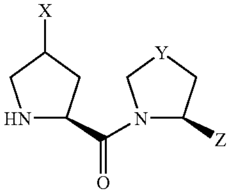
| Example No. | X | Y | Z | salt |
|---|---|---|---|---|
| 167 | 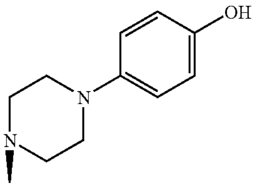 | S | H | 3HCl |
TABLE 18
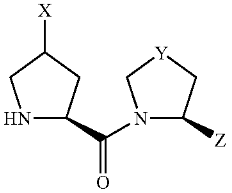
| Example No. | X | Y | Z | salt |
|---|---|---|---|---|
| 168 | 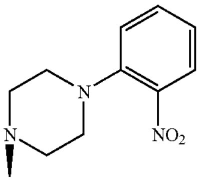 | S | H | 2HCl |
| 169 | 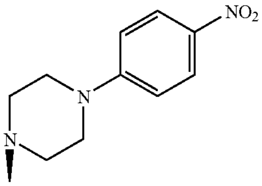 | S | H | 3HCl |
| 170 | 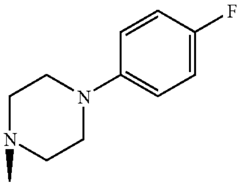 | S | H | 3HCl |
| 171 | 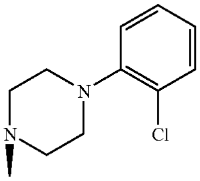 | S | H | 2HCl |

TABLE 18-continued
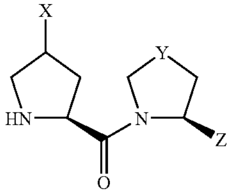
| Example No. | X | Y | Z | salt |
| --- | --- | --- | --- | --- |
| 172 | 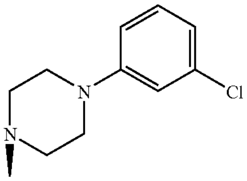 | S | H | 3HCl |
| 173 | 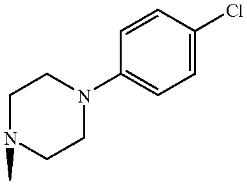 | S | H | 3HCl |
| 174 | 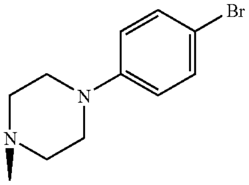 | S | H | 3HCl |
| 175 | 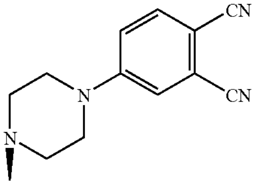 | S | H | 3HCl |
TABLE 19
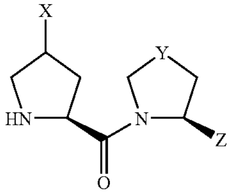
| Example No. | X | Y | Z | salt |
| --- | --- | --- | --- | --- |
| 176 | 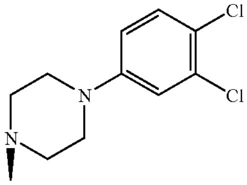 | S | H | 3HCl |
TABLE 19-continued
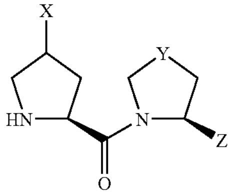
| Example No. | X | Y | Z | salt |
| --- | --- | --- | --- | --- |
| 177 | 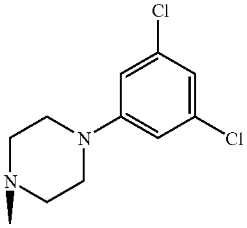 | S | H | 3HCl |
| 178 | 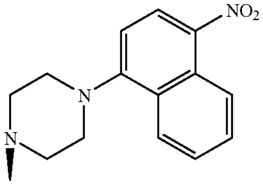 | S | H | 2HCl |
| 179 | 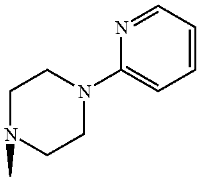 | S | H | 3HCl |
| 180 | 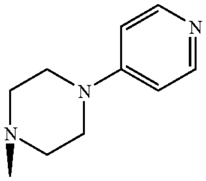 | S | H | 3HCl |
| 181 | 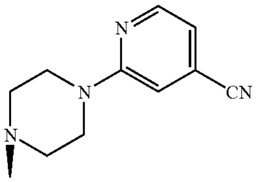 | S | H | 3HCl |
| 182 | 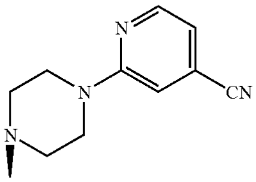 | $CH_2$ | H | 3HCl |

TABLE 20
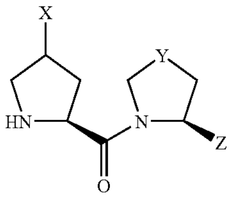
| Example No. | X | Y | Z | salt |
|---|---|---|---|---|
| 183 | 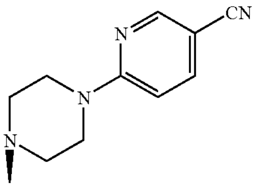 | S | H | 3HCl |
| 184 | 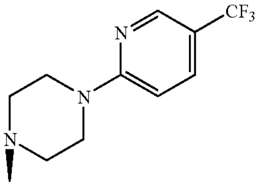 | S | H | 2HCl |
| 185 | 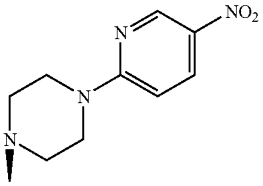 | S | H | 2HCl |
| 186 | 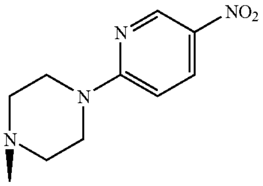 | $CH_2$ | H | 3HCl |
| 187 | 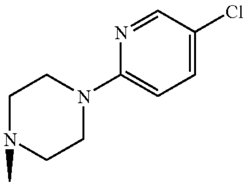 | S | H | 3HCl |
| 188 | 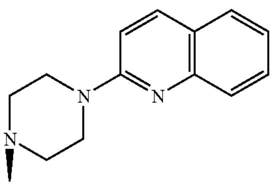 | S | H | 3HCl |
| 189 | 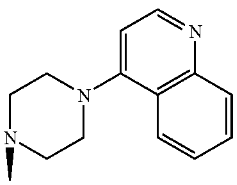 | S | H | 3HCl |
TABLE 20-continued
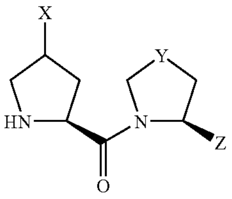
| Example No. | X | Y | Z | salt |
|---|---|---|---|---|
| 190 | 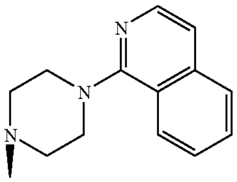 | S | H | 3HCl |
TABLE 21
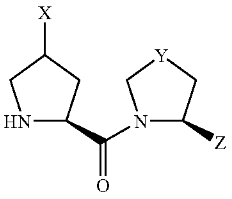
| Example No. | X | Y | Z | salt |
|---|---|---|---|---|
| 191 | 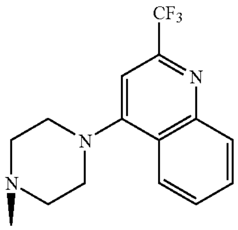 | S | H | 2HC |
| 192 | 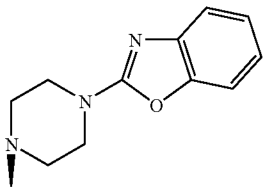 | S | H | 3HCl |
| 193 | 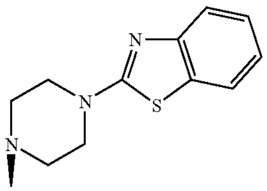 | S | H | 3HCl |
| 194 | 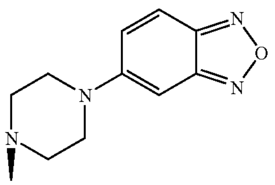 | S | H | 2HC |

TABLE 21-continued
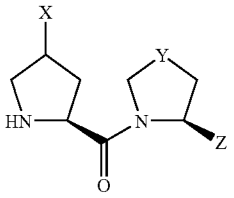
| Example No. | X | Y | Z | salt |
|---|---|---|---|---|
| 195 | 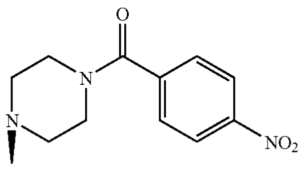 | S | H | 2HC |
| 196 | 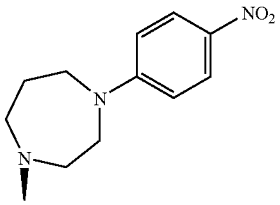 | S | H | 2HCl |
| 197 | 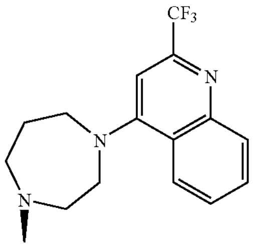 | S | H | 3HCl |
TABLE 22
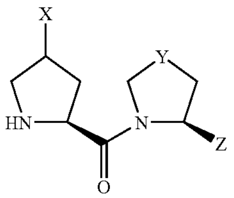
| Example No. | X | Y | Z | salt |
|---|---|---|---|---|
| 198 | 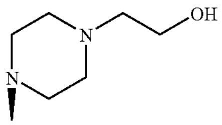 | S | H | 3HCl |
| 199 | 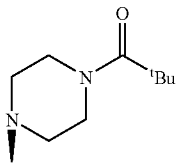 | S | H | 2HCl |
TABLE 22-continued
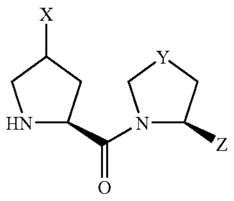
| Example No. | X | Y | Z | salt |
|---|---|---|---|---|
| 200 | 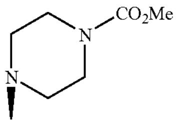 | S | H | 2HCl |
| 201 | 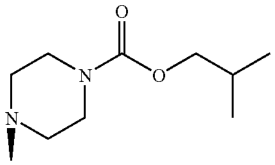 | S | H | 2HCl |
| 202 | 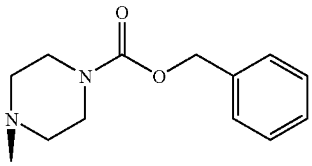 | S | H | 2HCl |
| 203 | 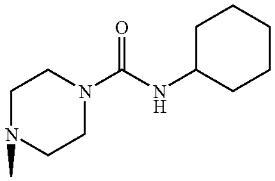 | S | H | 2HCl |
| 204 | 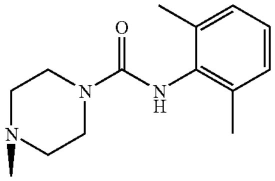 | S | H | 2HCl |
| 205 | 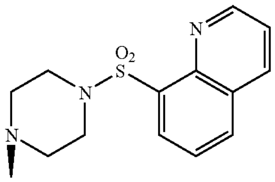 | S | H | 3HCl |

TABLE 23
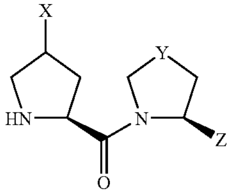
| Example No. | X | Y | Z | salt |
|---|---|---|---|---|
| 206 | 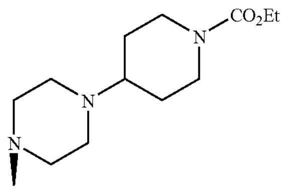 | S | H | 4HCl |
| 207 | 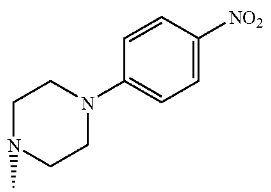 | S | H | 2HCl |
| 208 | 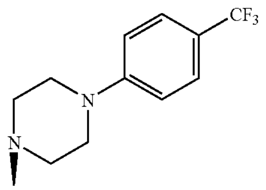 | S | H | 3HCl |
| 209 | 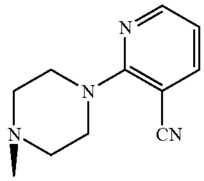 | S | H | 3HCl |
| 210 | 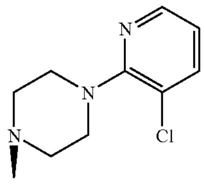 | S | H | 3HCl |
| 211 | 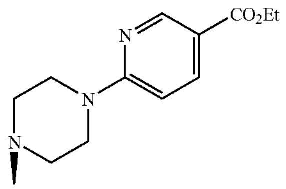 | S | H | 3HCl |
TABLE 23-continued
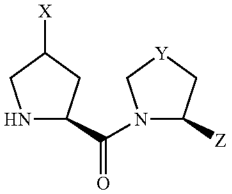
| Example No. | X | Y | Z | salt |
|---|---|---|---|---|
| 212 | 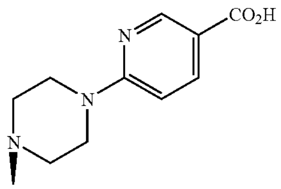 | S | H | 3HCl |
TABLE 24
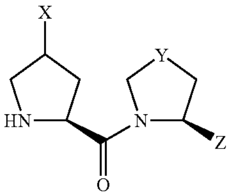
| Example No. | X | Y | Z | salt |
|---|---|---|---|---|
| 213 | 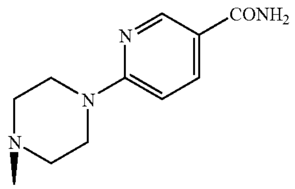 | S | H | 3HCl |
| 214 | 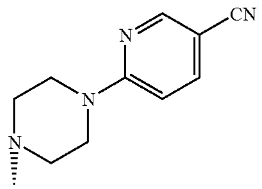 | S | H | 3HCl |
| 215 | 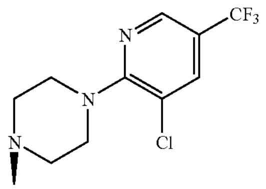 | S | H | 3HCl |
| 216 | 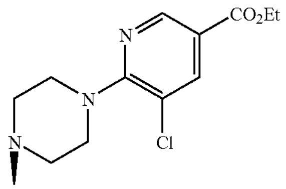 | S | H | 3HCl |

TABLE 24-continued
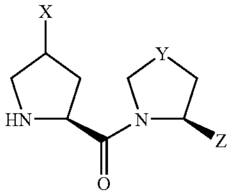
| Example No. | X | Y | Z | salt |
|---|---|---|---|---|
| 217 | 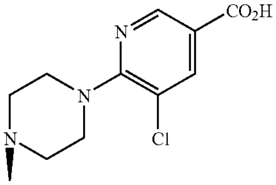 | S | H | 3HCl |
| 218 | 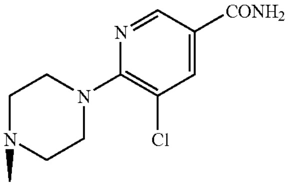 | S | H | 3HCl |
| 219 | 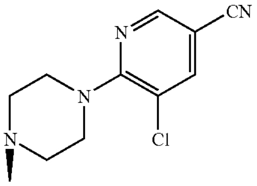 | S | H | 3HCl |
TABLE 25
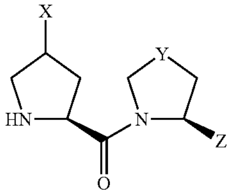
| Example No. | X | Y | Z | salt |
|---|---|---|---|---|
| 220 | 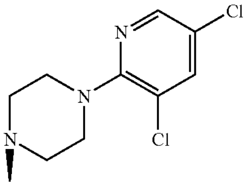 | S | H | 3HCl |
| 221 | 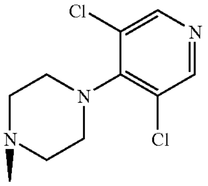 | S | H | 3HCl |
TABLE 25-continued
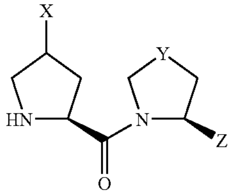
| Example No. | X | Y | Z | salt |
|---|---|---|---|---|
| 222 | 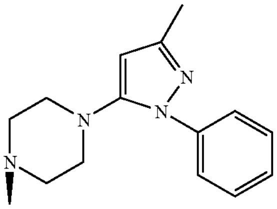 | S | H | 3HCl |
| 223 | 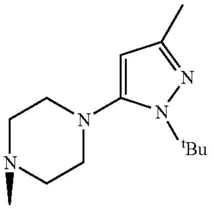 | S | H | 3HCl |
| 224 | 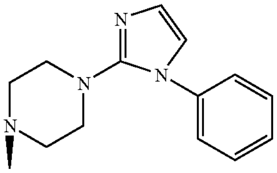 | S | H | 3HCl |
| 225 | 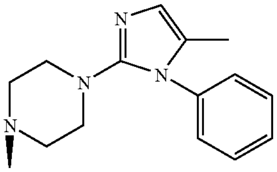 | S | H | 3HCl |
| 226 | 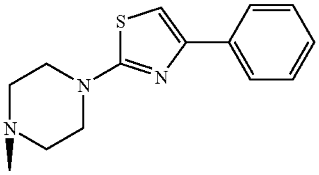 | S | H | 3HCl |

TABLE 26
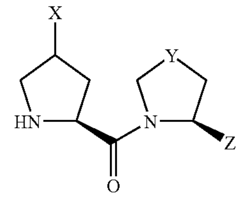
| Example No. | X | Y | Z | salt |
|---|---|---|---|---|
| 227 | 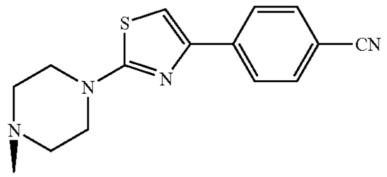 | S | H | 3HCl |
| 228 | 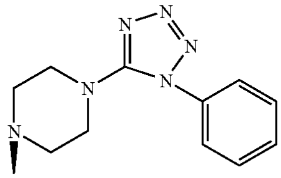 | S | H | 3HCl |
| 229 | 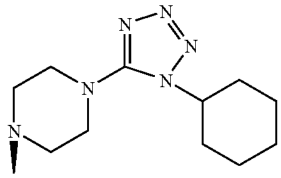 | S | H | 3HCl |
| 230 | 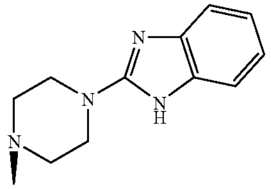 | S | H | 2HCl |
| 231 | 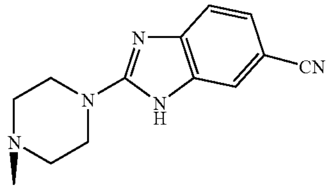 | S | H | 3HCl |
| 232 | 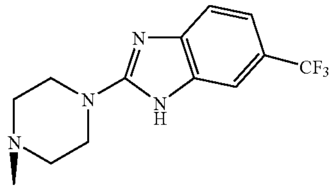 | S | H | 3HBr |
| 233 | 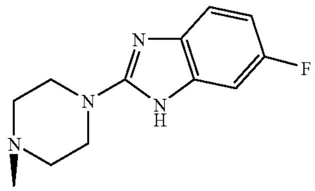 | S | H | 3HBr |

TABLE 27
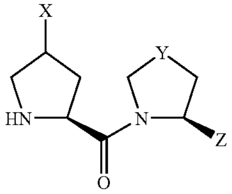
| Example No. | X | Y | Z | salt |
|---|---|---|---|---|
| 234 | 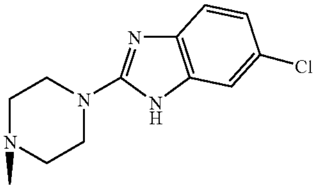 | S | H | 3HBr |
| 235 | 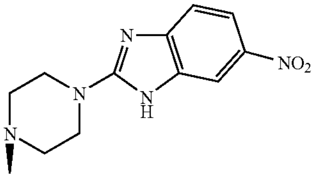 | S | H | 3HCl |
| 236 | 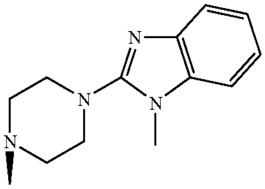 | S | H | 3HCl |
TABLE 27-continued
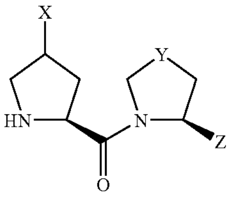
| Example No. | X | Y | Z | salt |
|---|---|---|---|---|
| 237 | 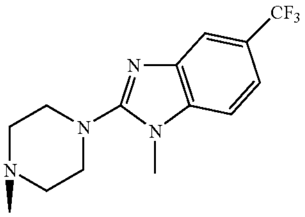 | S | H | 3HCl |
| 238 | 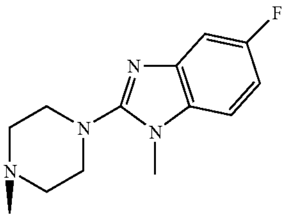 | S | H | 3HCl |
| 239 | 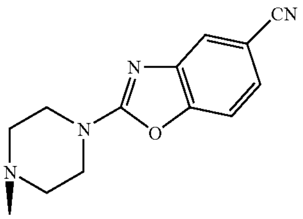 | S | H | 2HCl |
TABLE 28
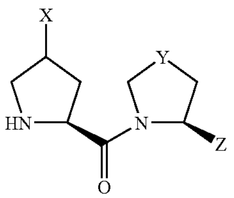
| Example No. | X | Y | Z | salt |
|---|---|---|---|---|
| 240 | 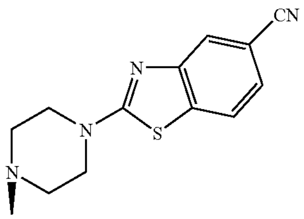 | S | H | 2HCl |

TABLE 28-continued
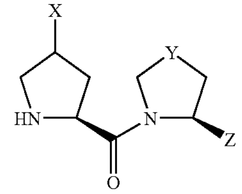
| Example No. | X | Y | Z | salt |
|---|---|---|---|---|
| 241 | 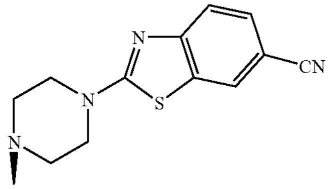 | S | H | 2HCl |
| 242 | 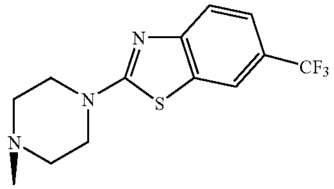 | S | H | 2HCl |
| 243 | 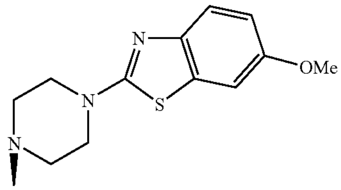 | S | H | 3HCl |
| 244 | 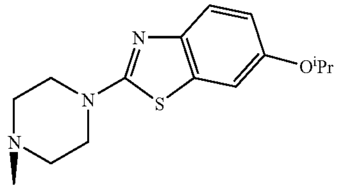 | S | H | 3HCl |
| 245 | 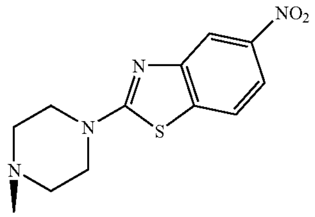 | S | H | 2HCl |

TABLE 29
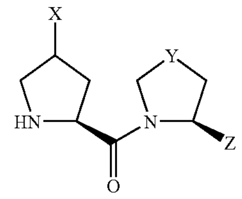
| Example No. | X | Y | Z | salt |
|---|---|---|---|---|
| 246 | 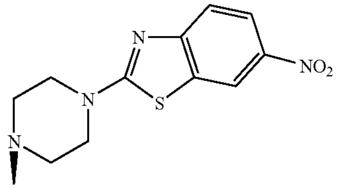 | S | H | 2HCl |
| 247 | 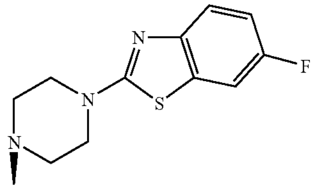 | S | H | 2HCl |
| 248 | 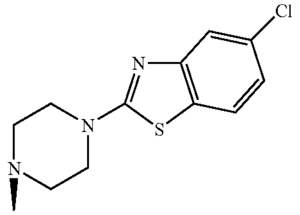 | S | H | 3HCl |
| 249 | 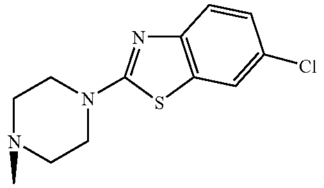 | S | H | 3HCl |
| 250 | 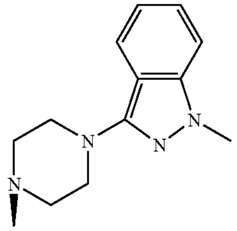 | S | H | 3HCl |
| 251 | 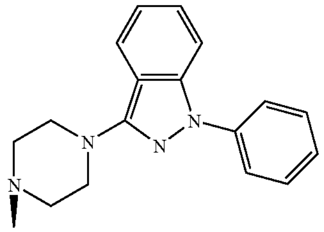 | S | H | 3HCl |

TABLE 30
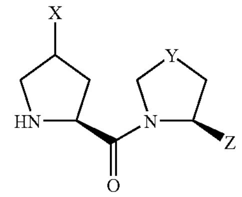
| Example No. | X | Y | Z | salt |
|---|---|---|---|---|
| 252 | 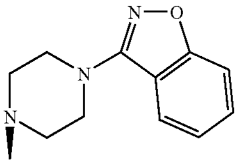 | S | H | 3HCl |
| 253 | 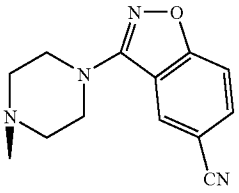 | S | H | 3HCl |
| 254 | 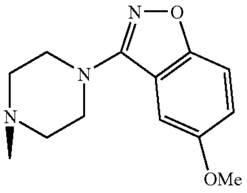 | S | H | 3HCl |
| 255 | 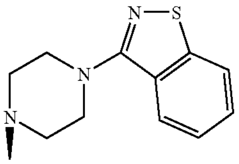 | S | H | $1.5(CO_2H)_2$ |
| 256 | 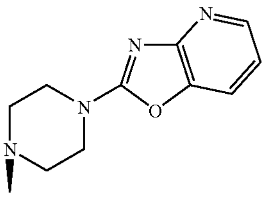 | S | H | 3HCl |
| 257 | 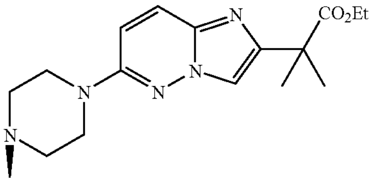 | S | H | 3HCl |
| 258 | 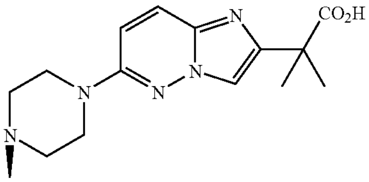 | S | H | 3HCl |

TABLE 31
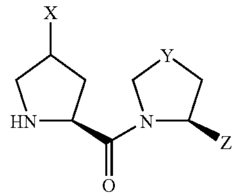
| Example No. | X | Y | Z | salt |
| --- | --- | --- | --- | --- |
| 259 | 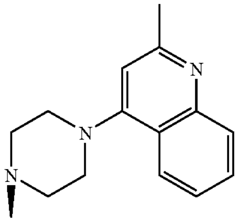 | S | H | 3HCl |
| 260 | 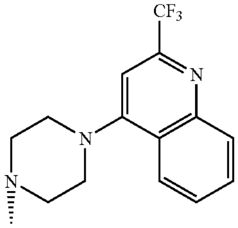 | S | H | 2HCl |
| 261 | 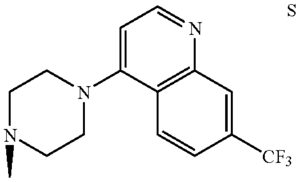 | S | H | 2HCl |
| 262 | 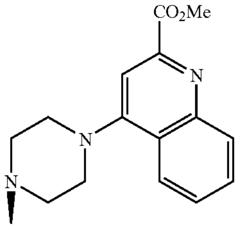 | S | H | 3HCl |
| 263 | 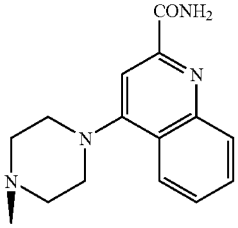 | S | H | 3HCl |
| 264 | 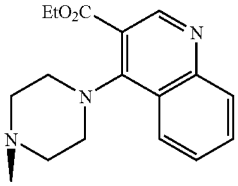 | S | H | 3HCl |
TABLE 32
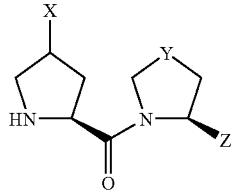
| Example No. | X | Y | Z | salt |
| --- | --- | --- | --- | --- |
| 265 | 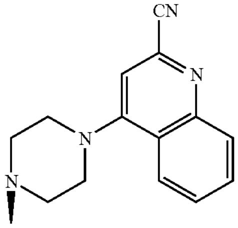 | S | H | 3HCl |
| 266 | 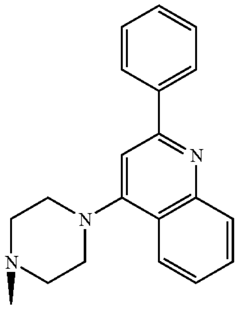 | S | H | 3HCl |
| 267 | 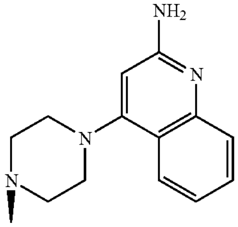 | S | H | 3HCl |
| 268 | 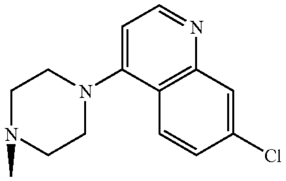 | S | H | 3HCl |
| 269 | 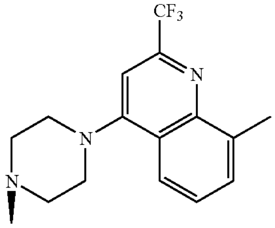 | S | H | 2HCl |

TABLE 32-continued
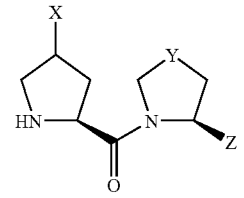
| Example No. | X | Y | Z | salt |
|---|---|---|---|---|
| 270 | 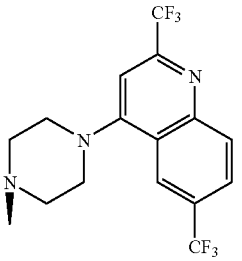 | S | H | 2HCl |
TABLE 33
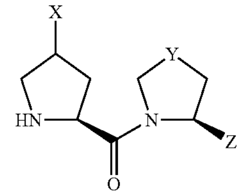
| Example No. | X | Y | Z | salt |
|---|---|---|---|---|
| 271 | 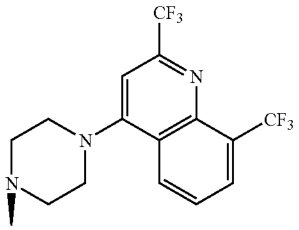 | S | H | 2HCl |
| 272 | 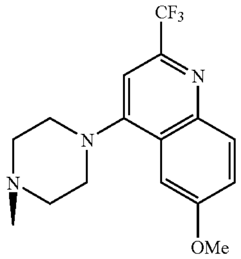 | S | H | 3HCl |
| 273 | 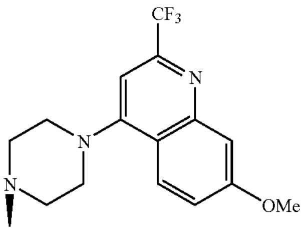 | S | H | 2HCl |
TABLE 33-continued
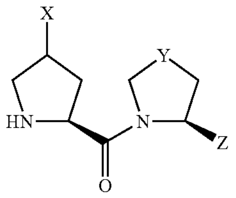
| Example No. | X | Y | Z | salt |
|---|---|---|---|---|
| 274 | 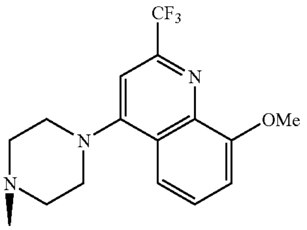 | S | H | 2HCl |
| 275 | 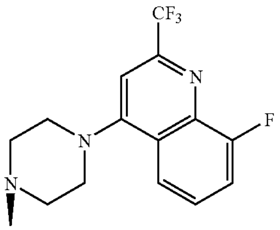 | S | H | 2HCl |
| 276 | 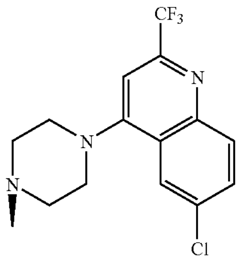 | S | H | 2HCl |
TABLE 34
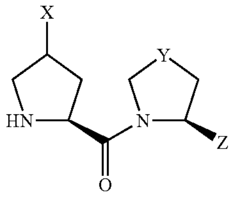
| Example No. | X | Y | Z | salt |
|---|---|---|---|---|
| 277 | 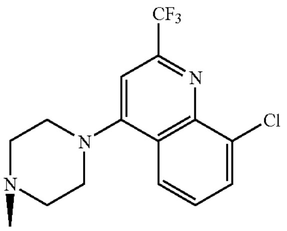 | S | H | 2HCl |

TABLE 34-continued
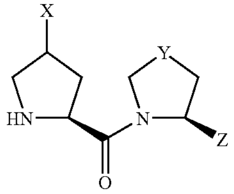
| Example No. | X | Y | Z | salt |
|---|---|---|---|---|
| 278 | 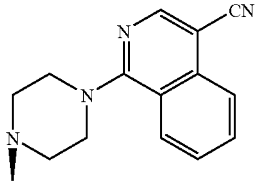 | S | H | 3HCl |
| 279 | 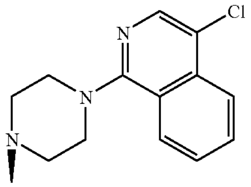 | S | H | 3HCl |
| 280 | 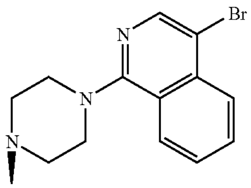 | S | H | 3HCl |
| 281 | 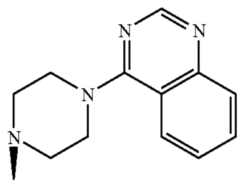 | S | H | 3HCl |
| 282 | 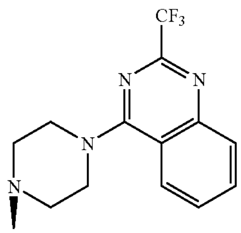 | S | H | — |
TABLE 35
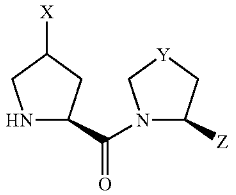
| Example No. | X | Y | Z | salt |
|---|---|---|---|---|
| 283 | 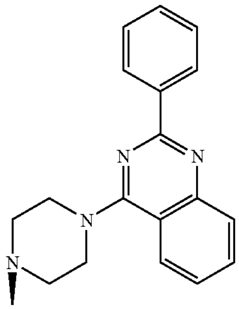 | S | H | 3HCl |
| 284 | 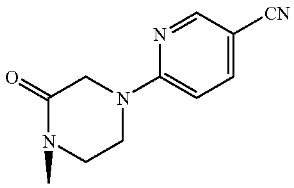 | S | H | 2HCl |
| 285 | 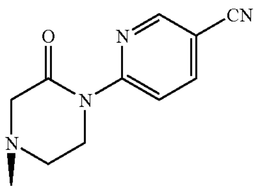 | S | H | 2HCl |
| 286 | 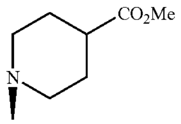 | S | H | 2HCl |
| 287 | 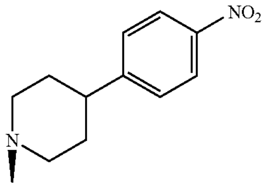 | S | H | 2HCl |
| 288 | 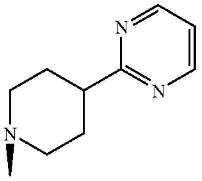 | S | H | 2HCl |

TABLE 35-continued
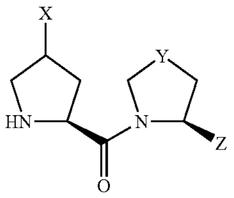
| Example No. | X | Y | Z | salt |
|---|---|---|---|---|
| 289 | 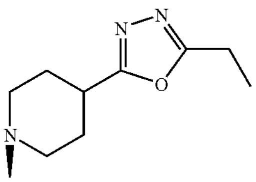 | S | H | 2HCl |
TABLE 36
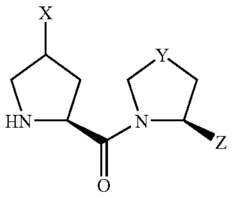
| Example No. | X | Y | Z | salt |
|---|---|---|---|---|
| 290 | 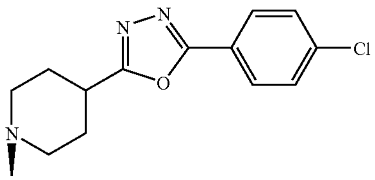 | S | H | 2HCl |
| 291 | 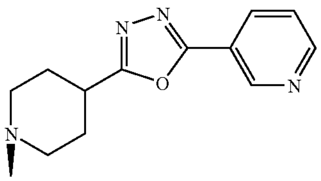 | S | H | 3HCl |
| 292 | 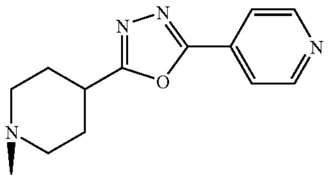 | S | H | 3HCl |
| 293 | 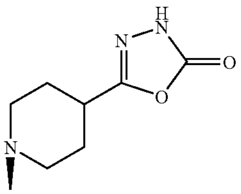 | S | H | 2HCl |
TABLE 36-continued
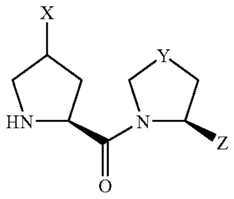
| Example No. | X | Y | Z | salt |
|---|---|---|---|---|
| 294 | 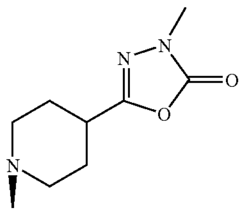 | S | H | 2HCl |
| 295 | 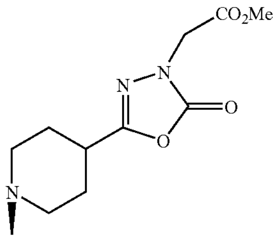 | S | H | 2HCl |
TABLE 37
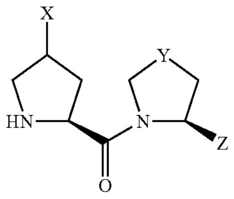
| Example No. | X | Y | Z | salt |
|---|---|---|---|---|
| 296 | 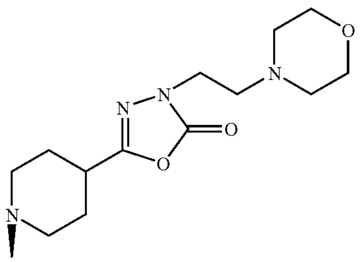 | S | H | 3HCl |
| 297 | 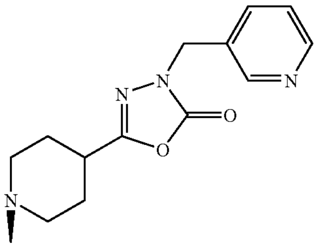 | S | H | 3HCl |

TABLE 37-continued
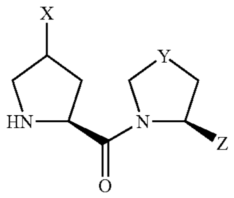
| Example No. | X | Y | Z | salt |
|---|---|---|---|---|
| 298 | 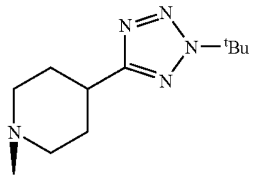 | S | H | 2HCl |
| 299 | 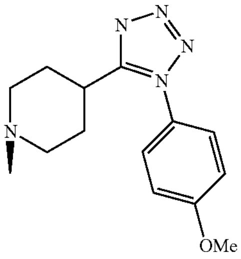 | S | H | 2HCl |
| 300 | 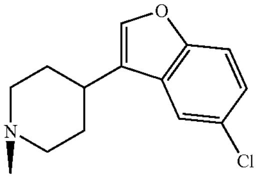 | S | H | 2HCl |
| 301 | 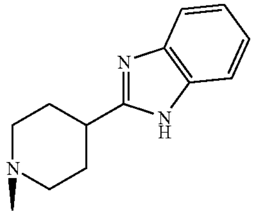 | S | H | 3HCl |
TABLE 38
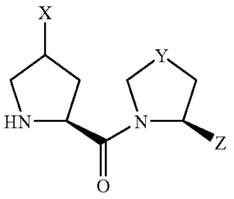
| Example No. | X | Y | Z | salt |
|---|---|---|---|---|
| 302 | 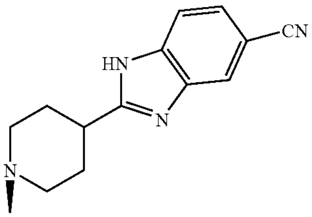 | S | H | 3HCl |
| 303 | 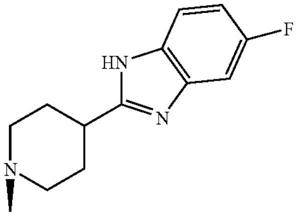 | S | H | 3HCl |
| 304 | 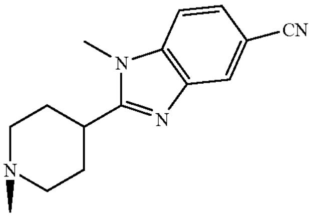 | S | H | 3HCl |
| 305 | 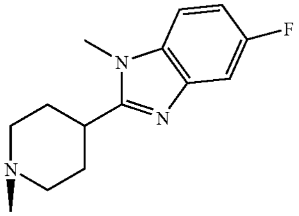 | S | H | 3HCl |
| 306 | 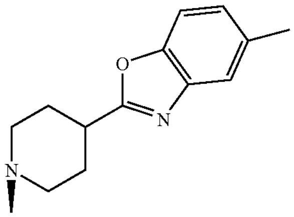 | S | H | — |
| 307 | 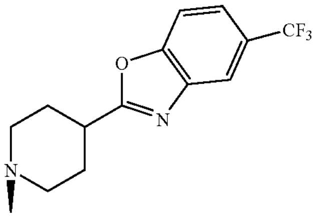 | S | H | — |

TABLE 39
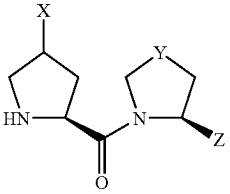
| Example No. | X | Y | Z | salt |
|---|---|---|---|---|
| 308 | 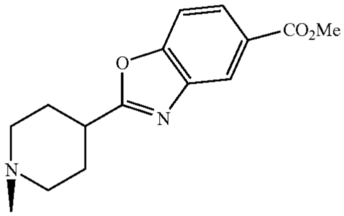 | S | H | — |
| 309 | 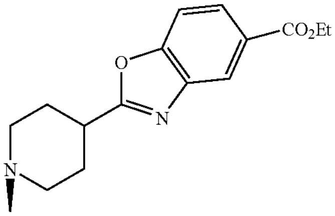 | S | H | — |
| 310 | 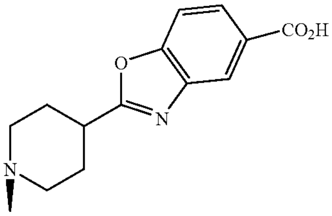 | S | H | 2HCl |
| 311 | 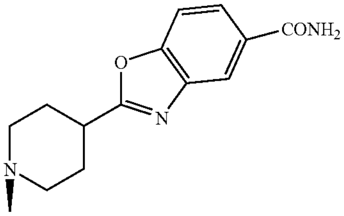 | S | H | — |
| 312 | 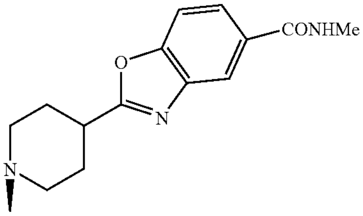 | S | H | — |
TABLE 39-continued
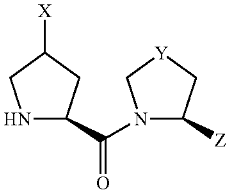
| Example No. | X | Y | Z | salt |
|---|---|---|---|---|
| 313 | 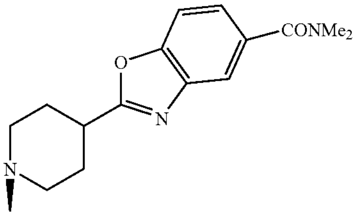 | S | H | 2HCl |
TABLE 40
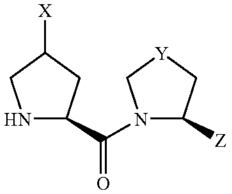
| Example No. | X | Y | Z | salt |
|---|---|---|---|---|
| 314 | 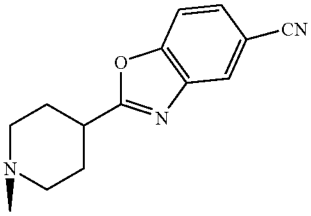 | S | H | — |
| 315 | 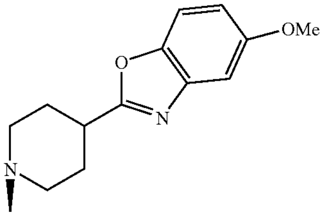 | S | H | 2HCl |
| 316 | 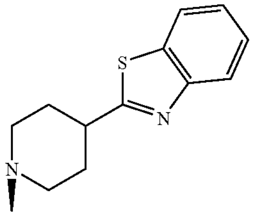 | S | H | 2HCl |

TABLE 40-continued

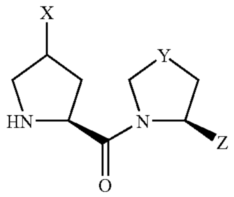

| Example No. | X | Y | Z | salt |
|---|---|---|---|---|
| 317 | 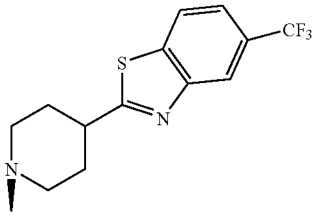 | S | H | — |
| 318 | 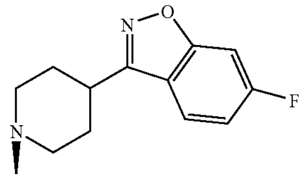 | S | H | 2HCl |
| 319 | 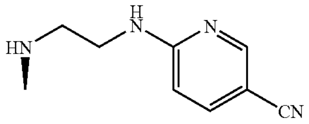 | S | H | 3HCl |
| 320 | 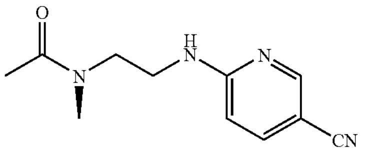 | S | H | 2HCl |

The compound of the present invention showed a potent DPP-IV inhibitory activity in Experimental Example 1 shown below.

Experimental Example 1

Plasma DPP-IV Inhibitory Activity

The plasma DPP-IV inhibitory activity of human and rat was measured by the fluorescence assay method. Using Gly-Pro-MCA (Peptide Institute Inc.) as a DPP-IV specific fluorescent substrate, reaction solutions having the following compositions and containing test substances having various concentrations were incubated at room temperature for 60 min and the measured (SPECTRA FLUOR, TECAN) fluorescent intensity (Exitation 360 nm/Emission 465 nm) was taken as the DPP-IV activity.

| | |
|---|---|
| Rat or human plasma (10-fold diluted solution) | 20 μL/well |
| fluorescent substrate (100 μmol/L) | 20 μL/well |

-continued

| | |
|---|---|
| test substance | 20 μL/well |
| buffer (0.003% Brij-35 containing PBS) | 140 μL/well |
| total amount | 200 μL/well |

The inhibitory rate relative to the solvent addition group was calculated and $IC_{50}$ values were determined by logistic analysis.

The $IC_{50}$ values of the plasma DPP-IV inhibitory activity of the present invention as determined by the method above are shown in the following table.

| Example compound No. | Human plasma DPP-IV Inhibitory activity $IC_{50}$ (nM) | Rat plasma DPP-IV Inhibitory activity $IC_{50}$ (nM) |
|---|---|---|
| 5 | 0.18 | 0.17 |
| 12 | 0.13 | 0.15 |
| 20 | 0.54 | 0.41 |
| 24 | 0.51 | 0.64 |
| 29 | 0.30 | 0.22 |
| 39 | 1.1 | 0.55 |
| 88 | 4.8 | 6.1 |
| 99 | 6.8 | 9.4 |
| 143 | 1.5 | 2.1 |
| 186 | 3.7 | 4.2 |
| 189 | 0.95 | 1.0 |
| 212 | 0.45 | 0.75 |
| 242 | 0.33 | 0.34 |
| 279 | 0.73 | 0.79 |
| 296 | 1.1 | 1.9 |
| 303 | 0.61 | 1.1 |

As shown in the following, the plasma DPP-IV inhibitory activity of the compound of Japanese Patent Application under PCT laid-open under kohyo No. 9-509921 and the compound of WO99/61431 is not sufficient.

| Known compound | Human plasma DPP-IV Inhibitory activity $IC_{50}$ (nM) |
|---|---|
| (S)-2-cyano-1-L-prolylpyrrolidine hydrochloride | 2.9 |
| 3-L-prolyl-1,3-thiazolidine | 538 |

INDUSTRIAL APPLICABILITY

From the foregoing Experimental Example and various pharmacological experiments, the compounds of the present invention exhibit a potent DPP-IV inhibitory activity and are useful for the prophylaxis or treatment of diabetes or the prophylaxis or treatment of obesity or the prophylaxis or treatment of HIV infection, cancer metastasis, dermopathy, prostatic hyperplasia, periodontitis or autoimmune disease, and the like.

This application is based on patent application Nos. 243217/2000 and 400296/2000 filed in Japan, the contents of which are hereby incorporated by reference.

What is claimed is:

1. An L-proline derivative of the formula (I)

(I)

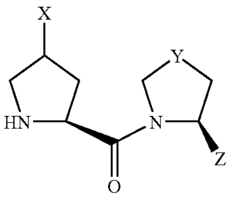

wherein

X is —$NR^1R^2$ wherein $R^1$ and $R^2$ may be the same or different and each is independently cycloalkylalkyl, arylalkyl, heteroaryl or heteroarylalkyl, or may be bonded to each other to form a heterocycle optionally containing 1 or 2 nitrogen atoms or oxygen atoms, the heterocycle optionally being condensed with an aromatic ring optionally having substituents, and the heterocycle optionally being a spiro ring, —$NR^3COR^4$ wherein $R^3$ and $R^4$ are the same or different and each is independently a hydrogen atom, alkyl, cycloalkyl, cycloalkylalkyl, aryl, arylalkyl, arylalkenyl, heteroaryl or heteroarylalkyl, —$NR^5CONR^6R^7$ or —$NR^5CH_2CH_2NR^6R^7$ wherein $R^5$, $R^6$ and $R^7$ are the same or different and each is independently hydrogen atom, alkyl, acyl, cycloalkyl, cycloalkylalkyl, aryl, arylalkyl, heteroaryl or heteroarylalkyl, or $R^6$ and $R^7$ may be bonded to each other to form a heterocycle optionally containing 1 or 2 nitrogen atoms or oxygen atoms, the heterocycle optionally being condensed with an aromatic ring optionally having substituents, —$NR^8SO_2R^9$ wherein $R^8$ and $R^9$ are the same or different and each is independently a hydrogen atom, alkyl, cycloalkyl, cycloalkylalkyl, aryl, arylalkyl, heteroaryl or heteroarylalkyl, or —$OR^{10}$ or —$OCOR^{11}$ wherein $R^{10}$ and $R^{11}$ are each a hydrogen atom, alkyl, cycloalkyl, cycloalkylalkyl, aryl, arylalkyl, heteroaryl or heteroarylalkyl, Y is $CH_2$, CH—OH, S, S═O or $SO_2$, Z is a hydrogen atom or a cyano, and of the above-mentioned groups, alkyl, aryl, arylalkyl, arylalkenyl, heteroaryl, heteroarylalkyl, cycloalkyl, cycloalkylalkyl and heterocycle each optionally have substituents, or a pharmaceutically acceptable salt thereof.

2. The L-proline derivative of claim 1, wherein X of the formula (I) is a group of the formula (II):

(II)

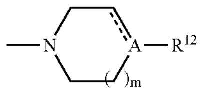

wherein

=== is a single bond or a double bond, $R^{12}$ is alkyl, cycloalkyl, cycloalkylalkyl, aryl, arylalkyl, heteroaryl, heteroarylalkyl, —$NR^{14}R^{15}$, —$OR^{16}$, —$COR^{17}$, —$CO_2R^{18}$, —$CONR^{19}R^{20}$ or —$SO_2R^{21}$ wherein $R^{14}R^{15}$, $R^{16}$, $R^{17}$, $R^{18}$, $R^{19}$, $R^{20}$ and $R^{21}$ are the same or different and each is independently a hydrogen atom, alkyl, cycloalkyl, cycloalkylalkyl, aryl, arylalkyl, heteroaryl, heteroarylalkyl or haloalkyl, or $R^{14}$ and $R^{15}$, and $R^{19}$ and $R^{20}$ may be bonded to each other to form heterocycles each optionally containing 1 or 2 nitrogen atoms or oxygen atoms, said heterocycle optionally being condensed with an aromatic ring optionally having substituents, m is 1 or 2, and A is a carbon atom or a nitrogen atom, provided that i) when A is a carbon atom, A may be substituted by a hydroxyl group, carboxyl or alkoxycarbonyl, and ii) when A is a nitrogen atom, === is a single bond, of the above-mentioned groups, alkyl, cycloalkyl, cycloalkylalkyl, aryl, arylalkyl, heteroaryl, heteroarylalkyl and heterocycle each optionally have substituents, or a pharmaceutically acceptable salt thereof.

3. The L-proline derivative of claim 1, wherein X of the formula (I) is a group of the formula (VI) or (VII):

(VI)

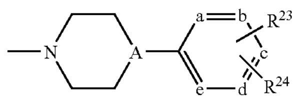

(VII)

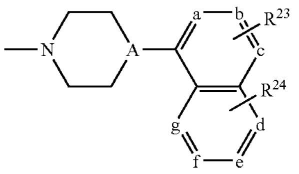

wherein $R^{23}$ and $R^{24}$ are the same or different and each is independently a hydrogen atom, alkyl, aryl, arylalkyl, heteroaryl, heteroarylalkyl, halogen, haloalkyl, cyano, nitro, —$NR^{25}R^{26}$, —$NHSO_2R^{27}$, —$OR^{28}$, —$COOR^{29}$, —$CONHSO_2R^{30}$, —$SO_2OR^{31}$, —$SO_2R^{32}$ or —$CONR^{33}R^{34}$ wherein $R^{25}$, $R^{26}$, $R^{27}$, $R^{28}$, $R^{29}$, $R^{30}$, $R^{31}$, $R^{32}$, $R^{33}$ and $R^{34}$ are the same or different and each is independently a hydrogen atom, alkyl, cycloalkyl, cycloalkylalkyl, aryl, arylalkyl, heteroaryl, heteroarylalkyl or haloalkyl, or $R^{25}$ and $R^{26}$, and $R^{33}$ and $R^{34}$ may be bonded to each other to form heterocycles each optionally containing 1 or 2 nitrogen atoms or oxygen atoms, said heterocycle optionally being condensed with an aromatic ring optionally having substituents, a, b, c, d, e, f and g are all carbon atoms, or any one or two thereof is(are) nitrogen atom(s) and the rest is a carbon atom, and A is a carbon atom or a nitrogen atom, provided that when A is a carbon atom, A may be substituted by a hydroxyl group, carboxyl or alkoxycarbonyl, and of the above-mentioned groups, alkyl, aryl, arylalkyl, heteroaryl, heteroarylalkyl, cycloalkyl, cycloalkylalkyl and heterocycle each optionally have substituents, or a pharmaceutically acceptable salt thereof.

4. The L-proline derivative of claim 3, wherein, in the formula (I), the asymmetric carbon, to which X is bonded, is expressed by an S configuration, X is a group of the formula (VI) or (VII), $R^{23}$ and $R^{24}$ are the same or different and each is nitro, cyano, $C_{1-6}$alkyl, $C_{1-6}$alkyloxy, halogen or haloalkyl, Y is a sulfur atom and Z is a hydrogen atom, or a pharmaceutically acceptable salt thereof.

5. The L-proline derivative of claim 1, which is 3-{(2S, 4S)-4-[4-(3-methyl-1-phenyl-5-pyrazolyl)-1-piperazinyl]-2-pyrrolidinylcarbonyl}-1,3-thiazolidine trihydrochloride.

6. 3-{(2S,4S)-4-[4-(3-methyl-1-phenyl-5-pyrazolyl)-1-piperazinyl]-2-pyrrolidinylcarbonyl}-1,3-thiazolidine or a salt thereof.

7. A pharmaceutical composition containing the L-proline derivative of any one of claims 1 to 4 or a pharmaceutically acceptable salt thereof, or the L-proline derivative of claim 5 or a pharmaceutically acceptable salt thereof, or the compound of claim 6, and a pharmacologically acceptable carrier.

8. A method for treating diabetes or obesity, which comprises administering to a mammal in need thereof a therapeutically effective amount of the L-proline derivative according to any one of claims 1 to 4 or 5 or 6, or a pharmaceutically acceptable salt thereof.

* * * * *

UNITED STATES PATENT AND TRADEMARK OFFICE
CERTIFICATE OF CORRECTION

PATENT NO. : 7,074,794 B2
APPLICATION NO. : 10/344255
DATED : July 11, 2006
INVENTOR(S) : Hiroshi Kitajima et al.

It is certified that error appears in the above-identified patent and that said Letters Patent is hereby corrected as shown below:

Title Page

In Section (30) Foreign Application Priority Data, please change the first application number of “2000-24217” to -- 2000-243217 --.

Signed and Sealed this

Sixth Day of February, 2007

JON W. DUDAS
*Director of the United States Patent and Trademark Office*